US012442015B2

(12) United States Patent
Alkan et al.

(10) Patent No.: US 12,442,015 B2
(45) Date of Patent: Oct. 14, 2025

(54) CLOSED-ENDED DNA VECTORS OBTAINABLE FROM CELL-FREE SYNTHESIS AND PROCESS FOR OBTAINING ceDNA VECTORS

(71) Applicant: Generation Bio Co., Cambridge, MA (US)

(72) Inventors: Ozan Alkan, Cambridge, MA (US); Robert Michael Kotin, Cambridge, MA (US); Matthew Stanton, Cambridge, MA (US); Douglas Anthony Kerr, Cambridge, MA (US); Carolyn Pelletier, Cambridge, MA (US)

(73) Assignee: Generation Bio Co., Cambridge, MA (US)

( * ) Notice: Subject to any disclaimer, the term of this patent is extended or adjusted under 35 U.S.C. 154(b) by 1188 days.

(21) Appl. No.: 16/962,005

(22) PCT Filed: Jan. 18, 2019

(86) PCT No.: PCT/US2019/014122

§ 371 (c)(1),
(2) Date: Jul. 14, 2020

(87) PCT Pub. No.: WO2019/143885

PCT Pub. Date: Jul. 25, 2019

(65) Prior Publication Data

US 2021/0071197 A1 Mar. 11, 2021

Related U.S. Application Data

(60) Provisional application No. 62/619,392, filed on Jan. 19, 2018.

(51) Int. Cl.
*C12N 15/85* (2006.01)

(52) U.S. Cl.
CPC ........ *C12N 15/85* (2013.01); *C12N 2800/105* (2013.01)

(58) Field of Classification Search
CPC .............. C12N 15/85; C12N 2800/105; C12N 2750/14143; C12N 2820/60; C12N 2830/48; C12N 15/86; C12N 15/63; C12N 2710/14043; A61K 39/12
See application file for complete search history.

(56) References Cited

U.S. PATENT DOCUMENTS

| | | | | |
|---|---|---|---|---|
| 11,066,679 | B2 * | 7/2021 | Kotin | A61P 3/08 |
| 2002/0164783 | A1 | 11/2002 | Feldhaus | |
| 2003/0211103 | A1 | 11/2003 | Buyse et al. | |
| 2009/0117615 | A1 | 5/2009 | Banzai et al. | |
| 2010/0105110 | A1 * | 4/2010 | Danthinne | C12N 7/00 435/235.1 |
| 2014/0107186 | A1 | 4/2014 | Garcia et al. | |
| 2014/0271551 | A1 | 9/2014 | Hirsch et al. | |
| 2019/0032083 | A1 * | 1/2019 | Kotin | A61K 48/0075 |
| 2022/0119840 | A1 * | 4/2022 | Kerr | A61K 31/437 |
| 2022/0195456 | A9 * | 6/2022 | Kotin | C12N 15/09 |
| 2022/0228171 | A1 * | 7/2022 | Alkan | C12N 15/86 |

FOREIGN PATENT DOCUMENTS

| | | |
|---|---|---|
| JP | 2010-046066 A | 3/2010 |
| WO | 1993/009239 A1 | 5/1993 |
| WO | 2017/152149 A1 | 9/2017 |
| WO | 2019/101596 A1 | 5/2019 |
| WO | 2019/161059 A1 | 8/2019 |
| WO | 2021/011842 A1 | 1/2021 |

OTHER PUBLICATIONS

Nahreini et al., Cloning and integration of DNA fragments in human cells via the inverted terminal repeats of the adeno-associated virus 2 genome. Gene. Oct. 1, 1992;119(2):265-72.
Dennis. Welfare issues of genetically modified animals. ILAR J. 2002;43(2):100-9.
Maksimenko et al., Cyclic oligonucleotides. II. Regularities in the formation of polycyclic structures. Bioorg Khim. Feb. 1997;23(2):127-33.
Muller et al., Spliceosomal peptide P140 for immunotherapy of systemic lupus erythematosus: results of an early phase II clinical trial. Arthritis Rheum. Dec. 2008;58(12):3873-83.
Xu et al., Drug delivery trends in clinical trials and translational medicine: challenges and opportunities in the delivery of nucleic acid-based therapeutics. J Pharm Sci. Jan. 2011;100(1):38-52.
Zhou et al., Developing tTA transgenic rats for inducible and reversible gene expression. Int J Biol Sci. 2009;5(2):171-81.

(Continued)

*Primary Examiner* — Jeremy C Flinders
*Assistant Examiner* — Alexander W Nicol
(74) *Attorney, Agent, or Firm* — McCarter & English, LLP; Marcie B. Clarke

(57) ABSTRACT

The application describes methods for synthetic synthesis and cell-free synthesis of DNA vectors, particularly closed-ended DNA vectors (e.g., ceDNA vectors) having linear and continuous structure for delivery and expression of a transgene. The present invention relates to an in vitro process for production of closed-ended DNA vectors, corresponding DNA vector products produced by the methods and uses thereof, and oligonucleotides and kits useful in the process of the invention. DNA vectors produced using the methods described herein are free from unwanted side effects due to contaminants introduced during production in cell lines, for example, bacterial or insect cell lines. Further provided herein are methods and cell lines for reliable gene expression in vitro, ex vivo and in vivo using the ceDNA vectors synthesized using the methods herein.

16 Claims, 52 Drawing Sheets

Specification includes a Sequence Listing.

(56) References Cited

OTHER PUBLICATIONS

International Search Report and Written Opinion for Application No. PCT/US2019/014122, dated Apr. 11, 2019, 14 pages.
International Preliminary Report on Patentability for Application No. PCT/US2019/014122, dated Jul. 30, 2020, 11 pages.
Cataldi et al., Hairpin-end conformation of adeno-associated virus genome determines interactions with DNA-repair pathways. Gene Ther. Jun. 2013;20(6):686-93.

* cited by examiner

ITR-1, Right

GCGCGCTCGCTCGCTCACTGAGGCCGGGCGACCAAAGGTCGCCCGACGCCCGGGCGGCCTCAGTGAGCGAGCGAGCGCGC

α β γ δ B B′ C δ γ β α

WT-L-oligo-1: ctAGGCCGCCCGGGCAAAGCCCGGGCGTCGGGCGACTTTGGTCGCCCGGC

- AvrII recognition placed in the stem, to recover rep binding sites if needed

WT-L-oligo-2: ctaggACTGAGGCCGCCCGGGCAAAGCCCGGGCGTCGGGCGACCTTTGGTCGCCCGGCCTCAGTc

- AvrII recognition site placed at the end of the stem predicted structure

Probability >= 99%
99% > Probability >= 95%
95% > Probability >= 90%
90% > Probability >= 80%
80% > Probability >= 70%
70% > Probability >= 60%
60% > Probability >= 50%
50% > Probability
ENERGY= -50.9 WT-L-oligo-2

WT-R-oligo-3: ggACTGAGGCCGCCCGGGCAAAGCCCGGGCGTCGGGCGACCTTTGGTCGCCCGGCCTCAGTcctgca

- Sbf1 recognition site placed at the end of the stem predicted structure

Probability >= 99%
99% > Probability >= 95%
95% > Probability >= 90%
90% > Probability >= 80%
80% > Probability >= 70%
70% > Probability >= 60%
60% > Probability >= 50%
50% > Probability
ENERGY= -50.9 WT-R-oligo-3

MU-R-oligo-1: GtgCGGGCGACCAAAGGTCGCCCGACGCCCGGGCGcaCTCA

- DraIII recognition placed in the stem, to recover rep binding sites if needed predicted structure Probability >= 99%
99% > Probability >= 95%
95% > Probability >= 90%
90% > Probability >= 80%
80% > Probability >= 70%
70% > Probability >= 60%
60% > Probability >= 50%
50% > Probability
ENERGY= -22.0 MU-R-oligo-1

MU-R-oligo-2: ggACTGAGGCCGGGCGACCAAAGGTCGCCCGACGCCCGGGCGGCCTCAGTcctgca

- Sbf1 recognition site placed at end of the stem predicted structure

Probability >= 99%
99% > Probability >= 95%
95% > Probability >= 90%
90% > Probability >= 80%
80% > Probability >= 70%
70% > Probability >= 60%
60% > Probability >= 50%
50% > Probability
ENERGY= -33.2 MU-R-oligo-2

MU-L-oligo-3: ctaggACTGAGGCCGCCCGGGCGTCGGGCGACCTTTGGTCGCCCGGCCTCAGTc

- AvrII recognition site placed at end of the stem predicted structure

Probability >= 99%
99% > Probability >= 95%
95% > Probability >= 90%
90% > Probability >= 80%
80% > Probability >= 70%
70% > Probability >= 60%
60% > Probability >= 50%
50% > Probability
ENERGY= -32.7 MU-L-oligo-3

MU-R-oligo-4 dITR R
56 bp

MU-R-oligo-4: ggACTGAGGCCGGGCGACCAAAGGTCGCCCGACGGCCTCAGTcctgca

- Sbf1 recognition site placed at end of the stem predicted structure

Probability >= 99%
99% > Probability >= 95%
95% > Probability >= 90%
90% > Probability >= 80%
80% > Probability >= 70%
70% > Probability >= 60%
60% > Probability >= 50%
50% > Probability
ENERGY= -32.8 MU-L-oligo-4

MU-L-oligo-5

MU-L-oligo-5: ctaggACTGAGGCCGTCGGGCGACCTTTGGTCGCCCGGCCTCAGTc

- AvrII recognition site placed at end of the stem predicted structure

Probability >= 99%
99% > Probability >= 95%
95% > Probability >= 90%
90% > Probability >= 80%
80% > Probability >= 70%
70% > Probability >= 60%
60% > Probability >= 50%
50% > Probability
ENERGY= -32.8 MU-L-oligo-5

MU-R-oligo-6

FL R ITR
75 bp

MU-R-oligo-6: ggACTGAGGCCCGGGCGACCAAAGGTCGCCCGACGCCCGGGCTTTGCCCGGGCGCCTCAGTcctgca

- Sbf1 recognition site placed at end of the stem predicted structure

Probability >= 99%
99% > Probability >= 95%
95% > Probability >= 90%
90% > Probability >= 80%
80% > Probability >= 70%
70% > Probability >= 60%
60% > Probability >= 50%
50% > Probability
ENERGY= -48.6 MU-R-oligo-6

Energy = -54.4

ITR-6, Right

Energy = -54.4

ITR-6, Left

Synthetic eGFP-ceDNA [wt/wt]

Synthetic eGFP-ceDNA

Control SF9-derived eGFP-ceDNA [wt/mu]

Synthetic eGFP-ceDNA [mu/mu]

SEQUENCE LISTING

```
<160> NUMBER OF SEQ ID NOS: 187

<210> SEQ ID NO 1
<211> LENGTH: 141
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

aggaacccct agtgatggag ttggccactc cctctctgcg cgctcgctcg ctcactgagg     60

ccgggcgacc aaaggtcgcc cgacgcccgg gctttgcccg ggcggcctca gtgagcgagc    120

gagcgcgcag ctgcctgcag g                                              141


<210> SEQ ID NO 2
<211> LENGTH: 141
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 2
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc t 141

<210> SEQ ID NO 3
<211> LENGTH: 130
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 3
aggaacccct agtgatggag ttggccactc cctctctgcg cgctcgctcg ctcactgagg 60
ccgggcgacc aaaggtcgcc cgacgcccgg gcggcctcag tgagcgagcg agcgcgcagc 120
tgcctgcagg 130

<210> SEQ ID NO 4
<211> LENGTH: 130
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 4
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct 130

<210> SEQ ID NO 5
<211> LENGTH: 143
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 5
ttgcccactc cctctctgcg cgctcgctcg ctcggtgggg cctgcggacc aaaggtccgc 60
agacggcaga ggtctcctct gccggcccca ccgagcgagc gacgcgcgca gagagggagt 120
gggcaactcc atcactaggg taa 143

<210> SEQ ID NO 6
<211> LENGTH: 144
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 6
ttggccactc cctctatgcg cactcgctcg ctcggtgggg cctggcgacc aaaggtcgcc 60
agacggacgt gggtttccac gtccggcccc accgagcgag cgagtgcgca tagagggagt 120
ggccaactcc atcactagag gtat 144

<210> SEQ ID NO 7

<211> LENGTH: 127
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 7
ttggccactc cctctatgcg cgctcgctca ctcactcggc cctggagacc aaaggtctcc 60
agactgccgg cctctggccg gcagggccga gtgagtgagc gagcgcgcat agagggagtg 120
gccaact 127

<210> SEQ ID NO 8
<211> LENGTH: 166
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 8 tccccctgt cgcgttcgct cgctcgctgg ctcgtttggg ggggcgacgg ccagagggcc 60
gtcgtctggc agctctttga gctgccaccc ccccaaacga gccagcgagc gagcgaacgc 120
gacagggggg agagtgccac actctcaagc aagggggttt tgtaag 166

<210> SEQ ID NO 9
<211> LENGTH: 144
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 9
ttgcccactc cctctaatgc gcgctcgctc gctcggtggg gcctgcggac caaaggtccg 60
cagacggcag aggtctcctc tgccggcccc accgagcgag cgagcgcgca tagagggagt 120
gggcaactcc atcactaggg gtat 144

<210> SEQ ID NO 10
<211> LENGTH: 143
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 10
ttaccctagt gatggagttg cccactccct ctctgcgcgc gtcgctcgct cggtggggcc 60
ggcagaggag acctctgccg tctgcggacc tttggtccgc aggccccacc gagcgagcga 120
gcgcgcagag agggagtggg caa 143

<210> SEQ ID NO 11
<211> LENGTH: 144
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 11
atacctctag tgatggagtt ggccactccc tctatgcgca ctcgctcgct cggtggggcc 60

-continued ggacgtggaa acccacgtcc gtctggcgac ctttggtcgc caggccccac cgagcgagcg 120
agtgcgcata gagggagtgg ccaa 144

<210> SEQ ID NO 12
<211> LENGTH: 127
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12
agttggccac attagctatg cgcgctcgct cactcactcg gccctggaga ccaaaggtct 60
ccagactgcc ggcctctggc cggcagggcc gagtgagtga gcgagcgcgc atagagggag 120
tggccaa 127

<210> SEQ ID NO 13
<211> LENGTH: 166
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13
cttacaaaac ccccttgctt gagagtgtgg cactctcccc cctgtcgcgt tcgctcgctc 60
gctggctcgt ttgggggggt ggcagctcaa agagctgcca gacgacggcc ctctggccgt 120 cgcccccccca aacgagccag cgagcgagcg aacgcgacag gggga 166

<210> SEQ ID NO 14
<211> LENGTH: 144
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14 ataccctag tgatggagtt gcccactccc tctatgcgcg ctcgctcgct cggtggggcc 60
ggcagaggag acctctgccg tctgcggacc tttggtccgc aggccccacc gagcgagcga 120
gcgcgcatta gagggagtgg gcaa 144

<210> SEQ ID NO 15
<211> LENGTH: 120
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15
aggaacccct agtgatggag ttggccactc cctctctgcg cgctcgctcg ctcactgagg 60
cgcacgcccg ggtttcccgg gcggcctcag tgagcgagcg agcgcgcagc tgcctgcagg 120

<210> SEQ ID NO 16
<211> LENGTH: 122
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16
aggaacccct agtgatggag ttggccactc cctctctgcg cgctcgctcg ctcactgagg 60
ccgacgcccg ggctttgccc gggcggcctc agtgagcgag cgagcgcgca gctgcctgca 120
gg 122

<210> SEQ ID NO 17
<211> LENGTH: 129
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 17
aggaacccct agtgatggag ttggccactc cctctctgcg cgctcgctcg ctcactgagg 60
ccgggcgacc aaaggtcgcc cgacgcccgg gcgcctcagt gagcgagcga gcgcgcagct 120
gcctgcagg 129

<210> SEQ ID NO 18
<211> LENGTH: 101
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 18
aggaacccct agtgatggag ttggccactc cctctctgcg cgctcgctcg ctcactgagg 60
ctttgcctca gtgagcgagc gagcgcgcag ctgcctgcag g 101

<210> SEQ ID NO 19
<211> LENGTH: 139
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 19
aggaacccct agtgatggag ttggccactc cctctctgcg cgctcgctcg ctcactgagg 60
ccgggcgaca aagtcgcccg acgcccgggc tttgcccggg cggcctcagt gagcgagcga 120
gcgcgcagct gcctgcagg 139

<210> SEQ ID NO 20
<211> LENGTH: 137
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 20
aggaacccct agtgatggag ttggccactc cctctctgcg cgctcgctcg ctcactgagg 60
ccgggcgaaa atcgcccgac gcccgggctt tgcccgggcg gcctcagtga gcgagcgagc 120
gcgcagctgc ctgcagg 137

<210> SEQ ID NO 21
<211> LENGTH: 135
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 21
aggaacccct agtgatggag ttggccactc cctctctgcg cgctcgctcg ctcactgagg 60
ccgggcgaaa cgcccgacgc ccgggctttg cccgggcggc ctcagtgagc gagcgagcgc 120
gcagctgcct gcagg 135

<210> SEQ ID NO 22
<211> LENGTH: 133
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 22
aggaacccct agtgatggag ttggccactc cctctctgcg cgctcgctcg ctcactgagg 60
ccgggcaaag cccgacgccc gggctttgcc cgggcggcct cagtgagcga gcgagcgcgc 120
agctgcctgc agg 133

<210> SEQ ID NO 23
<211> LENGTH: 139
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 23
aggaacccct agtgatggag ttggccactc cctctctgcg cgctcgctcg ctcactgagg 60
ccgggcgacc aaaggtcgcc cgacgcccgg gtttcccggg cggcctcagt gagcgagcga 120
gcgcgcagct gcctgcagg 139

<210> SEQ ID NO 24
<211> LENGTH: 137
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 24
aggaacccct agtgatggag ttggccactc cctctctgcg cgctcgctcg ctcactgagg 60
ccgggcgacc aaaggtcgcc cgacgcccgg tttccgggcg gcctcagtga gcgagcgagc 120
gcgcagctgc ctgcagg 137

<210> SEQ ID NO 25
<211> LENGTH: 135
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 25
aggaacccct agtgatggag ttggccactc cctctctgcg cgctcgctcg ctcactgagg 60
ccgggcgacc aaaggtcgcc cgacgcccgt ttcgggcggc ctcagtgagc gagcgagcgc 120
gcagctgcct gcagg 135

<210> SEQ ID NO 26
<211> LENGTH: 133
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 26
aggaacccct agtgatggag ttggccactc cctctctgcg cgctcgctcg ctcactgagg 60
ccgggcgacc aaaggtcgcc cgacgccctt tgggcggcct cagtgagcga gcgagcgcgc 120
agctgcctgc agg 133

<210> SEQ ID NO 27
<211> LENGTH: 131
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 27
aggaacccct agtgatggag ttggccactc cctctctgcg cgctcgctcg ctcactgagg 60
ccgggcgacc aaaggtcgcc cgacgccttt ggcggcctca gtgagcgagc gagcgcgcag 120
ctgcctgcag g 131

<210> SEQ ID NO 28
<211> LENGTH: 129
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 28
aggaacccct agtgatggag ttggccactc cctctctgcg cgctcgctcg ctcactgagg 60
ccgggcgacc aaaggtcgcc cgacgctttg cggcctcagt gagcgagcga gcgcgcagct 120
gcctgcagg 129

<210> SEQ ID NO 29
<211> LENGTH: 127
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 29
aggaacccct agtgatggag ttggccactc cctctctgcg cgctcgctcg ctcactgagg 60
ccgggcgacc aaaggtcgcc cgacgtttcg gcctcagtga gcgagcgagc gcgcagctgc 120
ctgcagg 127

<210> SEQ ID NO 30
<211> LENGTH: 122
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 30
aggaacccct agtgatggag ttggccactc cctctctgcg cgctcgctcg ctcactgagg 60
ccgggcgacc aaaggtcgcc cgacggcctc agtgagcgag cgagcgcgca gctgcctgca 120
gg 122

<210> SEQ ID NO 31
<211> LENGTH: 130
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 31
aggaacccct agtgatggag ttggccactc cctctctgcg cgctcgctcg ctcactgagg 60
ccgggcgacc aaaggtcgcc cgacgcccgg gcggcctcag tgagcgagcg agcgcgcagc 120
tgcctgcagg 130

<210> SEQ ID NO 32
<211> LENGTH: 120
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32
cctgcaggca gctgcgcgct cgctcgctca ctgaggccgc ccgggaaacc cgggcgtgcg 60
cctcagtgag cgagcgagcg cgcagagagg gagtggccaa ctccatcact aggggttcct 120

<210> SEQ ID NO 33
<211> LENGTH: 122
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 33
cctgcaggca gctgcgcgct cgctcgctca ctgaggccgt cgggcgacct ttggtcgccc 60
ggcctcagtg agcgagcgag cgcgcagaga gggagtggcc aactccatca ctaggggttc 120
ct 122

<210> SEQ ID NO 34
<211> LENGTH: 122
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34
cctgcaggca gctgcgcgct cgctcgctca ctgaggccgc ccgggcaaag cccgggcgtc 60
ggcctcagtg agcgagcgag cgcgcagaga gggagtggcc aactccatca ctaggggttc 120
ct 122

<210> SEQ ID NO 35
<211> LENGTH: 129
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 35
cctgcaggca gctgcgcgct cgctcgctca ctgaggcgcc cgggcgtcgg gcgacctttg     60
gtcgcccggc ctcagtgagc gagcgagcgc gcagagaggg agtggccaac tccatcacta    120
ggggttcct                                                             129

<210> SEQ ID NO 36
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
cctgcaggca gctgcgcgct cgctcgctca ctgaggcaaa gcctcagtga gcgagcgagc     60
gcgcagagag ggagtggcca actccatcac taggggttcc t                        101

<210> SEQ ID NO 37
<211> LENGTH: 139
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
cctgcaggca gctgcgcgct cgctcgctca ctgaggccgc ccgggcaaag cccgggcgtc     60
gggcgacttt gtcgcccggc ctcagtgagc gagcgagcgc gcagagaggg agtggccaac    120
tccatcacta ggggttcct                                                 139

<210> SEQ ID NO 38
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
cctgcaggca gctgcgcgct cgctcgctca ctgaggccgc ccgggcaaag cccgggcgtc     60
gggcgatttt cgcccggcct cagtgagcga gcgagcgcgc agagagggag tggccaactc    120
catcactagg ggttcct                                                   137

<210> SEQ ID NO 39
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
cctgcaggca gctgcgcgct cgctcgctca ctgaggccgc ccgggcaaag cccgggcgtc     60
gggcgtttcg cccggcctca gtgagcgagc gagcgcgcag agagggagtg gccaactcca    120
tcactagggg ttcct                                                     135

<210> SEQ ID NO 40

<211> LENGTH: 133
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 40
cctgcaggca gctgcgcgct cgctcgctca ctgaggccgc ccgggcaaag cccgggcgtc 60
gggctttgcc cggcctcagt gagcgagcga gcgcgcagag agggagtggc caactccatc 120
actaggggtt cct 133

<210> SEQ ID NO 41
<211> LENGTH: 139
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 41
cctgcaggca gctgcgcgct cgctcgctca ctgaggccgc ccgggaaacc cgggcgtcgg 60
gcgacctttg gtcgcccggc ctcagtgagc gagcgagcgc gcagagaggg agtggccaac 120
tccatcacta ggggttcct 139

<210> SEQ ID NO 42
<211> LENGTH: 137
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 42
cctgcaggca gctgcgcgct cgctcgctca ctgaggccgc ccggaaaccg ggcgtcgggc 60
gacctttggt cgcccggcct cagtgagcga gcgagcgcgc agagagggag tggccaactc 120
catcactagg ggttcct 137

<210> SEQ ID NO 43
<211> LENGTH: 135
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 43
cctgcaggca gctgcgcgct cgctcgctca ctgaggccgc ccgaaacggg cgtcgggcga 60
cctttggtcg cccggcctca gtgagcgagc gagcgcgcag agagggagtg gccaactcca 120
tcactagggg ttcct 135

<210> SEQ ID NO 44
<211> LENGTH: 133
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 44
cctgcaggca gctgcgcgct cgctcgctca ctgaggccgc ccaaagggcg tcgggcgacc 60

-continued

```
tttggtcgcc cggcctcagt gagcgagcga gcgcgcagag agggagtggc caactccatc    120

actaggggtt cct                                                        133


<210> SEQ ID NO 45
<211> LENGTH: 131
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45

cctgcaggca gctgcgcgct cgctcgctca ctgaggccgc caaaggcgtc gggcgacctt     60

tggtcgcccg gcctcagtga gcgagcgagc gcgcagagag ggagtggcca actccatcac    120

taggggttcc t                                                          131


<210> SEQ ID NO 46
<211> LENGTH: 129
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46

cctgcaggca gctgcgcgct cgctcgctca ctgaggccgc aaagcgtcgg gcgacctttg     60

gtcgcccggc ctcagtgagc gagcgagcgc gcagagaggg agtggccaac tccatcacta    120

ggggttcct                                                             129


<210> SEQ ID NO 47
<211> LENGTH: 127
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

cctgcaggca gctgcgcgct cgctcgctca ctgaggccga aacgtcgggc gacctttggt     60

cgcccggcct cagtgagcga gcgagcgcgc agagagggag tggccaactc catcactagg    120

ggttcct                                                               127


<210> SEQ ID NO 48
<211> LENGTH: 122
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48

aggaacccct agtgatggag ttggccactc cctctctgcg cgctcgctcg ctcactgagg     60

ccgggcgacc aaaggtcgcc cgacggcctc agtgagcgag cgagcgcgca gctgcctgca    120

gg                                                                    122


<210> SEQ ID NO 49
<211> LENGTH: 12
<212> TYPE: DNA
<213> ORGANISM: Artificial Sequence
<220> FEATURE:
<223> OTHER INFORMATION: Description of Artificial Sequence: Synthetic
```

oligonucleotide

<400> SEQUENCE: 49
cgatcgttcg at 12

<210> SEQ ID NO 50
<211> LENGTH: 12
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 50
atcgaaccat cg 12

<210> SEQ ID NO 51
<211> LENGTH: 12
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 51
atcgaacgat cg 12

<210> SEQ ID NO 52
<211> LENGTH: 165
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 52
aggaacccct agtgatggag ttggccactc cctctctgcg cgctcgctcg ctcactgagg 60
ccgcccgggc aaagcccggg cgtcgggcga cctttggtcg cccggcctca gtgagcgagc 120
gagcgcgcag agagggagtg gccaactcca tcactagggg ttcct 165

<210> SEQ ID NO 53
<211> LENGTH: 140
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 53
cccctagtga tggagttggc cactccctct ctgcgcgctc gctcgctcac tgaggccgcc 60
cgggcaaagc ccgggcgtcg ggcgaccttt ggtcgcccgg cctcagtgag cgagcgagcg 120
cgcagagaga tcactagggg 140

<210> SEQ ID NO 54
<211> LENGTH: 91
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 54
gcgcgctcgc tcgctcactg aggccgcccg ggcaaagccc gggcgtcggg cgacctttgg 60
tcgcccggcc tcagtgagcg agcgagcgcg c 91

<210> SEQ ID NO 55
<211> LENGTH: 91
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 55
gcgcgctcgc tcgctcactg aggccgggcg accaaaggtc gcccgacgcc cgggctttgc 60
ccgggcggcc tcagtgagcg agcgagcgcg c 91

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 60
gcgcgctcgc tcgctc 16

<210> SEQ ID NO 61
<211> LENGTH: 6
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 61 ggttga 6

<210> SEQ ID NO 62
<211> LENGTH: 4
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 62 agtt 4

<210> SEQ ID NO 63
<211> LENGTH: 6
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 63 ggttgg 6

<210> SEQ ID NO 64
<211> LENGTH: 6
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 64 agttgg 6

<210> SEQ ID NO 65
<211> LENGTH: 6
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 65 agttga 6

<210> SEQ ID NO 66
<211> LENGTH: 6
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 66 rrttrr 6

<210> SEQ ID NO 67
<211> LENGTH: 581
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67
gagcatctta ccgccattta ttcccatatt tgttctgttt ttcttgattt gggtatacat 60
ttaaatgtta ataaaacaaa atggtggggc aatcatttac atttttaggg atatgtaatt 120
actagttcag gtgtattgcc acaagacaaa catgttaaga aactttcccg ttatttacgc 180
tctgttcctg ttaatcaacc tctggattac aaaatttgtg aaagattgac tgatattctt 240
aactatgttg ctccttttac gctgtgtgga tatgctgctt tatagcctct gtatctagct 300
attgcttccc gtacggcttt cgttttctcc tccttgtata aatcctggtt gctgtctctt 360
ttagaggagt tgtggcccgt tgtccgtcaa cgtggcgtgg tgtgctctgt gtttgctgac 420
gcaaccccca ctggctgggg cattgccacc acctgtcaac tcctttctgg gactttcgct 480
ttccccctcc cgatcgccac ggcagaactc atcgccgcct gccttgcccg ctgctggaca 540
ggggctaggt tgctgggcac tgataattcc gtggtgttgt c 581

<210> SEQ ID NO 68
<211> LENGTH: 225
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 68
tgtgccttct agttgccagc catctgttgt ttgcccctcc cccgtgcctt ccttgaccct 60
ggaaggtgcc actcccactg tcctttccta ataaaatgag gaaattgcat cgcattgtct 120
gagtaggtgt cattctattc tggggggtgg ggtggggcag gacagcaagg gggaggattg 180
ggaagacaat agcaggcatg ctggggatgc ggtgggctct atggc 225

<210> SEQ ID NO 69
<211> LENGTH: 8
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 69 actgaggc 8

<210> SEQ ID NO 70
<211> LENGTH: 8
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 70 gcctcagt 8

<210> SEQ ID NO 71
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 71
gagcgagcga gcgcgc 16

<210> SEQ ID NO 72
<211> LENGTH: 1923
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 72
tcaatattgg ccattagcca tattattcat tggttatata gcataaatca atattggcta 60
ttggccattg catacgttgt atctatatca taatatgtac atttatattg gctcatgtcc 120
aatatgaccg ccatgttggc attgattatt gactagttat taatagtaat caattacggg 180
gtcattagtt catagcccat atatggagtt ccgcgttaca taacttacgg taaatggccc 240
gcctggctga ccgcccaacg acccccgccc attgacgtca ataatgacgt atgttcccat 300
agtaacgcca atagggactt tccattgacg tcaatgggtg gagtatttac ggtaaactgc 360
ccacttggca gtacatcaag tgtatcatat gccaagtccg ccccctattg acgtcaatga 420
cggtaaatgg cccgcctggc attatgccca gtacatgacc ttacgggact ttcctacttg 480
gcagtacatc tacgtattag tcatcgctat taccatggtc gaggtgagcc ccacgttctg 540
cttcactctc cccatctccc ccccctcccc acccccaatt ttgtatttat ttatttttta 600
attattttgt gcagcgatgg gggcgggggg gggggggggg cgcgcgccag gcggggcggg 660
gcggggcgag gggcggggcg gggcgaggcg gagaggtgcg gcggcagcca atcagagcgg 720
cgcgctccga aagtttcctt ttatggcgag gcggcggcgg cggcggccct ataaaaagcg 780
aagcgcgcgg cgggcgggag tcgctgcgac gctgccttcg ccccgtgccc cgctccgccg 840
ccgcctcgcg ccgcccgccc cggctctgac tgaccgcgtt actcccacag gtgagcgggc 900
gggacggccc ttctcctccg ggctgtaatt agcgcttggt ttaatgacgg cttgtttctt 960
ttctgtggct gcgtgaaagc cttgaggggc tccgggaggg ccctttgtgc ggggggggagc 1020 ggctcggggg gtgcgtgcgt gtgtgtgtgc gtggggagcg ccgcgtgcgg cccgcgctgc 1080
ccggcggctg tgagcgctgc gggcgcggcg cggggctttg tgcgctccgc agtgtgcgcg 1140
aggggagcgc ggccgggggc ggtgccccgc ggtgcggggg gggctgcgag gggaacaaag 1200
gctgcgtgcg gggtgtgtgc gtgggggggt gagcaggggg tgtgggcgcg gcggtcgggc 1260
tgtaaccccc ccctgcaccc ccctccccga gttgctgagc acggcccggc ttcgggtgcg 1320
gggctccgta cggggcgtgg cgcggggctc gccgtgccgg gcggggggtg gcggcaggtg 1380
ggggtgccgg gcggggcggg gccgcctcgg gccggggagg gctcggggga ggggcgcggc 1440
ggcccccgga gcgccggcgg ctgtcgaggc gcggcgagcc gcagccattg ccttttatgg 1500
taatcgtgcg agagggcgca gggacttcct ttgtcccaaa tctgtgcgga gccgaaatct 1560
gggaggcgcc gccgcacccc ctctagcggg cgcggggcga agcggtgcgg cgccggcagg 1620
aaggaaatgg gcggggaggg ccttcgtgcg tcgccgcgcc gccgtcccct tctccctctc 1680
cagcctcggg gctgtccgcg gggggacggc tgccttcggg ggggacgggg cagggcgggg 1740
ttcggcttct ggcgtgtgac cggcggctct agagcctctg ctaaccatgt tttagccttc 1800
ttctttttcc tacagctcct gggcaacgtg ctggttattg tgctgtctca tcatttgtcg 1860
acagaattcc tcgaagatcc gaaggggttc aagcttggca ttccggtact gttggtaaag 1920
cca 1923

<210> SEQ ID NO 73
<211> LENGTH: 1272
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 73
aggctcagag gcacacagga gtttctgggc tcaccctgcc cccttccaac ccctcagttc 60
ccatcctcca gcagctgttt gtgtgctgcc tctgaagtcc acactgaaca aacttcagcc 120

```
tactcatgtc cctaaaatgg gcaaacattg caagcagcaa acagcaaaca cacagccctc    180
cctgcctgct gaccttggag ctggggcaga ggtcagagac ctctctgggc ccatgccacc    240
tccaacatcc actcgacccc ttggaatttc ggtggagagg agcagaggtt gtcctggcgt    300
ggtttaggta gtgtgagagg gtccgggttc aaaaccactt gctgggtggg gagtcgtcag    360
taagtggcta tgccccgacc ccgaagcctg tttccccatc tgtacaatgg aaatgataaa    420
gacgcccatc tgatagggtt tttgtggcaa ataaacattt ggtttttttg ttttgttttg    480
ttttgttttt tgagatggag gtttgctctg tcgcccaggc tggagtgcag tgacacaatc    540
tcatctcacc acaaccttcc cctgcctcag cctcccaagt agctgggatt acaagcatgt    600
gccaccacac ctggctaatt ttctattttt agtagagacg ggtttctcca tgttggtcag    660
cctcagcctc ccaagtaact gggattacag gcctgtgcca ccacacccgg ctaatttttt    720
ctatttttga cagggacggg gtttcaccat gttggtcagg ctggtctaga ggtaccggat    780
cttgctacca gtggaacagc cactaaggat tctgcagtga gagcagaggg ccagctaagt    840
ggtactctcc cagagactgt ctgactcacg ccaccccctc caccttggac acaggacgct    900
gtggtttctg agccaggtac aatgactcct ttcggtaagt gcagtggaag ctgtacactg    960
cccaggcaaa gcgtccgggc agcgtaggcg ggcgactcag atcccagcca gtggacttag   1020
cccctgtttg ctcctccgat aactggggtg accttggtta atattcacca gcagcctccc   1080
ccgttgcccc tctggatcca ctgcttaaat acggacgagg acagggccct gtctcctcag   1140
cttcaggcac caccactgac ctgggacagt gaatccggac tctaaggtaa atataaaatt   1200
tttaagtgta taatgtgtta aactactgat tctaattgtt tctctctttt agattccaac   1260
ctttggaact ga                                                        1272
```

```
<210> SEQ ID NO 74
<211> LENGTH: 1177
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74
```

```
ggctcagagg ctcagaggca cacaggagtt tctgggctca ccctgccccc ttccaacccc     60
tcagttccca tcctccagca gctgtttgtg tgctgcctct gaagtccaca ctgaacaaac    120
ttcagcctac tcatgtccct aaaatgggca aacattgcaa gcagcaaaca gcaaacacac    180
agccctccct gcctgctgac cttggagctg gggcagaggt cagagacctc tctgggccca    240
tgccacctcc aacatccact cgaccccttg gaatttcggt ggagaggagc agaggttgtc    300
ctggcgtggt ttaggtagtg tgagagggtc cgggttcaaa accacttgct gggtggggag    360
tcgtcagtaa gtggctatgc cccgaccccg aagcctgttt ccccatctgt acaatggaaa    420
tgataaagac gcccatctga tagggttttt gtggcaaata aacatttggt ttttttgttt    480
tgttttgttt tgttttttga gatggaggtt tgctctgtcg cccaggctgg agtgcagtga    540
cacaatctca tctcaccaca accttcccct gcctcagcct cccaagtagc tgggattaca    600
agcatgtgcc accacacctg gctaattttc tatttttagt agagacgggt ttctccatgt    660
tggtcagcct cagcctccca agtaactggg attacaggcc tgtgccacca cacccggcta    720
atttttctta tttttgacag ggacggggtt tcaccatgtt ggtcaggctg gtctagaggt    780
accggatctt gctaccagtg gaacagccac taaggattct gcagtgagag cagagggcca    840
```

gctaagtggt actctcccag agactgtctg actcacgcca ccccctccac cttggacaca 900
ggacgctgtg gtttctgagc caggtacaat gactcctttc ggtaagtgca gtggaagctg 960
tacactgccc aggcaaagcg tccgggcagc gtaggcgggc gactcagatc ccagccagtg 1020
gacttagccc ctgtttgctc ctccgataac tggggtgacc ttggttaata ttcaccagca 1080
gcctcccccg ttgcccctct ggatccactg cttaaatacg gacgaggaca gggccctgtc 1140
tcctcagctt caggcaccac cactgacctg ggacagt 1177

<210> SEQ ID NO 75
<211> LENGTH: 547
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 75
ccctaaaatg ggcaaacatt gcaagcagca aacagcaaac acacagccct ccctgcctgc 60
tgaccttgga gctggggcag aggtcagaga cctctctggg cccatgccac ctccaacatc 120
cactcgaccc cttggaattt ttcggtggag aggagcagag gttgtcctgg cgtggtttag 180
gtagtgtgag aggggaatga ctcctttcgg taagtgcagt ggaagctgta cactgcccag 240
gcaaagcgtc cgggcagcgt aggcgggcga ctcagatccc agccagtgga cttagcccct 300
gtttgctcct ccgataactg gggtgacctt ggttaatatt caccagcagc ctcccccgtt 360
gcccctctgg atccactgct taaatacgga cgaggacagg gccctgtctc ctcagcttca 420
ggcaccacca ctgacctggg acagtgaatc cggactctaa ggtaaatata aaatttttaa 480
gtgtataatg tgttaaacta ctgattctaa ttgtttctct cttttagatt ccaacctttg 540
gaactga 547

<210> SEQ ID NO 76
<211> LENGTH: 556
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 76
ccctaaaatg ggcaaacatt gcaagcagca aacagcaaac acacagccct ccctgcctgc 60
tgaccttgga gctggggcag aggtcagaga cctctctggg cccatgccac ctccaacatc 120
cactcgaccc cttggaattt cggtggagag gagcagaggt tgtcctggcg tggtttaggt 180
agtgtgagag gggaatgact cctttcggta agtgcagtgg aagctgtaca ctgcccaggc 240
aaagcgtccg ggcagcgtag gcgggcgact cagatcccag ccagtggact tagcccctgt 300
ttgctcctcc gataactggg gtgaccttgg ttaatattca ccagcagcct cccccgttgc 360
ccctctggat ccactgctta aatacggacg aggacactcg agggccctgt ctcctcagct 420
tcaggcacca ccactgacct gggacagtga atccggacat cgattctaag gtaaatataa 480
aatttttaag tgtataattt gttaaactac tgattctaat tgtttctctc ttttagattc 540
caacctttgg aactga 556

<210> SEQ ID NO 77
<211> LENGTH: 1179
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 77

```
ggctccggtg cccgtcagtg ggcagagcgc acatcgccca cagtccccga gaagttgggg     60

ggaggggtcg gcaattgaac cggtgcctag agaaggtggc gcggggtaaa ctgggaaagt    120

gatgtcgtgt actggctccg cctttttccc gagggtgggg gagaaccgta tataagtgca    180

gtagtcgccg tgaacgttct ttttcgcaac gggtttgccg ccagaacaca ggtaagtgcc    240

gtgtgtggtt cccgcgggcc tggcctcttt acgggttatg gcccttgcgt gccttgaatt    300

acttccacct ggctgcagta cgtgattctt gatcccgagc ttcgggttgg aagtgggtgg    360

gagagttcga ggccttgcgc ttaaggagcc ccttcgcctc gtgcttgagt tgaggcctgg    420

cctgggcgct ggggccgccg cgtgcgaatc tggtggcacc ttcgcgcctg tctcgctgct    480

ttcgataagt ctctagccat ttaaaatttt tgatgacctg ctgcgacgct ttttttctgg    540

caagatagtc ttgtaaatgc gggccaagat ctgcacactg gtatttcggt ttttggggcc    600

gcgggcggcg acggggcccg tgcgtcccag cgcacatgtt cggcgaggcg gggcctgcga    660

gcgcggccac cgagaatcgg acgggggtag tctcaagctg gccggcctgc tctggtgcct    720

ggtctcgcgc cgccgtgtat cgccccgccc tgggcggcaa ggctggcccg gtcggcacca    780

gttgcgtgag cggaaagatg gccgcttccc ggccctgctg cagggagctc aaaatggagg    840

acgcggcgct cgggagagcg ggcgggtgag tcacccacac aaaggaaaag ggcctttccg    900

tcctcagccg tcgcttcatg tgactccacg gagtaccggg cgccgtccag gcacctcgat    960

tagttctcga gcttttggag tacgtcgtct ttaggttggg gggaggggtt ttatgcgatg   1020

gagtttcccc acactgagtg ggtggagact gaagttaggc cagcttggca cttgatgtaa   1080

ttctccttgg aatttgccct ttttgagttt ggatcttggt tcattctcaa gcctcagaca   1140

gtggttcaaa gtttttttct tccatttcag gtgtcgtga                          1179
```

<210> SEQ ID NO 78
<211> LENGTH: 141
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 78

```
aataaacgat aacgccgttg gtggcgtgag gcatgtaaaa ggttacatca ttatcttgtt     60

cgccatccgg ttggtataaa tagacgttca tgttggtttt tgtttcagtt gcaagttggc    120

tgcggcgcgc gcagcacctt t                                              141
```

<210> SEQ ID NO 79
<211> LENGTH: 317
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 79

```
ggtgtggaaa gtccccaggc tccccagcag gcagaagtat gcaaagcatg catctcaatt     60

agtcagcaac caggtgtgga aagtccccag gctccccagc aggcagaagt atgcaaagca    120
```

-continued

```
tgcatctcaa ttagtcagca accatagtcc cgcccctaac tccgcccatc ccgcccctaa    180

ctccgcccag ttccgcccat tctccgcccc atggctgact aattttttt atttatgcag    240

aggccgaggc cgcctcggcc tctgagctat tccagaagta gtgaggaggc ttttttggag    300

gcctaggctt ttgcaaa                                                   317


<210> SEQ ID NO 80
<211> LENGTH: 241
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80

gagggcctat ttcccatgat tccttcatat ttgcatatac gatacaaggc tgttagagag     60

ataattggaa ttaatttgac tgtaaacaca aagatattag tacaaaatac gtgacgtaga    120

aagtaataat ttcttgggta gtttgcagtt ttaaaattat gttttaaaat ggactatcat    180

atgcttaccg taacttgaaa gtatttcgat ttcttggctt tatatatctt gtggaaagga    240

c                                                                    241


<210> SEQ ID NO 81
<211> LENGTH: 215
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81

gaacgctgac gtcatcaacc cgctccaagg aatcgcgggc ccagtgtcac taggcgggaa     60

cacccagcgc gcgtgcgccc tggcaggaag atggctgtga gggacagggg agtggcgccc    120

tgcaatattt gcatgtcgct atgtgttctg ggaaatcacc ataaacgtga aatgtctttg    180

gatttgggaa tcgtataaga actgtatgag accac                               215


<210> SEQ ID NO 82
<211> LENGTH: 546
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82

ccctaaaatg ggcaaacatt gcaagcagca aacagcaaac acacagccct ccctgcctgc     60

tgaccttgga gctggggcag aggtcagaga cctctctggg cccatgccac ctccaacatc    120

cactcgaccc cttggaattt ttcggtggag aggagcagag gttgtcctgg cgtggtttag    180

gtagtgtgag aggggaatga ctcctttcgg taagtgcagt ggaagctgta cactgcccag    240

gcaaagcgtc cgggcagcgt aggcgggcga ctcagatccc agccagtgga cttagcccct    300

gtttgctcct ccgataactg gggtgacctt ggttaatatt caccagcagc ctcccccgtt    360

gcccctctgg atccactgct taaatacgga cgaggacagg gccctgtctc ctcagcttca    420

ggcaccacca ctgacctggg acagtgaatc cggactctaa ggtaaatata aaatttttaa    480

gtgtataatg tgttaaacta ctgattctaa ttgtttctct cttttagatt ccaacctttg    540

gaactg                                                               546
```

<210> SEQ ID NO 83
<211> LENGTH: 576
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 83
tagtaatcaa ttacggggtc attagttcat agcccatata tggagttccg cgttacataa 60
cttacggtaa atggcccgcc tggctgaccg cccaacgacc cccgcccatt gacgtcaata 120
atgacgtatg ttcccatagt aacgccaata gggactttcc attgacgtca atgggtggag 180
tatttacggt aaactgccca cttggcagta catcaagtgt atcatatgcc aagtacgccc 240
cctattgacg tcaatgacgg taaatggccc gcctggcatt atgcccagta catgacctta 300
tgggactttc ctacttggca gtacatctac gtattagtca tcgctattac catggtgatg 360
cggttttggc agtacatcaa tgggcgtgga tagcggtttg actcacgggg atttccaagt 420
ctccacccca ttgacgtcaa tgggagtttg ttttggcacc aaaatcaacg ggactttcca 480
aaatgtcgta acaactccgc cccattgacg caaatgggcg gtaggcgtgt acggtgggag 540
gtctatataa gcagagctgg tttagtgaac cgtcag 576

<210> SEQ ID NO 84
<211> LENGTH: 150
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 84
ataaacgata acgccgttgg tggcgtgagg catgtaaaag gttacatcat tatcttgttc 60
gccatccggt tggtataaat agacgttcat gttggttttt gtttcagttg caagttggct 120
gcggcgcgcg cagcaccttt gcggccatct 150

<210> SEQ ID NO 85
<211> LENGTH: 1313
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 85
ggagccgaga gtaattcata caaaaggagg gatcgccttc gcaaggggag agcccaggga 60
ccgtccctaa attctcacag acccaaatcc ctgtagccgc cccacgacag cgcgaggagc 120
atgcgcccag ggctgagcgc gggtagatca gagcacacaa gctcacagtc cccggcggtg 180
gggggagggg cgcgctgagc gggggccagg gagctggcgc ggggcaaact gggaaagtgg 240
tgtcgtgtgc tggctccgcc ctcttcccga gggtggggga gaacggtata taagtgcggt 300
agtcgccttg gacgttcttt ttcgcaacgg gtttgccgtc agaacgcagg tgagtggcgg 360
gtgtggcttc cgcgggcccc ggagctggag ccctgctctg agcgggccgg gctgatatgc 420
gagtgtcgtc cgcagggttt agctgtgagc attcccactt cgagtggcgg gcggtgcggg 480
ggtgagagtg cgaggcctag cggcaacccc gtagcctcgc ctcgtgtccg gcttgaggcc 540
tagcgtggtg tccgccgccg cgtgccactc cggccgcact atgcgttttt tgtccttgct 600

```
gccctcgatt gccttccagc agcatgggct aacaaaggga gggtgtgggg ctcactctta    660

aggagcccat gaagcttacg ttggatagga atggaagggc aggaggggcg actggggccc    720

gcccgccttc ggagcacatg tccgacgcca cctggatggg gcgaggcctg tggctttccg    780

aagcaatcgg gcgtgagttt agcctacctg ggccatgtgg ccctagcact gggcacggtc    840

tggcctggcg gtgccgcgtt cccttgcctc ccaacaaggg tgaggccgtc ccgcccggca    900

ccagttgctt gcgcggaaag atggccgctc ccggggccct gttgcaagga gctcaaaatg    960

gaggacgcgg cagcccggtg gagcgggcgg gtgagtcacc cacacaaagg aagagggcct   1020

tgcccctcgc cggccgctgc ttcctgtgac cccgtggtct atcggccgca tagtcacctc   1080

gggcttctct tgagcaccgc tcgtcgcggc ggggggaggg gatctaatgg cgttggagtt   1140

tgttcacatt tggtgggtgg agactagtca ggccagcctg gcgctggaag tcattcttgg   1200

aatttgcccc tttgagtttg gagcgaggct aattctcaag cctcttagcg gttcaaaggt   1260

attttctaaa cccgtttcca ggtgttgtga aagccaccgc taattcaaag caa          1313
```

```
<210> SEQ ID NO 86
<211> LENGTH: 213
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86

taagatacat tgatgagttt ggacaaacca caactagaat gcagtgaaaa aaatgcttta     60

tttgtgaaat ttgtgatgct attgctttat ttgtaaccat tataagctgc aataaacaag    120

ttaacaacaa caattgcatt cattttatgt ttcaggttca gggggaggtg tgggaggttt    180

tttaaagcaa gtaaaacctc tacaaatgtg gta                                 213
```

```
<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Pro Lys Lys Lys Arg Lys Val
1               5
```

```
<210> SEQ ID NO 88
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Met Asp Trp Thr Trp Arg Ile Leu Phe Leu Val Ala Ala Ala Thr Gly
1               5                   10                  15

Ala His Ser
```

```
<210> SEQ ID NO 89
<211> LENGTH: 19
<212> TYPE: PRT
<213> ORGANISM: Artificial Sequence
<220> FEATURE:
```

<223> OTHER INFORMATION: Description of Artificial Sequence: Synthetic peptide

<400> SEQUENCE: 89

Met Leu Pro Ser Gln Leu Ile Gly Phe Leu Leu Leu Trp Val Pro Ala
1 5 10 15

Ser Arg Gly

<210> SEQ ID NO 90
<211> LENGTH: 7
<212> TYPE: PRT
<213> ORGANISM: Simian virus 40

<400> SEQUENCE: 90

Pro Lys Lys Lys Arg Lys Val
1 5

<210> SEQ ID NO 91
<211> LENGTH: 21
<212> TYPE: DNA
<213> ORGANISM: Simian virus 40

<400> SEQUENCE: 91
cccaagaaga agaggaaggt g 21

<210> SEQ ID NO 92
<211> LENGTH: 16
<212> TYPE: PRT
<213> ORGANISM: Unknown
<220> FEATURE:
<223> OTHER INFORMATION: Description of Unknown: Nucleoplasmin bipartite NLS sequence

<400> SEQUENCE: 92

Lys Arg Pro Ala Ala Thr Lys Lys Ala Gly Gln Ala Lys Lys Lys Lys
1 5 10 15

<210> SEQ ID NO 93
<211> LENGTH: 9
<212> TYPE: PRT
<213> ORGANISM: Unknown
<220> FEATURE:
<223> OTHER INFORMATION: Description of Unknown: C-myc NLS sequence

<400> SEQUENCE: 93

Pro Ala Ala Lys Arg Val Lys Leu Asp
1 5

<210> SEQ ID NO 94
<211> LENGTH: 11
<212> TYPE: PRT
<213> ORGANISM: Unknown
<220> FEATURE:
<223> OTHER INFORMATION: Description of Unknown: C-myc NLS sequence

<400> SEQUENCE: 94

Arg Gln Arg Arg Asn Glu Leu Lys Arg Ser Pro
1 5 10

<210> SEQ ID NO 95
<211> LENGTH: 38
<212> TYPE: PRT
<213> ORGANISM: Homo sapiens

<400> SEQUENCE: 95

Asn Gln Ser Ser Asn Phe Gly Pro Met Lys Gly Gly Asn Phe Gly Gly
1 5 10 15

Arg Ser Ser Gly Pro Tyr Gly Gly Gly Gly Gln Tyr Phe Ala Lys Pro
20 25 30

Arg Asn Gln Gly Gly Tyr
35

<210> SEQ ID NO 96
<211> LENGTH: 42
<212> TYPE: PRT
<213> ORGANISM: Unknown
<220> FEATURE:
<223> OTHER INFORMATION: Description of Unknown:
IBB domain from importin-alpha sequence

<400> SEQUENCE: 96

Arg Met Arg Ile Glx Phe Lys Asn Lys Gly Lys Asp Thr Ala Glu Leu
1 5 10 15

Arg Arg Arg Arg Val Glu Val Ser Val Glu Leu Arg Lys Ala Lys Lys
20 25 30

Asp Glu Gln Ile Leu Lys Arg Arg Asn Val
35 40

<210> SEQ ID NO 97
<211> LENGTH: 8
<212> TYPE: PRT
<213> ORGANISM: Unknown
<220> FEATURE:
<223> OTHER INFORMATION: Description of Unknown:
Myoma T protein sequence

<400> SEQUENCE: 97

Val Ser Arg Lys Arg Pro Arg Pro
1 5

<210> SEQ ID NO 98
<211> LENGTH: 8
<212> TYPE: PRT
<213> ORGANISM: Unknown
<220> FEATURE:
<223> OTHER INFORMATION: Description of Unknown:
Myoma T protein sequence

<400> SEQUENCE: 98

Pro Pro Lys Lys Ala Arg Glu Asp
1 5

<210> SEQ ID NO 99
<211> LENGTH: 8
<212> TYPE: PRT
<213> ORGANISM: Homo sapiens

<400> SEQUENCE: 99

Pro Gln Pro Lys Lys Lys Pro Leu
1 5

<210> SEQ ID NO 100
<211> LENGTH: 12
<212> TYPE: PRT
<213> ORGANISM: Mus musculus

<400> SEQUENCE: 100

Ser Ala Leu Ile Lys Lys Lys Lys Lys Met Ala Pro 1 5 10

<210> SEQ ID NO 101
<211> LENGTH: 70
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 101
gcgcgctcgc tcgctcactg aggccgcccg ggaaacccgg gcgtgcgcct cagtgagcga 60
gcgagcgcgc 70

<210> SEQ ID NO 102
<211> LENGTH: 70
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 102
gcgcgctcgc tcgctcactg aggcgcacgc ccgggtttcc cgggcggcct cagtgagcga 60
gcgagcgcgc 70

<210> SEQ ID NO 103
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 103
gcgcgctcgc tcgctcactg aggccgtcgg gcgacctttg gtcgcccggc ctcagtgagc 60
gagcgagcgc gc 72

<210> SEQ ID NO 104
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 104
gcgcgctcgc tcgctcactg aggccgggcg accaaaggtc gcccgacggc ctcagtgagc 60
gagcgagcgc gc 72

<210> SEQ ID NO 105
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 105
gcgcgctcgc tcgctcactg aggccgcccg ggcaaagccc gggcgtcggc ctcagtgagc 60
gagcgagcgc gc 72

<210> SEQ ID NO 106

<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 106
gcgcgctcgc tcgctcactg aggccgacgc ccgggctttg cccgggcggc ctcagtgagc 60
gagcgagcgc gc 72

<210> SEQ ID NO 107
<211> LENGTH: 83
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 107
gcgcgctcgc tcgctcactg aggccgcccg ggcaaagccc gggcgtcggg ctttgcccgg 60
cctcagtgag cgagcgagcg cgc 83

<210> SEQ ID NO 108
<211> LENGTH: 83
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 108
gcgcgctcgc tcgctcactg aggccgggca aagcccgacg cccgggcttt gcccgggcgg 60
cctcagtgag cgagcgagcg cgc 83

<210> SEQ ID NO 109
<211> LENGTH: 77
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 109
gcgcgctcgc tcgctcactg aggccgaaac gtcgggcgac ctttggtcgc ccggcctcag 60
tgagcgagcg agcgcgc 77

<210> SEQ ID NO 110
<211> LENGTH: 77
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 110
gcgcgctcgc tcgctcactg aggccgggcg accaaaggtc gcccgacgtt tcggcctcag 60
tgagcgagcg agcgcgc 77

<210> SEQ ID NO 111
<211> LENGTH: 51
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 111
gcgcgctcgc tcgctcactg aggcaaagcc tcagtgagcg agcgagcgcg c 51

<210> SEQ ID NO 112
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 112
gcgcgctcgc tcgctcactg aggctttgcc tcagtgagcg agcgagcgcg c 51

<210> SEQ ID NO 113
<211> LENGTH: 80
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 113
gcgcgctcgc tcgctcactg aggccgcccg ggcgtcgggc gacctttggt cgcccggcct 60
cagtgagcga gcgagcgcgc 80

<210> SEQ ID NO 114
<211> LENGTH: 80
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 114
gcgcgctcgc tcgctcactg aggccgggcg accaaaggtc gcccgacgcc cgggcggcct 60
cagtgagcga gcgagcgcgc 80

<210> SEQ ID NO 115
<211> LENGTH: 79
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 115
gcgcgctcgc tcgctcactg aggcgcccgg gcgtcgggcg acctttggtc gcccggcctc 60
agtgagcgag cgagcgcgc 79

<210> SEQ ID NO 116
<211> LENGTH: 79
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 116
gcgcgctcgc tcgctcactg aggccgggcg accaaaggtc gcccgacgcc cgggcgcctc 60
agtgagcgag cgagcgcgc 79

<210> SEQ ID NO 117
<211> LENGTH: 5
<212> TYPE: PRT
<213> ORGANISM: Influenza virus

<400> SEQUENCE: 117

Asp Arg Leu Arg Arg
1 5

<210> SEQ ID NO 118
<211> LENGTH: 7
<212> TYPE: PRT
<213> ORGANISM: Influenza virus

<400> SEQUENCE: 118

Pro Lys Gln Lys Lys Arg Lys
1 5

<210> SEQ ID NO 119
<211> LENGTH: 10
<212> TYPE: PRT
<213> ORGANISM: Hepatitis delta virus

<400> SEQUENCE: 119

Arg Lys Leu Lys Lys Lys Ile Lys Lys Leu
1 5 10

<210> SEQ ID NO 120
<211> LENGTH: 10
<212> TYPE: PRT
<213> ORGANISM: Mus musculus

<400> SEQUENCE: 120

Arg Glu Lys Lys Lys Phe Leu Lys Arg Arg
1 5 10

<210> SEQ ID NO 121
<211> LENGTH: 20
<212> TYPE: PRT
<213> ORGANISM: Homo sapiens

<400> SEQUENCE: 121

Lys Arg Lys Gly Asp Glu Val Asp Gly Val Asp Glu Val Ala Lys Lys
1 5 10 15

Lys Ser Lys Lys
20

<210> SEQ ID NO 122
<211> LENGTH: 17
<212> TYPE: PRT
<213> ORGANISM: Homo sapiens

<400> SEQUENCE: 122

Arg Lys Cys Leu Gln Ala Gly Met Asn Leu Glu Ala Arg Lys Thr Lys
1 5 10 15

Lys

<210> SEQ ID NO 123
<211> LENGTH: 8
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 123 gtttaaac 8

<210> SEQ ID NO 124
<211> LENGTH: 8
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 124 ttaattaa 8

<210> SEQ ID NO 125
<211> LENGTH: 141
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 125
aataaacgat aacgccgttg gtggcgtgag gcatgtaaaa ggttacatca ttatcttgtt 60
cgccatccgg ttggtataaa tagacgttca tgttggtttt tgtttcagtt gcaagttggc 120
tgcggcgcgc gcagcacctt t 141

<210> SEQ ID NO 126

<400> SEQUENCE: 126

000

<210> SEQ ID NO 127
<211> LENGTH: 72
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 127
gcgcgctcgc tcgctcactg aggccgggcg accaaaggtc gcccgacggc ctcagtgagc 60
gagcgagcgc gc 72

<210> SEQ ID NO 128
<211> LENGTH: 122
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 128
aggaacccct agtgatggag ttggccactc cctctctgcg cgctcgctcg ctcactgagg 60
ccgggcgacc aaaggtcgcc cgacggcctc agtgagcgag cgagcgcgca gctgcctgca 120
gg 122

<210> SEQ ID NO 129
<211> LENGTH: 1260
<212> TYPE: DNA

<213> ORGANISM: Adeno-associated virus - 2

<400> SEQUENCE: 129
atggagctgg tcgggtggct cgtggacaag ggGattacct cggagaagca gtggatccag 60
gaggaccagg cctcatacat ctccttcaat gcggcctcca actcgcggtc ccaaatcaag 120
gctgccttgg acaatgcggg aaagattatg agcctgacta aaaccgcccc cgactacctg 180
gtgggccagc agcccgtgga ggacatttcc agcaatcgga tttataaaat tttggaacta 240
aacgggtacg atccccaata tgcggcttcc gtctttctgg gatgggccac gaaaaagttc 300
ggcaagagga acaccatctg gctgtttggg cctgcaacta ccgggaagac caacatcgcg 360
gaggccatag cccacactgt gcccttctac gggtgcgtaa actggaccaa tgagaacttt 420
cccttcaacg actgtgtcga caagatggtg atctggtggg aggaggggaa gatgaccgcc 480
aaggtcgtgg agtcggccaa agccattctc ggaggaagca aggtgcgcgt ggaccagaaa 540
tgcaagtcct cggcccagat agacccgact cccgtgatcg tcacctccaa caccaacatg 600
tgcgccgtga ttgacgggaa ctcaacgacc ttcgaacacc agcagccgtt gcaagaccgg 660
atgttcaaat ttgaactcac ccgccgtctg gatcatgact ttgggaaggt caccaagcag 720
gaagtcaaag actttttccg gtgggcaaag gatcacgtgg ttgaggtgga gcatgaattc 780
tacgtcaaaa agggtggagc caagaaaaga cccgccccca gtgacgcaga tataagtgag 840
cccaaacggg tgcgcgagtc agttgcgcag ccatcgacgt cagacgcgga agcttcgatc 900
aactacgcag acaggtacca aaacaaatgt tctcgtcacg tgggcatgaa tctgatgctg 960
tttccctgca gacaatgcga gagaatgaat cagaattcaa atatctgctt cactcacgga 1020
cagaaagact gtttagagtg ctttcccgtg tcagaatctc aacccgtttc tgtcgtcaaa 1080
aaggcgtatc agaaactgtg ctacattcat catatcatgg gaaaggtgcc agacgcttgc 1140
actgcctgcg atctggtcaa tgtggatttg gatgactgca tctttgaaca ataaatgatt 1200
taaatcaggt atggctgccg atggttatct tccagattgg ctcgaggaca ctctctctga 1260

<210> SEQ ID NO 130
<211> LENGTH: 1932
<212> TYPE: DNA
<213> ORGANISM: Adeno-associated virus - 2

<400> SEQUENCE: 130
atgccggggt tttacgagat tgtgattaag gtccccagcg accttgacga gcatctgccc 60
ggcatttctg acagctttgt gaactgggtg gccgagaagg aatgggagtt gccgccagat 120
tctgacatgg atctgaatct gattgagcag gcacccctga ccgtggccga gaagctgcag 180
cgcgactttc tgacggaatg gcgccgtgtg agtaaggccc cggaggccct tttctttgtg 240
caatttgaga agggagagag ctacttccac atgcacgtgc tcgtggaaac caccggggtg 300
aaatccatgg ttttgggacg tttcctgagt cagattcgcg aaaaactgat tcagagaatt 360
taccgcggga tcgagccgac tttgccaaac tggttcgcgg tcacaaagac cagaaatggc 420
gccggaggcg ggaacaaggt ggtggatgag tgctacatcc ccaattactt gctccccaaa 480
acccagcctg agctccagtg ggcgtggact aatatggaac agtatttaag cgcctgtttg 540
aatctcacgg agcgtaaacg gttggtggcg cagcatctga cgcacgtgtc gcagacgcag 600
gagcagaaca aagagaatca gaatcccaat tctgatgcgc cggtgatcag atcaaaaact 660
tcagccaggt acatggagct ggtcgggtgg ctcgtggaca aggggattac ctcggagaag 720
cagtggatcc aggaggacca ggcctcatac atctccttca atgcggcctc caactcgcgg 780

```
tcccaaatca aggctgcctt ggacaatgcg ggaaagatta tgagcctgac taaaaccgcc    840

cccgactacc tggtgggcca gcagcccgtg gaggacattt ccagcaatcg gatttataaa    900

attttggaac taaacgggta cgatccccaa tatgcggctt ccgtctttct gggatgggcc    960

acgaaaaagt tcggcaagag gaacaccatc tggctgtttg ggcctgcaac taccgggaag   1020

accaacatcg cggaggccat agcccacact gtgcccttct acgggtgcgt aaactggacc   1080

aatgagaact ttcccttcaa cgactgtgtc gacaagatgg tgatctggtg ggaggagggg   1140

aagatgaccg ccaaggtcgt ggagtcggcc aaagccattc tcggaggaag caaggtgcgc   1200

gtggaccaga aatgcaagtc ctcggcccag atagacccga ctcccgtgat cgtcacctcc   1260

aacaccaaca tgtgcgccgt gattgacggg aactcaacga ccttcgaaca ccagcagccg   1320

ttgcaagacc ggatgttcaa atttgaactc acccgccgtc tggatcatga ctttgggaag   1380

gtcaccaagc aggaagtcaa agactttttc cggtgggcaa aggatcacgt ggttgaggtg   1440

gagcatgaat tctacgtcaa aaagggtgga gccaagaaaa gacccgcccc cagtgacgca   1500

gatataagtg agcccaaacg ggtgcgcgag tcagttgcgc agccatcgac gtcagacgcg   1560

gaagcttcga tcaactacgc agacaggtac caaaacaaat gttctcgtca cgtgggcatg   1620

aatctgatgc tgtttccctg cagacaatgc gagagaatga atcagaattc aaatatctgc   1680

ttcactcacg gacagaaaga ctgtttagag tgctttcccg tgtcagaatc tcaacccgtt   1740

tctgtcgtca aaaaggcgta tcagaaactg tgctacattc atcatatcat gggaaaggtg   1800

ccagacgctt gcactgcctg cgatctggtc aatgtggatt tggatgactg catctttgaa   1860

caataaatga tttaaatcag gtatggctgc cgatggttat cttccagatt ggctcgagga   1920

cactctctct ga                                                       1932
```

```
<210> SEQ ID NO 131
<211> LENGTH: 1876
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131
```

```
cgcagccacc atggcggggt tttacgagat tgtgattaag gtccccagcg accttgacgg     60

gcatctgccc ggcatttctg acagctttgt gaactgggtg gccgagaagg aatgggagtt    120

gccgccagat tctgacatgg atctgaatct gattgagcag gcacccctga ccgtggccga    180

gaagctgcag cgcgactttc tgacggaatg gcgccgtgtg agtaaggccc cggaggccct    240

tttctttgtg caatttgaga agggagagag ctacttccac atgcacgtgc tcgtggaaac    300

caccggggtg aaatccatgg ttttgggacg tttcctgagt cagattcgcg aaaaactgat    360

tcagagaatt taccgcggga tcgagccgac tttgccaaac tggttcgcgg tcacaaagac    420

cagaaatggc gccggaggcg ggaacaaggt ggtggatgag tgctacatcc ccaattactt    480

gctccccaaa acccagcctg agctccagtg ggcgtggact aatatggaac agtatttaag    540

cgcctgtttg aatctcacgg agcgtaaacg gttggtggcg cagcatctga cgcacgtgtc    600

gcagacgcag gagcagaaca aagagaatca gaatcccaat tctgatgcgc cggtgatcag    660

atcaaaaact tcagccaggt acatggagct ggtcgggtgg ctcgtggaca aggggattac    720

ctcggagaag cagtggatcc aggaggacca ggcctcatac atctccttca atgcggcctc    780

caactcgcgg tcccaaatca aggctgcctt ggacaatgcg ggaaagatta tgagcctgac    840
```

```
taaaaccgcc cccgactacc tggtgggcca gcagcccgtg gaggacattt ccagcaatcg    900
gatttataaa attttggaac taaacgggta cgatccccaa tatgcggctt ccgtctttct    960
gggatgggcc acgaaaaagt tcggcaagag gaacaccatc tggctgtttg ggcctgcaac   1020
taccgggaag accaacatcg cggaggccat agcccacact gtgcccttct acgggtgcgt   1080
aaactggacc aatgagaact ttcccttcaa cgactgtgtc gacaagatgg tgatctggtg   1140
ggaggagggg aagatgaccg ccaaggtcgt ggagtcggcc aaagccattc tcggaggaag   1200
caaggtgcgc gtggaccaga aatgcaagtc ctcggcccag atagacccga ctcccgtgat   1260
cgtcacctcc aacaccaaca tgtgcgccgt gattgacggg aactcaacga ccttcgaaca   1320
ccagcagccg ttgcaagacc ggatgttcaa atttgaactc acccgccgtc tggatcatga   1380
ctttgggaag gtcaccaagc aggaagtcaa agactttttc cggtgggcaa aggatcacgt   1440
ggttgaggtg gagcatgaat tctacgtcaa aaagggtgga gccaagaaaa gacccgcccc   1500
cagtgacgca gatataagtg agcccaaacg ggtgcgcgag tcagttgcgc agccatcgac   1560
gtcagacgcg gaagcttcga tcaactacgc agacaggtac caaaacaaat gttctcgtca   1620
cgtgggcatg aatctgatgc tgtttccctg cagacaatgc gagagaatga atcagaattc   1680
aaatatctgc ttcactcacg gacagaaaga ctgtttagag tgctttcccg tgtcagaatc   1740
tcaacccgtt tctgtcgtca aaaaggcgta tcagaaactg tgctacattc atcatatcat   1800
gggaaaggtg ccagacgctt gcactgcctg cgatctggtc aatgtggatt tggatgactg   1860
catctttgaa caataa                                                   1876
```

<210> SEQ ID NO 132
<211> LENGTH: 1194
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 132

```
atggagctgg tcgggtggct cgtggacaag ggggattacct cggagaagca gtggatccag     60
gaggaccagg cctcatacat ctccttcaat gcggcctcca actcgcggtc ccaaatcaag    120
gctgccttgg acaatgcggg aaagattatg agcctgacta aaaccgcccc cgactacctg    180
gtgggccagc agcccgtgga ggacatttcc agcaatcgga tttataaaat tttggaacta    240
aacgggtacg atccccaata tgcggcttcc gtctttctgg gatgggccac gaaaaagttc    300
ggcaagagga acaccatctg gctgtttggg cctgcaacta ccgggaagac caacatcgcg    360
gaggccatag cccacactgt gcccttctac gggtgcgtaa actggaccaa tgagaacttt    420
cccttcaacg actgtgtcga caagatggtg atctggtggg aggaggggaa gatgaccgcc    480
aaggtcgtgg agtcggccaa agccattctc ggaggaagca aggtgcgcgt ggaccagaaa    540
tgcaagtcct cggcccagat agacccgact cccgtgatcg tcacctccaa caccaacatg    600
tgcgccgtga ttgacgggaa ctcaacgacc ttcgaacacc agcagccgtt gcaagaccgg    660
atgttcaaat ttgaactcac ccgccgtctg gatcatgact ttgggaaggt caccaagcag    720
gaagtcaaag actttttccg gtgggcaaag gatcacgtgg ttgaggtgga gcatgaattc    780
tacgtcaaaa agggtggagc caagaaaaga cccgcccccca gtgacgcaga tataagtgag    840
cccaaacggg tgcgcgagtc agttgcgcag ccatcgacgt cagacgcgga agcttcgatc    900
aactacgcag accgctacca aaacaaatgt tctcgtcacg tgggcatgaa tctgatgctg    960
```

```
tttccctgca gacaatgcga gagaatgaat cagaattcaa atatctgctt cactcacgga   1020

cagaaagact gtttagagtg ctttcccgtg tcagaatctc aacccgtttc tgtcgtcaaa   1080

aaggcgtatc agaaactgtg ctacattcat catatcatgg gaaaggtgcc agacgcttgc   1140

actgcctgcg atctggtcaa tgtggatttg gatgactgca tctttgaaca ataa         1194
```

<210> SEQ ID NO 133
<211> LENGTH: 1876
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 133

```
cgcagccacc atggcggggt tttacgagat tgtgattaag gtccccagcg accttgacgg     60

gcatctgccc ggcatttctg acagctttgt gaactgggtg gccgagaagg aatgggagtt    120

gccgccagat tctgacatgg atctgaatct gattgagcag gcacccctga ccgtggccga    180

gaagctgcag cgcgactttc tgacggaatg gcgccgtgtg agtaaggccc cggaggccct    240

tttctttgtg caatttgaga agggagagag ctacttccac atgcacgtgc tcgtggaaac    300

caccggggtg aaatccatgg ttttgggacg tttcctgagt cagattcgcg aaaaactgat    360

tcagagaatt taccgcggga tcgagccgac tttgccaaac tggttcgcgg tcacaaagac    420

cagaaatggc gccggaggcg ggaacaaggt ggtggatgag tgctacatcc ccaattactt    480

gctccccaaa acccagcctg agctccagtg ggcgtggact aatatggaac agtatttaag    540

cgcctgtttg aatctcacgg agcgtaaacg gttggtggcg cagcatctga cgcacgtgtc    600

gcagacgcag gagcagaaca aagagaatca gaatcccaat tctgatgcgc cggtgatcag    660

atcaaaaact tcagccaggt acatggagct ggtcgggtgg ctcgtggaca aggggattac    720

ctcggagaag cagtggatcc aggaggacca ggcctcatac atctccttca atgcggcctc    780

caactcgcgg tcccaaatca aggctgcctt ggacaatgcg ggaaagatta tgagcctgac    840

taaaaccgcc cccgactacc tggtgggcca gcagcccgtg gaggacattt ccagcaatcg    900

gatttataaa attttggaac taaacgggta cgatccccaa tatgcggctt ccgtctttct    960

gggatgggcc acgaaaaagt tcggcaagag gaacaccatc tggctgtttg ggcctgcaac   1020

taccgggaag accaacatcg cggaggccat agcccacact gtgcccttct acgggtgcgt   1080

aaactggacc aatgagaact ttcccttcaa cgactgtgtc gacaagatgg tgatctggtg   1140

ggaggagggg aagatgaccg ccaaggtcgt ggagtcggcc aaagccattc tcggaggaag   1200

caaggtgcgc gtggaccaga aatgcaagtc ctcggcccag atagacccga ctcccgtgat   1260

cgtcacctcc aacaccaaca tgtgcgccgt gattgacggg aactcaacga ccttcgaaca   1320

ccagcagccg ttgcaagacc ggatgttcaa atttgaactc acccgccgtc tggatcatga   1380

ctttgggaag gtcaccaagc aggaagtcaa agactttttc cggtgggcaa aggatcacgt   1440

ggttgaggtg gagcatgaat tctacgtcaa aaagggtgga gccaagaaaa gacccgcccc   1500

cagtgacgca gatataagtg agcccaaacg ggtgcgcgag tcagttgcgc agccatcgac   1560

gtcagacgcg gaagcttcga tcaactacgc agacaggtac caaaacaaat gttctcgtca   1620

cgtgggcatg aatctgatgc tgtttccctg cagacaatgc gagagaatga atcagaattc   1680

aaatatctgc ttcactcacg gacagaaaga ctgtttagag tgctttcccg tgtcagaatc   1740

tcaacccgtt tctgtcgtca aaaaggcgta tcagaaactg tgctacattc atcatatcat   1800
```

-continued gggaaaggtg ccagacgctt gcactgcctg cgatctggtc aatgtggatt tggatgactg 1860
catctttgaa caataa 1876

<210> SEQ ID NO 134
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 134
ctaggccgcc cgggcaaagc ccgggcgtcg ggcgaccttt ggtcgcccgg c 51

<210> SEQ ID NO 135
<211> LENGTH: 65
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 135
ctaggactga ggccgcccgg gcaaagcccg ggcgtcgggc gacctttggt cgcccggcct 60
cagtc 65

<210> SEQ ID NO 136
<211> LENGTH: 67
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 136
ggactgaggc cgcccgggca aagcccgggc gtcgggcgac ctttggtcgc ccggcctcag 60
tcctgca 67

<210> SEQ ID NO 137
<211> LENGTH: 41
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 137
gtgcgggcga ccaaaggtcg cccgacgccc gggcgcactc a 41

<210> SEQ ID NO 138
<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 138
ggactgaggc cgggcgacca aaggtcgccc gacgcccggg cggcctcagt cctgca 56

<210> SEQ ID NO 139
<211> LENGTH: 54
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 139
ctaggactga ggccgcccgg gcgtcgggcg acctttggtc gcccggcctc agtc 54

<210> SEQ ID NO 140
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 140
ggactgaggc cgggcgacca aaggtcgccc gacggcctca gtcctgca 48

<210> SEQ ID NO 141
<211> LENGTH: 46
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 141
ctaggactga ggccgtcggg cgacctttgg tcgcccggcc tcagtc 46

<210> SEQ ID NO 142
<211> LENGTH: 67
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 142
ggactgaggc ccgggcgacc aaaggtcgcc cgacgcccgg gctttgcccg ggcgcctcag 60
tcctgca 67

<210> SEQ ID NO 143
<211> LENGTH: 47
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 143
atacctaggc acgcgtgtta ctagttatta atagtaatca attacgg 47

<210> SEQ ID NO 144
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 144
atacctaggg gccgcacgcg tgttactag 29

<210> SEQ ID NO 145
<211> LENGTH: 42
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 145
atacactcag tgcctgcagg cacgtggtcc ggagatccag ac 42

<210> SEQ ID NO 146
<211> LENGTH: 3754
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 146
cctaggtgag cgagcgagcg cgcagagagg gagtggccaa ctccatcact aggggttcct 60
tgtagttaat gattaacccg ccatgctact tatcgcggcc gctcaatatt ggccattagc 120
catattattc attggttata tagcataaat caatattggc tattggccat tgcatacgtt 180
gtatctatat cataatatgt acatttatat tggctcatgt ccaatatgac cgccatgttg 240
gcattgatta ttgactagtt attaatagta atcaattacg gggtcattag ttcatagccc 300
atatatggag ttccgcgtta cataacttac ggtaaatggc ccgcctggct gaccgcccaa 360
cgacccccgc ccattgacgt caataatgac gtatgttccc atagtaacgc caatagggac 420
tttccattga cgtcaatggg tggagtattt acggtaaact gcccacttgg cagtacatca 480
agtgtatcat atgccaagtc cgccccctat tgacgtcaat gacggtaaat ggcccgcctg 540
gcattatgcc cagtacatga ccttacggga ctttcctact tggcagtaca tctacgtatt 600
agtcatcgct attaccatgg tcgaggtgag ccccacgttc tgcttcactc tccccatctc 660
ccccccctcc ccacccccaa ttttgtattt atttattttt taattatttt gtgcagcgat 720
gggggcgggg gggggggggg ggcgcgcgcc aggcggggcg gggcggggcg aggggcgggg 780
cggggcgagg cggagaggtg cggcggcagc caatcagagc ggcgcgctcc gaaagtttcc 840
ttttatggcg aggcggcggc ggcggcggcc ctataaaaag cgaagcgcgc ggcgggcggg 900
agtcgctgcg acgctgcctt cgccccgtgc cccgctccgc cgccgcctcg cgccgcccgc 960
cccggctctg actgaccgcg ttactcccac aggtgagcgg gcgggacggc ccttctcctc 1020
cgggctgtaa ttagcgcttg gtttaatgac ggcttgtttc ttttctgtgg ctgcgtgaaa 1080
gccttgaggg gctccgggag ggccctttgt gcgggggga gcggctcggg gggtgcgtgc 1140
gtgtgtgtgt gcgtggggag cgccgcgtgc ggcccgcgct gcccggcggc tgtgagcgct 1200
gcgggcgcgg cgcggggctt tgtgcgctcc gcagtgtgcg cgaggggagc gcggccgggg 1260
gcggtgcccc gcggtgcggg gggggctgcg aggggaacaa aggctgcgtg cggggtgtgt 1320
gcgtgggggg gtgagcaggg ggtgtgggcg cggcggtcgg gctgtaaccc ccccctgcac 1380
ccccctcccc gagttgctga gcacggcccg gcttcgggtg cggggctccg tacggggcgt 1440
ggcgcggggc tcgccgtgcc gggcgggggg tggcggcagg tgggggtgcc gggcggggcg 1500
gggccgcctc gggccgggga gggctcgggg gaggggcgcg gcggcccccg gagcgccggc 1560
ggctgtcgag gcgcggcgag ccgcagccat tgccttttat ggtaatcgtg cgagagggcg 1620
cagggacttc ctttgtccca aatctgtgcg gagccgaaat ctgggaggcg ccgccgcacc 1680
ccctctagcg ggcgcggggc gaagcggtgc ggcgccggca ggaaggaaat gggcggggag 1740
ggccttcgtg cgtcgccgcg ccgccgtccc cttctccctc tccagcctcg gggctgtccg 1800

```
cggggggacg gctgccttcg ggggggacgg ggcagggcgg ggttcggctt ctggcgtgtg   1860
accggcggct ctagagcctc tgctaaccat gttttagcct tcttcttttt cctacagctc   1920
ctgggcaacg tgctggttat tgtgctgtct catcatttgt cgacagaatt cctcgaagat   1980
ccgaaggggt tcaagcttgg cattccggta ctgttggtaa agccagttta aacgccgcca   2040
ccatggtgag caagggcgag gagctgttca ccggggtggt gcccatcctg gtcgagctgg   2100
acggcgacgt aaacggccac aagttcagcg tgtccggcga gggcgagggc gatgccacct   2160
acggcaagct gaccctgaag ttcatctgca ccaccggcaa gctgcccgtg ccctggccca   2220
ccctcgtgac caccctgacc tacggcgtgc agtgcttcag ccgctacccc gaccacatga   2280
agcagcacga cttcttcaag tccgccatgc ccgaaggcta cgtccaggag cgcaccatct   2340
tcttcaagga cgacggcaac tacaagaccc gcgccgaggt gaagttcgag ggcgacaccc   2400
tggtgaaccg catcgagctg aagggcatcg acttcaagga ggacggcaac atcctggggc   2460
acaagctgga gtacaactac aacagccaca acgtctatat catggccgac aagcagaaga   2520
acggcatcaa ggtgaacttc aagatccgcc acaacatcga ggacggcagc gtgcagctcg   2580
ccgaccacta ccagcagaac acccccatcg gcgacggccc cgtgctgctg cccgacaacc   2640
actacctgag cacccagtcc gccctgagca aagaccccaa cgagaagcgc gatcacatgg   2700
tcctgctgga gttcgtgacc gccgccggga tcactctcgg catggacgag ctgtacaagt   2760
aattaattaa gagcatctta ccgccattta ttcccatatt tgttctgttt ttcttgattt   2820
gggtatacat ttaaatgtta ataaaacaaa atggtggggc aatcatttac atttttaggg   2880
atatgtaatt actagttcag gtgtattgcc acaagacaaa catgttaaga aactttcccg   2940
ttatttacgc tctgttcctg ttaatcaacc tctggattac aaaatttgtg aaagattgac   3000
tgatattctt aactatgttg ctccttttac gctgtgtgga tatgctgctt tatagcctct   3060
gtatctagct attgcttccc gtacggcttt cgttttctcc tccttgtata aatcctggtt   3120
gctgtctctt ttagaggagt tgtggcccgt tgtccgtcaa cgtggcgtgg tgtgctctgt   3180
gtttgctgac gcaaccccca ctggctgggg cattgccacc acctgtcaac tcctttctgg   3240
gactttcgct ttccccctcc cgatcgccac ggcagaactc atcgccgcct gccttgcccg   3300
ctgctggaca ggggctaggt tgctgggcac tgataattcc gtggtgttgt ctgtgccttc   3360
tagttgccag ccatctgttg tttgcccctc ccccgtgcct tccttgaccc tggaaggtgc   3420
cactcccact gtcctttcct aataaaatga ggaaattgca tcgcattgtc tgagtaggtg   3480
tcattctatt ctggggggtg gggtggggca ggacagcaag ggggaggatt gggaagacaa   3540
tagcaggcat gctggggatg cggtgggctc tatggctcta gagcatggct acgtagataa   3600
gtagcatggc gggttaatca ttaactacac ctgcagcagg aacccctagt gatggagttg   3660
gccactccct ctctgcgcgc tcgctcgctc cctgcaggac tgaggccggg cgaccaaagg   3720
tcgcccgacg cccgggcggc ctcagtcctg cagg                               3754
```

<210> SEQ ID NO 147
<211> LENGTH: 8418
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 147

```
ggcagctgcg cgctcgctcg ctcacctagg ccgcccgggc aaagcccggg cgtcgggcga     60
```

-continued

```
cctttggtcg cccggcctag gtgagcgagc gagcgcgcag agagggagtg gccaactcca    120
tcactagggg ttccttgtag ttaatgatta acccgccatg ctacttatcg cggccgctca    180
atattggcca ttagccatat tattcattgg ttatatagca taaatcaata ttggctattg    240
gccattgcat acgttgtatc tatatcataa tatgtacatt tatattggct catgtccaat    300
atgaccgcca tgttggcatt gattattgac tagttattaa tagtaatcaa ttacggggtc    360
attagttcat agcccatata tggagttccg cgttacataa cttacggtaa atggcccgcc    420
tggctgaccg cccaacgacc cccgcccatt gacgtcaata atgacgtatg ttcccatagt    480
aacgccaata gggactttcc attgacgtca atgggtggag tatttacggt aaactgccca    540
cttggcagta catcaagtgt atcatatgcc aagtccgccc cctattgacg tcaatgacgg    600
taaatggccc gcctggcatt atgcccagta catgacctta cgggactttc ctacttggca    660
gtacatctac gtattagtca tcgctattac catggtcgag gtgagcccca cgttctgctt    720
cactctcccc atctcccccc cctccccacc cccaattttg tatttattta tttttaatt     780
attttgtgca gcgatggggg cggggggggg gggggggcgc gcgccaggcg gggcggggcg    840
gggcgagggg cggggcgggg cgaggcggag aggtgcggcg gcagccaatc agagcggcgc    900
gctccgaaag tttcctttta tggcgaggcg gcggcggcgg cggccctata aaaagcgaag    960
cgcgcggcgg gcgggagtcg ctgcgacgct gccttcgccc cgtgccccgc tccgccgccg   1020
cctcgcgccg cccgccccgg ctctgactga ccgcgttact cccacaggtg agcgggcggg   1080
acggcccttc tcctccgggc tgtaattagc gcttggttta atgacggctt gtttcttttc   1140
tgtggctgcg tgaaagcctt gaggggctcc gggagggccc tttgtgcggg gggagcggc    1200
tcgggggtg cgtgcgtgtg tgtgtgcgtg gggagcgccg cgtgcggccc gcgctgcccg    1260
gcggctgtga gcgctgcggg cgcggcgcgg ggctttgtgc gctccgcagt gtgcgcgagg   1320
ggagcgcggc cgggggcggt gccccgcggt gcgggggggg ctgcgagggg aacaaaggct   1380
gcgtgcgggg tgtgtgcgtg ggggggtgag cagggggtgt gggcgcggcg gtcgggctgt   1440
aacccccccc tgcacccccc tccccgagtt gctgagcacg gcccggcttc gggtgcgggg   1500
ctccgtacgg ggcgtggcgc ggggctcgcc gtgccgggcg gggggtggcg gcaggtgggg   1560
gtgccgggcg gggcggggcc gcctcgggcc ggggagggct cgggggaggg gcgcggcggc   1620
ccccggagcg ccggcggctg tcgaggcgcg gcgagccgca gccattgcct tttatggtaa   1680
tcgtgcgaga gggcgcaggg acttcctttg tcccaaatct gtgcggagcc gaaatctggg   1740
aggcgccgcc gcaccccctc tagcgggcgc ggggcgaagc ggtgcggcgc cggcaggaag   1800
gaaatgggcg gggagggcct tcgtgcgtcg ccgcgccgcc gtccccttct ccctctccag   1860
cctcggggct gtccgcgggg ggacggctgc cttcgggggg gacggggcag ggcggggttc   1920
ggcttctggc gtgtgaccgg cggctctaga gcctctgcta accatgtttt agccttcttc   1980
tttttcctac agctcctggg caacgtgctg gttattgtgc tgtctcatca tttgtcgaca   2040
gaattcctcg aagatccgaa ggggttcaag cttggcattc cggtactgtt ggtaaagcca   2100
gtttaaacgc cgccaccatg gtgagcaagg gcgaggagct gttcaccggg gtggtgccca   2160
tcctggtcga gctggacggc gacgtaaacg gccacaagtt cagcgtgtcc ggcgagggcg   2220
agggcgatgc cacctacggc aagctgaccc tgaagttcat ctgcaccacc ggcaagctgc   2280
ccgtgccctg gcccaccctc gtgaccaccc tgacctacgg cgtgcagtgc ttcagccgct   2340
accccgacca catgaagcag cacgacttct tcaagtccgc catgcccgaa ggctacgtcc   2400
```

-continued

```
aggagcgcac catcttcttc aaggacgacg gcaactacaa gacccgcgcc gaggtgaagt   2460
tcgagggcga caccctggtg aaccgcatcg agctgaaggg catcgacttc aaggaggacg   2520
gcaacatcct ggggcacaag ctggagtaca actacaacag ccacaacgtc tatatcatgg   2580
ccgacaagca gaagaacggc atcaaggtga acttcaagat ccgccacaac atcgaggacg   2640
gcagcgtgca gctcgccgac cactaccagc agaacacccc catcggcgac ggccccgtgc   2700
tgctgcccga caaccactac ctgagcaccc agtccgccct gagcaaagac cccaacgaga   2760
agcgcgatca catggtcctg ctggagttcg tgaccgccgc cgggatcact ctcggcatgg   2820
acgagctgta caagtaatta attaagagca tcttaccgcc atttattccc atatttgttc   2880
tgtttttctt gatttgggta tacatttaaa tgttaataaa acaaaatggt ggggcaatca   2940
tttacatttt tagggatatg taattactag ttcaggtgta ttgccacaag acaaacatgt   3000
taagaaactt tcccgttatt tacgctctgt tcctgttaat caacctctgg attacaaaat   3060
ttgtgaaaga ttgactgata ttcttaacta tgttgctcct tttacgctgt gtggatatgc   3120
tgctttatag cctctgtatc tagctattgc ttcccgtacg gctttcgttt tctcctcctt   3180
gtataaatcc tggttgctgt ctcttttaga ggagttgtgg cccgttgtcc gtcaacgtgg   3240
cgtggtgtgc tctgtgtttg ctgacgcaac ccccactggc tggggcattg ccaccacctg   3300
tcaactcctt tctgggactt tcgctttccc cctcccgatc gccacggcag aactcatcgc   3360
cgcctgcctt gcccgctgct ggacaggggc taggttgctg ggcactgata attccgtggt   3420
gttgtctgtg ccttctagtt gccagccatc tgttgtttgc ccctcccccg tgccttcctt   3480
gaccctggaa ggtgccactc ccactgtcct ttcctaataa aatgaggaaa ttgcatcgca   3540
ttgtctgagt aggtgtcatt ctattctggg gggtggggtg gggcaggaca gcaaggggga   3600
ggattgggaa gacaatagca ggcatgctgg ggatgcggtg ggctctatgg ctctagagca   3660
tggctacgta gataagtagc atggcgggtt aatcattaac tacacctgca gcaggaaccc   3720
ctagtgatgg agttggccac tccctctctg cgcgctcgct cgctccctgc aggactgagg   3780
ccgggcgacc aaaggtcgcc cgacgcccgg gcggcctcag tcctgcaggg agcgagcgag   3840
cgcgcagctg cctgcacggg cgcgccggta ccgggagatg ggggaggcta actgaaacac   3900
ggaaggagac aataccggaa ggaacccgcg ctatgacggc aataaaaaga cagaataaaa   3960
cgcacgggtg ttgggtcgtt tgttcataaa cgcggggttc ggtcccaggg ctggcactct   4020
gtcgataccc caccgagacc ccattgggac caatacgccc gcgtttcttc cttttcccca   4080
ccccaacccc caagttcggg tgaaggccca gggctcgcag ccaacgtcgg ggcggcaagc   4140
cctgccatag ccactacggg tacgtaggcc aaccactaga actatagcta gagtcctggg   4200
cgaacaaacg atgctcgcct tccagaaaac cgaggatgcg aaccacttca tccggggtca   4260
gcaccaccgg caagcgccgc gacggccgag gtctaccgat ctcctgaagc cagggcagat   4320
ccgtgcacag caccttgccg tagaagaaca gcaaggccgc caatgcctga cgatgcgtgg   4380
agaccgaaac cttgcgctcg ttcgccagcc aggacagaaa tgcctcgact tcgctgctgc   4440
ccaaggttgc cgggtgacgc acaccgtgga aacggatgaa ggcacgaacc cagttgacat   4500
aagcctgttc ggttcgtaaa ctgtaatgca agtagcgtat gcgctcacgc aactggtcca   4560
gaaccttgac cgaacgcagc ggtggtaacg gcgcagtggc ggttttcatg gcttgttatg   4620
actgtttttt tgtacagtct atgcctcggg catccaagca gcaagcgcgt tacgccgtgg   4680
gtcgatgttt gatgttatgg agcagcaacg atgttacgca gcagcaacga tgttacgcag   4740
cagggcagtc gccctaaaac aaagttaggt ggctcaagta tgggcatcat tcgcacatgt   4800
```

```
aggctcggcc ctgaccaagt caaatccatg cgggctgctc ttgatctttt cggtcgtgag   4860
ttcggagacg tagccaccta ctcccaacat cagccggact ccgattacct cgggaacttg   4920
ctccgtagta agacattcat cgcgcttgct gccttcgacc aagaagcggt tgttggcgct   4980
ctcgcggctt acgttctgcc caggtttgag cagccgcgta gtgagatcta tatctatgat   5040
ctcgcagtct ccggcgagca ccggaggcag ggcattgcca ccgcgctcat caatctcctc   5100
aagcatgagg ccaacgcgct tggtgcttat gtgatctacg tgcaagcaga ttacggtgac   5160
gatcccgcag tggctctcta tacaaagttg ggcatacggg aagaagtgat gcactttgat   5220
atcgacccaa gtaccgccac ctaacaattc gttcaagccg agatcggctt cccggccgcg   5280
gagttgttcg gtaaattgtc acaacgccgc gaatatagtc tttaccatgc ccttggccac   5340
gcccctcttt aatacgacgg gcaatttgca cttcagaaaa tgaagagttt gctttagcca   5400
taacaaaagt ccagtatgct tttcacagc ataactggac tgatttcagt ttacaactat   5460
tctgtctagt ttaagacttt attgtcatag tttagatcta ttttgttcag tttaagactt   5520
tattgtccgc ccacacccgc ttacgcaggg catccattta ttactcaacc gtaaccgatt   5580
ttgccaggtt acgcggctgg tctgcggtgt gaaataccgc acagatgcgt aaggagaaaa   5640
taccgcatca ggcgctcttc cgcttcctcg ctcactgact cgctgcgctc ggtcgttcgg   5700
ctgcggcgag cggtatcagc tcactcaaag gcggtaatac ggttatccac agaatcaggg   5760
gataacgcag gaaagaacat gtgagcaaaa ggccagcaaa aggccaggaa ccgtaaaaag   5820
gccgcgttgc tggcgttttt ccataggctc cgcccccctg acgagcatca caaaaatcga   5880
cgctcaagtc agaggtggcg aaacccgaca ggactataaa gataccaggc gtttccccct   5940
ggaagctccc tcgtgcgctc tcctgttccg accctgccgc ttaccggata cctgtccgcc   6000
tttctccctt cgggaagcgt ggcgctttct caatgctcac gctgtaggta tctcagttcg   6060
gtgtaggtcg ttcgctccaa gctgggctgt gtgcacgaac cccccgttca gcccgaccgc   6120
tgcgccttat ccggtaacta tcgtcttgag tccaacccgg taagacacga cttatcgcca   6180
ctggcagcag ccactggtaa caggattagc agagcgaggt atgtaggcgg tgctacagag   6240
ttcttgaagt ggtggcctaa ctacggctac actagaagga cagtatttgg tatctgcgct   6300
ctgctgaagc cagttacctt cggaaaaaga gttggtagct cttgatccgg caaacaaacc   6360
accgctggta gcggtggttt ttttgtttgc aagcagcaga ttacgcgcag aaaaaaagga   6420
tctcaagaag atcctttgat cttttctacg gggtctgacg ctcagtggaa cgaaaactca   6480
cgttaaggga ttttggtcat gagattatca aaaaggatct tcacctagat ccttttaaat   6540
taaaaatgaa gttttaaatc aatctaaagt atatatgagt aaacttggtc tgacagttac   6600
caatgcttaa tcagtgaggc acctatctca gcgatctgtc tatttcgttc atccatagtt   6660
gcctgactcc ccgtcgtgta gataactacg atacgggagg gcttaccatc tggccccagt   6720
gctgcaatga taccgcgaga cccacgctca ccggctccag atttatcagc aataaaccag   6780
ccagccggaa gggccgagcg cagaagtggt cctgcaactt tatccgcctc catccagtct   6840
attaattgtt gccgggaagc tagagtaagt agttcgccag ttaatagttt gcgcaacgtt   6900
gttgccattg ctacaggcat cgtggtgtca cgctcgtcgt ttggtatggc ttcattcagc   6960
tccggttccc aacgatcaag gcgagttaca tgatccccca tgttgtgcaa aaaagcggtt   7020
agctccttcg gtcctccgat cgttgtcaga agtaagttgg ccgcagtgtt atcactcatg   7080
gttatggcag cactgcataa ttctcttact gtcatgccat ccgtaagatg cttttctgtg   7140
```

actggtgagt actcaaccaa gtcattctga gaatagtgta tgcggcgacc gagttgctct 7200
tgcccggcgt caatacggga taataccgcg ccacatagca gaactttaaa agtgctcatc 7260
attggaaaac gttcttcggg gcgaaaactc tcaaggatct taccgctgtt gagatccagt 7320
tcgatgtaac ccactcgtgc acccaactga tcttcagcat cttttacttt caccagcgtt 7380
tctgggtgag caaaaacagg aaggcaaaat gccgcaaaaa agggaataag ggcgacacgg 7440
aaatgttgaa tactcatact cttccttttt caatattatt gaagcattta tcagggttat 7500
tgtctcatga gcggatacat atttgaatgt atttagaaaa ataaacaaat aggggttccg 7560
cgcacatttc cccgaaaagt gccacctgaa attgtaaacg ttaatatttt gttaaaattc 7620
gcgttaaatt tttgttaaat cagctcattt tttaaccaat aggccgaaat cggcaaaatc 7680
ccttataaat caaaagaata gaccgagata gggttgagtg ttgttccagt ttggaacaag 7740
agtccactat taaagaacgt ggactccaac gtcaaagggc gaaaaaccgt ctatcagggc 7800
gatggcccac tacgtgaacc atcaccctaa tcaagttttt tggggtcgag gtgccgtaaa 7860
gcactaaatc ggaaccctaa agggagcccc cgatttagag cttgacgggg aaagccggcg 7920
aacgtggcga gaaaggaagg gaagaaagcg aaaggagcgg gcgctagggc gctggcaagt 7980
gtagcggtca cgctgcgcgt aaccaccaca cccgccgcgc ttaatgcgcc gctacagggc 8040
gcgtcccatt cgccattcag gctgcaaata agcgttgata ttcagtcaat tacaaacatt 8100
aataacgaag agatgacaga aaaattttca ttctgtgaca gagaaaaagt agccgaagat 8160
gacggtttgt cacatggagt tggcaggatg tttgattaaa aacataacag gaagaaaaat 8220
gccccgctgt gggcggacaa aatagttggg aactgggagg ggtggaaatg gagtttttaa 8280
ggattattta gggaagagtg acaaaataga tgggaactgg gtgtagcgtc gtaagctaat 8340
acgaaaatta aaaatgacaa aatagtttgg aactagattt cacttatctg gttcggatct 8400
cctagtgagc tccctgca 8418

<210> SEQ ID NO 148
<211> LENGTH: 225
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 148
tgtgccttct agttgccagc catctgttgt ttgcccctcc cccgtgcctt ccttgaccct 60
ggaaggtgcc actcccactg tcctttccta ataaaatgag gaaattgcat cgcattgtct 120
gagtaggtgt cattctattc tggggggtgg ggtggggcag gacagcaagg gggaggattg 180
ggaagacaat agcaggcatg ctggggatgc ggtgggctct atggc 225

<210> SEQ ID NO 149
<211> LENGTH: 1177
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 149
ggctcagagg ctcagaggca cacaggagtt tctgggctca ccctgccccc ttccaacccc 60
tcagttccca tcctccagca gctgtttgtg tgctgcctct gaagtccaca ctgaacaaac 120
ttcagcctac tcatgtccct aaaatgggca aacattgcaa gcagcaaaca gcaaacacac 180

-continued

```
agccctccct gcctgctgac cttggagctg gggcagaggt cagagacctc tctgggccca    240

tgccacctcc aacatccact cgaccccttg gaatttcggt ggagaggagc agaggttgtc    300

ctggcgtggt ttaggtagtg tgagagggtc cgggttcaaa accacttgct gggtggggag    360

tcgtcagtaa gtggctatgc cccgaccccg aagcctgttt ccccatctgt acaatggaaa    420

tgataaagac gcccatctga tagggttttt gtggcaaata aacatttggt ttttttgttt    480

tgttttgttt tgtttttga gatggaggtt tgctctgtcg cccaggctgg agtgcagtga    540

cacaatctca tctcaccaca accttcccct gcctcagcct cccaagtagc tgggattaca    600

agcatgtgcc accacacctg gctaattttc tatttttagt agagacgggt ttctccatgt    660

tggtcagcct cagcctccca agtaactggg attacaggcc tgtgccacca cacccggcta    720

attttttcta tttttgacag ggacggggtt tcaccatgtt ggtcaggctg gtctagaggt    780

accggatctt gctaccagtg gaacagccac taaggattct gcagtgagag cagagggcca    840

gctaagtggt actctcccag agactgtctg actcacgcca ccccctccac cttggacaca    900

ggacgctgtg gtttctgagc caggtacaat gactcctttc ggtaagtgca gtggaagctg    960

tacactgccc aggcaaagcg tccgggcagc gtaggcgggc gactcagatc ccagccagtg   1020

gacttagccc ctgtttgctc ctccgataac tggggtgacc ttggttaata ttcaccagca   1080

gcctcccccg ttgcccctct ggatccactg cttaaatacg gacgaggaca gggccctgtc   1140

tcctcagctt caggcaccac cactgacctg ggacagt                            1177
```

```
<210> SEQ ID NO 150

<400> SEQUENCE: 150

000
```

```
<210> SEQ ID NO 151
<211> LENGTH: 573
<212> TYPE: DNA
<213> ORGANISM: Mus musculus

<400> SEQUENCE: 151

gtaagagttt tatgtttttt catctctgct tgtatttttc tagtaatgga agcctggtat     60

tttaaaatag ttaaattttc ctttagtgct gatttctaga ttattattac tgttgttgtt    120

gttattattg tcattatttg catctgagaa cccttaggtg gttatattat tgatatattt    180

ttggtatctt tgatgacaat aatgggggat tttgaaagct tagctttaaa tttcttttaa    240

ttaaaaaaaa atgctaggca gaatgactca aattacgttg gatacagttg aatttattac    300

ggtctcatag ggcctgcctg ctcgaccatg ctatactaaa aattaaaagt gtgtgttact    360

aattttataa atggagtttc catttatatt tacctttatt tcttatttac cattgtctta    420

gtagatattt acaaacatga cagaaacact aaatcttgag tttgaatgca cagatataaa    480

cacttaacgg gttttaaaaa taataatgtt ggtgaaaaaa tataactttg agtgtagcag    540

agaggaacca ttgccacctt cagattttcc tgt                                 573
```

```
<210> SEQ ID NO 152
<211> LENGTH: 1993
<212> TYPE: DNA
<213> ORGANISM: Mus musculus

<400> SEQUENCE: 152

acgatcggga actggcatct tcagggagta gcttaggtca gtgaagagaa gaacaaaaag     60
```

cagcatatta cagttagttg tcttcatcaa tctttaaata tgttgtgtgg tttttctctc 120
cctgtttcca cagacaagag tgagatcgcc catcggtata atgatttggg agaacaacat 180
ttcaaaggcc tgtaagttat aatgctgaaa gcccacttaa tatttctggt agtattagtt 240
aaagttttaa aacacctttt tccaccttga gtgtgagaat tgtagagcag tgctgtccag 300
tagaaatgtg tgcattgaca gaaagactgt ggatctgtgc tgagcaatgt ggcagccaga 360
gatcacaagg ctatcaagca ctttgcacat ggcaagtgta actgagaagc acacattcaa 420
ataatagtta attttaattg aatgtatcta gccatgtgtg gctagtagct cctttcctgg 480
agagagaatc tggagcccac atctaacttg ttaagtctgg aatcttattt tttatttctg 540
gaaaggtcta tgaactatag ttttgggggc agctcactta ctaactttta atgcaataag 600
atctcatggt atcttgagaa cattattttg tctctttgta gtactgaaac cttatacatg 660
tgaagtaagg ggtctatact taagtcacat ctccaacctt agtaatgttt taatgtagta 720
aaaaaatgag taattaattt atttttagaa ggtcaatagt atcatgtatt ccaaataaca 780
gaggtatatg gttagaaaag aaacaattca aaggacttat ataatatcta gccttgacaa 840
tgaataaatt tagagagtag tttgcctgtt tgcctcatgt tcataaatct attgacacat 900
atgtgcatct gcacttcagc atggtagaag tccatattcc tttgcttgga aaggcaggtg 960
ttcccattac gcctcagaga atagctgacg ggaagaggct ttctagatag ttgtatgaaa 1020
gatatacaaa atctcgcagg tatacacagg catgatttgc tggttgggag agccacttgc 1080
ctcatactga ggtttttgtg tctgcttttc agagtcctga ttgccttttc ccagtatctc 1140
cagaaatgct catacgatga gcatgccaaa ttagtgcagg aagtaacaga ctttgcaaag 1200
acgtgtgttg ccgatgagtc tgccgccaac tgtgacaaat cccttgtgag taccttctga 1260
ttttgtggat ctactttcct gctttctgga actctgtttc aaagccaatc atgactccat 1320
cacttaaggc cccgggaaca ctgtggcaga gggcagcaga gagattgata aagccagggt 1380
gatgggaatt ttctgtggga ctccatttca tagtaattgc agaagctaca atacactcaa 1440
aaagtctcac cacatgactg cccaaatggg agcttgacag tgacagtgac agtagatatg 1500
ccaaagtgga tgagggaaag accacaagag ctaaaccctg taaaaagaac tgtaggcaac 1560
taaggaatgc agagagaaga agttgccttg gaagagcata ccaactgcct ctccaatacc 1620
aatggtcatc cctaaaacat acgtatgaat aacatgcaga ctaagcaggc tacatttagg 1680
aatatacatg tatttacata aatgtatatg catgtaacaa caatgaatga aaactgaggt 1740
catggatctg aaagagagca agggggctta catgagaggg tttggaggga ggggttggag 1800
ggagggaggt attattcttt agttttacag ggaacgtagt aaaaacatag gcttctccca 1860
aaggagcaga gcccatgagg agctgtgcaa ggttccccag cttgatttta cctgctcctc 1920
aaattccctt gatttgtttt tattataatg actttactcc tagcttttag tgtcagatag 1980
aaaacatgga agg 1993

<210> SEQ ID NO 153
<211> LENGTH: 1350
<212> TYPE: DNA
<213> ORGANISM: Homo sapiens

<400> SEQUENCE: 153
taggaggctg aggcaggagg atcgcttgag cccaggagtt cgagaccagc ctgggcaaca 60
tagtgtgatc ttgtatctat aaaaataaac aaaattagct tggtgtggtg gcgcctgtag 120

-continued

```
tccccagcca cttggagggg tgaggtgaga ggattgcttg agcccgggat ggtccaggct    180
gcagtgagcc atgatcgtgc cactgcactc cagcctgggc gacagagtga gaccctgtct    240
cacaacaaca acaacaacaa caaaaaggct gagctgcacc atgcttgacc cagtttctta    300
aaattgttgt caaagcttca ttcactccat ggtgctatag agcacaagat tttatttggt    360
gagatggtgc tttcatgaat tcccccaaca gagccaagct ctccatctag tggacaggga    420
agctagcagc aaaccttccc ttcactacaa aacttcattg cttggccaaa aagagagtta    480
attcaatgta gacatctatg taggcaatta aaaacctatt gatgtataaa acagtttgca    540
ttcatggagg gcaactaaat acattctagg actttataaa agatcacttt ttatttatgc    600
acagggtgga acaagatgga ttatcaagtg tcaagtccaa tctatgacat caattattat    660
acatcggagc cctgccaaaa aatcaatgtg aagcaaatcg cagcccgcct cctgcctccg    720
ctctactcac tggtgttcat ctttggtttt gtgggcaaca tgctggtcat cctcatcctg    780
ataaactgca aaaggctgaa gagcatgact gacatctacc tgctcaacct ggccatctct    840
gacctgtttt tccttcttac tgtcccettc tgggctcact atgctgccgc ccagtgggac    900
tttggaaata caatgtgtca actcttgaca gggctctatt ttataggctt cttctctgga    960
atcttcttca tcatcctcct gacaatcgat aggtacctgg ctgtcgtcca tgctgtgttt   1020
gctttaaaag ccaggacggt cacctttggg gtggtgacaa gtgtgatcac ttgggtggtg   1080
gctgtgtttg cgtctctccc aggaatcatc tttaccagat ctcaaaaaga aggtcttcat   1140
tacacctgca gctctcattt tccatacagt cagtatcaat tctggaagaa tttccagaca   1200
ttaaagatag tcatcttggg gctggtcctg ccgctgcttg tcatggtcat ctgctactcg   1260
ggaatcctaa aaactctgct tcggtgtcga aatgagaaga agaggcacag ggctgtgagg   1320
cttatcttca ccatcatgat tgtttatttt                                     1350
```

<210> SEQ ID NO 154
<211> LENGTH: 1223
<212> TYPE: DNA
<213> ORGANISM: Homo sapiens

<400> SEQUENCE: 154

```
tgacagagac tcttgggatg acgcactgct gcatcaaccc catcatctat gcctttgtcg     60
gggagaagtt cagaaactac ctcttagtct tcttccaaaa gcacattgcc aaacgcttct    120
gcaaatgctg ttctattttc cagcaagagg ctcccgagcg agcaagctca gtttacaccc    180
gatccactgg ggagcaggaa atatctgtgg gcttgtgaca cggactcaag tgggctggtg    240
acccagtcag agttgtgcac atggcttagt tttcatacac agcctgggct gggggtgggg    300
tgggagaggt ctttttttaaa aggaagttac tgttatagag ggtctaagat tcatccattt    360
atttggcatc tgtttaaagt agattagatc ttttaagccc atcaattata gaaagccaaa    420
tcaaaatatg ttgatgaaaa atagcaacct ttttatctcc ccttcacatg catcaagtta    480
ttgacaaact ctcccttcac tccgaaagtt ccttatgtat atttaaaaga aagcctcaga    540
gaattgctga ttcttgagtt tagtgatctg aacagaaata ccaaaattat ttcagaaatg    600
tacaactttt tacctagtac aaggcaacat ataggttgta aatgtgttta aaacaggtct    660
ttgtcttgct atggggagaa aagacatgaa tatgattagt aaagaaatga cacttttcat    720
gtgtgatttc ccctccaagg tatggttaat aagtttcact gacttagaac caggcgagag    780
acttgtggcc tgggagagct ggggaagctt cttaaatgag aaggaatttg agttggatca    840
tctattgctg gcaaagacag aagcctcact gcaagcactg catgggcaag cttggctgta    900
```

gaaggagaca gagctggttg ggaagacatg gggaggaagg acaaggctag atcatgaaga 960
accttgacgg cattgctccg tctaagtcat gagctgagca gggagatcct ggttggtgtt 1020
gcagaaggtt tactctgtgg ccaaaggagg gtcaggaagg atgagcattt agggcaagga 1080
gaccaccaac agccctcagg tcagggtgag gatggcctct gctaagctca aggcgtgagg 1140
atgggaagga gggaggtatt cgtaaggatg ggaaggaggg aggtattcgt gcagcatatg 1200
aggatgcaga gtcagcagaa ctg 1223

<210> SEQ ID NO 155
<211> LENGTH: 215
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 155
gaacgctgac gtcatcaacc cgctccaagg aatcgcgggc ccagtgtcac taggcgggaa 60
cacccagcgc gcgtgcgccc tggcaggaag atggctgtga gggacagggg agtggcgccc 120
tgcaatattt gcatgtcgct atgtgttctg ggaaatcacc ataaacgtga aatgtctttg 180
gatttgggaa tcttataagt tctgtatgag accac 215

<210> SEQ ID NO 156
<211> LENGTH: 141
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 156
cctgcaggca gctgcgcgct cgctcgctca cctaggccgc ccgggcaaag cccgggcgtc 60
gggcgacctt tggtcgcccg gcctaggtga gcgagcgagc gcgcagagag ggagtggcca 120
actccatcac taggggttcc t 141

<210> SEQ ID NO 157
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 157
gcgcgctcgc tcgctcacc 19

<210> SEQ ID NO 158
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 158
ctaggtgagc gagcgagcgc gc 22

<210> SEQ ID NO 159
<211> LENGTH: 75
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 159
cctgcaggac tgaggccgcc cgggcaaagc ccgggcgtcg ggcgaccttt ggtcgcccgg 60
cctcagtcct gcagg 75

<210> SEQ ID NO 160
<211> LENGTH: 130
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 160
aggaacccct agtgatggag ttggccactc cctctctgcg cgctcgctcg ctcactgagt 60
gcgggcgacc aaaggtcgcc cgacgcccgg gcgcactcag tgagcgagcg agcgcgcagc 120
tgcctgcagg 130

<210> SEQ ID NO 161
<211> LENGTH: 142
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 161
cctgcaggca gctgcgcgct cgctcgctcc ctaggactga ggccgcccgg gcgtcgggcg 60
acctttggtc gcccggcctc agtcctaggg agcgagcgag cgcgcagaga gggagtggcc 120
aactccatca ctaggggttc ct 142

<210> SEQ ID NO 162
<211> LENGTH: 80
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 162
gcgcgctcgc tcgctcactg agtgcgggcg accaaaggtc gcccgacgcc cgggcgcact 60
cagtgagcga gcgagcgcgc 80

<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 163
gcgcgctcgc tcgctcactg a 21

<210> SEQ ID NO 164
<211> LENGTH: 18
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 164
gtgagcgagc gagcgcgc 18

<210> SEQ ID NO 165
<211> LENGTH: 89
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 165
gcgcgctcgc tcgctcactg aggccgcccg ggcaaagccc gggcgtcggg cgactttgtc 60
gcccggcctc agtgagcgag cgagcgcgc 89

<210> SEQ ID NO 166
<211> LENGTH: 89
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 166
gcgcgctcgc tcgctcactg aggccgggcg acaaagtcgc ccgacgcccg ggctttgccc 60
gggcggcctc agtgagcgag cgagcgcgc 89

<210> SEQ ID NO 167
<211> LENGTH: 87
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 167
gcgcgctcgc tcgctcactg aggccgcccg ggcaaagccc gggcgtcggg cgattttcgc 60
ccggcctcag tgagcgagcg agcgcgc 87

<210> SEQ ID NO 168
<211> LENGTH: 87
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 168
gcgcgctcgc tcgctcactg aggccgggcg aaaatcgccc gacgcccggg ctttgcccgg 60
gcggcctcag tgagcgagcg agcgcgc 87

<210> SEQ ID NO 169
<211> LENGTH: 85
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 169
gcgcgctcgc tcgctcactg aggccgcccg ggcaaagccc gggcgtcggg cgtttcgccc 60
ggcctcagtg agcgagcgag cgcgc 85

<210> SEQ ID NO 170
<211> LENGTH: 85
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 170
gcgcgctcgc tcgctcactg aggccgggcg aaacgcccga cgcccgggct ttgcccgggc 60
ggcctcagtg agcgagcgag cgcgc 85

<210> SEQ ID NO 171
<211> LENGTH: 89
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 171
gcgcgctcgc tcgctcactg aggccgcccg ggaaacccgg gcgtcgggcg acctttggtc 60
gcccggcctc agtgagcgag cgagcgcgc 89

<210> SEQ ID NO 172
<211> LENGTH: 89
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 172
gcgcgctcgc tcgctcactg aggccgggcg accaaaggtc gcccgacgcc cgggtttccc 60
gggcggcctc agtgagcgag cgagcgcgc 89

<210> SEQ ID NO 173
<211> LENGTH: 87
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 173
gcgcgctcgc tcgctcactg aggccgcccg gaaaccgggc gtcgggcgac ctttggtcgc 60
ccggcctcag tgagcgagcg agcgcgc 87

<210> SEQ ID NO 174
<211> LENGTH: 87
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 174
gcgcgctcgc tcgctcactg aggccgggcg accaaaggtc gcccgacgcc cggtttccgg 60
gcggcctcag tgagcgagcg agcgcgc 87

<210> SEQ ID NO 175
<211> LENGTH: 85
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 175
gcgcgctcgc tcgctcactg aggccgcccg aaacgggcgt cgggcgacct ttggtcgccc 60
ggcctcagtg agcgagcgag cgcgc 85

<210> SEQ ID NO 176
<211> LENGTH: 85
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 176
gcgcgctcgc tcgctcactg aggccgggcg accaaaggtc gcccgacgcc cgtttcgggc 60
ggcctcagtg agcgagcgag cgcgc 85

<210> SEQ ID NO 177
<211> LENGTH: 83
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 177
gcgcgctcgc tcgctcactg aggccgccca aagggcgtcg ggcgaccttt ggtcgcccgg 60
cctcagtgag cgagcgagcg cgc 83

<210> SEQ ID NO 178
<211> LENGTH: 83
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 178
gcgcgctcgc tcgctcactg aggccgggcg accaaaggtc gcccgacgcc ctttgggcgg 60
cctcagtgag cgagcgagcg cgc 83

<210> SEQ ID NO 179
<211> LENGTH: 81
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 179
gcgcgctcgc tcgctcactg aggccgccaa aggcgtcggg cgacctttgg tcgcccggcc 60
tcagtgagcg agcgagcgcg c 81

<210> SEQ ID NO 180
<211> LENGTH: 81
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 180
gcgcgctcgc tcgctcactg aggccgggcg accaaaggtc gcccgacgcc tttggcggcc 60
tcagtgagcg agcgagcgcg c 81

<210> SEQ ID NO 181
<211> LENGTH: 79
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 181
gcgcgctcgc tcgctcactg aggccgcaaa gcgtcgggcg acctttggtc gcccggcctc 60
agtgagcgag cgagcgcgc 79

<210> SEQ ID NO 182
<211> LENGTH: 79
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 182
gcgcgctcgc tcgctcactg aggccgggcg accaaaggtc gcccgacgct ttgcggcctc 60
agtgagcgag cgagcgcgc 79

<210> SEQ ID NO 183
<211> LENGTH: 81
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 183
ctgcgcgctc gctcgctcac tgaggccgaa acgtcgggcg acctttggtc gcccggcctc 60
agtgagcgag cgagcgcgca g 81

<210> SEQ ID NO 184
<211> LENGTH: 81
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 184
ctgcgcgctc gctcgctcac tgaggccggg cgaccaaagg tcgcccgacg tttcggcctc 60
agtgagcgag cgagcgcgca g 81

<210> SEQ ID NO 185
<211> LENGTH: 72
<212> TYPE: DNA
<213> ORGANISM: Artificial Sequence
<220> FEATURE:
<223> OTHER INFORMATION: Description of Artificial Sequence: Synthetic
oligonucleotide -continued

```
<400> SEQUENCE: 185

gcgcgctcgc tcgctcactg aggccgggcg accaaaggtc gcccgacggc ctcagtgagc     60

gagcgagcgc gc                                                         72


<210> SEQ ID NO 186
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186

gcgcgctcgc tcgctcactg aggccgggcg accaaaggtc gcccgacgcc cgggcggcct     60

cagtgagcga gcgagcgcgc                                                 80


<210> SEQ ID NO 187
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187

gcgcgctcgc tcgctcactg aggcgcccgg gcgtcgggcg acctttggtc gcccggcctc     60

agtgagcgag cgagcgcgc                                                  79
```

CLOSED-ENDED DNA VECTORS OBTAINABLE FROM CELL-FREE SYNTHESIS AND PROCESS FOR OBTAINING ceDNA VECTORS

CROSS REFERENCE TO RELATED APPLICATIONS

This application is a 35 U.S.C. § 371 National Stage filing of International Application No. PCT/US2019/014122, filed on Jan. 18, 2019, which in turn claims benefit under 35 U.S.C. § 119(e) of U.S. Provisional Application No. 62/619,392, filed on Jan. 19, 2018. The contents of each of the aforementioned applications are incorporated herein by reference in their entireties.

SEQUENCE LISTING

The instant application contains a Sequence Listing which has been submitted electronically in ASCII format and is hereby incorporated by reference in its entirety. Said ASCII copy, created on Jan. 17, 2019, is named 080170-091310-WOPT_SL.txt and is 102,804 bytes in size.

TECHNICAL FIELD

The present invention relates to the field of gene therapy, including production of non-viral vectors for the purpose of expressing a transgene or isolated polynucleotides in a subject or cell. For example, the present disclosure provides cell-free methods of synthesizing non-viral DNA vectors. The disclosure also relates to the nucleic acid constructs produced thereby and methods of their use.

BACKGROUND

Gene therapy aims to improve clinical outcomes for patients suffering from either genetic mutations or acquired diseases caused by an aberration in the gene expression profile. Gene therapy includes the treatment or prevention of medical conditions resulting from defective genes or abnormal regulation or expression, e.g. underexpression or overexpression, that can result in a disorder, disease, malignancy, etc. For example, a disease or disorder caused by a defective gene might be treated, prevented or ameliorated by delivery of a corrective genetic material to a patient, or might be treated, prevented or ameliorated by altering or silencing a defective gene, e.g., with a corrective genetic material to a patient resulting in the therapeutic expression of the genetic material within the patient.

The basis of gene therapy is to supply a transcription cassette with an active gene product (sometimes referred to as a transgene), e.g., that can result in a positive gain-of-function effect, a negative loss-of-function effect, or another outcome. Gene therapy can also be used to treat a disease or malignancy caused by other factors. Human monogenic disorders can be treated by the delivery and expression of a normal gene to the target cells. Delivery and expression of a corrective gene in the patient's target cells can be carried out via numerous methods, including the use of engineered viruses and viral gene delivery vectors. Among the many virus-derived vectors available (e.g., recombinant retrovirus, recombinant lentivirus, recombinant adenovirus, and the like), recombinant adeno-associated virus (rAAV) is gaining popularity as a versatile vector in gene therapy.

Adeno-associated viruses (AAV) belong to the parvoviridae family and more specifically constitute the dependoparvovirus genus. Vectors derived from AAV (i.e., recombinant AAV (rAVV) or AAV vectors) are attractive for delivering genetic material because (i) they are able to infect (transduce) a wide variety of non-dividing and dividing cell types including myocytes and neurons; (ii) they are devoid of the virus structural genes, thereby diminishing the host cell responses to virus infection, e.g., interferon-mediated responses; (iii) wild-type viruses are considered non-pathologic in humans; (iv) in contrast to wild type AAV, which are capable of integrating into the host cell genome, replication-deficient AAV vectors lack the rep gene and generally persist as episomes, thus limiting the risk of insertional mutagenesis or genotoxicity; and (v) in comparison to other vector systems, AAV vectors are generally considered to be relatively poor immunogens and therefore do not trigger a significant immune response (see ii), thus gaining persistence of the vector DNA and potentially, long-term expression of the therapeutic transgenes.

However, there are several major deficiencies in using AAV particles as a gene delivery vector. One major drawback associated with rAAV is its limited viral packaging capacity of about 4.5 kb of heterologous DNA (Dong et al., 1996; Athanasopoulos et al., 2004; Lai et al., 2010), and as a result, use of AAV vectors has been limited to less than 150,000 Da protein coding capacity. The second drawback is that as a result of the prevalence of wild-type AAV infection in the population, candidates for rAAV gene therapy have to be screened for the presence of neutralizing antibodies that eliminate the vector from the patient. A third drawback is related to the capsid immunogenicity that prevents re-administration to patients that were not excluded from an initial treatment. The immune system in the patient can respond to the vector which effectively acts as a "booster" shot to stimulate the immune system generating high titer anti-AAV antibodies that preclude future treatments. Some recent reports indicate concerns with immunogenicity in high dose situations. Another notable drawback is that the onset of AAV-mediated gene expression is relatively slow, given that single-stranded AAV DNA must be converted to double-stranded DNA prior to heterologous gene expression.

Additionally, conventional AAV virions with capsids are produced by introducing a plasmid or plasmids containing the AAV genome, rep genes, and cap genes (Grimm et al., 1998). However, such encapsidated AAV virus vectors were found to inefficiently transduce certain cell and tissue types and the capsids also induce an immune response.

Accordingly, use of adeno-associated virus (AAV) vectors for gene therapy is limited due to the single administration to patients (owing to the patient immune response), the limited range of transgene genetic material suitable for delivery in AAV vectors due to minimal viral packaging capacity (about 4.5 kb), and slow AAV-mediated gene expression.

Closed-ended DNA vectors have been developed that are capable of delivering one or more desired transgenes in vivo for therapeutic or other purposes, and which avoid the above-described liabilities of AAV and other virus vector systems. However, methods of producing such ceDNA vectors have relied upon traditional bacterial or insect cell production methods. Such methods can result in contaminants (e.g., nucleic acid contaminants) from the cells used to produce the vectors that are inconvenient or costly to remove and which may have undesirable side effects if included in a ceDNA therapeutic formulation. Accordingly, there is need in the field for a technology that allows for the generation of recombinant vectors to be used in methods of controlling gene expression with minimal off-target effects such as those introduced by such contaminants or other artifacts of the purification method. The methods provided herein lessen or avoid such problems.

BRIEF DESCRIPTION OF THE INVENTION

Conventional methods for production of viral and virally-derived DNA typically use eukaryotic cells, e.g., mammalian or insect cells. One commonly used insect cell line is Sf9. However, not only do these cells both contain enzymes and other proteins which may have a deleterious effect on the DNA to be replicated, but the process of purifying the desired DNA from cell lysates introduces cellular nucleic acids whose presence can make purification of the desired DNA product more difficult. Further, such impurities or contaminants can have a range of deleterious and/or unwanted effects in the subject to which the desired DNA is administered. Additionally, such traditional cell-based production methods can have issues with respect to the quantity of DNA vector product produced, and it is not uncommon for significant engineering of the cell line itself or the production technology to be required to produce desirable yields. The technology described herein relates to a synthetic production method that can readily produce closed circle hairpin loop-containing DNA vectors such as, but not limited to, close-ended DNA vectors (ceDNA vectors) in higher purities and quantities than by conventional means, avoiding the concerns detailed above.

The invention described herein provides synthetic production methods to produce closed-ended DNA vectors using a synthetic production system, which can be a cell-free system. In some embodiments, the closed-ended DNA vector is a ceDNA vector, which can be used in methods of controlling gene expression in a cell, tissue or system or to introduce new genetic material into a desired cell, tissue or system. In one particular embodiment, the technology described herein relates to novel cell-free methods of making DNA vectors containing modified AAV inverted terminal repeat sequences (ITRs) and, e.g., one or more expressible transgenes. The methods disclosed herein can be used to produce any closed-ended hairpin loop-containing DNA vector in a cell free system, including but not limited to capsid-free, linear duplex DNA molecules, herein referred to ceDNA vectors, formed from a single strand of DNA with covalently-closed ends (linear, continuous and non-encapsidated structure).

One exemplary synthetic production method to generate a closed-ended DNA vector, exemplified using the production of a ceDNA vector as disclosed herein, relates to excising the entire molecule that forms the closed-ended DNA vector from a double-stranded DNA construct. In such an embodiment, a double-stranded DNA construct is provided with, in 5' to 3' order: a first restriction endonuclease site; an upstream ITR; an expression cassette; a downstream ITR; and a second restriction endonuclease site. The double-stranded DNA construct is then contacted with one or more restriction endonucleases to generate double-stranded breaks at both of the restriction endonuclease cleavage sites. One endonuclease can target both sites, or each site can be targeted by a different endonuclease as long as the restriction sites are not present within the closed-ended vector template region. This excises the sequence between the restriction endonuclease sites from the rest of the double-stranded DNA construct. This excised molecule will have free 5' and 3' ends, which are then ligated in order to form a ceDNA vector. In some aspects, the excised molecule is first annealed to facilitate hairpin formation prior to ligation of the free 5' and 3' ends. In some aspects, the unwanted double-stranded DNA construct backbone is cleaved by one or more restriction endonucleases specific for a unique cleavage site in the backbone so that it is degraded and more readily eliminated during purification.

Another exemplary method of producing a DNA vector, e.g., a ceDNA vector, using the synthetic production method as disclosed herein involves the assembly of various oligonucleotides to form the complete vector. In such an embodiment, a DNA vector, e.g., ceDNA vector is produced by synthesizing a 5' oligonucleotide and a 3' ITR oligonucleotide, which in some embodiments, are in a hairpin or other three-dimensional configuration (e.g., holliday junction configuration), and ligating the 5' and 3' ITR oligonucleotides to a double-stranded polynucleotide comprising an expression cassette or heterologous nucleic acid sequence. Optionally, a step is added subjecting the oligo(s) to conditions that facilitate the folding of the oligo into a three-dimensional configuration prior to the ligation step. FIG. 11B shows an exemplary method of generating a ceDNA vector comprising ligating a 5' ITR oligonucleotide and a 3' ITR oligonucleotide to a double stranded polynucleotide comprising an expression cassette. In some embodiments, the 5' and 3' ITR oligonucleotides are 5' and 3' hairpin oligonucleotides or have a hairpin structure or different three-dimensional configuration (e.g., a T- or Y-shaped Holliday junction), and can optionally be provided by in vitro DNA synthesis. In some embodiments, the 5' and 3' ITR oligonucleotides have been cleaved with a restriction endonuclease to have complementary sticky ends to the double-stranded polynucleotide that has corresponding restriction endonuclease sticky ends. In some embodiments, the end of the hairpin of the 5' ITR oligonucleotide has a sticky end that is complementary to the 5' sense strand and 3' antisense strand of the double-stranded polynucleotide. In some embodiments, the end of the hairpin of the 3' ITR oligonucleotide has a sticky end that is complementary to the 3' sense strand and 5' antisense strand of the double-stranded polynucleotide. In some embodiments, the ends of the hairpin of the 5' ITR oligonucleotide and the 3' ITR oligonucleotide have different restriction endonuclease sticky ends, such that directed ligation to each end of the double-stranded polynucleotide can be achieved. In some embodiments, the ends of one or both of the ITR oligonucleotides do not have overhangs and such ITR oligo(s) are ligated to the double-stranded polynucleotide by blunt end-joining. In some aspects, the unwanted double-stranded DNA polynucleotide backbone is cleaved by one or more restriction endonucleases specific for a unique cleavage site in the backbone so that it is degraded and more readily eliminated during purification.

Another exemplary method of producing a DNA vector, (e.g., ceDNA vector) involves the formation of a single-stranded linear DNA comprising an expression cassette and subsequently closing the DNA molecule with ligation. In this embodiment, the DNA vector is prepared by synthesizing through any art-known means a single-stranded linear DNA comprising in the 5' to 3' direction a first sense first ITR, a sense expression cassette sequence, a sense second ITR, an antisense second ITR, an antisense expression cassette sequence, and an antisense first ITR, and then ligating the free ends in order to form a closed-ended ceDNA vector. In one embodiment, using the production of a ceDNA vector as an exemplary DNA vector to be produced, the resulting single-stranded DNA molecule for production of a ceDNA vector comprises, from 5' to 3':

a sense first ITR;
a sense expression cassette sequence;
a sense second ITR;
an antisense second ITR;
an antisense expression cassette sequence; and
an antisense first ITR.

In this exemplary method, in one embodiment, oligonucleotides may be synthesized that encompass one or more of the sense first ITR, the sense expression cassette sequence, the sense second ITR, the antisense second ITR, the antisense expression cassette sequence, and the antisense first ITR. One or more of such oligonucleotides may be ligated in order to form the single-stranded DNA molecule as shown above. Once the single-stranded DNA molecule has been formed, the free 3' and 5' ends of the molecule may be joined by ligation, forming the ceDNA vector.

Another exemplary method of producing a closed-ended DNA vector is by synthesis of a single-stranded sequence comprising at least one ITR flanking an expression cassette sequence and which also comprises an antisense expression cassette sequence. In one nonlimiting example, ceDNA vector is produced by the method as follows.

A single-stranded sequence comprising in order from 5' to 3':
a sense first ITR;
a sense expression cassette sequence;
a sense second ITR; and
an antisense expression cassette sequence
is provided. In one embodiment the single-stranded sequence may be synthesized directly through any art-known method. In another embodiment, the single-stranded sequence may be constructed by joining by ligation two or more oligos comprising one or more of the sense first ITR, sense expression cassette sequence, sense second ITR and antisense expression cassette sequence.

In yet another embodiment, the single-stranded sequence may be obtained by excision of the sequence from a double-stranded DNA construct with subsequent separation of the strands from the excised double-stranded fragment. More specifically, a double-stranded DNA construct comprising a first restriction site, the sense first ITR, the sense expression cassette sequence, the sense second ITR, the antisense expression cassette sequence, and a second restriction site in 5' to 3' order is provided. The region between the two restriction endonuclease cleavage sites is excised by cleavage with at least one restriction endonuclease recognizing such cleavage site(s). The resulting excised double-stranded DNA fragment is treated such that the sense and antisense strands are separated into the desired single-stranded sequence fragments.

The single-stranded sequence is subjected to an annealing step to facilitate the formation of one or more hairpin loop by the sense first ITR and/or the sense second ITR, and the complementary binding of the sense expression cassette sequence to the antisense expression cassette sequence. The result is a closed-ended structure that did not require ligation to form. Annealing parameters and techniques are well known in the art.

In all aspects of the synthetic production methods to generate DNA vectors as disclosed herein, the ligation step can be a chemical ligation step or an enzymatic ligation step. In some embodiments, ligation can be conducted using a ligation-competent enzyme, e.g., DNA ligase, e.g. to ligate 5' and 3' sticky overhangs, or blunt ends. In some embodiments, the ligation enzyme is a ligase enzyme other than a Rep protein. In some embodiments, the ligation enzyme is an AAV Rep protein.

In all aspects of the synthetic methods to generate DNA vectors as disclosed herein, the method is an in vitro method. In a preferred embodiment, the method is a cell-free method, i.e., not performed in, or in the presence of a cell, e.g., an insect cell.

It will be appreciated by one of ordinary skill in the art that one or more enzymes for the synthetic production method or one or more of the oligonucleotide components can be produced from a cell and used in the methods of the invention in purified form. Accordingly, in some embodiments, the synthetic production method is a cell-free method, however, a restriction enzyme and/or ligase enzyme can be produced from a cell. In one embodiment, a cell, such as a bacterial cell, comprising an expression vector expressing one or more of the restriction endonucleases or the ligase enzymes can be present. Therefore, while the methods disclosed herein are primarily directed to cell-free synthetic methods to generate the DNA vectors disclosed herein, also encompassed in one embodiment are synthetic production methods where a cell, e.g., bacterial cell but not an insect cell is present and can be used to express one or more of the enzymes required in the method.

One aspect of the technology described herein is use the synthetic production methods to generate ceDNA vectors. The ceDNA vectors described herein are capsid-free, linear duplex DNA molecules formed from a continuous strand of complementary DNA with covalently-closed ends (linear, continuous and non-encapsidated structure), which comprise a 5' inverted terminal repeat (ITR) sequence and a 3' ITR sequence, where the 5' ITR and the 3' ITR can have the same symmetrical three-dimensional organization with respect to each other, (i.e., symmetrical or substantially symmetrical), or alternatively, the 5' ITR and the 3' ITR can have different three-dimensional organization with respect to each other (i.e., asymmetrical ITRs). In addition, the ITRs can be from the same or different serotypes. In some embodiments, a ceDNA vector can comprise ITR sequences that have a symmetrical three-dimensional spatial organization such that their structure is the same shape in geometrical space, or have the same A, C-C' and B-B' loops in 3D space (i.e., they are the same or are mirror images with respect to each other). In some embodiments, one ITR can be from one AAV serotype, and the other ITR can be from a different AAV serotype.

Accordingly, some aspects of the technology described herein relate to synthetic production of a ceDNA vector that comprises ITR sequences selected from any of: (i) at least one WT ITR and at least one modified AAV inverted terminal repeat (ITR) (e.g., asymmetric modified ITRs); (ii) two modified ITRs where the mod-ITR pair have a different three-dimensional spatial organization with respect to each other (e.g., asymmetric modified ITRs), or (iii) symmetrical or substantially symmetrical WT-WT ITR pair, where each WT-ITR has the same three-dimensional spatial organization, or (iv) symmetrical or substantially symmetrical modified ITR pair, where each mod-ITR has the same three-dimensional spatial organization.

Aspects of the invention relate to synthetic production methods to produce the ceDNA vectors useful for expression of a desired transgene in a cell, tissue, organ, system, or subject as described herein. In particular, provided herein are methods for producing closed-ended DNA vectors, including but not limited to, ceDNA vectors in a cell-free environment, thereby limiting the amount of impurities and preventing introduction of contaminants during the production process that could impact the efficacy and/or safety of a given vector product. Such methods can be used to synthesize a DNA vector, for example a ceDNA vector, expressing any desired transgene. Transgenes can be selected for treatment of a given disease, promoting optimal health, prevention of disease onset, for diagnostic purposes, or as desired by one of skill in the art for a given application.

In another embodiment of this aspect and all other aspects provided herein, the transgene encodes a protein of interest, e.g., where a protein of interest is a receptor, a toxin, a hormone, an enzyme, or a cell surface protein. In another embodiment of this aspect and all other aspects provided herein, the protein of interest is a receptor. In another embodiment of this aspect and all other aspects provided herein, the protein of interest is an enzyme. Exemplary genes to be targeted and proteins of interest are described in detail in the methods of use and methods of treatment sections herein.

In some embodiments, the present application may be defined in any of the following paragraphs:

1. A method of preparing a closed-ended DNA vector comprising: (i) providing a first single-stranded ITR molecule comprising a first ITR; (ii) providing a second single-stranded ITR molecule comprising a second ITR; (iii) providing a double-stranded polynucleotide comprising an expression cassette sequence; and ligating the 5' and 3' ends of the first ITR molecule to a first end of the double-stranded molecule and ligating the 5' and 3' ends of the second ITR molecule to the second end of the double stranded molecule to form the DNA vector.
2. A method of preparing a closed-ended DNA vector comprising:

contacting a double-stranded DNA construct comprising: (i) an expression cassette; (ii) a first ITR on the upstream (5'-end) of the expression cassette; (iii) a second ITR on the downstream (3'-end) of the expression cassette; (iii) and at least two restriction endonuclease cleavage sites flanking the ITRs such that the restriction endonucleases are distal to the expression cassette with one or more restriction endonucleases that can cleave the double-stranded DNA construct at the restriction endonuclease cleavage sites to excise the sequences between the restriction endonuclease cleavage sites from the double-stranded DNA construct; and ligating the 5' and 3' ends of the excised sequence to form a closed-ended DNA vector.

3. A method of preparing a DNA vector comprising:

synthesizing a single-stranded DNA molecule comprising in order in the 5' to 3' direction:

a sense first ITR;

a sense expression cassette sequence;

a sense second ITR;

an antisense second ITR;

an antisense expression cassette sequence; and an antisense first ITR;

forming a hairpin-comprising polynucleotide from the single-stranded molecule; and ligating the 5' and 3' ends to form the closed-ended DNA vector.

4. A method of preparing a closed-ended DNA vector comprising: synthesizing a single-stranded DNA molecule comprising in order in the 5' to 3' direction:

a sense first ITR;

a sense expression cassette sequence;

a sense second ITR; and an antisense expression cassette sequence;

and annealing the molecule.

5. A method of preparing a closed-ended DNA vector comprising: providing a double-stranded DNA construct comprising in order in the 5' to 3' direction:

a first restriction endonuclease cleavage site;

a sense first ITR;

a sense expression cassette sequence;

a sense second ITR;

an antisense expression cassette sequence; and a second restriction endonuclease cleavage site;

contacting the double-stranded DNA construct with one or more restriction endonucleases that can cleave the double-stranded DNA construct at the first restriction endonuclease cleavage site and the second restriction endonuclease cleavage site to excise the double-stranded sequence between the restriction endonuclease cleavage sites from the double-stranded polynucleotide; separating the excised double-stranded sequence into a sense strand and an antisense strand; and performing an annealing step wherein each of the sense strand and the antisense strand forms a closed-ended DNA vector.

6. The method of any of the proceeding paragraphs, wherein the double-stranded DNA construct is a bacmid, plasmid, minicircle, or a linear double-stranded DNA molecule.
7. The method of any of the proceeding paragraphs, wherein a single restriction endonuclease is used to effect the excision.
8. The method of any of the proceeding paragraphs, wherein two different restriction endonucleases are used to effect the excision.
9. The method of any of the proceeding paragraphs, wherein at least one of the sense first ITR, the sense expression cassette sequence, the sense second ITR, the antisense second ITR, the antisense expression cassette sequence, and the antisense first ITR are synthesized.
10. The method of any of the proceeding paragraphs, wherein the single-stranded DNA molecule is constructed by synthesizing one or more of the sense first ITR, the sense expression cassette sequence, the sense second ITR, the antisense second ITR, the antisense expression cassette sequence, and the antisense first ITR as oligonucleotides and ligating such oligonucleotides to form the single-stranded DNA molecule.
11. The method of any of the proceeding paragraphs, wherein the single-stranded DNA molecule is provided by excision of the molecule from a double-stranded DNA polynucleotide, followed by denaturation of the excised double-stranded fragment to produce the single-stranded DNA molecule.
12. The method of any of the proceeding paragraphs, wherein the step of forming a hairpin-comprising polynucleotide from the single-stranded molecule is effected by annealing the single-stranded molecule under conditions whereby one or more of the ITRs forms a hairpin loop.
13. The method of any of the proceeding paragraphs, wherein at least one of the first ITR and the second ITR are synthesized.
14. The method of any of the proceeding paragraphs, wherein the double-stranded expression cassette sequence was obtained by excision from a double-stranded DNA construct comprising the expression cassette sequence.
15. The method of any of the proceeding paragraphs, wherein within the double-stranded DNA construct the expression cassette sequence is flanked at the 5' end by a first restriction endonuclease cleavage site and at the 3' end by a second restriction endonuclease cleavage site.

16. The method of any of the proceeding paragraphs, wherein the double-stranded DNA construct is a bacmid, plasmid, minicircle, or a linear double-stranded DNA molecule.
17. The method of any of the proceeding paragraphs, wherein the first restriction endonuclease and the second restriction endonuclease are the same restriction endonuclease.
18. The method of any of the proceeding paragraphs, wherein the first restriction endonuclease and the second restriction endonuclease are different restriction endonucleases.
19. The method of any of the preceding paragraphs, wherein at least one of the first ITR and the second ITR are annealed prior to ligation to the expression cassette sequence.
20. The method of any of the preceding paragraphs, wherein at least one of the first ITR and the second ITR comprises an overhang region complementary to the first end of the expression cassette sequence or the second end of the expression cassette sequence, respectively.
21. The method of any of the proceeding paragraphs, wherein the ligation is selected from a chemical ligation and a protein-assisted ligation.
22. The method of any of the proceeding paragraphs, wherein the ligation is effected by T4 ligase or an AAV Rep protein.
23. The method of any of the proceeding paragraphs, wherein the first ITR is selected from a wild-type ITR and a modified ITR.
24. The method of any of the proceeding paragraphs, wherein the second ITR is selected from a wild-type ITR and a modified ITR.
25. The method of any of the preceding paragraphs, wherein at least one of the first ITR and the second ITR comprises at least one RBE site.
26. The method of any of the preceding paragraphs wherein at least one of the first ITR and the second ITR is an AAV ITR or an AAV-derived ITR.
27. The method of any of the proceeding paragraphs, wherein the sequence of the first ITR is selected from any of the left ITR sequences set forth in Table 3, Table 4B or Table 5 or SEQ ID NO: 2, 5-9, 32-48.
28. The method of any of the proceeding paragraphs, wherein the sequence of the second ITR is selected from any of the right ITR sequences set forth in Table 3, Table 4A or Table 5 or SEQ ID NO: 1, 3, 10-14, 15-31.
29. The method of any of the proceeding paragraphs, wherein the expression cassette sequence comprises at least one cis-regulatory element.
30. The method of any of the proceeding paragraphs, wherein the cis-regulatory element is selected from the group consisting of a promoter, an enhancer, a post-transcriptional regulatory element and a polyadenylation signal.
31. The method of any of the proceeding paragraphs, wherein the posttranscriptional regulatory element comprises a WHP posttranscriptional regulatory element (WPRE).
32. The method of any of the proceeding paragraphs, wherein the promoter is selected from the group consisting of a CAG promoter, an AAT promoter, an LP1 promoter, and an EF1a promoter.
33. The method of any of the preceding paragraphs, wherein the expression cassette sequence comprises a transgene sequence.
34. The method of any of the proceeding paragraphs, wherein the transgene sequence is at least 2000 nucleotides in length.
35. The method of any of the proceeding paragraphs, wherein the transgene sequence encodes a protein.
36. The method of any of the proceeding paragraphs, wherein the transgene sequence encodes a reporter protein, a therapeutic protein, an antigen, a gene editing protein, or a cytotoxic protein.
37. The method of any of the proceeding paragraphs, wherein the transgene sequence is a functional nucleotide sequence.
38. The method of any of the preceding paragraphs, wherein the closed-ended DNA vector is a ceDNA vector.
39. The method of any of the proceeding paragraphs, wherein the ceDNA vector is purified.
40. A closed-ended DNA vector generated by the method of any of the preceding paragraphs.
41. A pharmaceutical composition comprising the closed-ended DNA vector of any of the proceeding paragraphs and optionally, an excipient.
42. An isolated closed-ended DNA vector obtained by or obtainable by a process according to any of paragraphs 1-6 or 6-39.
43. A genetic medicine comprising an isolated closed-ended DNA vector obtained by the process according to any of the proceeding paragraphs.
44. A cell comprising a the closed-ended DNA vector of paragraph 40.
45. A transgenic animal comprising the closed ended DNA vector of paragraph 40.
46. A method of treating a subject by administering a closed-ended DNA vector obtained by or obtainable by a process according to any of paragraphs 1-5 or 6-39.
47. A method for delivering a therapeutic protein to a subject, the method comprising: administering to a subject a composition comprising a closed-ended DNA vector of paragraph 40, or obtained by or obtainable by a process according to any of paragraphs 1-5, or 6-39, wherein at least one heterologous nucleotide sequence encodes a transgene or a therapeutic protein.
48. The method of paragraph 47, wherein the therapeutic protein is a therapeutic antibody, a reporter protein, a therapeutic protein, an antigen, a gene editing protein, or a cytotoxic protein.
49. A kit comprising a closed-ended DNA vector of paragraph 40, or obtained by or obtainable by a process according to any of paragraphs 1-5, or 6-39, and a nanocarrier, packaged in a container with a packet insert.
50. A kit for producing a closed-ended DNA vector obtained by or obtainable by a process according to any of paragraphs 1-5, or 6-39.
51. A kit for producing a closed-ended DNA vector obtained by or obtainable by a process according to any of paragraphs 1-39, comprising a first-single stranded ITR molecule comprising a first ITR, a second single-stranded ITR molecule comprising a second ITR and at least one reagent for ligation of the first-single stranded ITR molecule and second single-stranded ITR molecule to a double stranded polynucleotide molecule.

52. A kit for producing a closed-ended DNA vector obtained by or obtainable by a process according to any of paragraphs 2-39, comprising: (i) a double-stranded DNA construct comprising an expression cassette; a first ITR on the upstream (5'-end) of the expression cassette; a second ITR on the downstream (3'-end) of the expression cassette; and at least two restriction endonuclease cleavage sites flanking the ITRs such that the restriction endonucleases are distal to the expression cassette, wherein the expression cassette has a restriction endonuclease site for insertion of a transgene, and (ii) at least one ligation reagent for ligation
53. A kit for producing a closed-ended DNA vector obtained by or obtainable by a process according to any of paragraphs 3-39, comprising: (i) single-stranded DNA molecule comprising in order in the 5' to 3' direction: a sense first ITR; a sense expression cassette sequence; a sense second ITR; an antisense second ITR; an antisense expression cassette sequence; and an antisense first ITR; wherein the sense expression cassette sequence and the antisense expression cassette sequence have a restriction endonuclease site for insertion of a transgene, and (i) at least one ligation reagent for ligation.
54. A kit for producing a closed-ended DNA vector obtained by or obtainable by a process according to any of paragraphs 4-39, comprising: (i) a single stranded-DNA molecule comprising in order of 5' to 3' direction: a sense first ITR; a sense expression cassette sequence; a sense second ITR; and an antisense expression cassette sequence; wherein the sense expression cassette sequence and the antisense expression cassette sequence have a restriction endonuclease site for insertion of a transgene, and (ii) at least one ligation reagent for ligation.
55. A kit for producing a closed-ended DNA vector obtained by or obtainable by a process according to any of paragraphs 5-39, comprising: (i) a double-stranded DNA construct comprising in order in the 5' to 3' direction: a first restriction endonuclease cleavage site; a sense first ITR; a sense expression cassette sequence; a sense second ITR; an antisense expression cassette sequence; and a second restriction endonuclease cleavage site; wherein the sense expression cassette sequence and the antisense expression cassette sequence have a restriction endonuclease site for insertion of a transgene, and (ii) at least one ligation reagent for ligation.
56. The kit of any of paragraphs 49-55, wherein the at least one reagent for ligation is a reagent for chemical ligation.
57. The kit of any of paragraphs 49-56, wherein the at least one reagent for ligation is a reagent for protein-assisted ligation.
58. The kit of any of paragraphs 49-57, wherein the ligation is effected by T4 ligation or an AAV Rep protein.
59. The kit of any of paragraphs 49-58, wherein the first-single stranded ITR molecule and second single-stranded ITR molecule comprise a restriction endonuclease cleave site at their ends.
60. The kit of any of paragraphs 49-59, wherein the kit further comprises at least one restriction endonuclease enzyme.

In some embodiments, one aspect of the technology described herein relates to a synthetically produced non-viral capsid-free DNA vector with covalently-closed ends (ceDNA vector), wherein the ceDNA vector comprises at least one heterologous nucleotide sequence, operably positioned between wild-type inverted terminal repeat sequences, wherein optionally the heterologous nucleic acid sequence encodes a transgene, and wherein the vector is not in a viral capsid.

In some embodiments, one aspect of the technology described herein relates to a synthetically produced non-viral capsid-free DNA vector with covalently-closed ends (ceDNA vector), wherein the ceDNA vector comprises at least one heterologous nucleotide sequence, operably positioned between asymmetric inverted terminal repeat sequences (asymmetric ITRs), wherein at least one of the asymmetric ITRs comprises a functional terminal resolution site and a Rep binding site, and optionally the heterologous nucleic acid sequence encodes a transgene, and wherein the vector is not in a viral capsid.

In some embodiments, one aspect of the technology described herein relates to a synthetically produced non-viral capsid-free DNA vector with covalently-closed ends (ceDNA vector), wherein the ceDNA vector comprises at least one heterologous nucleotide sequence, operably positioned between symmetric mutant inverted terminal repeat sequences, wherein at least one of the ITRs comprises a functional terminal resolution site and a Rep binding site, and optionally the heterologous nucleic acid sequence encodes a transgene, and wherein the vector is not in a viral capsid.

These and other aspects of the invention are described in further detail below.

DESCRIPTION OF DRAWINGS

Embodiments of the present disclosure, briefly summarized above and discussed in greater detail below, can be understood by reference to the illustrative embodiments of the disclosure depicted in the appended drawings. However, the appended drawings illustrate only typical embodiments of the disclosure and are therefore not to be considered limiting of scope, for the disclosure may admit to other equally effective embodiments.

FIG. 4C shows schematic expected bands for an exemplary ceDNA either left uncut or digested with a restriction endonuclease and then subjected to electrophoresis on either a native gel or a denaturing gel. The leftmost schematic is a native gel, and shows multiple bands suggesting that in its duplex and uncut form ceDNA exists in at least monomeric and dimeric states, visible as a faster-migrating smaller monomer and a slower-migrating dimer that is twice the size of the monomer. The schematic second from the left shows that when ceDNA is cut with a restriction endonuclease, the original bands are gone and faster-migrating (e.g., smaller) bands appear, corresponding to the expected fragment sizes remaining after the cleavage. Under denaturing conditions, the original duplex DNA is single-stranded and migrates as a species twice as large as observed on native gel because the complementary strands are covalently linked. Thus in the second schematic from the right, the digested ceDNA shows a similar banding distribution to that observed on native gel, but the bands migrate as fragments twice the size of their native gel counterparts. The rightmost schematic shows that uncut ceDNA under denaturing conditions migrates as a single-stranded open circle, and thus the observed bands are twice the size of those observed under native conditions where the circle is not open. In this figure "kb" is used to indicate relative size of nucleotide molecules based, depending on context, on either nucleotide chain length (e.g., for the single stranded molecules observed in denaturing conditions) or number of basepairs (e.g., for the double-stranded molecules observed in native conditions). FIG. 4D shows DNA having a non-continuous structure. The ceDNA can be cut by a restriction endonuclease, having a single recognition site on the ceDNA vector, and generate two DNA fragments with different sizes (1 kb and 2 kb) in both neutral and denaturing conditions. FIG. 4D also shows a ceDNA having a linear and continuous structure. The ceDNA vector can be cut by the restriction endonuclease, and generate two DNA fragments that migrate as 1 kb and 2 kb in neutral conditions, but in denaturing conditions, the stands remain connected and produce single strands that migrate as 2 kb and 4 kb.

FIG. 6A shows an exemplary oligonucleotide (WT-L-oligo-1) for generating a 5' WT-ITR with ArvII restriction sites. FIG. 6A discloses the top sequence as SEQ ID NO: 156, the ideal structure as SEQ ID NOS 134, 158, and 157, respectively, in order of appearance, the predicted structure as SEQ ID NO: 134, and the WT-L-oligo-1 as SEQ ID NO: 134. FIG. 6B shows an exemplary oligonucleotide (WT-L-oligo-2) for generating a 5' WT-ITR with ArvII restriction sites. FIG. 6B discloses SEQ ID NOS 135 and 135, respectively, in order of appearance.

FIG. 6C shows another exemplary oligonucleotide (WT-R-oligo-3) for generating a 3' WT-ITR with SbfI restriction sites. FIG. 6C discloses SEQ ID NOS 159, 136, and 136, respectively, in order of appearance. FIG. 6D shows another exemplary oligonucleotide (MU-R-oligo-1) for generating a 3' mod-ITR with DraIII restriction sites. FIG. 6D discloses SEQ ID NOS 160, 137, and 137, respectively, in order of appearance.

FIG. 7A shows an exemplary oligonucleotide (WT-L-oligo-1) for generating a 5' WT-ITR with ArvII restriction sites. FIG. 8A discloses SEQ ID NOS 138 and 138, respectively, in order of appearance. FIG. 7B shows an exemplary oligonucleotide (WT-L-oligo-2) for generating a 5' WT-ITR with ArvII restriction sites. FIG. 8B discloses SEQ ID NOS 161, 139, and 139, respectively, in order of appearance. FIG. 7C shows another exemplary oligonucleotide (WT-R-oligo-3) for generating a 3' WT-ITR with SbfI restriction sites. FIG. 8C discloses SEQ ID NOS 140 and 140, respectively, in order of appearance. FIG. 7D shows another exemplary oligonucleotide (MU-R-oligo-1) for generating a 3' mod-ITR with DraIII restriction sites. FIG. 8D discloses SEQ ID NOS 141 and 141, respectively, in order of appearance. FIG. 7E shows another exemplary oligonucleotide (MU-R-oligo-6) (SEQ ID NO: 142) for generating a 3' mod-ITR with SbfI restriction sites. FIG. 8E discloses SEQ ID NOS 142 and 142, respectively, in order of appearance.

FIG. 8 discloses SEQ ID NOS 160 and 162, respectively, in order of appearance. FIG. 9 discloses SEQ ID NOS 134, 158, and 157, respectively, in order of appearance on the left-hand side, and SEQ ID NOS 163, 137, and 164, respectively, in order of appearance on the right-hand side.

DETAILED DESCRIPTION OF THE INVENTION

Figure 1A:
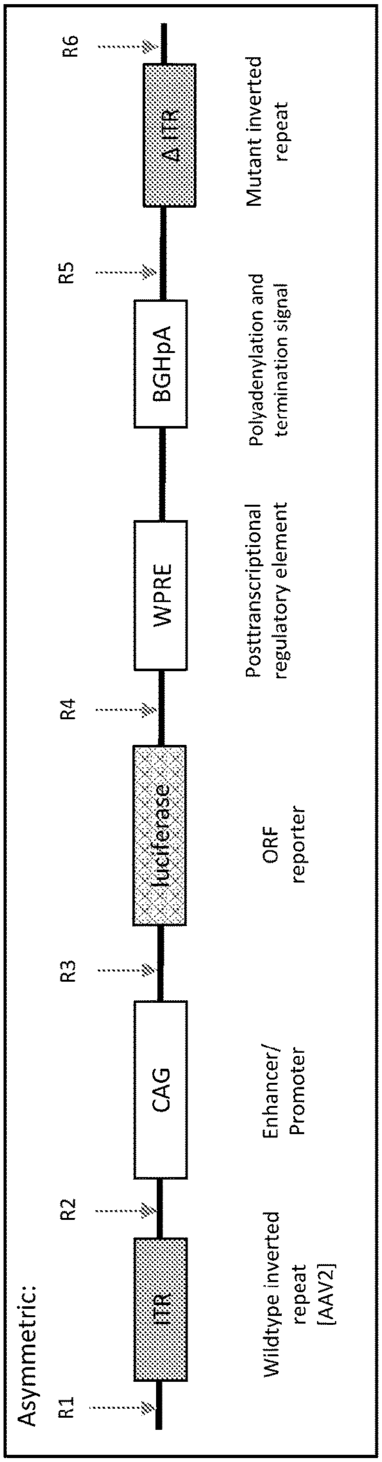
FIG. 1A illustrates an exemplary structure of a ceDNA vector comprising asymmetric ITRs. In this embodiment, the exemplary ceDNA vector comprises an expression cassette containing CAG promoter, WPRE, and BGHpA. An open reading frame (ORF) encoding a transgene, e.g., a luciferase transgene is inserted into the cloning site (R3/R4) between the CAG promoter and WPRE. The expression cassette is flanked by two inverted terminal repeats (ITRs)—the wild-type AAV2 ITR on the upstream (5'-end) and the modified ITR on the downstream (3'-end) of the expression cassette, therefore the two ITRs flanking the expression cassette are asymmetric with respect to each other.

The methods and compositions provided herein are based, in part, on the discovery of a synthetic production method useful for generating closed-ended DNA vectors, including, but not limited to ceDNA vectors that have fewer impurities and/or higher yield as compared to DNA vectors produced in an insect cell line, such as the Sf9 cell line, and/or where the production process is streamlined or made more efficient or cost-effective relative to traditional cell-based production methods. In one embodiment, cells are not used to replicate the DNA vectors, and thus the production is cell-free. Accordingly, provided herein is a method of synthesizing closed-ended DNA vectors without using cells. In some embodiments, provided herein is a method of synthesizing closed-ended DNA vectors without using insect cells. Also provided herein are closed-ended DNA vector compositions produced using the synthetic production methods herein, including ceDNA vector compositions, and use of such closed-ended DNA vectors and ceDNA vectors.

The present invention relates to an in vitro process for production of closed-ended DNA vectors, corresponding DNA vector products produced by the methods herein and uses thereof, and oligonucleotides and kits useful in the process of the invention.

The closed-ended DNA vectors made by the methods described herein are advantageous over other vectors in that they can be used more safely to express a transgene in a cell, tissue or subject. That is, undesirable side effects can potentially be minimized by generating the linear vectors by such cell-free methods since the resulting vectors are free of bacterial or insect cell contaminants. The synthetic production methods may also result in greater purity of the desired vector. The synthetic production method may also be more efficient and/or cost effective than traditional cell-based production methods for such vectors.

The vectors synthesized as described herein can express any desired transgene, for example, a transgene to treat or cure a given disease. One of ordinary skill in the art will readily recognize that any transgene used in conventional gene therapy methods with conventional recombinant vectors can be adapted for expression by e.g., ceDNA vectors made by the synthetic methods described herein.

I. Definitions

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), Fields Virology, $6^{th}$ Edition, published by Lippincott Williams & Wilkins, Philadelphia, PA, USA (2013), Knipe, D. M. and Howley, P. M. (ed.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, $4^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

As used herein, the terms "cell-free production", "synthetic closed-ended DNA vector production" and "synthetic production" and their grammatically related counterparts are used interchangeably and refer to the production of one or more molecules in a manner that does not involve replication or other multiplication of the molecule by or inside of a cell or using a cellular extract. Synthetic production avoids contamination of the produced molecule with cellular contaminants (e.g., cellular proteins or cellular nucleic acids) and further avoids unwanted cellular-specific modification of the molecule during the production process (e.g., methylation or glycosylation or other post-translational modification).

As used herein, the terms "heterologous nucleotide sequence" and "transgene" are used interchangeably and refer to a nucleic acid of interest (other than a nucleic acid encoding a capsid polypeptide) that is incorporated into and may be delivered and expressed by a ceDNA vector as disclosed herein.

As used herein, the terms "expression cassette" and "transcription cassette" and "gene expression unit" are used interchangeably and refer to a linear stretch of nucleic acids that includes a transgene that is operably linked to one or more promoters or other regulatory sequences sufficient to direct transcription of the transgene, but which does not comprise capsid-encoding sequences, other vector sequences or inverted terminal repeat regions. An expression cassette may additionally comprise one or more cis-acting sequences (e.g., promoters, enhancers, or repressors), one or more introns, and one or more post-transcriptional regulatory elements.

The terms "polynucleotide" and "nucleic acid," used interchangeably herein, refer to a polymeric form of nucleotides of any length, either ribonucleotides or deoxyribonucleotides. Thus, this term includes single, double, or multi-stranded DNA or RNA, genomic DNA, cDNA, DNA-RNA hybrids, or a polymer including purine and pyrimidine bases or other natural, chemically or biochemically modified, non-natural, or derivatized nucleotide bases. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as "oligomers" or "oligos" and may be isolated from genes, or chemically synthesized by methods known in the art. The terms "polynucleotide" and "nucleic acid" should be understood to include, as applicable to the embodiments being described, single-stranded (such as sense or antisense) and double-stranded polynucleotides.

The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present disclosure. An "expression cassette" includes a DNA coding sequence operably linked to a promoter.

By "hybridizable" or "complementary" or "substantially complementary" it is meant that a nucleic acid (e.g., RNA) includes a sequence of nucleotides that enables it to non-covalently bind, i.e. form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymidine (T), adenine (A) pairing with uracil (U), and guanine (G) pairing with cytosine (C). In addition, it is also known in the art that for hybridization between two RNA molecules (e.g., dsRNA), guanine (G) base pairs with uracil (U). For example, G/U base-pairing is partially responsible for the degeneracy (i.e., redundancy) of the genetic code in the context of tRNA anti-codon base-pairing with codons in mRNA. In the context of this disclosure, a guanine (G) of a protein-binding segment (dsRNA duplex) of a subject DNA-targeting RNA molecule is considered complementary to a uracil (U), and vice versa. As such, when a G/U base-pair can be made at a given nucleotide position a protein-binding segment (dsRNA duplex) of a subject DNA-targeting RNA molecule, the position is not considered to be non-complementary, but is instead considered to be complementary.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

A DNA sequence that "encodes" a particular RNA or protein gene product is a DNA nucleic acid sequence that is transcribed into the particular RNA and/or protein. A DNA polynucleotide may encode an RNA (mRNA) that is translated into protein, or a DNA polynucleotide may encode an RNA that is not translated into protein (e.g., tRNA, rRNA, or a DNA-targeting RNA; also called "non-coding" RNA or "ncRNA").

As used herein, the term "genomic safe harbor gene" or "safe harbor gene" refers to a gene or loci that a nucleic acid sequence can be inserted such that the sequence can integrate and function in a predictable manner (e.g., express a protein of interest) without significant negative consequences to endogenous gene activity, or the promotion of cancer. In some embodiments, a safe harbor gene is also a loci or gene where an inserted nucleic acid sequence can be expressed efficiently and at higher levels than a non-safe harbor site.

As used herein, the term "gene delivery" means a process by which foreign DNA is transferred to host cells for applications of gene therapy.

As used herein, the term "terminal repeat" or "TR" includes any viral terminal repeat or synthetic sequence that comprises at least one minimal required origin of replication and a region comprising a palindrome hairpin structure. A Rep-binding sequence ("RBS") (also referred to as RBE (Rep-binding element)) and a terminal resolution site ("TRS") together constitute a "minimal required origin of replication" and thus the TR comprises at least one RBS and at least one TRS. TRs that are the inverse complement of one another within a given stretch of polynucleotide sequence are typically each referred to as an "inverted terminal repeat" or "ITR". In the context of a virus, ITRs mediate replication, virus packaging, integration and provirus rescue. As was unexpectedly found in the invention herein, TRs that are not inverse complements across their full length can still perform the traditional functions of ITRs, and thus the term ITR is used herein to refer to a TR in a ceDNA genome or ceDNA vector that is capable of mediating replication of ceDNA vector. It will be understood by one of ordinary skill in the art that in complex ceDNA vector configurations more than two ITRs or asymmetric ITR pairs may be present. The ITR can be an AAV ITR or a non-AAV ITR, or can be derived from an AAV ITR or a non-AAV ITR. For example, the ITR can be derived from the family Parvoviridae, which encompasses parvoviruses and dependoviruses (e.g., canine parvovirus, bovine parvovirus, mouse parvovirus, porcine parvovirus, human parvovirus B-19), or the SV40 hairpin that serves as the origin of SV40 replication can be used as an ITR, which can further be modified by truncation, substitution, deletion, insertion and/or addition. Parvoviridae family viruses consist of two subfamilies: Parvovirinae, which infect vertebrates, and Densovirinae, which infect invertebrates. Dependoparvoviruses include the viral family of the adeno-associated viruses (AAV) which are capable of replication in vertebrate hosts including, but not limited to, human, primate, bovine, canine, equine and ovine species. For convenience herein, an ITR located 5' to (upstream of) an expression cassette in a ceDNA vector is referred to as a "5' ITR" or a "left ITR", and an ITR located 3' to (downstream of) an expression cassette in a ceDNA vector is referred to as a "3' ITR" or a "right ITR".

A "wild-type ITR" or "WT-ITR" refers to the sequence of a naturally occurring ITR sequence in an AAV or other dependovirus that retains, e.g., Rep binding activity and Rep nicking ability. The nucleotide sequence of a WT-ITR from any AAV serotype may slightly vary from the canonical naturally occurring sequence due to degeneracy of the genetic code or drift, and therefore WT-ITR sequences encompassed for use herein include WT-ITR sequences as result of naturally occurring changes taking place during the production process (e.g., a replication error).

As used herein, the term “substantially symmetrical WT-ITRs” or a “substantially symmetrical WT-ITR pair” refers to a pair of WT-ITRs within a single ceDNA genome or ceDNA vector that are both wild type ITRs that have an inverse complement sequence across their entire length. For example, an ITR can be considered to be a wild-type sequence, even if it has one or more nucleotides that deviate from the canonical naturally occurring sequence, so long as the changes do not affect the properties and overall three-dimensional structure of the sequence. In some aspects, the deviating nucleotides represent conservative sequence changes. As one non-limiting example, a sequence that has at least 95%, 96%, 97%, 98%, or 99% sequence identity to the canonical sequence (as measured, e.g., using BLAST at default settings), and also has a symmetrical three-dimensional spatial organization to the other WT-ITR such that their 3D structures are the same shape in geometrical space. The substantially symmetrical WT-ITR has the same A, C-C' and B-B' loops in 3D space. A substantially symmetrical WT-ITR can be functionally confirmed as WT by determining that it has an operable Rep binding site (RBE or RBE') and terminal resolution site (trs) that pairs with the appropriate Rep protein. One can optionally test other functions, including transgene expression under permissive conditions.

As used herein, the phrases of “modified ITR” or “mod-ITR” or “mutant ITR” are used interchangeably herein and refer to an ITR that has a mutation in at least one or more nucleotides as compared to the WT-ITR from the same serotype. The mutation can result in a change in one or more of A, C, C', B, B' regions in the ITR, and can result in a change in the three-dimensional spatial organization (i.e. its 3D structure in geometric space) as compared to the 3D spatial organization of a WT-ITR of the same serotype.

As used herein, the term “asymmetric ITRs” also referred to as “asymmetric ITR pairs” refers to a pair of ITRs within a single ceDNA genome or ceDNA vector that are not inverse complements across their full length. As one non-limiting example, an asymmetric ITR pair does not have a symmetrical three-dimensional spatial organization to their cognate ITR such that their 3D structures are different shapes in geometrical space. Stated differently, an asymmetrical ITR pair have the different overall geometric structure, i.e., they have different organization of their A, C-C' and B-B' loops in 3D space (e.g., one ITR may have a short C-C' arm and/or short B-B' arm as compared to the cognate ITR). The difference in sequence between the two ITRs may be due to one or more nucleotide addition, deletion, truncation, or point mutation. In one embodiment, one ITR of the asymmetric ITR pair may be a wild-type AAV ITR sequence and the other ITR a modified ITR as defined herein (e.g., a non-wild-type or synthetic ITR sequence). In another embodiment, neither ITRs of the asymmetric ITR pair is a wild-type AAV sequence and the two ITRs are modified ITRs that have different shapes in geometrical space (i.e., a different overall geometric structure). In some embodiments, one mod-ITRs of an asymmetric ITR pair can have a short C-C' arm and the other ITR can have a different modification (e.g., a single arm, or a short B-B' arm etc.) such that they have different three-dimensional spatial organization as compared to the cognate asymmetric mod-ITR.

As used herein, the term “symmetric ITRs” refers to a pair of ITRs within a single ceDNA genome or ceDNA vector that are mutated or modified relative to wild-type dependoviral ITR sequences and are inverse complements across their full length. Neither ITRs are wild type ITR AAV2 sequences (i.e., they are a modified ITR, also referred to as a mutant ITR), and can have a difference in sequence from the wild type ITR due to nucleotide addition, deletion, substitution, truncation, or point mutation. For convenience herein, an ITR located 5' to (upstream of) an expression cassette in a ceDNA vector is referred to as a “5' ITR” or a “left ITR”, and an IFR located 3' to (downstream of) an expression cassette in a ceDNA vector is referred to as a “3' ITR” or a “right ITR”.

As used herein, the terms “substantially symmetrical modified-ITRs” or a “substantially symmetrical mod-ITR pair” refers to a pair of modified-ITRs within a single ceDNA genome or ceDNA vector that are both that have an inverse complement sequence across their entire length. For example, the a modified ITR can be considered substantially symmetrical, even if it has some nucleotide sequences that deviate from the inverse complement sequence so long as the changes do not affect the properties and overall shape. As one non-limiting example, a sequence that has at least 85%, 90%, 95%, 96%, 97%, 98%, or 99% sequence identity to the canonical sequence (as measured using BLAST at default settings), and also has a symmetrical three-dimensional spatial organization to their cognate modified ITR such that their 3D structures are the same shape in geometrical space. Stated differently, a substantially symmetrical modified-ITR pair have the same A, C-C' and B-B' loops organized in 3D space. In some embodiments, the ITRs from a mod-ITR pair may have different reverse complement nucleotide sequences but still have the same symmetrical three-dimensional spatial organization—that is both ITRs have mutations that result in the same overall 3D shape. For example, one ITR (e.g., 5' ITR) in a mod-ITR pair can be from one serotype, and the other ITR (e.g., 3' ITR) can be from a different serotype, however, both can have the same corresponding mutation (e.g., if the 5'ITR has a deletion in the C region, the cognate modified 3'ITR from a different serotype has a deletion at the corresponding position in the C' region), such that the modified ITR pair has the same symmetrical three-dimensional spatial organization. In such embodiments, each ITR in a modified ITR pair can be from different serotypes (e.g. AAV1, 2, 3, 4, 5, 6, 7, 8, 9, 10, 11, and 12) such as the combination of AAV2 and AAV6, with the modification in one ITR reflected in the corresponding position in the cognate ITR from a different serotype. In one embodiment, a substantially symmetrical modified ITR pair refers to a pair of modified ITRs (mod-ITRs) so long as the difference in nucleotide sequences between the ITRs does not affect the properties or overall shape and they have substantially the same shape in 3D space. As a non-limiting example, a mod-ITR that has at least 95%, 96%, 97%, 98% or 99% sequence identity to the canonical mod-ITR as determined by standard means well known in the art such as BLAST (Basic Local Alignment Search Tool), or BLASTN at default settings, and also has a symmetrical three-dimensional spatial organization such that their 3D structure is the same shape in geometric space. A substantially symmetrical mod-ITR pair has the same A, C-C' and B-B' loops in 3D space, e.g., if a modified ITR in a substantially symmetrical mod-ITR pair has a deletion of a C-C' arm, then the cognate mod-ITR has the corresponding deletion of the C-C' loop and also has a similar 3D structure of the remaining A and B-B' loops in the same shape in geometric space of its cognate mod-ITR.

The term “flanking” refers to a relative position of one nucleic acid sequence with respect to another nucleic acid sequence. Generally, in the sequence ABC, B is flanked by A and C. The same is true for the arrangement A×B×C. Thus, a flanking sequence precedes or follows a flanked sequence but need not be contiguous with, or immediately adjacent to the flanked sequence. In one embodiment, the term flanking refers to terminal repeats at each end of the linear duplex ceDNA vector.

As used herein, the term "ceDNA genome" refers to an expression cassette that further incorporates at least one inverted terminal repeat region. A ceDNA genome may further comprise one or more spacer regions. In some embodiments the ceDNA genome is incorporated as an intermolecular duplex polynucleotide of DNA into a plasmid or viral genome.

As used herein, the term "ceDNA spacer region" refers to an intervening sequence that separates functional elements in the ceDNA vector or ceDNA genome. In some embodiments, ceDNA spacer regions keep two functional elements at a desired distance for optimal functionality. In some embodiments, ceDNA spacer regions provide or add to the genetic stability of the ceDNA genome within e.g., a plasmid or baculovirus. In some embodiments, ceDNA spacer regions facilitate ready genetic manipulation of the ceDNA genome by providing a convenient location for cloning sites and the like. For example, in certain aspects, an oligonucleotide "polylinker" containing several restriction endonuclease sites, or a non-open reading frame sequence designed to have no known protein (e.g., transcription factor) binding sites can be positioned in the ceDNA genome to separate the cis-acting factors, e.g., inserting a 6mer, 12mer, 18mer, 24mer, 48mer, 86mer, 176mer, etc. between the terminal resolution site and the upstream transcriptional regulatory element. Similarly, the spacer may be incorporated between the polyadenylation signal sequence and the 3'-terminal resolution site.

As used herein, the terms "Rep binding site, "Rep binding element, "RBE" and "RBS" are used interchangeably and refer to a binding site for Rep protein (e.g., AAV Rep 78 or AAV Rep 68) which upon binding by a Rep protein permits the Rep protein to perform its site-specific endonuclease activity on the sequence incorporating the RBS. An RBS sequence and its inverse complement together form a single RBS. RBS sequences are known in the art, and include, for example, 5'-GCGCGCTCGCTCGCTC-3' (SEQ ID NO: 60), an RBS sequence identified in AAV2. Any known RBS sequence may be used in the embodiments of the invention, including other known AAV RBS sequences and other naturally known or synthetic RBS sequences. Without being bound by theory it is thought that he nuclease domain of a Rep protein binds to the duplex nucleotide sequence GCTC, and thus the two known AAV Rep proteins bind directly to and stably assemble on the duplex oligonucleotide, 5'-(GCGC)(GCTC)(GCTC)(GCTC)-3' (SEQ ID NO: 60). In addition, soluble aggregated conformers (i.e., undefined number of inter-associated Rep proteins) dissociate and bind to oligonucleotides that contain Rep binding sites. Each Rep protein interacts with both the nitrogenous bases and phosphodiester backbone on each strand. The interactions with the nitrogenous bases provide sequence specificity whereas the interactions with the phosphodiester backbone are non- or less-sequence specific and stabilize the protein-DNA complex.

As used herein, the terms "terminal resolution site" and "TRS" are used interchangeably herein and refer to a region at which Rep forms a tyrosine-phosphodiester bond with the 5' thymidine generating a 3' OH that serves as a substrate for DNA extension via a cellular DNA polymerase, e.g., DNA pol delta or DNA pol epsilon. Alternatively, the Rep-thymidine complex may participate in a coordinated ligation reaction. In some embodiments, a TRS minimally encompasses a non-base-paired thymidine. In some embodiments, the nicking efficiency of the TRS can be controlled at least in part by its distance within the same molecule from the RBS. When the acceptor substrate is the complementary ITR, then the resulting product is an intramolecular duplex. TRS sequences are known in the art, and include, for example, 5'-GGTTGA-3' (SEQ ID NO: 61), the hexanucleotide sequence identified in AAV2. Any known TRS sequence may be used in the embodiments of the invention, including other known AAV TRS sequences and other naturally known or synthetic TRS sequences such as AGTT (SEQ ID NO: 62), GGTTGG (SEQ ID NO: 63), AGTTGG (SEQ ID NO: 64), AGTTGA (SEQ ID NO: 65), and other motifs such as RRTTRR (SEQ ID NO: 66).

As used herein, the term "ceDNA-plasmid" refers to a plasmid that comprises a ceDNA genome as an intermolecular duplex.

As used herein, the term "ceDNA-bacmid" refers to an infectious baculovirus genome comprising a ceDNA genome as an intermolecular duplex that is capable of propagating in *E. coli* as a plasmid, and so can operate as a shuttle vector for baculovirus.

As used herein, the term "ceDNA-baculovirus" refers to a baculovirus that comprises a ceDNA genome as an intermolecular duplex within the baculovirus genome.

As used herein, the terms "ceDNA-baculovirus infected insect cell" and "ceDNA-BIIC" are used interchangeably, and refer to an invertebrate host cell (including, but not limited to an insect cell (e.g., an Sf9 cell)) infected with a ceDNA-baculovirus.

As used herein, the term "closed-ended DNA vector" refers to a capsid-free DNA vector with at least one covalently closed end and where at least part of the vector has an intramolecular duplex structure.

As used herein, the terms "ceDNA vector" and "ceDNA" are used interchangeably and refer to a closed-ended DNA vector comprising at least one terminal palindrome. In some embodiments, the ceDNA comprises two covalently-closed ends.

As defined herein, "reporters" refer to proteins that can be used to provide detectable read-outs. Reporters generally produce a measurable signal such as fluorescence, color, or luminescence. Reporter protein coding sequences encode proteins whose presence in the cell or organism is readily observed. For example, fluorescent proteins cause a cell to fluoresce when excited with light of a particular wavelength, luciferases cause a cell to catalyze a reaction that produces light, and enzymes such as β-galactosidase convert a substrate to a colored product. Exemplary reporter polypeptides useful for experimental or diagnostic purposes include, but are not limited to β-lactamase, β-galactosidase (LacZ), alkaline phosphatase (AP), thymidine kinase (TK), green fluorescent protein (GFP) and other fluorescent proteins, chloramphenicol acetyltransferase (CAT), luciferase, and others well known in the art.

As used herein, the term "effector protein" refers to a polypeptide that provides a detectable read-out, either as, for example, a reporter polypeptide, or more appropriately, as a polypeptide that kills a cell, e.g., a toxin, or an agent that renders a cell susceptible to killing with a chosen agent or lack thereof. Effector proteins include any protein or peptide that directly targets or damages the host cell's DNA and/or RNA. For example, effector proteins can include, but are not limited to, a restriction endonuclease that targets a host cell DNA sequence (whether genomic or on an extrachromosomal element), a protease that degrades a polypeptide target necessary for cell survival, a DNA gyrase inhibitor, and a ribonuclease-type toxin. In some embodiments, the expression of an effector protein controlled by a synthetic biological circuit as described herein can participate as a factor in another synthetic biological circuit to thereby expand the range and complexity of a biological circuit system's responsiveness.

Transcriptional regulators refer to transcriptional activators and repressors that either activate or repress transcription of a gene of interest. Promoters are regions of nucleic acid that initiate transcription of a particular gene Transcriptional activators typically bind nearby to transcriptional promoters and recruit RNA polymerase to directly initiate transcription. Repressors bind to transcriptional promoters and sterically hinder transcriptional initiation by RNA polymerase. Other transcriptional regulators may serve as either an activator or a repressor depending on where they bind and cellular and environmental conditions. Non-limiting examples of transcriptional regulator classes include, but are not limited to homeodomain proteins, zinc-finger proteins, winged-helix (forkhead) proteins, and leucine-zipper proteins.

As used herein, a "repressor protein" or "inducer protein" is a protein that binds to a regulatory sequence element and represses or activates, respectively, the transcription of sequences operatively linked to the regulatory sequence element. Preferred repressor and inducer proteins as described herein are sensitive to the presence or absence of at least one input agent or environmental input. Preferred proteins as described herein are modular in form, comprising, for example, separable DNA-binding and input agent-binding or responsive elements or domains.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutically active substances is well known in the art. Supplementary active ingredients can also be incorporated into the compositions. The phrase "pharmaceutically-acceptable" refers to molecular entities and compositions that do not produce a toxic, an allergic, or similar untoward reaction when administered to a host.

As used herein, an "input agent responsive domain" is a domain of a transcription factor that binds to or otherwise responds to a condition or input agent in a manner that renders a linked DNA binding fusion domain responsive to the presence of that condition or input. In one embodiment, the presence of the condition or input results in a conformational change in the input agent responsive domain, or in a protein to which it is fused, that modifies the transcription-modulating activity of the transcription factor.

The term "in vivo" refers to assays or processes that occur in or within an organism, such as a multicellular animal. In some of the aspects described herein, a method or use can be said to occur "in vivo" when a unicellular organism, such as a bacterium, is used. The term "ex vivo" refers to methods and uses that are performed using a living cell with an intact membrane that is outside of the body of a multicellular animal or plant, e.g., explants, cultured cells, including primary cells and cell lines, transformed cell lines, and extracted tissue or cells, including blood cells, among others. The term "in vitro" refers to assays and methods that do not require the presence of a cell with an intact membrane, such as cellular extracts, and can refer to the introducing of a programmable synthetic biological circuit in a non-cellular system, such as a medium not comprising cells or cellular systems, such as cellular extracts.

The term "promoter," as used herein, refers to any nucleic acid sequence that regulates the expression of another nucleic acid sequence by driving transcription of the nucleic acid sequence, which can be a heterologous target gene encoding a protein or an RNA. Promoters can be constitutive, inducible, repressible, tissue-specific, or any combination thereof. A promoter is a control region of a nucleic acid sequence at which initiation and rate of transcription of the remainder of a nucleic acid sequence are controlled. A promoter can also contain genetic elements at which regulatory proteins and molecules can bind, such as RNA polymerase and other transcription factors. In some embodiments of the aspects described herein, a promoter can drive the expression of a transcription factor that regulates the expression of the promoter itself. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the expression of transgenes in the ceDNA vectors disclosed herein. A promoter sequence may be bounded at its 3' terminus by the transcription initiation site and extends upstream (5' direction) to include the minimum number of bases or elements necessary to initiate transcription at levels detectable above background.

The term "enhancer" as used herein refers to a cis-acting regulatory sequence (e.g., 50-1,500 base pairs) that binds one or more proteins (e.g., activator proteins, or transcription factor) to increase transcriptional activation of a nucleic acid sequence. Enhancers can be positioned up to 1,000,000 base pars upstream of the gene start site or downstream of the gene start site that they regulate. An enhancer can be positioned within an intronic region, or in the exonic region of an unrelated gene.

A promoter can be said to drive expression or drive transcription of the nucleic acid sequence that it regulates. The phrases "operably linked," "operatively positioned," "operatively linked," "under control," and "under transcriptional control" indicate that a promoter is in a correct functional location and/or orientation in relation to a nucleic acid sequence it regulates to control transcriptional initiation and/or expression of that sequence. An "inverted promoter," as used herein, refers to a promoter in which the nucleic acid sequence is in the reverse orientation, such that what was the coding strand is now the non-coding strand, and vice versa. Inverted promoter sequences can be used in various embodiments to regulate the state of a switch. In addition, in various embodiments, a promoter can be used in conjunction with an enhancer.

A promoter can be one naturally associated with a gene or sequence, as can be obtained by isolating the 5' non-coding sequences located upstream of the coding segment and/or exon of a given gene or sequence. Such a promoter can be referred to as "endogenous." Similarly, in some embodiments, an enhancer can be one naturally associated with a nucleic acid sequence, located either downstream or upstream of that sequence.

In some embodiments, a coding nucleic acid segment is positioned under the control of a "recombinant promoter" or "heterologous promoter," both of which refer to a promoter that is not normally associated with the encoded nucleic acid sequence it is operably linked to in its natural environment. A recombinant or heterologous enhancer refers to an enhancer not normally associated with a given nucleic acid sequence in its natural environment. Such promoters or enhancers can include promoters or enhancers of other genes; promoters or enhancers isolated from any other prokaryotic, viral, or eukaryotic cell; and synthetic promoters or enhancers that are not "naturally occurring," i.e., comprise different elements of different transcriptional regulatory regions, and/or mutations that alter expression through methods of genetic engineering that are known in the art. In addition to producing nucleic acid sequences of promoters and enhancers synthetically, promoter sequences can be produced using recombinant cloning and/or nucleic acid amplification technology, including PCR, in connection with the synthetic biological circuits and modules disclosed herein (see, e.g., U.S. Pat. Nos. 4,683,202, 5,928,906, each incorporated herein by reference). Furthermore, it is contemplated that control sequences that direct transcription and/or expression of sequences within non-nuclear organelles such as mitochondria, chloroplasts, and the like, can be employed as well.

As described herein, an "inducible promoter" is one that is characterized by initiating or enhancing transcriptional activity when in the presence of, influenced by, or contacted by an inducer or inducing agent. An "inducer" or "inducing agent," as defined herein, can be endogenous, or a normally exogenous compound or protein that is administered in such a way as to be active in inducing transcriptional activity from the inducible promoter. In some embodiments, the inducer or inducing agent, i.e., a chemical, a compound or a protein, can itself be the result of transcription or expression of a nucleic acid sequence (i.e., an inducer can be an inducer protein expressed by another component or module), which itself can be under the control or an inducible promoter. In some embodiments, an inducible promoter is induced in the absence of certain agents, such as a repressor. Examples of inducible promoters include but are not limited to, tetracycline, metallothionine, ecdysone, mammalian viruses (e.g., the adenovirus late promoter; and the mouse mammary tumor virus long terminal repeat (MMTV-LTR)) and other steroid-responsive promoters, rapamycin responsive promoters and the like.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate transcription of a non-coding sequence (e.g., DNA-targeting RNA) or a coding sequence (e.g., site-directed modifying polypeptide, or Cas9/Csn1 polypeptide) and/or regulate translation of an encoded polypeptide.

"Operably linked" refers to a juxtaposition wherein the components so described are in a relationship permitting them to function in their intended manner. For instance, a promoter is operably linked to a coding sequence if the promoter affects its transcription or expression. An "expression cassette" includes a heterologous DNA sequence that is operably linked to a promoter or other regulatory sequence sufficient to direct transcription of the transgene in the ceDNA vector. Suitable promoters include, for example, tissue specific promoters. Promoters can also be of AAV origin.

The term "subject" as used herein refers to a human or animal, to whom treatment, including prophylactic treatment, with the ceDNA vector according to the present invention, is provided. Usually the animal is a vertebrate such as, but not limited to a primate, rodent, domestic animal or game animal. Primates include but are not limited to, chimpanzees, cynomolgous monkeys, spider monkeys, and macaques, e.g., Rhesus. Rodents include mice, rats, woodchucks, ferrets, rabbits and hamsters. Domestic and game animals include, but are not limited to, cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In certain embodiments of the aspects described herein, the subject is a mammal, e.g., a primate or a human. A subject can be male or female. Additionally, a subject can be an infant or a child. In some embodiments, the subject can be a neonate or an unborn subject, e.g., the subject is in utero. Preferably, the subject is a mammal. The mammal can be a human, non-human primate, mouse, rat, dog, cat, horse, or cow, but is not limited to these examples. Mammals other than humans can be advantageously used as subjects that represent animal models of diseases and disorders. In addition, the methods and compositions described herein can be used for domesticated animals and/or pets. A human subject can be of any age, gender, race or ethnic group, e.g., Caucasian (white), Asian, African, black, African American, African European, Hispanic, Mideastern, etc. In some embodiments, the subject can be a patient or other subject in a clinical setting. In some embodiments, the subject is already undergoing treatment. In some embodiments, the subject is an embryo, a fetus, neonate, infant, child, adolescent, or adult. In some embodiments, the subject is a human fetus, human neonate, human infant, human child, human adolescent, or human adult. In some embodiments, the subject is an animal embryo, or non-human embryo or non-human primate embryo. In some embodiments, the subject is a human embryo.

As used herein, the term "host cell", includes any cell type that is susceptible to transformation, transfection, transduction, and the like with a nucleic acid construct or ceDNA expression vector of the present disclosure. As non-limiting examples, a host cell can be an isolated primary cell, pluripotent stem cells, $CD34^+$ cells), induced pluripotent stem cells, or any of a number of immortalized cell lines (e.g., HepG2 cells). Alternatively, a host cell can be an in situ or in vivo cell in a tissue, organ or organism.

The term "exogenous" refers to a substance present in a cell other than its native source. The term "exogenous" when used herein can refer to a nucleic acid (e.g., a nucleic acid encoding a polypeptide) or a polypeptide that has been introduced by a process involving the hand of man into a biological system such as a cell or organism in which it is not normally found and one wishes to introduce the nucleic acid or polypeptide into such a cell or organism. Alternatively, "exogenous" can refer to a nucleic acid or a polypeptide that has been introduced by a process involving the hand of man into a biological system such as a cell or organism in which it is found in relatively low amounts and one wishes to increase the amount of the nucleic acid or polypeptide in the cell or organism, e.g., to create ectopic expression or levels. In contrast, the term "endogenous" refers to a substance that is native to the biological system or cell.

The term "sequence identity" refers to the relatedness between two nucleotide sequences. For purposes of the present disclosure, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows: (Identical Deoxyribonucleotides.times.100)/(Length of Alignment-Total Number of Gaps in Alignment). The length of the alignment is preferably at least 10 nucleotides, preferably at least 25 nucleotides more preferred at least 50 nucleotides and most preferred at least 100 nucleotides.

The term "homology" or "homologous" as used herein is defined as the percentage of nucleotide residues in the homology arm that are identical to the nucleotide residues in the corresponding sequence on the target chromosome, after aligning the sequences and introducing gaps, if necessary, to achieve the maximum percent sequence identity. Alignment for purposes of determining percent nucleotide sequence homology can be achieved in various ways that are within the skill in the art, for instance, using publicly available computer software such as BLAST, BLAST-2, ALIGN, ClustalW2 or Megalign (DNASTAR) software. Those skilled in the art can determine appropriate parameters for aligning sequences, including any algorithms needed to achieve maximal alignment over the full length of the sequences being compared. In some embodiments, a nucleic acid sequence (e.g., DNA sequence), for example of a homology arm of a repair template, is considered "homologous" when the sequence is at least 70%, at least 75%, at least 80%, at least 85%, at least 90%, at least 91%, at least 92%, at least 93%, at least 94%, at least 95%, at least 96%, at least 97%, at least 98%, at least 99%, or more, identical to the corresponding native or unedited nucleic acid sequence (e.g., genomic sequence) of the host cell.

The term "heterologous," as used herein, means a nucleotide or polypeptide sequence that is not found in the native nucleic acid or protein, respectively. A heterologous nucleic acid sequence may be linked to a naturally-occurring nucleic acid sequence (or a variant thereof) (e.g., by genetic engineering) to generate a chimeric nucleotide sequence encoding a chimeric polypeptide. A heterologous nucleic acid sequence may be linked to a variant polypeptide (e.g., by genetic engineering) to generate a nucleotide sequence encoding a fusion variant polypeptide.

A "vector" or "expression vector" is a replicon, such as plasmid, bacmid, phage, virus, virion, or cosmid, to which another DNA segment, i.e. an "insert", may be attached so as to bring about the replication of the attached segment in a cell. A vector can be a nucleic acid construct designed for delivery to a host cell or for transfer between different host cells. As used herein, a vector can be viral or non-viral in origin and/or in final form, however for the purpose of the present disclosure, a "vector" generally refers to a ceDNA vector, as that term is used herein. The term "vector" encompasses any genetic element that is capable of replication when associated with the proper control elements and that can transfer gene sequences to cells. In some embodiments, a vector can be an expression vector or recombinant vector.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g., 5' untranslated (5'UTR) or "leader" sequences and 3' UTR or "trailer" sequences, as well as intervening sequences (introns) between individual coding segments (exons).

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

The phrase "genetic disease" as used herein refers to a disease, partially or completely, directly or indirectly, caused by one or more abnormalities in the genome, especially a condition that is present from birth. The abnormality may be a mutation, an insertion or a deletion. The abnormality may affect the coding sequence of the gene or its regulatory sequence. The genetic disease may be, but not limited to DMD, hemophilia, cystic fibrosis, Huntington's chorea, familial hypercholesterolemia (LDL receptor defect), hepatoblastoma, Wilson's disease, congenital hepatic *porphyria*, inherited disorders of hepatic metabolism, Lesch Nyhan syndrome, sickle cell anemia, thalassaemias, xeroderma pigmentosum, Fanconi's anemia, retinitis pigmentosa, ataxia telangiectasia, Bloom's syndrome, retinoblastoma, and Tay-Sachs disease.

As used herein the term "comprising" or "comprises" is used in reference to compositions, methods, and respective component(s) thereof, that are essential to the method or composition, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Other than in the operating examples, or where otherwise indicated, all numbers expressing quantities of ingredients or reaction conditions used herein should be understood as modified in all instances by the term "about." The term "about" when used in connection with percentages can mean±1%. The present invention is further explained in detail by the following examples, but the scope of the invention should not be limited thereto.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

II. Detailed Synthetic Production Method of Circular DNA Vectors, Including ceDNA Vectors The technology described herein is directed in general to methods for generating closed-ended DNA vectors in the absence of cells or cell lines. As such, the resulting vectors have fewer impurities than comparable vectors made using conventional cell production methodologies.

A. Synthetic Production Method in General

In some embodiments, disclosed herein is a process for synthesis of closed-ended DNA vectors including ceDNA vectors which does not require use of any microbiological steps. In some embodiments, the process allows for synthesis of closed-ended DNA vectors in a system using enzymatic cleavage steps using restriction endonucleases and ligation steps to generate the closed-ended DNA vectors. In nearly all embodiments, the synthetic system for DNA vector production is a cell-free system. In some embodiments, the cell-free system is an insect cell-free system.

It will be appreciated by one of ordinary skill in the art that one or more enzymes for the synthetic production method or one or more of the oligonucleotide components can be produced from a cell and used in the methods of the invention in purified form. Accordingly, in some embodiments, the synthetic production method is a cell-free method, however, a restriction enzyme and/or ligase enzyme can be produced from a cell.

In one embodiment, a restriction endonuclease and/or a ligation-competent protein can be expressed or provided from an expression vector in a cell, e.g., bacterial cell. In one embodiment, a cell, such as a bacterial cell, comprising an expression vector expressing one or more of the restriction endonucleases or the ligase enzymes can be present. Therefore, while the methods disclosed herein are primarily directed to cell-free synthetic methods to generate the DNA vectors disclosed herein, also encompassed in one embodiment are synthetic production methods where a cell, e.g., bacterial cell but not an insect cell is present and can be used to express one or more of the enzymes required in the method. In such embodiments, the cell expressing a restriction endonuclease and/or ligation-competent protein is not an insect cell. In all embodiments where a cell is present and expresses one or more restriction endonucleases or ligation-competent proteins, the cell does not replicate the close-ended DNA vector. Stated differently, the intracellular machinery of the cell does not replicate, or is not involved in the replication of the DNA vector.

In some embodiments, synthesis of closed-ended DNA vectors (e.g., ceDNA vectors) described herein is carried out in an in vitro cell-free process starting from either a double-stranded DNA construct or one or more oligonucleotides. The double-stranded DNA construct or one or more oligonucleotides are cleaved with restriction endonucleases and ligated to form the DNA molecules. In some embodiments, the oligonucleotides which can be synthesized chemically, thus avoiding use of large starting templates encoding the entirety of the desired sequence which would typically need to be propagated in bacteria. Once a desired DNA sequence is synthesized, it can be cleaved and ligated with other oligonucleotides as disclosed herein. The use of multiple oligonucleotides in the generation of closed-ended DNA vectors using the methods disclosed herein allows for a modular approach to DNA vector generation, enabling tailoring and/or specific selection of the terminal repeats, e.g., ITRs, as well as the spacing of the terminal repeats, and also selection of the heterologous nucleic acid sequence in the synthetically produced closed-ended DNA vectors.

B. Method of the Synthetic Production of DNA Vectors

Certain methods for the production of a ceDNA vector comprising an with various ITR configurations using cell-based methods are described in Example 1 of International applications PCT/US18/49996, filed Sep. 7, 2018, and PCT/US2018/064242, filed Dec. 6, 2018 each of which are incorporated herein in their entirety by reference.

In contrast, the methods provided herein relate to a synthetic production method, e.g., in some embodiments, a cell-free production method, and is also referred to herein as "synthetic closed-ended DNA vector production"" or "synthetic production".

Herein, a synthetic production method of a closed-ended DNA vector is exemplified and described using the synthetic production of a ceDNA vector. In some embodiments, the synthetic production method is a cell-free method, e.g., insect cell-free method. In some embodiments, the synthetic production method occurs in the absence of bacmids, or baculovirus, or both. In alternative embodiments, the synthetic production method can encompass use of cells, e.g., bacterial cells, e.g., cells expressing a restriction endonuclease, and/or ligation-competent Rep protein, or the like. In such an embodiment, the cells can be a cell line that has a polynucleotide vector template stably integrated, and can be used to introduce a restriction endonuclease protein and/or a ligase competent protein e.g., such as but not limited to, a Rep protein to the reaction mixture comprising the oligonucleotides used in the synthetic production methods described herein.

Examples of the process for generating and isolating ceDNA vectors generated using the synthetic production method as disclosed herein are described in FIGS. 4A-4E and the specific examples in the Examples section below.

In all aspects of the synthetic production methods to generate closed-ended DNA vectors as disclosed herein, the ligation step can be a chemical ligation step or an enzymatic ligation step. In some embodiments, ligation can be conducted using a ligation-competent enzyme, e.g., DNA ligase, e.g. to ligate 5' and 3' sticky overhangs, or blunt ends. In some embodiments, the ligation enzyme is a ligase enzyme other than a Rep protein. In some embodiments, the ligation enzyme is an AAV Rep protein.

In all aspects of the synthetic methods to generate closed-ended DNA vectors as disclosed herein, the method is an in vitro method. In a preferred embodiment, the method is a cell-free method, i.e., not performed in, or in the presence of a cell, e.g., an insect cell. In alternative embodiments, one or more enzymes for the synthetic production method can be produced from, or expressed from a cell, e.g., a non-insect cell. For example, in some embodiments, a cell, such as a bacterial cell, comprising an expression vector expressing one or more of the restriction endonucleases or the ligase enzymes can be present. Therefore, while the methods disclosed herein are primarily directed to cell-free synthetic methods to generate the closed-ended DNA vectors disclosed herein, also encompassed are synthetic production methods where a cell, e.g., bacterial cell can be used to express one or more of the enzymes required in the method.

(i) Synthetic Production Method from a Double Stranded DNA Construct

In one aspect, a closed-ended DNA vector is generated by excising the entire molecule that forms the closed-ended DNA vector from a double-stranded DNA construct, followed by ligation of the ends to close the molecule. In such an embodiment, a double-stranded DNA construct is provided with, in 5' to 3' order: a first restriction endonuclease site; an upstream ITR; an expression cassette; a downstream ITR; and a second restriction endonuclease site. The double-stranded DNA construct is then contacted with one or more restriction endonucleases to generate double-stranded breaks at both of the restriction endonuclease cleavage sites. One endonuclease can target both sites, or each site can be targeted by a different endonuclease as long as the restriction sites are not present within the closed-ended vector template region. This excises the sequence between the restriction endonuclease sites from the rest of the double-stranded DNA construct. This excised molecule will have free 5' and 3' ends, which are then ligated in order to form a closed-ended DNA vector. The ligation can be effected by using a protein with ligating functions, such as e.g. Rep or phage protein, or by chemical ligation. In some aspects, the vector length in the 5' to 3' direction is greater than the maximum length known to be encapsidated in an AAV virion. In some aspects, length is greater than 4.6 kb, or greater than 5 kb, or greater than 6 kb. In some aspects, the excised molecule is first annealed to facilitate hairpin formation prior to ligation of the free 5' and 3' ends. In some aspects, the unwanted double-stranded DNA construct backbone is cleaved by one or more restriction endonucleases specific for a unique cleavage site in the backbone so that it is degraded and more readily eliminated during purification. In some aspects, the foregoing method can further comprise a step of heating or melting the excised dsDNA molecule to form single-stranded polynucleotides prior to the ligation step. In some aspects, the two restriction endonuclease sites are identical in sequence. In some aspects, the two restriction endonuclease sites can be cleaved to provide blunt ends.

(ii) Synthetic Production Method from a Single-Stranded Molecule (Variant 1)

Another exemplary method of producing a closed-ended DNA vector, e.g., ceDNA vector using the synthetic production method as disclosed herein uses a single-stranded linear DNA with closed ends and comprises two ITRs which flank an expression cassette, first in the sense direction followed by the antisense direction. Accordingly, in some embodiments, the method comprises a) synthesizing a single-stranded molecule containing, from 5' to 3': a sense first ITR; a sense expression cassette sequence; a sense second ITR; an antisense second ITR; an antisense expression cassette sequence; and an antisense first ITR; b) facilitating the formation of at least one hairpin loop within the single stranded molecule c) and ligating the 5' and 3' ends to form the ceDNA vector. Various methods of synthesizing oligonucleotides and polynucleotides are known in the art, e.g., in vitro or in silico synthesis of oligonucleotides and any method known in the art can be used in step a). The terms "sense" and "antisense" in the foregoing method refer to the orientation of the structural element on the polynucleotide. The sense and antisense versions of an element are the reverse complement of each other. A hairpin loop sequence can be any nucleotide sequence, preferably one that will not hybridize to form a dsDNA along its entire length. Methods of ligating DNA to form linear double strand structures are known in the art, non-limiting examples use viral proteins, e.g. Rep, or phage, or pox, proteins, or chemical ligation.

In this embodiment, the closed-ended DNA vector, e.g., ceDNA vector is produced by providing a single-stranded linear DNA sequence encoding the expression cassette flanked by sense and antisense ITRs, which is then made closed-ended by ligation. Using the production of a ceDNA vector as an exemplary closed-ended DNA vector produced, a single-stranded DNA molecule for production of a ceDNA vector comprises, from 5' to 3':

a sense first ITR;
a sense expression cassette sequence;
a sense second ITR;
an antisense second ITR;
an antisense expression cassette sequence; and
an antisense first ITR.

In this exemplary method, the oligonucleotides are ligated in order as shown above, and the antisense first ITR complementary to the sense first ITR, and likewise the antisense second ITR and the antisense expression cassette sequence are complementary to the sense second ITR and the sense expression cassette sequence, respectively. The ligation step joins the free 5' and 3' ends and results in the formation of the closed-ended DNA vector, ceDNA.

In all aspects of the synthetic production methods to generate closed-ended DNA vectors as disclosed herein, the ligation step can be a chemical ligation step or an enzymatic ligation step. In some embodiments, ligation can be conducted using a ligation-competent enzyme, e.g., DNA ligase, e.g. to ligate 5' and 3' sticky overhangs, or blunt ends. In some embodiments, the ligation enzyme is a ligase enzyme other than a Rep protein. In some embodiments, the ligation enzyme is an AAV Rep protein.

(iii) Synthetic Production Using 5' and 3' ITR Oligonucleotides

Another aspect comprises: a) synthesizing (and/or providing) a first single-stranded ITR molecule comprising a first ITR; b) synthesizing (and/or providing) a second single-stranded ITR molecule comprising a second ITR; c) providing a double-stranded polynucleotide comprising an expression cassette sequence; and d) ligating the 5' and 3' ends of the first ITR molecule to a first end of the double-stranded molecule and ligating the 5' and 3' ends of the second ITR molecule to the second end of the double stranded molecule to form the DNA vector. Prior to the ligation step, the ITR molecules and/or the double-stranded polynucleotide can be contact with restriction enzymes to generate compatible ends, e.g., overhangs to ensure proper ligation at the desired locations. In some embodiments, the three elements are provided with blunt ends. The ligations of the each ITR with the double-stranded polynucleotide can be sequential or concurrent. In one embodiment, the ligation step involves ligation of a single stranded 5' to 3'oligo that forms a hairpin.

Figure 11A:
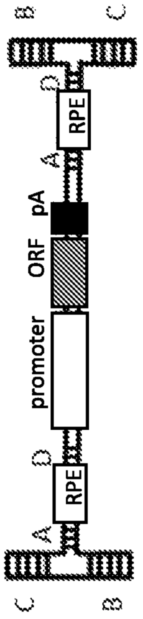
FIG. 11A is a schematic representation of a ceDNA vector, showing an ITR comprising two hairpin loops (the B and C regions) and the A and D region comprising an RPE and optionally a TRS flanking either side of the cassette comprising the gene of interest, an optional promoter/enhancer region, an optional posttranscriptional response element (e.g., the woodchuck hepatitis virus posttranscriptional regulatory element (WPRE), and an optional polyadenylation signal (e.g., from bovine growth hormone, BGHpA).
Figure 11B:
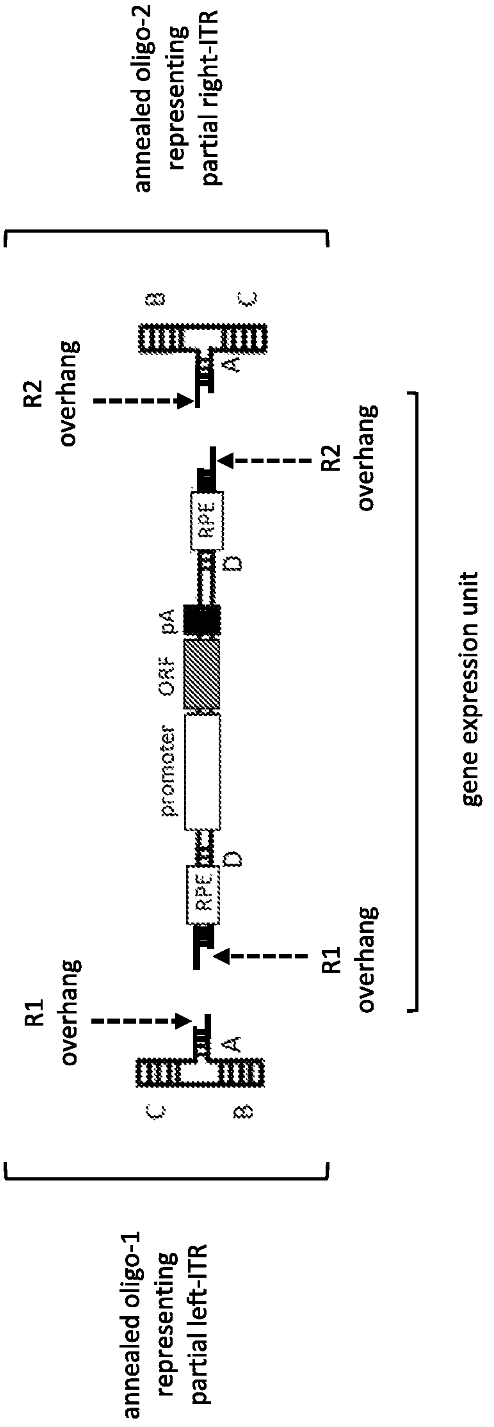
FIG. 11B shows a schematic representation of the different oligos that are synthesized and joined to form the final ceDNA vector.

In such an embodiment, a closed-ended DNA vector, e.g., ceDNA vector is produced by synthesizing a 5' and a 3' ITR oligonucleotide, which in some embodiments, are in a hairpin or other three-dimensional configuration (e.g., T- or Y-Holliday junction configuration), and ligating the 5' and 3' ITR oligonucleotides to a double-stranded polynucleotide comprising an expression cassette or heterologous nucleic acid sequence. Optionally, a step is added subjecting the oligo(s) to conditions that facilitate the folding of the oligo into a three-dimensional configuration prior to the ligation step. FIG. 11B shows an exemplary method of generating a ceDNA vector comprising ligating a 5' ITR oligonucleotide and a 3' ITR oligonucleotide to a double-stranded polynucleotide comprising an expression cassette. In some embodiments, the 5' and a 3' ITR oligonucleotides are 5' and 3' hairpin oligonucleotides or have a different three-dimensional configuration (e.g., Holliday junction), and can optionally be provided by in vitro DNA synthesis. In some embodiments, the 5' and a 3' ITR oligonucleotides have been cleaved with a restriction endonuclease to have complementary sticky ends to the double-stranded polynucleotide that has corresponding restriction endonuclease sticky ends. In some embodiments, the ends of the hairpin of the 5' ITR oligonucleotide has a sticky end that is complementary to the 5' sense strand and 3' antisense strand of the double-stranded polynucleotide. In some embodiments, the end of the hairpin of the 3' ITR oligonucleotide has a sticky end that is complementary to the 3' sense strand and 5' antisense strand of the double-stranded polynucleotide. In some embodiments, the ends of the hairpin of the 5' ITR oligonucleotide and the 3' ITR oligonucleotide have different restriction endonuclease sticky ends, such that directed ligation to the double-stranded polynucleotide can be achieved. In some embodiments, the ends of one or both of the ITR oligonucleotides do not have overhangs and such ITR oligo(s) are ligated to the double-stranded polynucleotide by blunt end-joining. The ITR molecules in the foregoing method can be synthesized and/or ligated by any method known in the art. Various methods of synthesizing oligonucleotides and polynucleotides are known in the art, e.g., solid-phase DNA synthesis, phosphoramidite DNA synthesis, and PCR. The ITR molecules can also be excised from a DNA construct comprising the ITR. Various methods of ligation nucleic acids are known in the art, e.g., chemical ligation or ligation with ligation-competent protein, e.g., a ligase, AAV Rep, or topoisomerase.

(iv) Synthetic Production Method not Requiring Ligation

In some embodiments, the synthetic production of a closed-ended DNA vector is by synthesis of a single-stranded sequence comprising at least one ITR flanking an expression cassette sequence and which also comprises an antisense expression cassette sequence. In one nonlimiting example, ceDNA vector is produced by the method as follows.

A single-stranded sequence comprising in order from 5' to 3':

a sense first ITR;
a sense expression cassette sequence;
a sense second ITR; and
an antisense expression cassette sequence is provided. In one embodiment the single-stranded sequence may be synthesized directly through any art-known method. In another embodiment, the single-stranded sequence may be constructed by joining by ligation two or more oligos comprising one or more of the sense first ITR, sense expression cassette sequence, sense second ITR and antisense expression cassette sequence.

In yet another embodiment, the single-stranded sequence may be obtained by excision of the sequence from a double-stranded DNA construct with subsequent separation of the strands from the excised double-stranded fragment. More specifically, a double-stranded DNA construct comprising a first restriction site, the sense first ITR, the sense expression cassette sequence, the sense second ITR, the antisense expression cassette sequence, and a second restriction site in 5' to 3' order is provided. The region between the two restriction endonuclease cleavage sites is excised by cleavage with at least one restriction endonuclease recognizing such cleavage site(s). The resulting excised double-stranded DNA fragment is treated such that the sense and antisense strands are separated into the desired single-stranded sequence fragments.

The single-stranded sequence is subjected to an annealing step to facilitate the formation of one or more hairpin loop by the sense first ITR and/or the sense second ITR, and the complementary binding of the sense expression cassette sequence to the antisense expression cassette sequence. The result is a closed-ended structure that did not require ligation to form. Annealing parameters and techniques are well known in the art.

In some embodiments the modified ITR comprises a polynucleotide of SEQ ID NO: 4, the wild-type ITR comprises a polynucleotide of SEQ ID NO: 1.

Figure 4A:
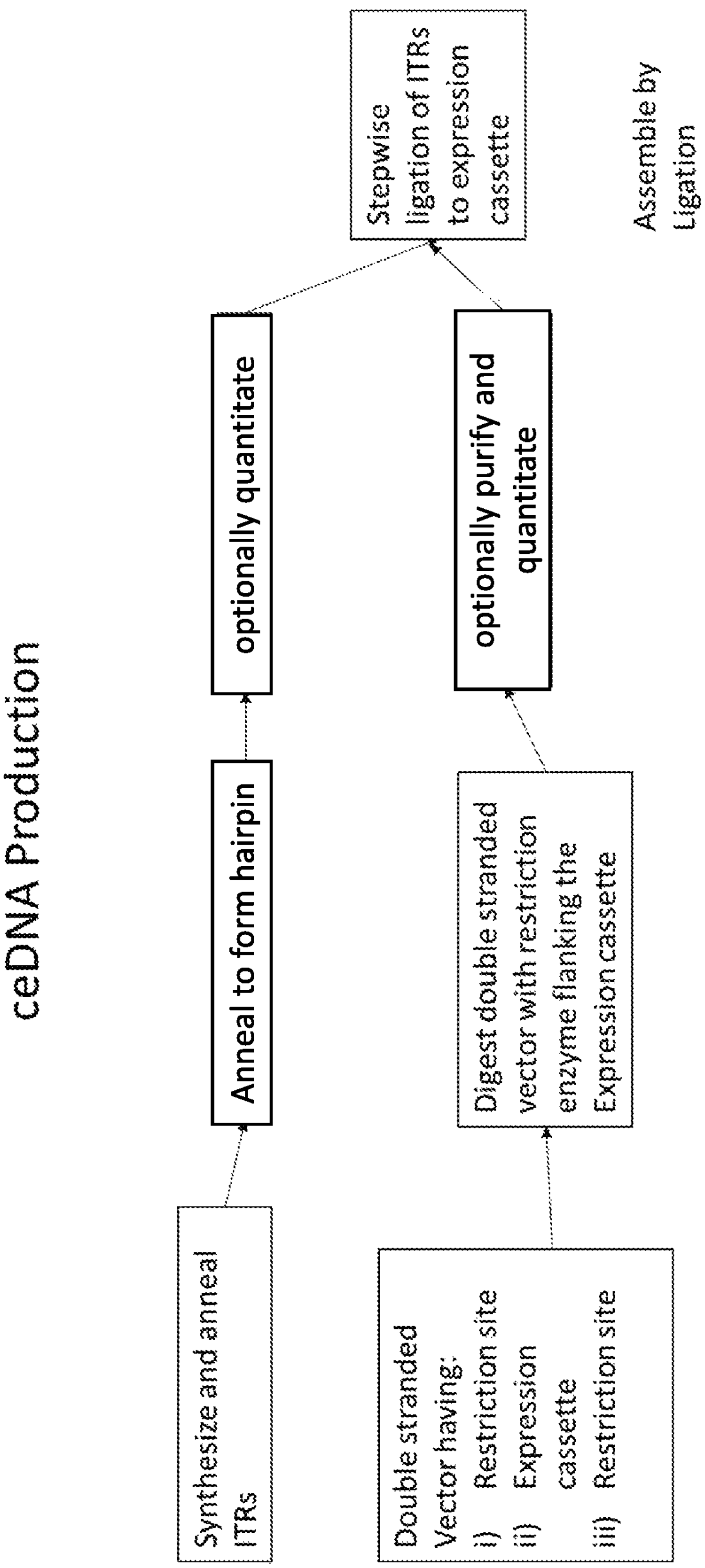
FIG. 4A is a schematic illustrating one embodiment of cell-free synthesis for making ceDNA. The products of the method in FIG. 4A can be isolated and characterized according to the downstream process in FIG. 4B.
Figure 4B:
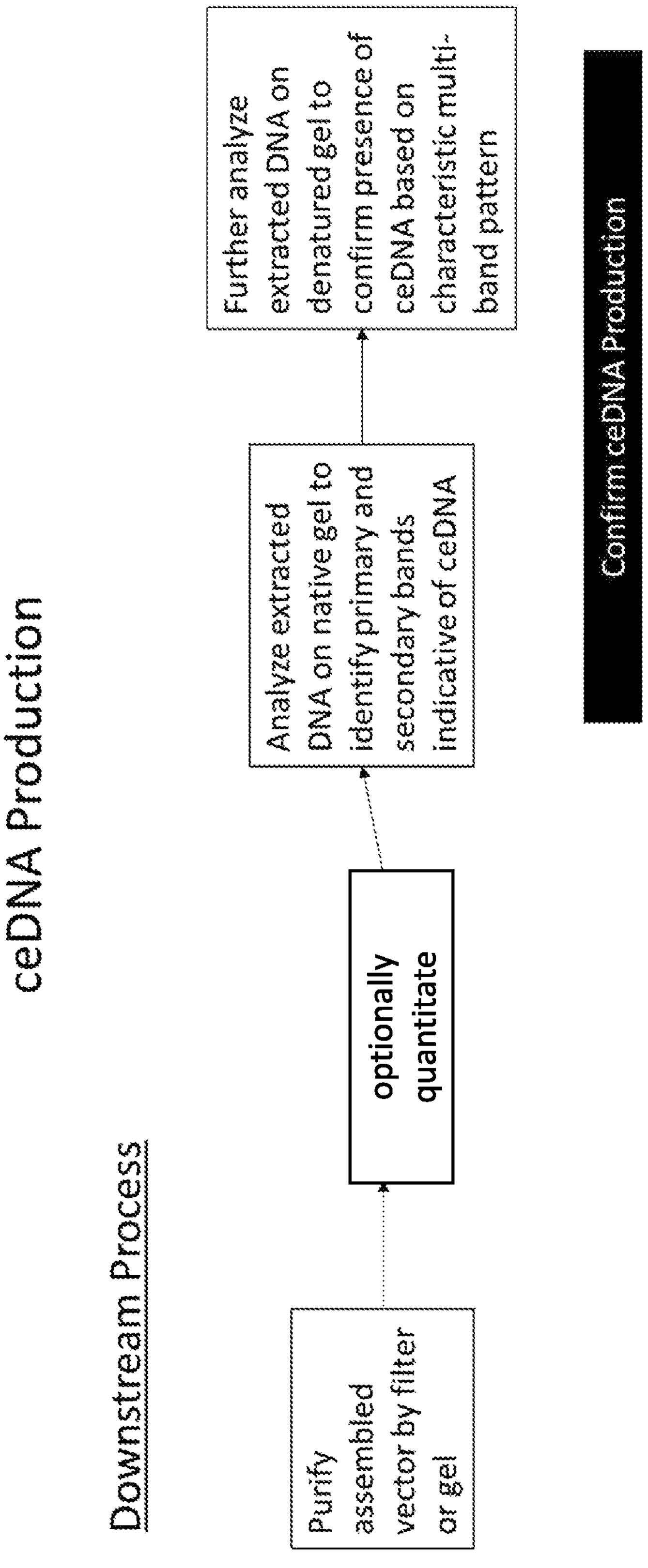
FIG. 4B illustrates a nonlimiting biochemical method to confirm ceDNA production.
Figure 4C:
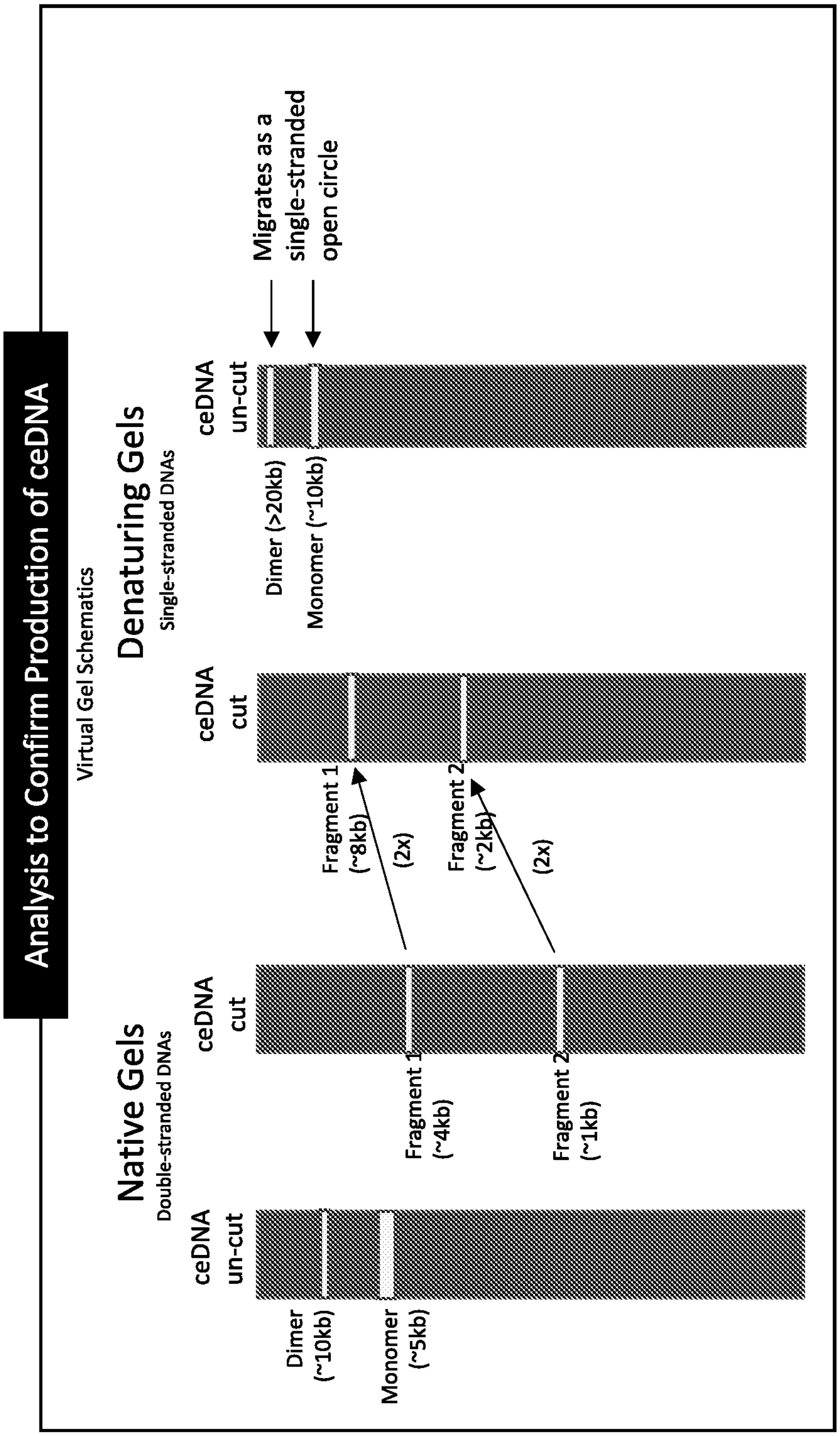
FIG. 4C and FIG. 4D are schematic illustrations describing a process for identifying the presence of ceDNA obtained during the cell-free ceDNA production process in FIG. 4A.

DNA vectors produced by the methods provided herein preferably have a linear and continuous structure rather than a non-continuous structure, as determined by restriction enzyme digestion assay (FIG. 4C). The linear and continuous structure is believed to be more stable from attack by cellular endonucleases, as well as less likely to be recombined and cause mutagenesis. Thus, vectors in the linear and continuous structure are preferred in some embodiments. The continuous, linear, single strand intramolecular duplex DNA vectors can have covalently bound terminal ends, without sequences encoding AAV capsid proteins. These DNA vectors are structurally distinct from plasmids, which are circular duplex nucleic acid molecules of bacterial origin. The complimentary strands of plasmids may be separated following denaturation whereas these DNA-vectors have complimentary strands and are a single DNA molecule. Preferably, vectors can be produced without DNA base methylation of prokaryotic type unlike plasmids.

Figure 5:
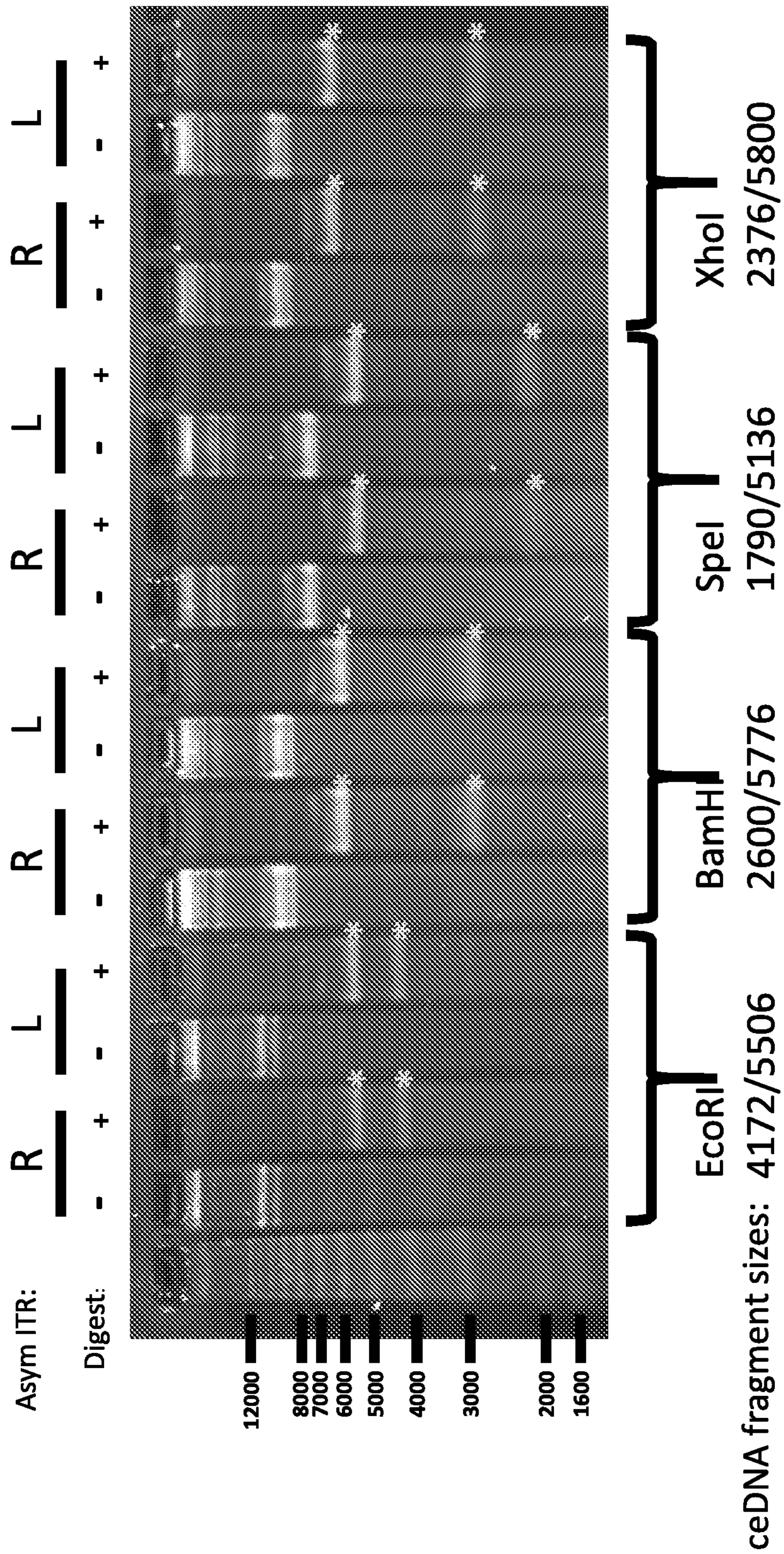
FIG. 5 is an exemplary picture of a denaturing gel running examples of ceDNA vectors with (+) or without (−) digestion with endonucleases (EcoRI for ceDNA construct 1 and 2; BamHI for ceDNA construct 3 and 4; SpeI for ceDNA construct 5 and 6; and XhoI for ceDNA construct 7 and 8). Sizes of bands highlighted with an asterisk were determined and provided on the bottom of the picture.
Figure 6A:
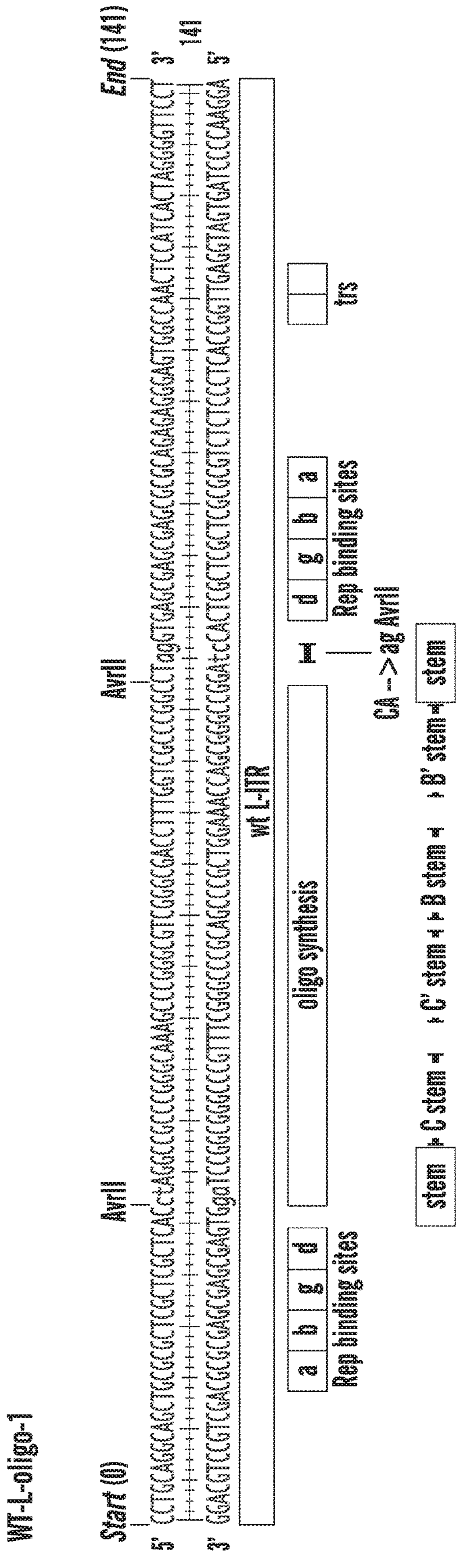
FIG. 6A-6D show exemplary ITRs and exemplary oligos for synthesizing ITRs for use in the embodiments described herein.
Figure 6A:
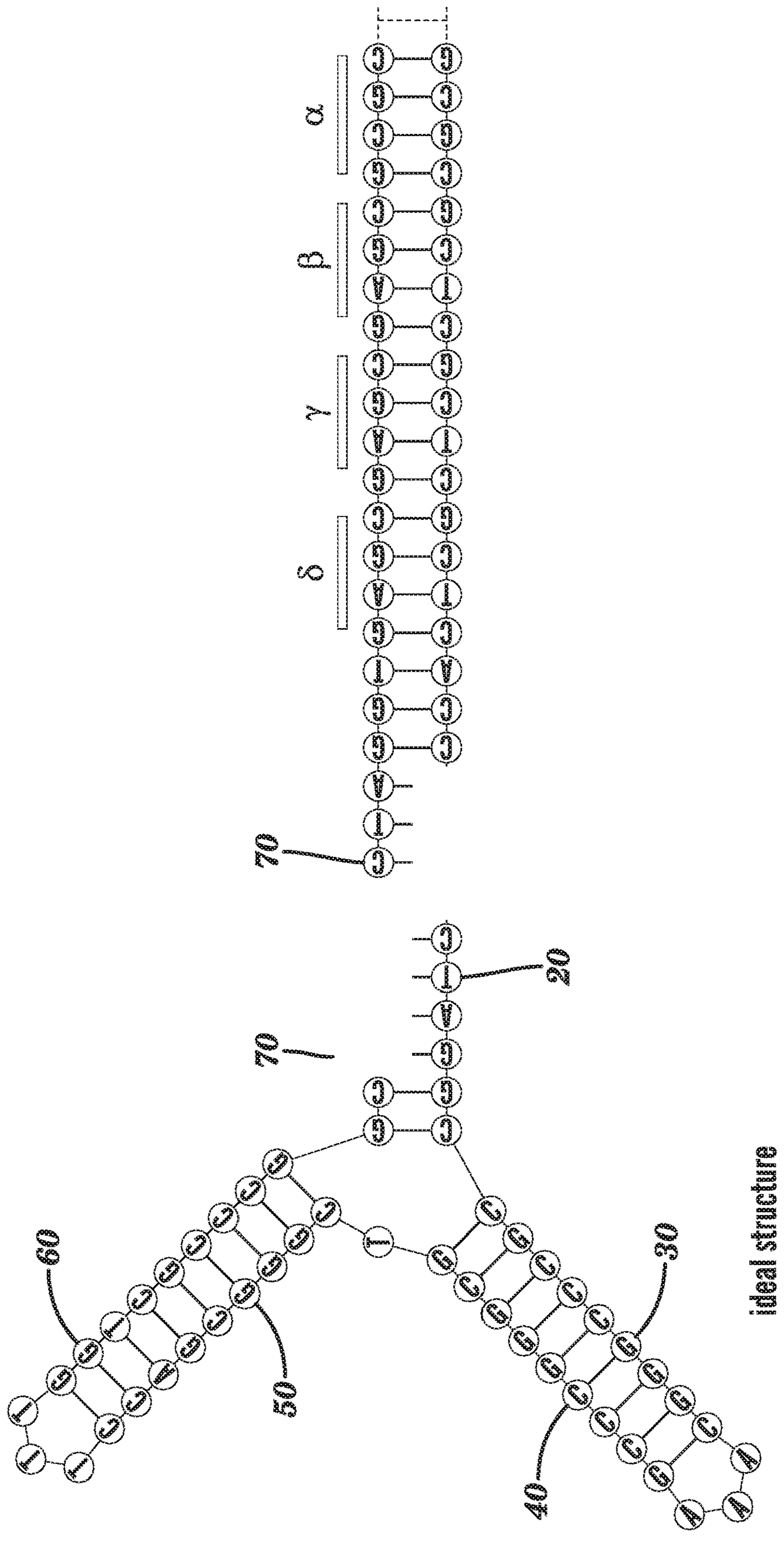
Figure 6A:
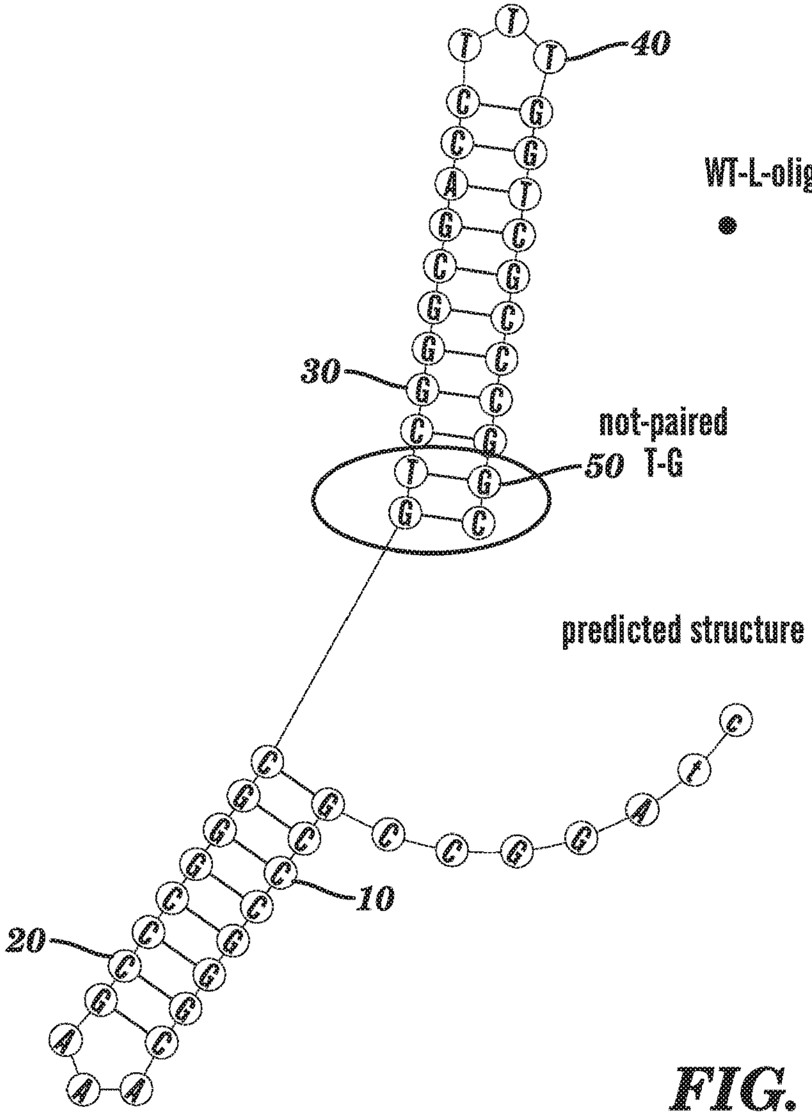
Figure 6B:
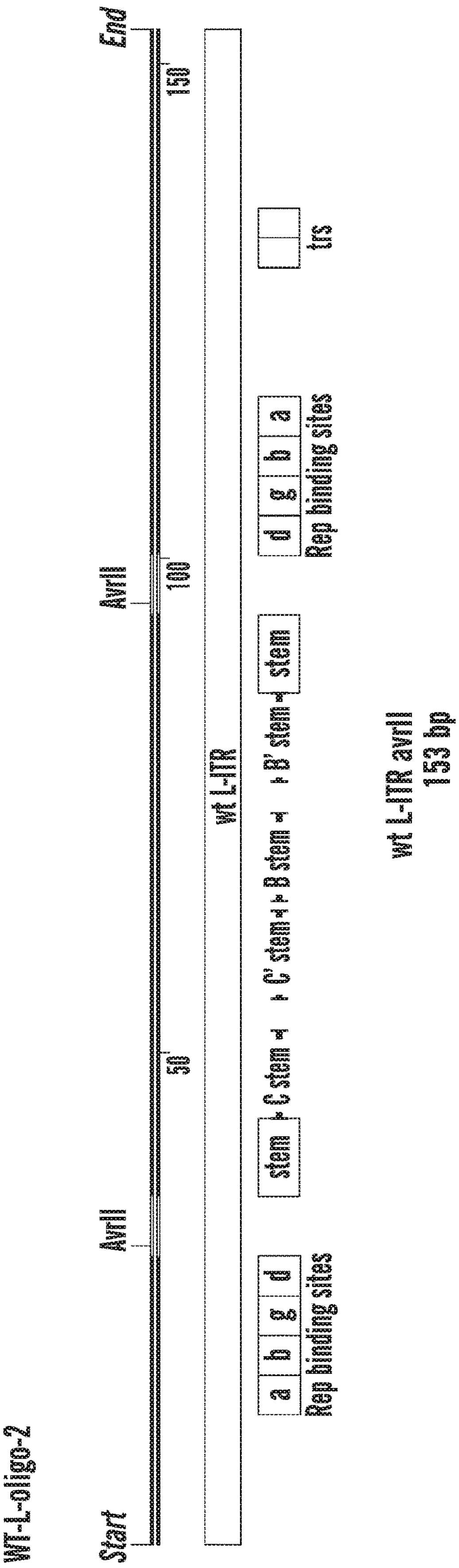
Figure 6B:
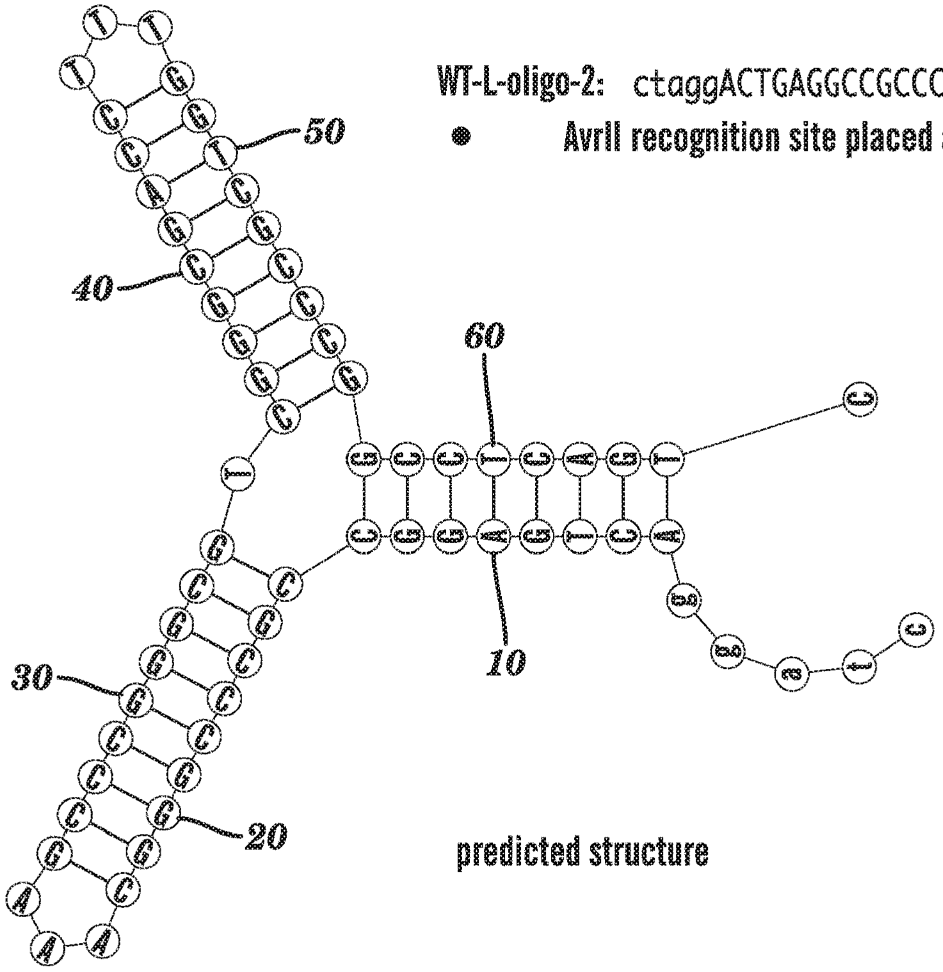
Figure 6C:
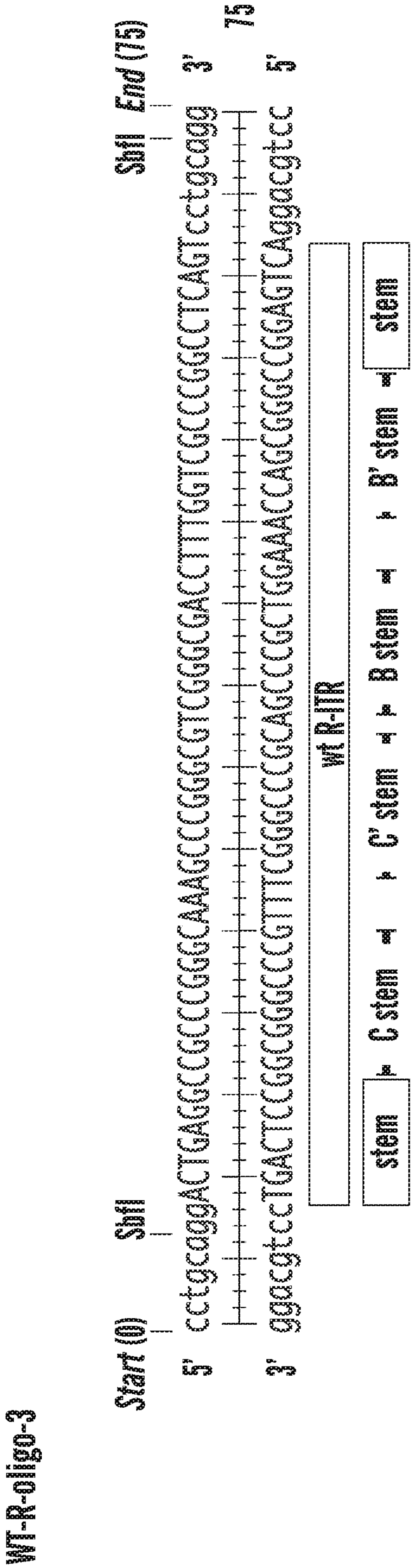
Figure 6C:
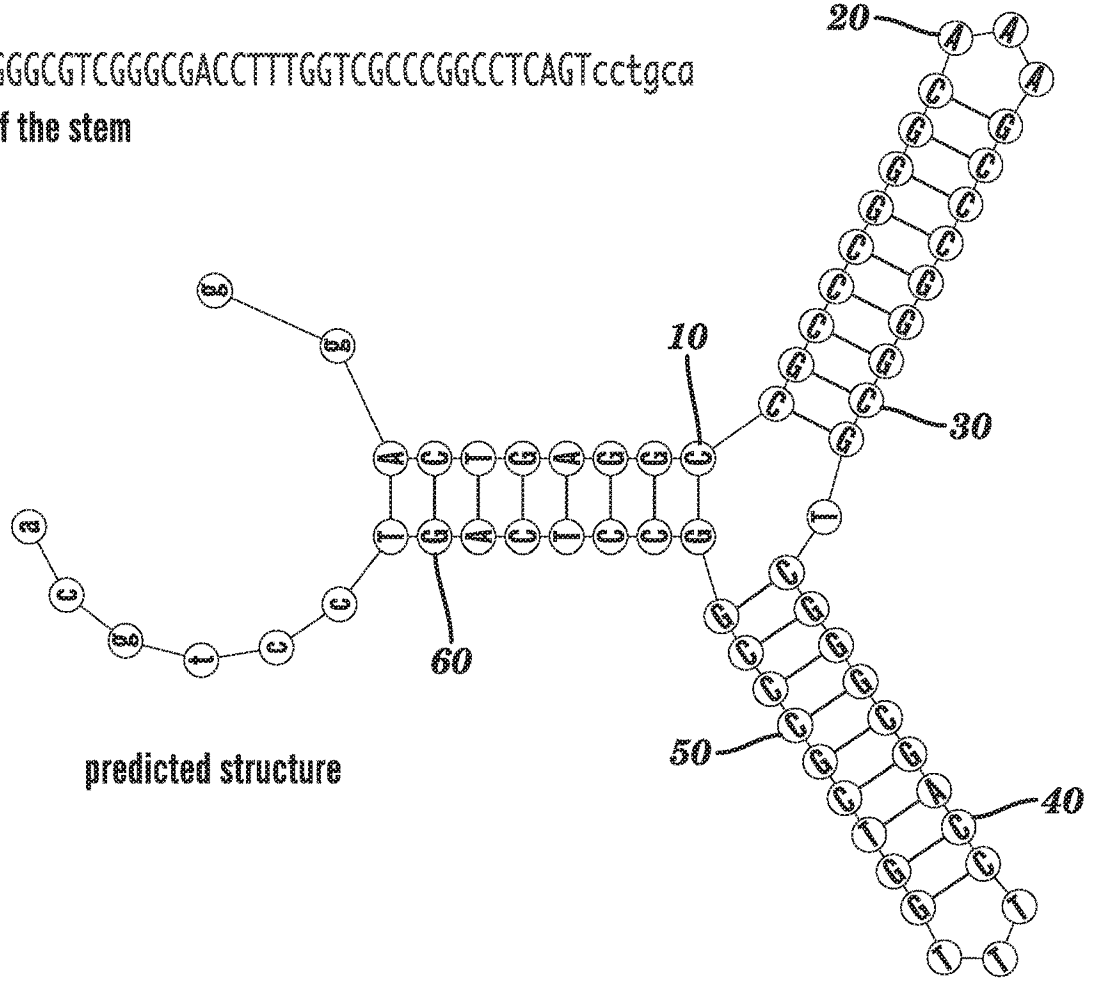
Figure 6D:
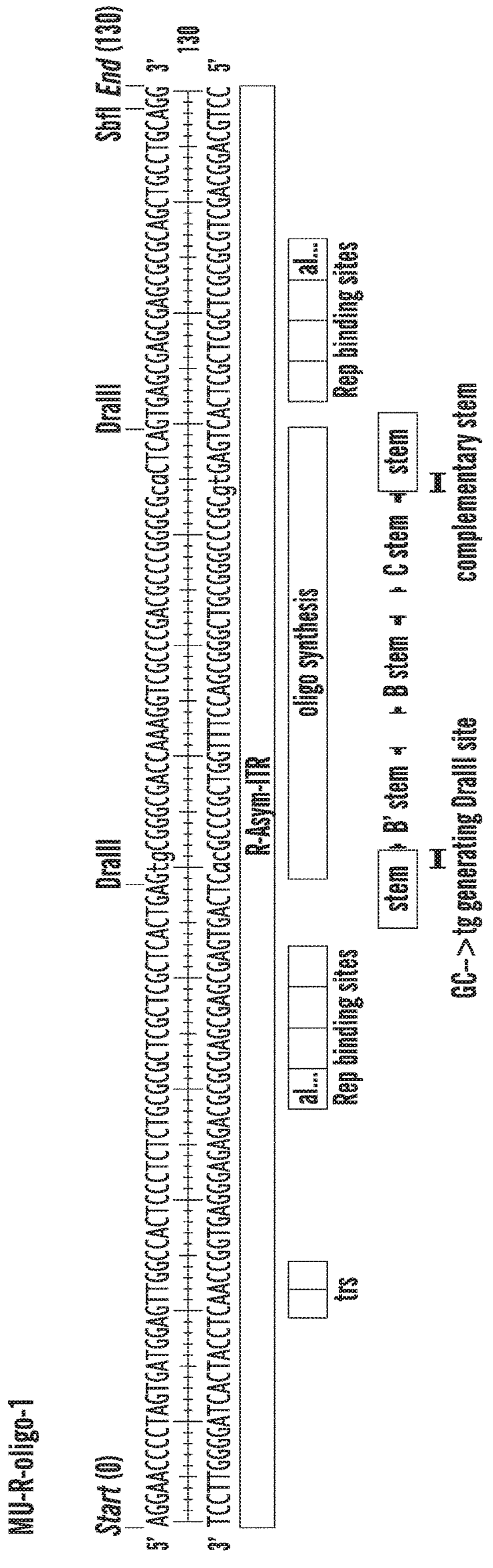
Figure 6D:
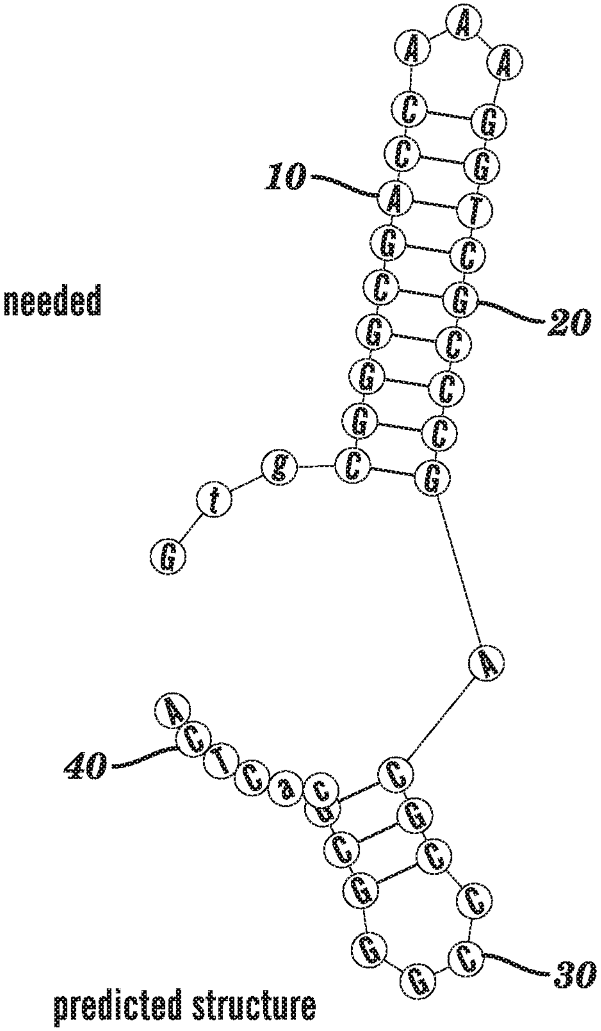

FIG. 5 is a gel confirming the production of ceDNA from multiple ceDNA plasmid constructs using the method described in the Examples. The ceDNA is confirmed by a characteristic band pattern in the gel, as discussed with respect to FIG. 4C above in the Examples.

C. Isolating and Purifying ceDNA Vectors:

Methods to generate and isolate a ceDNA vector, which is an exemplary closed-ended DNA vector, are described herein. For example, a closed-ended DNA vector, e.g., ceDNA vector produced by the synthetic methods described herein can be harvested or collected at an appropriate time after the last ligation reaction and can be optimized to achieve a high-yield production of the ceDNA vectors. The closed-ended DNA vector, e.g., ceDNA vectors can be purified by any means known to those of skill in the art for purification of DNA. In one embodiment, ceDNA vectors are purified as DNA molecules. Generally, any art-known nucleic acid purification methods can be adopted, as well as commercially available DNA extraction kits.

Alternatively, purification can be implemented by subjecting a reaction mixture to chromatographic separation. As one non-limiting example, the process can be performed by loading the reaction mixture on an ion exchange column (e.g. SARTOBIND Q®) which retains nucleic acids, and then eluting (e.g. with a 1.2 M NaCl solution) and performing a further chromatographic purification on a gel filtration column (e.g. 6 fast flow GE). The DNA vector, e.g., ceDNA vector is then recovered by, e.g., precipitation.

The presence of the ceDNA vector can be confirmed by digesting the vector DNA isolated from the cells with a restriction enzyme having a single recognition site on the DNA vector and analyzing both digested and undigested DNA material using gel electrophoresis to confirm the presence of characteristic bands of linear and continuous DNA as compared to linear and non-continuous DNA. FIG. 4B and FIG. 4C illustrate one embodiment for identifying the presence of the closed ended ceDNA vectors produced by the processes herein.

FIG. 5 of International application PCT/US18/49996 shows a gel confirming the production of ceDNA from multiple ceDNA-plasmid constructs using the method described in the Examples. The ceDNA is confirmed by a characteristic band pattern in the gel, as discussed with respect to FIG. 4C in the Examples.

In some embodiments, the closed-ended DNA vectors produced by the synthetic production methods disclosed herein can be delivered to a target cell in vitro or in vivo by various suitable methods as discussed herein. Vectors alone can be applied or injected. Vectors can be delivered to a cell without the help of a transfection reagent or other physical means. Alternatively, vectors can be delivered using a transfection reagent or other physical means that facilitates entry of DNA into a cell, e.g., liposomes, alcohols, polylysine-rich compounds, arginine-rich compounds calcium phosphate, microvesicles, microinjection, and the like.

D. Circular DNA Vectors Produced Using the Synthetic Production Method

Provided herein are various methods of in vitro production of DNA molecules and closed-ended DNA vectors. In some embodiments, the closed-ended DNA vector is a ceDNA vector, as described herein. In alternative embodiments, the closed-ended DNA vector is, e.g., a dumbbell DNA vector or a dog-bone DNA vector (see e.g., WO2010/0086626, the contents of which is incorporated by reference herein in its entirety). (2017): 65.

III. ceDNA Vector in General

In some embodiments, a closed-ended DNA vector produced using the synthetic process as described herein is a ceDNA vector, including ceDNA vectors that can express a transgene. The ceDNA vectors described herein are not limited by size, thereby permitting, for example, expression of all of the components necessary for expression of a transgene from a single vector. The ceDNA vector is preferably duplex, e.g. self-complementary, over at least a portion of the molecule, such as the expression cassette (e.g. ceDNA is not a double stranded circular molecule). The ceDNA vector has covalently closed ends, and thus is resistant to exonuclease digestion (e.g. exonuclease I or exonuclease III), e.g. for over an hour at 37° C.

In general, a ceDNA vector produced using the synthetic process as described herein, comprises in the 5' to 3' direction: a first adeno-associated virus (AAV) inverted terminal repeat (ITR), a nucleotide sequence of interest (for example an expression cassette as described herein) and a second AAV ITR. The ITR sequences selected from any of: (i) at least one WT ITR and at least one modified AAV inverted terminal repeat (mod-ITR) (e.g., asymmetric modified ITRs); (ii) two modified ITRs where the mod-ITR pair have a different three-dimensional spatial organization with respect to each other (e.g., asymmetric modified ITRs), or (iii) symmetrical or substantially symmetrical WT-WT ITR pair, where each WT-ITR has the same three-dimensional spatial organization, or (iv) symmetrical or substantially symmetrical modified ITR pair, where each mod-ITR has the same three-dimensional spatial organization.

Encompassed herein are methods and compositions comprising the ceDNA vector produced using the synthetic process as described herein, which may further include a delivery system, such as but not limited to, a liposome nanoparticle delivery system. Non-limiting exemplary liposome nanoparticle systems encompassed for use are disclosed herein. In some aspects, the disclosure provides for a lipid nanoparticle comprising ceDNA and an ionizable lipid. For example, a lipid nanoparticle formulation that is made and loaded with a ceDNA vector obtained by the process is disclosed in International Application PCT/US2018/050042, filed on Sep. 7, 2018, which is incorporated herein.

The ceDNA vectors produced using the synthetic process as described herein have no packaging constraints imposed by the limiting space within the viral capsid. This permits the insertion of control elements, e.g., regulatory switches as disclosed herein, large transgenes, multiple transgenes etc.

FIG. 1A-1E show schematics of non-limiting, exemplary ceDNA vectors, or the corresponding sequence of ceDNA plasmids. ceDNA vectors are capsid-free and can be obtained from a plasmid encoding in this order: a first ITR, an expression cassette comprising a transgene and a second ITR. The expression cassette may include one or more regulatory sequences that allows and/or controls the expression of the transgene, e.g., where the expression cassette can comprise one or more of, in this order: an enhancer/promoter, an ORF reporter (transgene), a post-transcription regulatory element (e.g., WPRE), and a polyadenylation and termination signal (e.g., BGH polyA).

The expression cassette can also comprise an internal ribosome entry site (IRES) and/or a 2A element. The cis-regulatory elements include, but are not limited to, a promoter, a riboswitch, an insulator, a mir-regulatable element, a post-transcriptional regulatory element, a tissue- and cell type-specific promoter and an enhancer. In some embodiments the ITR can act as the promoter for the transgene. In some embodiments, the ceDNA vector comprises additional components to regulate expression of the transgene, for example, a regulatory switch, which are described herein in the section entitled "Regulatory Switches" for controlling and regulating the expression of the transgene, and can include if desired, a regulatory switch which is a kill switch to enable controlled cell death of a cell comprising a ceDNA vector.

The expression cassette can comprise more than 4000 nucleotides, 5000 nucleotides, 10,000 nucleotides or 20,000 nucleotides, or 30,000 nucleotides, or 40,000 nucleotides or 50,000 nucleotides, or any range between about 4000-10,000 nucleotides or 10,000-50,000 nucleotides, or more than 50,000 nucleotides. In some embodiments, the expression cassette can comprise a transgene in the range of 500 to 50,000 nucleotides in length. In some embodiments, the expression cassette can comprise a transgene in the range of 500 to 75,000 nucleotides in length. In some embodiments, the expression cassette can comprise a transgene which is in the range of 500 to 10,000 nucleotides in length. In some embodiments, the expression cassette can comprise a transgene which is in the range of 1000 to 10,000 nucleotides in length. In some embodiments, the expression cassette can comprise a transgene which is in the range of 500 to 5,000 nucleotides in length. The ceDNA vectors do not have the size limitations of encapsidated AAV vectors, thus enable delivery of a large-size expression cassette to provide efficient transgene. In some embodiments, the ceDNA vector is devoid of prokaryote-specific methylation.

A ceDNA expression cassette can include, for example, an expressible exogenous sequence (e.g., open reading frame) or transgene that encodes a protein that is either absent, inactive, or insufficient activity in the recipient subject or a gene that encodes a protein having a desired biological or a therapeutic effect. The transgene can encode a gene product that can function to correct the expression of a defective gene or transcript. In principle, the expression cassette can include any gene that encodes a protein, polypeptide or RNA that is either reduced or absent due to a mutation or which conveys a therapeutic benefit when overexpressed is considered to be within the scope of the disclosure.

The expression cassette can comprise any transgene useful for treating a disease or disorder in a subject. A ceDNA vector produced using the synthetic process as described herein can be used to deliver and express any gene of interest in the subject, which includes but are not limited to, nucleic acids encoding polypeptides, or non-coding nucleic acids (e.g., RNAi, miRs etc.), as well as exogenous genes and nucleotide sequences, including virus sequences in a subjects' genome, e.g., HIV virus sequences and the like. Preferably a ceDNA vector disclosed herein is used for therapeutic purposes (e.g., for medical, diagnostic, or veterinary uses) or immunogenic polypeptides. In certain embodiments, a ceDNA vector is useful to express any gene of interest in the subject, which includes one or more polypeptides, peptides, ribozymes, peptide nucleic acids, siRNAs, RNAis, antisense oligonucleotides, antisense polynucleotides, or RNAs (coding or non-coding; e.g., siRNAs, shRNAs, micro-RNAs, and their antisense counterparts (e.g., antagoMiR)), antibodies, antigen binding fragments, or any combination thereof.

The expression cassette can also encode polypeptides, sense or antisense oligonucleotides, or RNAs (coding or non-coding; e.g., siRNAs, shRNAs, micro-RNAs, and their antisense counterparts (e.g., antagoMiR)). Expression cassettes can include an exogenous sequence that encodes a reporter protein to be used for experimental or diagnostic purposes, such as β-lactamase, β-galactosidase (LacZ), alkaline phosphatase, thymidine kinase, green fluorescent protein (GFP), chloramphenicol acetyltransferase (CAT), luciferase, and others well known in the art.

Sequences provided in the expression cassette, expression construct of a ceDNA vector described herein can be codon optimized for the target host cell. As used herein, the term "codon optimized" or "codon optimization" refers to the process of modifying a nucleic acid sequence for enhanced expression in the cells of the vertebrate of interest, e.g., mouse or human, by replacing at least one, more than one, or a significant number of codons of the native sequence (e.g., a prokaryotic sequence) with codons that are more frequently or most frequently used in the genes of that vertebrate. Various species exhibit particular bias for certain codons of a particular amino acid. Typically, codon optimization does not alter the amino acid sequence of the original translated protein. Optimized codons can be determined using e.g., Aptagen's Gene Forge® codon optimization and custom gene synthesis platform (Aptagen, Inc., 2190 Fox Mill Rd. Suite 300, Herndon, Va. 20171) or another publicly available database.

In some embodiments, a transgene expressed by the ceDNA vector is a therapeutic gene. In some embodiments, a therapeutic gene is an antibody, or antibody fragment, or antigen-binding fragment thereof, e.g., a neutralizing antibody or antibody fragment and the like.

In particular, a therapeutic gene is one or more therapeutic agent(s), including, but not limited to, for example, protein(s), polypeptide(s), peptide(s), enzyme(s), antibodies, antigen binding fragments, as well as variants, and/or active fragments thereof, for use in the treatment, prophylaxis, and/or amelioration of one or more symptoms of a disease, dysfunction, injury, and/or disorder. Exemplary therapeutic genes are described herein in the section entitled "Method of Treatment".

There are many structural features of ceDNA vectors that differ from plasmid-based expression vectors. ceDNA vectors produced by the synthetic methods herein may possess one or more of the following features: the lack of original (i.e. not inserted) bacterial DNA, the lack of a prokaryotic origin of replication, being self-containing, i.e., they do not require any sequences other than the two ITRs, including the Rep binding and terminal resolution sites (RBS and TRS), and an exogenous sequence between the ITRs, the presence of ITR sequences that form hairpins, and the absence of bacterial-type DNA methylation or indeed any other methylation associated with production in a given cell type and considered abnormal by a mammalian host. In general, it is preferred for the present vectors not to contain any prokaryotic DNA but it is contemplated that some prokaryotic DNA may be inserted as an exogenous sequence, as a non-limiting example in a promoter or enhancer region. Another important feature distinguishing ceDNA vectors from plasmid expression vectors is that ceDNA vectors are single-stranded linear DNA having closed ends, while plasmids are always double-stranded DNA.

ceDNA vectors produced by the synthetic methods provided herein preferably have a linear and continuous structure rather than a non-continuous structure, as determined by restriction enzyme digestion assay (FIG. 4C). The linear and continuous structure is believed to be more stable from attack by cellular endonucleases, as well as less likely to be recombined and cause mutagenesis. Thus, a ceDNA vector in the linear and continuous structure is a preferred embodiment. The continuous, linear, single strand intramolecular duplex ceDNA vector can have covalently bound terminal ends, without sequences encoding AAV capsid proteins. These ceDNA vectors are structurally distinct from plasmids (including ceDNA plasmids described herein), which are circular duplex nucleic acid molecules of bacterial origin. The complimentary strands of plasmids may be separated following denaturation to produce two nucleic acid molecules, whereas in contrast, ceDNA vectors, while having complimentary strands, are a single DNA molecule and therefore even if denatured, remain a single molecule. In some embodiments, ceDNA vectors as described herein can be produced without DNA base methylation of prokaryotic type, unlike plasmids. Therefore, the ceDNA vectors and ceDNA-plasmids are different both in term of structure (in particular, linear versus circular) and also in view of the methods used for producing and purifying these different objects (see below), and also in view of their DNA methylation which is of prokaryotic type for ceDNA-plasmids and of eukaryotic type for the ceDNA vector.

There are several advantages of using a ceDNA vector as described herein over plasmid-based expression vectors, such advantages include, but are not limited to: 1) plasmids contain bacterial DNA sequences and are subjected to prokaryotic-specific methylation, e.g., 6-methyl adenosine and 5-methyl cytosine methylation, whereas capsid-free AAV vector sequences are of eukaryotic origin and do not undergo prokaryotic-specific methylation; as a result, capsid-free AAV vectors are less likely to induce inflammatory and immune responses compared to plasmids; 2) while plasmids require the presence of a resistance gene during the production process, ceDNA vectors do not; 3) while a circular plasmid is not delivered to the nucleus upon introduction into a cell and requires overloading to bypass degradation by cellular nucleases, ceDNA vectors contain viral cis-elements, i.e., ITRs, that confer resistance to nucleases and can be designed to be targeted and delivered to the nucleus. It is hypothesized that the minimal defining elements indispensable for ITR function are a Rep-binding site (RBS; 5'-GCGCGCTCGCTCGCTC-3' (SEQ ID NO: 60) for AAV2) and a terminal resolution site (TRS; 5'-AGTTGG-3' (SEQ ID NO: 64) for AAV2) plus a variable palindromic sequence allowing for hairpin formation; and 4) ceDNA vectors do not have the over-representation of CpG dinucleotides often found in prokaryote-derived plasmids that reportedly binds a member of the Toll-like family of receptors, eliciting a T cell-mediated immune response. In contrast, transductions with capsid-free AAV vectors disclosed herein can efficiently target cell and tissue-types that are difficult to transduce with conventional AAV virions using various delivery reagent.

IV. ITRs

As disclosed herein, ceDNA vectors contain a transgene or heterologous nucleic acid sequence positioned between two inverted terminal repeat (ITR) sequences, where the ITR sequences can be an asymmetrical ITR pair or a symmetrical- or substantially symmetrical ITR pair, as these terms are defined herein. A ceDNA vector as disclosed herein can comprise ITR sequences that are selected from any of: (i) at least one WT ITR and at least one modified AAV inverted terminal repeat (mod-ITR) (e.g., asymmetric modified ITRs); (ii) two modified ITRs where the mod-ITR pair have a different three-dimensional spatial organization with respect to each other (e.g., asymmetric modified ITRs), or (iii) symmetrical or substantially symmetrical WT-WT ITR pair, where each WT-ITR has the same three-dimensional spatial organization, or (iv) symmetrical or substantially symmetrical modified ITR pair, where each mod-ITR has the same three-dimensional spatial organization, where the methods of the present disclosure may further include a delivery system, such as but not limited to a liposome nanoparticle delivery system.

In some embodiments, the ITR sequence can be from viruses of the Parvoviridae family, which includes two subfamilies: Parvovirinae, which infect vertebrates, and Densovirinae, which infect insects. The subfamily Parvovirinae (referred to as the parvoviruses) includes the genus Dependovirus, the members of which, under most conditions, require coinfection with a helper virus such as adenovirus or herpes virus for productive infection. The genus Dependovirus includes adeno-associated virus (AAV), which normally infects humans (e.g., serotypes 2, 3A, 3B, 5, and 6) or primates (e.g., serotypes 1 and 4), and related viruses that infect other warm-blooded animals (e.g., bovine, canine, equine, and ovine adeno-associated viruses). The parvoviruses and other members of the Parvoviridae family are generally described in Kenneth I. Berns, "Parvoviridae: The Viruses and Their Replication," Chapter 69 in FIELDS VIROLOGY (3d Ed. 1996).

While ITRs exemplified in the specification and Examples herein are AAV2 WT-ITRs, one of ordinary skill in the art is aware that one can as stated above use ITRs from any known parvovirus, for example a dependovirus such as AAV (e.g., AAV1, AAV2, AAV3, AAV4, AAV5, AAV 5, AAV7, AAV8, AAV9, AAV10, AAV 11, AAV12, AAVrh8, AAVrh10, AAV-DJ, and AAV-DJ8 genome. E.g., NCBI: NC 002077; NC 001401; NC001729; NC001829; NC006152; NC 006260; NC 006261), chimeric ITRs, or ITRs from any synthetic AAV. In some embodiments, the AAV can infect warm-blooded animals, e.g., avian (AAAV), bovine (BAAV), canine, equine, and ovine adeno-associated viruses. In some embodiments the ITR is from B19 parvovirus (GenBank Accession No: NC 000883), Minute Virus from Mouse (MVM) (GenBank Accession No. NC 001510); goose parvovirus (GenBank Accession No. NC 001701); snake parvovirus 1 (GenBank Accession No. NC 006148). In some embodiments, the 5' WT-ITR can be from one serotype and the 3' WT-ITR from a different serotype, as discussed herein.

An ordinarily skilled artisan is aware that ITR sequences have a common structure of a double-stranded Holliday junction, which typically is a T-shaped or Y-shaped hairpin structure (see e.g., FIG. 2A and FIG. 3A), where each WT-ITR is formed by two palindromic arms or loops (B-B' and C-C') embedded in a larger palindromic arm (A-A'), and a single stranded D sequence, (where the order of these palindromic sequences defines the flip or flop orientation of the ITR). See, for example, structural analysis and sequence comparison of ITRs from different AAV serotypes (AAV1-AAV6) and described in Grimm et al., J. Virology, 2006; 80(1); 426-439; Yan et al., J. Virology, 2005; 364-379; Duan et al., Virology 1999; 261; 8-14. One of ordinary skill in the art can readily determine WT-ITR sequences from any AAV serotype for use in a ceDNA vector or ceDNA-plasmid based on the exemplary AAV2 ITR sequences provided herein. See, for example, the sequence comparison of ITRs from different AAV serotypes (AAV1-AAV6, and avian AAV (AAAV) and bovine AAV (BAAV)) described in Grimm et al., J. Virology, 2006; 80(1); 426-439; that show the % identity of the left ITR of AAV2 to the left ITR from other serotypes: AAV-1 (84%), AAV-3 (86%), AAV-4 (79%), AAV-5 (58%), AAV-6 (left ITR) (100%) and AAV-6 (right ITR) (82%).

A. Symmetrical ITR pairs

In some embodiments, a ceDNA vector as described herein comprises, in the 5' to 3' direction: a first adeno-associated virus (AAV) inverted terminal repeat (ITR), a nucleotide sequence of interest (for example an expression cassette as described herein) and a second AAV ITR, where the first ITR (5' ITR) and the second ITR (3' ITR) are symmetric, or substantially symmetrical with respect to each other—that is, a ceDNA vector can comprise ITR sequences that have a symmetrical three-dimensional spatial organization such that their structure is the same shape in geometrical space, or have the same A, C-C' and B-B' loops in 3D space. In such an embodiment, a symmetrical ITR pair, or substantially symmetrical ITR pair can be modified ITRs (e.g., mod-ITRs) that are not wild-type ITRs. A mod-ITR pair can have the same sequence which has one or more modifications from wild-type ITR and are reverse complements (inverted) of each other. In alternative embodiments, a modified ITR pair are substantially symmetrical as defined herein, that is, the modified ITR pair can have a different sequence but have corresponding or the same symmetrical three-dimensional shape.

(i) Wildtype ITRs

In some embodiments, the symmetrical ITRs, or substantially symmetrical ITRs are wild type (WT-ITRs) as described herein. That is, both ITRs have a wild type sequence, but do not necessarily have to be WT-ITRs from the same AAV serotype. That is, in some embodiments, one WT-ITR can be from one AAV serotype, and the other WT-ITR can be from a different AAV serotype. In such an embodiment, a WT-ITR pair are substantially symmetrical as defined herein, that is, they can have one or more conservative nucleotide modification while still retaining the symmetrical three-dimensional spatial organization.

Accordingly, as disclosed herein, ceDNA vectors contain a transgene or heterologous nucleic acid sequence positioned between two flanking wild-type inverted terminal repeat (WT-ITR) sequences, that are either the reverse complement (inverted) of each other, or alternatively, are substantially symmetrical relative to each other—that is a WT-ITR pair have symmetrical three-dimensional spatial organization. In some embodiments, a wild-type ITR sequence (e.g. AAV WT-ITR) comprises a functional Rep binding site (RBS; e.g. 5'-GCGCGCTCGCTCGCTC-3' for AAV2, SEQ ID NO: 60) and a functional terminal resolution site (TRS; e.g. 5'-AGTT-3', SEQ ID NO: 62).

In one aspect, ceDNA vectors are obtainable from a vector polynucleotide that encodes a heterologous nucleic acid operatively positioned between two WT inverted terminal repeat sequences (WT-ITRs) (e.g. AAV WT-ITRs). That is, both ITRs have a wild type sequence, but do not necessarily have to be WT-ITRs from the same AAV serotype. That is, in some embodiments, one WT-ITR can be from one AAV serotype, and the other WT-ITR can be from a different AAV serotype. In such an embodiment, the WT-ITR pair are substantially symmetrical as defined herein, that is, they can have one or more conservative nucleotide modification while still retaining the symmetrical three-dimensional spatial organization. In some embodiments, the 5' WT-ITR is from one AAV serotype, and the 3' WT-ITR is from the same or a different AAV serotype. In some embodiments, the 5' WT-ITR and the 3'WT-ITR are mirror images of each other, that is they are symmetrical. In some embodiments, the 5' WT-ITR and the 3' WT-ITR are from the same AAV serotype.

WT ITRs are well known. In one embodiment the two ITRs are from the same AAV2 serotype. In certain embodiments one can use WT from other serotypes. There are a number of serotypes that are homologous, e.g. AAV2, AAV4, AAV6, AAV8. In one embodiment, closely homologous ITRs (e.g. ITRs with a similar loop structure) can be used. In another embodiment, one can use AAV WT ITRs that are more diverse, e.g., AAV2 and AAV5, and still another embodiment, one can use an ITR that is substantially WT—that is, it has the basic loop structure of the WT but some conservative nucleotide changes that do not alter or affect the properties. When using WT-ITRs from the same viral serotype, one or more regulatory sequences may further be used. In certain embodiments, the regulatory sequence is a regulatory switch that permits modulation of the activity of the ceDNA.

In some embodiments, one aspect of the technology described herein relates to a synthetically produced ceDNA vector, wherein the ceDNA vector comprises at least one heterologous nucleotide sequence, operably positioned between two wild-type inverted terminal repeat sequences (WT-ITRs), wherein the WT-ITRs can be from the same serotype, different serotypes or substantially symmetrical with respect to each other (i.e., have the symmetrical three-dimensional spatial organization such that their structure is the same shape in geometrical space, or have the same A, C-C' and B-B' loops in 3D space). In some embodiments, the symmetric WT-ITRs comprises a functional terminal resolution site and a Rep binding site. In some embodiments, the heterologous nucleic acid sequence encodes a transgene, and wherein the vector is not in a viral capsid.

In some embodiments, the WT-ITRs are the same but the reverse complement of each other. For example, the sequence AACG in the 5' ITR may be CGTT (i.e., the reverse complement) in the 3' ITR at the corresponding site. In one example, the 5' WT-ITR sense strand comprises the sequence of ATCGATCG and the corresponding 3' WT-ITR sense strand comprises CGATCGAT (i.e., the reverse complement of ATCGATCG). In some embodiments, the WT-ITRs ceDNA further comprises a terminal resolution site and a replication protein binding site (RPS) (sometimes referred to as a replicative protein binding site), e.g. a Rep binding site.

Exemplary WT-ITR sequences for use in the ceDNA vectors comprising WT-ITRs are shown in Table 2 herein, which shows pairs of WT-ITRs (5' WT-ITR and the 3' WT-ITR).

As an exemplary example, the present disclosure provides a synthetically produced ceDNA vector comprising a promoter operably linked to a transgene (e.g., heterologous nucleic acid sequence), with or without the regulatory switch, where the ceDNA is devoid of capsid proteins and is: (a) produced from a ceDNA-plasmid (e.g., see FIGS. 1F-1G) that encodes WT-ITRs, where each WT-ITR has the same number of intramolecularly duplexed base pairs in its hairpin secondary configuration (preferably excluding deletion of any AAA or TTT terminal loop in this configuration compared to these reference sequences), and (b) is identified as ceDNA using the assay for the identification of ceDNA by agarose gel electrophoresis under native gel and denaturing conditions in Example 1.

In some embodiments, the flanking WT-ITRs are substantially symmetrical to each other. In this embodiment the 5' WT-ITR can be from one serotype of AAV, and the 3' WT-ITR from a different serotype of AAV, such that the WT-ITRs are not identical reverse complements. For example, the 5' WT-ITR can be from AAV2, and the 3' WT-ITR from a different serotype (e.g. AAV1, 3, 4, 5, 6, 7, 8, 9, 10, 11, and 12. In some embodiments, WT-ITRs can be selected from two different parvoviruses selected from any to of: AAV1, AAV2, AAV3, AAV4, AAV5, AAV6, AAV7, AAV8, AAV9, AAV10, AAV11, AAV12, AAV13, snake parvovirus (e.g., royal python parvovirus), bovine parvovirus, goat parvovirus, avian parvovirus, canine parvovirus, equine parvovirus, shrimp parvovirus, porcine parvovirus, or insect AAV. In some embodiments, such a combination of WT ITRs is the combination of WT-ITRs from AAV2 and AAV6. In one embodiment, the substantially symmetrical WT-ITRs are when one is inverted relative to the other ITR at least 90% identical, at least 95% identical, at least 96% . . . 97% . . . 98% . . . 99% . . . 99.5% and all points in between, and has the same symmetrical three-dimensional spatial organization. In some embodiments, a WT-ITR pair are substantially symmetrical as they have symmetrical three-dimensional spatial organization, e.g., have the same 3D organization of the A, C-C'. B-B' and D arms. In one embodiment, a substantially symmetrical WT-ITR pair are inverted relative to the other, and are at least 95% identical, at least 96% . . . 97% . . . 98% . . . 99% . . . 99.5% and all points in between, to each other, and one WT-ITR retains the Rep-binding site (RBS) of 5'-GCGCGCTCGCTCGCTC-3' (SEQ ID NO: 60) and a terminal resolution site (trs). In some embodiments, a substantially symmetrical WT-ITR pair are inverted relative to each other, and are at least 95% identical, at least 96% . . . 97% . . . 98% . . . 99% . . . 99.5% and all points in between, to each other, and one WT-ITR retains the Rep-binding site (RBS) of 5'-GCGCGCTCGCTCGCTC-3' (SEQ ID NO: 60) and a terminal resolution site (trs) and in addition to a variable palindromic sequence allowing for hairpin secondary structure formation. Homology can be determined by standard means well known in the art such as BLAST (Basic Local Alignment Search Tool), BLASTN at default setting.

In some embodiments, the structural element of the ITR can be any structural element that is involved in the functional interaction of the ITR with a large Rep protein (e.g., Rep 78 or Rep 68). In certain embodiments, the structural element provides selectivity to the interaction of an ITR with a large Rep protein, i.e., determines at least in part which Rep protein functionally interacts with the ITR. In other embodiments, the structural element physically interacts with a large Rep protein when the Rep protein is bound to the ITR. Each structural element can be, e.g., a secondary structure of the ITR, a nucleotide sequence of the ITR, a spacing between two or more elements, or a combination of any of the above. In one embodiment, the structural elements are selected from the group consisting of an A and an A' arm, a B and a B' arm, a C and a C' arm, a D arm, a Rep binding site (RBE) and an RBE' (i.e., complementary RBE sequence), and a terminal resolution sire (trs).

By way of example only, Table 1 indicates exemplary combinations of WT-ITRs.

Table 1: Exemplary combinations of WT-ITRs from the same serotype or different serotypes, or different parvoviruses. The order shown is not indicative of the ITR position, for example, "AAV1, AAV2" demonstrates that the ceDNA can comprise a WT-AAV1 ITR in the 5' position, and a WT-AAV2 ITR in the 3' position, or vice versa, a WT-AAV2 ITR the 5' position, and a WT-AAV1 ITR in the 3' position. Abbreviations: AAV serotype 1 (AAV1), AAV serotype 2 (AAV2), AAV serotype 3 (AAV3), AAV serotype 4 (AAV4), AAV serotype 5 (AAV5), AAV serotype 6 (AAV6), AAV serotype 7 (AAV7), AAV serotype 8 (AAV8), AAV serotype 9 (AAV9), AAV serotype 10 (AAV10), AAV serotype 11 (AAV 11), or AAV serotype 12 (AAV12); AAVrh8, AAVrh10, AAV-DJ, and AAV-DJ8 genome (E.g., NCBI: NC 002077; NC 001401; NC001729; NC001829; NC006152; NC 006260; NC 006261), ITRs from warm-blooded animals (avian AAV (AAAV), bovine AAV (BAAV), canine, equine, and ovine AAV), ITRs from B19 parvoviris (GenBank Accession No: NC 000883), Minute Virus from Mouse (MVM) (GenBank Accession No. NC 001510); Goose: goose parvovirus (GenBank Accession No. NC 001701); snake: snake parvovirus 1 (GenBank Accession No. NC 006148).

TABLE 1

| | | | | |
|---|---|---|---|---|
| AAV1, AAV1 | AAV2, AAV2 | AAV3, AAV3 | AAV4, AAV4 | AAV5, AAV5 |
| AAV1, AAV2 | AAV2, AAV3 | AAV3, AAV4 | AAV4, AAV5 | AAV5, AAV6 |

TABLE 1-continued

| | | | | |
|---|---|---|---|---|
| AAV1, AAV3 | AAV2, AAV4 | AAV3, AAV5 | AAV4, AAV6 | AAV5, AAV7 |
| AAV1, AAV4 | AAV2, AAV5 | AAV3, AAV6 | AAV4, AAV7 | AAV5, AAV8 |
| AAV1, AAV5 | AAV2, AAV6 | AAV3, AAV7 | AAV4, AAV8 | AAV5, AAV9 |
| AAV1, AAV6 | AAV2, AAV7 | AAV3, AAV8 | AAV4, AAV9 | AAV5, AAV10 |
| AAV1, AAV7 | AAV2, AAV8 | AAV3, AAV9 | AAV4, AAV10 | AAV5, AAV11 |
| AAV1, AAV8 | AAV2, AAV9 | AAV3, AAV10 | AAV4, AAV11 | AAV5, AAV12 |
| AAV1, AAV9 | AAV2, AAV10 | AAV3, AAV11 | AAV4, AAV12 | AAV5, AAVRH8 |
| AAV1, AAV10 | AAV2, AAV11 | AAV3, AAV12 | AAV4, AAVRH8 | AAV5, AAVRH10 |
| AAV1, AAV11 | AAV2, AAV12 | AAV3, AAVRH8 | AAV4, AAVRH10 | AAV5, AAV13 |
| AAV1, AAV12 | AAV2, AAVRH8 | AAV3, AAVRH10 | AAV4, AAV13 | AAV5, AAVDJ |
| AAV1, AAVRH8 | AAV2, AAVRH10 | AAV3, AAV13 | AAV4, AAVDJ | AAV5, AAVDJ8 |
| AAV1, AAVRH10 | AAV2, AAV13 | AAV3, AAVDJ | AAV4, AAVDJ8 | AAV5, AVIAN |
| AAV1, AAV13 | AAV2, AAVDJ | AAV3, AAVDJ8 | AAV4, AVIAN | AAV5, BOVINE |
| AAV1, AAVDJ | AAV2, AAVDJ8 | AAV3, AVIAN | AAV4, BOVINE | AAV5, CANINE |
| AAV1, AAVDJ8 | AAV2, AVIAN | AAV3, BOVINE | AAV4, CANINE | AAV5, EQUINE |
| AAV1, AVIAN | AAV2, BOVINE | AAV3, CANINE | AAV4, EQUINE | AAV5, GOAT |
| AAV1, BOVINE | AAV2, CANINE | AAV3, EQUINE | AAV4, GOAT | AAV5, SHRIMP |
| AAV1, CANINE | AAV2, EQUINE | AAV3, GOAT | AAV4, SHRIMP | AAV5, PORCINE |
| AAV1, EQUINE | AAV2, GOAT | AAV3, SHRIMP | AAV4, PORCINE | AAV5, INSECT |
| AAV1, GOAT | AAV2, SHRIMP | AAV3, PORCINE | AAV4, INSECT | AAV5, OVINE |
| AAV1, SHRIMP | AAV2, PORCINE | AAV3, INSECT | AAV4, OVINE | AAV5, B19 |
| AAV1, PORCINE | AAV2, INSECT | AAV3, OVINE | AAV4, B19 | AAV5, MVM |
| AAV1, INSECT | AAV2, OVINE | AAV3, B19 | AAV4, MVM | AAV5, GOOSE |
| AAV1, OVINE | AAV2, B19 | AAV3, MVM | AAV4, GOOSE | AAV5, SNAKE |
| AAV1, B19 | AAV2, MVM | AAV3, GOOSE | AAV4, SNAKE | |
| AAV1, MVM | AAV2, GOOSE | AAV3, SNAKE | | |
| AAV1, GOOSE | AAV2, SNAKE | | | |
| AAV1, SNAKE | | | | |
| AAV6, AAV6 | AAV7, AAV7 | AAV8, AAV8 | AAV9, AAV9 | AAV10, AAV10 |
| AAV6, AAV7 | AAV7, AAV8 | AAV8, AAV9 | AAV9, AAV10 | AAV10, AAV11 |
| AAV6, AAV8 | AAV7, AAV9 | AAV8, AAV10 | AAV9, AAV11 | AAV10, AAV12 |
| AAV6, AAV9 | AAV7, AAV10 | AAV8, AAV11 | AAV9, AAV12 | AAV10, AAVRH8 |
| AAV6, AAV10 | AAV7, AAV11 | AAV8, AAV12 | AAV9, AAVRH8 | AAV10, AAVRH10 |
| AAV6, AAV11 | AAV7, AAV12 | AAV8, AAVRH8 | AAV9, AAVRH10 | AAV10, AAV13 |
| AAV6, AAV12 | AAV7, AAVRH8 | AAV8, AAVRH10 | AAV9, AAV13 | AAV10, AAVDJ |
| AAV6, AAVRH8 | AAV7, AAVRH10 | AAV8, AAV13 | AAV9, AAVDJ | AAV10, AAVDJ8 |
| AAV6, AAVRH10 | AAV7, AAV13 | AAV8, AAVDJ | AAV9, AAVDJ8 | AAV10, AVIAN |
| AAV6, AAV13 | AAV7, AAVDJ | AAV8, AAVDJ8 | AAV9, AVIAN | AAV10, BOVINE |
| AAV6, AAVDJ | AAV7, AAVDJ8 | AAV8, AVIAN | AAV9, BOVINE | AAV10, CANINE |
| AAV6, AAVDJ8 | AAV7, AVIAN | AAV8, BOVINE | AAV9, CANINE | AAV10, EQUINE |
| AAV6, AVIAN | AAV7, BOVINE | AAV8, CANINE | AAV9, EQUINE | AAV10, GOAT |
| AAV6, BOVINE | AAV7, CANINE | AAV8, EQUINE | AAV9, GOAT | AAV10, SHRIMP |
| AAV6, CANINE | AAV7, EQUINE | AAV8, GOAT | AAV9, SHRIMP | AAV10, PORCINE |
| AAV6, EQUINE | AAV7, GOAT | AAV8, SHRIMP | AAV9, PORCINE | AAV10, INSECT |
| AAV6, GOAT | AAV7, SHRIMP | AAV8, PORCINE | AAV9, INSECT | AAV10, OVINE |
| AAV6, SHRIMP | AAV7, PORCINE | AAV8, INSECT | AAV9, OVINE | AAV10, B19 |
| AAV6, PORCINE | AAV7, INSECT | AAV8, OVINE | AAV9, B19 | AAV10, MVM |
| AAV6, INSECT | AAV7, OVINE | AAV8, B19 | AAV9, MVM | AAV10, GOOSE |
| AAV6, OVINE | AAV7, B19 | AAV8, MVM | AAV9, GOOSE | AAV10, SNAKE |
| AAV6, B19 | AAV7, MVM | AAV8, GOOSE | AAV9, SNAKE | |
| AAV6, MVM | AAV7, GOOSE | AAV8, SNAKE | | |
| AAV6, GOOSE | AAV7, SNAKE | | | |
| AAV6, SNAKE | | | | |
| AAV11, AAV11 | AAV12, AAV12 | AAVRH8, AAVRH8 | AAVRH10, AAVRH10 | AAV13, AAV13 |
| AAV11, AAV12 | AAV12, AAVRH8 | AAVRH8, AAVRH10 | AAVRH10, AAV13 | AAV13, AAVDJ |
| AAV11, AAVRH8 | AAV12, AAVRH10 | AAVRH8, AAV13 | AAVRH10, AAVDJ | AAV13, AAVDJ8 |
| AAV11, AAVRH10 | AAV12, AAV13 | AAVRH8, AAVDJ | AAVRH10, AAVDJ8 | AAV13, AVIAN |
| AAV11, AAV13 | AAV12, AAVDJ | AAVRH8, AAVDJ8 | AAVRH10, AVIAN | AAV13, BOVINE |
| AAV11, AAVDJ | AAV12, AAVDJ8 | AAVRH8, AVIAN | AAVRH10, BOVINE | AAV13, CANINE |
| AAV11, AAVDJ8 | AAV12, AVIAN | AAVRH8, BOVINE | AAVRH10, CANINE | AAV13, EQUINE |
| AAV11, AVIAN | AAV12, BOVINE | AAVRH8, CANINE | AAVRH10, EQUINE | AAV13, GOAT |
| AAV11, BOVINE | AAV12, CANINE | AAVRH8, EQUINE | AAVRH10, GOAT | AAV13, SHRIMP |
| AAV11, CANINE | AAV12, EQUINE | AAVRH8, GOAT | AAVRH10, SHRIMP | AAV13, PORCINE |
| AAV11, EQUINE | AAV12, GOAT | AAVRH8, SHRIMP | AAVRH10, PORCINE | AAV13, INSECT |
| AAV11, GOAT | AAV12, SHRIMP | AAVRH8, PORCINE | AAVRH10, INSECT | AAV13, OVINE |
| AAV11, SHRIMP | AAV12, PORCINE | AAVRH8, INSECT | AAVRH10, OVINE | AAV13, B19 |
| AAV11, PORCINE | AAV12, INSECT | AAVRH8, OVINE | AAVRH10, B19 | AAV13, MVM |
| AAV11, INSECT | AAV12, OVINE | AAVRH8, B19 | AAVRH10, MVM | AAV13, GOOSE |
| AAV11, OVINE | AAV12, B19 | AAVRH8, MVM | AAVRH10, GOOSE | AAV13, SNAKE |
| AAV11, B19 | AAV12, MVM | AAVRH8, GOOSE | AAVRH10, SNAKE | |
| AAV11, MVM | AAV12, GOOSE | AAVRH8, SNAKE | | |
| AAV11, GOOSE | AAV12, SNAKE | | | |
| AAV11, SNAKE | | | | |
| AAVDJ, AAVDJ | AAVDJ8, AVVDJ8 | AVIAN, AVIAN | BOVINE, BOVINE | CANINE, CANINE |
| AAVDJ, AAVDJ8 | AAVDJ8, AVIAN | AVIAN, BOVINE | BOVINE, CANINE | CANINE, EQUINE |
| AAVDJ, AVIAN | AAVDJ8, BOVINE | AVIAN, CANINE | BOVINE, EQUINE | CANINE, GOAT |
| AAVDJ, BOVINE | AAVDJ8, CANINE | AVIAN, EQUINE | BOVINE, GOAT | CANINE, SHRIMP |
| AAVDJ, CANINE | AAVDJ8, EQUINE | AVIAN, GOAT | BOVINE, SHRIMP | CANINE, PORCINE |
| AAVDJ, EQUINE | AAVDJ8, GOAT | AVIAN, SHRIMP | BOVINE, PORCINE | CANINE, INSECT |
| AAVDJ, GOAT | AAVDJ8, SHRIMP | AVIAN, PORCINE | BOVINE, INSECT | CANINE, OVINE |

TABLE 1-continued

| | | | | |
|---|---|---|---|---|
| AAVDJ, SHRIMP | AAVDJ8, PORCINE | AVIAN, INSECT | BOVINE, OVINE | CANINE, B19 |
| AAVDJ, PORCINE | AAVDJ8, INSECT | AVIAN, OVINE | BOVINE, B19 | CANINE, MVM |
| AAVDJ, INSECT | AAVDJ8, OVINE | AVIAN, B19 | BOVINE, MVM | CANINE, GOOSE |
| AAVDJ, OVINE | AAVDJ8, B19 | AVIAN, MVM | BOVINE, GOOSE | CANINE, SNAKE |
| AAVDJ, B19 | AAVDJ8, MVM | AVIAN, GOOSE | BOVINE, SNAKE | |
| AAVDJ, MVM | AAVDJ8, GOOSE | AVIAN, SNAKE | | |
| AAVDJ, GOOSE | AAVDJ8, SNAKE | | | |
| AAVDJ, SNAKE | | | | |
| EQUINE, EQUINE | GOAT, GOAT | SHRIMP, SHRIMP | PORCINE, PORCINE | INSECT, INSECT |
| EQUINE, GOAT | GOAT, SHRIMP | SHRIMP, PORCINE | PORCINE, INSECT | INSECT, OVINE |
| EQUINE, SHRIMP | GOAT, PORCINE | SHRIMP, INSECT | PORCINE, OVINE | INSECT, B19 |
| EQUINE, PORCINE | GOAT, INSECT | SHRIMP, OVINE | PORCINE, B19 | INSECT, MVM |
| EQUINE, INSECT | GOAT, OVINE | SHRIMP, B19 | PORCINE, MVM | INSECT, GOOSE |
| EQUINE, OVINE | GOAT, B19 | SHRIMP, MVM | PORCINE, GOOSE | INSECT, SNAKE |
| EQUINE, B19 | GOAT, MVM | SHRIMP, GOOSE | PORCINE, SNAKE | |
| EQUINE, MVM | GOAT, GOOSE | SHRIMP, SNAKE | | |
| EQUINE, GOOSE | GOAT, SNAKE | | | |
| EQUINE, SNAKE | | | | |
| OVINE, OVINE | B19, B19 | MVM, MVM | GOOSE, GOOSE | SNAKE, SNAKE |
| OVINE, B19 | B19, MVM | MVM, GOOSE | GOOSE, SNAKE | |
| OVINE, MVM | B19, GOOSE | MVM, SNAKE | | |
| OVINE, GOOSE | B19, SNAKE | | | |
| OVINE, SNAKE | | | | |

By way of example only, Table 2 shows the sequences of exemplary WT-ITRs from some different AAV serotypes.

TABLE 2

| AAV serotype | 5' WT-ITR (LEFT) | 3' WT-ITR (RIGHT) |
|---|---|---|
| AAV1 | 5'-<br>TTGCCCACTCCCTCTCTGCGCGCTCGC<br>TCGCTCGGTGGGGCCTGCGGACCAAA<br>GGTCCGCAGACGGCAGAGGTCTCCTC<br>TGCCGGCCCCACCGAGCGAGCGACGC<br>GCGCAGAGAGGGAGTGGGCAACTCCA<br>TCACTAGGGTAA-3'<br>(SEQ ID NO: 5) | 5'-<br>TTACCCTAGTGATGGAGTTGCCCACTC<br>CCTCTCTGCGCGCGTCGCTCGCTCGGT<br>GGGGCCGGCAGAGGAGACCTCTGCCG<br>TCTGCGGACCTTTGGTCCGCAGGCCCC<br>ACCGAGCGAGCGAGCGCGCAGAGAGG<br>GAGTGGGCAA-3' (SEQ ID NO: 10) |
| AAV2 | CCTGCAGGCAGCTGCGCGCTCGCTCG<br>CTCACTGAGGCCGCCCGGGCAAAGCC<br>CGGGCGTCGGGCGACCTTTGGTCGCC<br>CGGCCTCAGTGAGCGAGCGAGCGCGC<br>AGAGAGGGAGTGGCCAACTCCATCAC<br>TAGGGGTTCCT (SEQ ID NO: 2) | AGGAACCCCTAGTGATGGAGTTGGCCA<br>CTCCCTCTCTGCGCGCTCGCTCGCTCAC<br>TGAGGCCGGGCGACCAAAGGTCGCCC<br>GACGCCCGGGCTTTGCCCGGGCGGCCT<br>CAGTGAGCGAGCGAGCGCGCAGCTGC<br>CTGCAGG (SEQ ID NO: 1) |
| AAV3 | 5'-<br>TTGGCCACTCCCTCTATGCGCACTCGC<br>TCGCTCGGTGGGGCCTGGCGACCAAA<br>GGTCGCCAGACGGACGTGGGTTTCCA<br>CGTCCGGCCCCACCGAGCGAGCGAGT<br>GCGCATAGAGGGAGTGGCCAACTCCA<br>TCACTAGAGGTAT-3' (SEQ ID NO:6) | 5'-<br>ATACCTCTAGTGATGGAGTTGGCCACT<br>CCCTCTATGCGCACTCGCTCGCTCGGT<br>GGGGCCGGACGTGGAAACCCACGTCC<br>GTCTGGCGACCTTTGGTCGCCAGGCCC<br>CACCGAGCGAGCGAGTGCGCATAGAG<br>GGAGTGGCCAA-3' (SEQ ID NO: 11) |
| AAV4 | 5'-<br>TTGGCCACTCCCTCTATGCGCGCTCGC<br>TCACTCACTCGGCCCTGGAGACCAAA<br>GGTCTCCAGACTGCCGGCCTCTGGCC<br>GGCAGGGCCGAGTGAGTGAGCGAGC<br>GCGCATAGAGGGAGTGGCCAACT-3'<br>(SEQ ID NO: 7) | 5'-<br>AGTTGGCCACATTAGCTATGCGCGCTC<br>GCTCACTCACTCGGCCCTGGAGACCAA<br>AGGTCTCCAGACTGCCGGCCTCTGGCC<br>GGCAGGGCCGAGTGAGTGAGCGAGCG<br>CGCATAGAGGGAGTGGCCAA-3' (SEQ ID<br>NO: 12) |
| AAV5 | 5'-<br>TCCCCCCTGTCGCGTTCGCTCGCTCGC<br>TGGCTCGTTTGGGGGGGCGACGGCCA<br>GAGGGCCGTCGTCTGGCAGCTCTTTG<br>AGCTGCCACCCCCCCAAACGAGCCAG<br>CGAGCGAGCGAACGCGACAGGGGGG<br>AGAGTGCCACACTCTCAAGCAAGGGG<br>GTTTTGTAAG-3' (SEQ ID NO: 8) | 5'-<br>CTTACAAAACCCCCTTGCTTGAGAGTG<br>TGGCACTCTCCCCCCTGTCGCGTTCGCT<br>CGCTCGCTGGCTCGTTTGGGGGGGTGG<br>CAGCTCAAAGAGCTGCCAGACGACGG<br>CCCTCTGGCCGTCGCCCCCCCAAACGA<br>GCCAGCGAGCGAGCGAACGCGACAGG<br>GGGGA-3' (SEQ ID NO: 13) |
| AAV6 | 5'-<br>TTGCCCACTCCCTCTAATGCGCGCTCG<br>CTCGCTCGGTGGGGCCTGCGGACCAA<br>AGGTCCGCAGACGGCAGAGGTCTCCT | 5'-<br>ATACCCCTAGTGATGGAGTTGCCCACT<br>CCCTCTATGCGCGCTCGCTCGCTCGGT<br>GGGGCCGGCAGAGGAGACCTCTGCCG |

TABLE 2-continued

| AAV serotype | 5' WT-ITR (LEFT) | 3' WT-ITR (RIGHT) |
|---|---|---|
| | CTGCCGGCCCCACCGAGCGAGCGAGC GCGCATAGAGGGAGTGGGCAACTCCA TCACTAGGGGTAT-3' (SEQ ID NO: 9) | TCTGCGGACCTTTGGTCCGCAGGCCCC ACCGAGCGAGCGAGCGCGCATTAGAG GGAGTGGGCAA (SEQ ID NO: 14) |

In some embodiments, the nucleotide sequence of the WT-ITR sequence can be modified (e.g., by modifying 1, 2, 3, 4 or 5, or more nucleotides or any range therein), whereby the modification is a substitution for a complementary nucleotide, e.g., G for a C, and vice versa, and T for an A, and vice versa.

In certain embodiments of the present invention, the synthetically produced ceDNA vector does not have a WT-ITR consisting of the nucleotide sequence selected from any of: SEQ ID NOs: 1, 2, 5-14. In alternative embodiments of the present invention, if a ceDNA vector has a WT-ITR comprising the nucleotide sequence selected from any of: SEQ ID NOs: 1, 2, 5-14, then the flanking ITR is also WT and the ceDNA vector comprises a regulatory switch, e.g., as disclosed herein and in International application PCT/US18/49996 (e.g., see Table 11 of PCT/US18/49996). In some embodiments, the ceDNA vector comprises a regulatory switch as disclosed herein and a WT-ITR selected having the nucleotide sequence selected from any of the group consisting of: SEQ ID NO: 1, 2, 5-14.

Figure 2A:
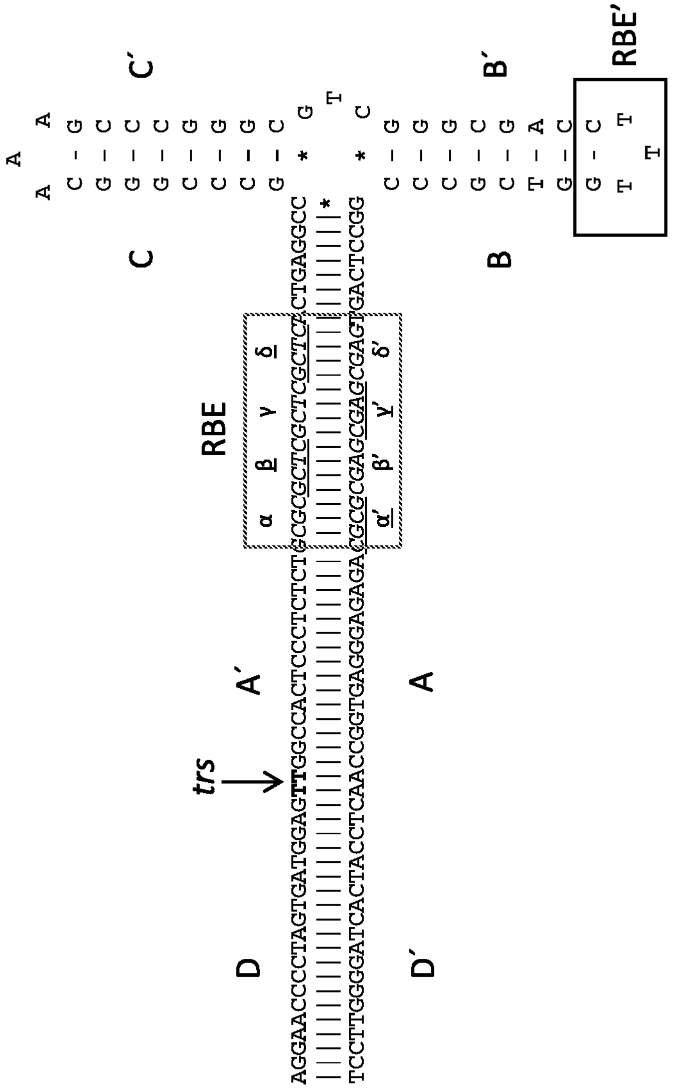
FIG. 2A provides the T-shaped stem-loop structure of a wild-type left ITR of AAV2 (SEQ ID NO: 52) with identification of A-A' arm, B-B' arm, C-C' arm, two Rep binding sites (RBE and RBE') and also shows the terminal resolution site (trs). The RBE contains a series of 4 duplex tetramers that are believed to interact with either Rep 78 or Rep 68. In addition, the RBE' is also believed to interact with Rep complex assembled on the wild-type ITR or mutated ITR in the construct. The D and D' regions contain transcription factor binding sites and other conserved structure.
Figure 2B:
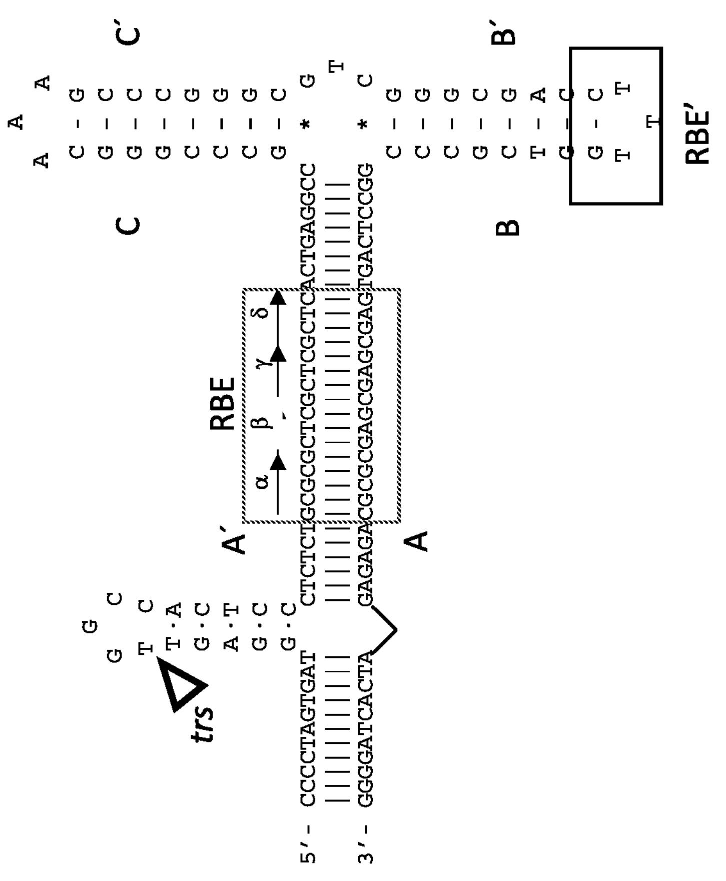
FIG. 2B shows proposed Rep-catalyzed nicking and ligating activities in a wild-type left ITR (SEQ ID NO: 53), including the T-shaped stem-loop structure of the wild-type left ITR of AAV2 with identification of A-A' arm, B-B' arm, C-C' arm, two Rep Binding sites (RBE and RBE') and also shows the terminal resolution site (trs), and the D and D' region comprising several transcription factor binding sites and other conserved structure.
Figure 3A:
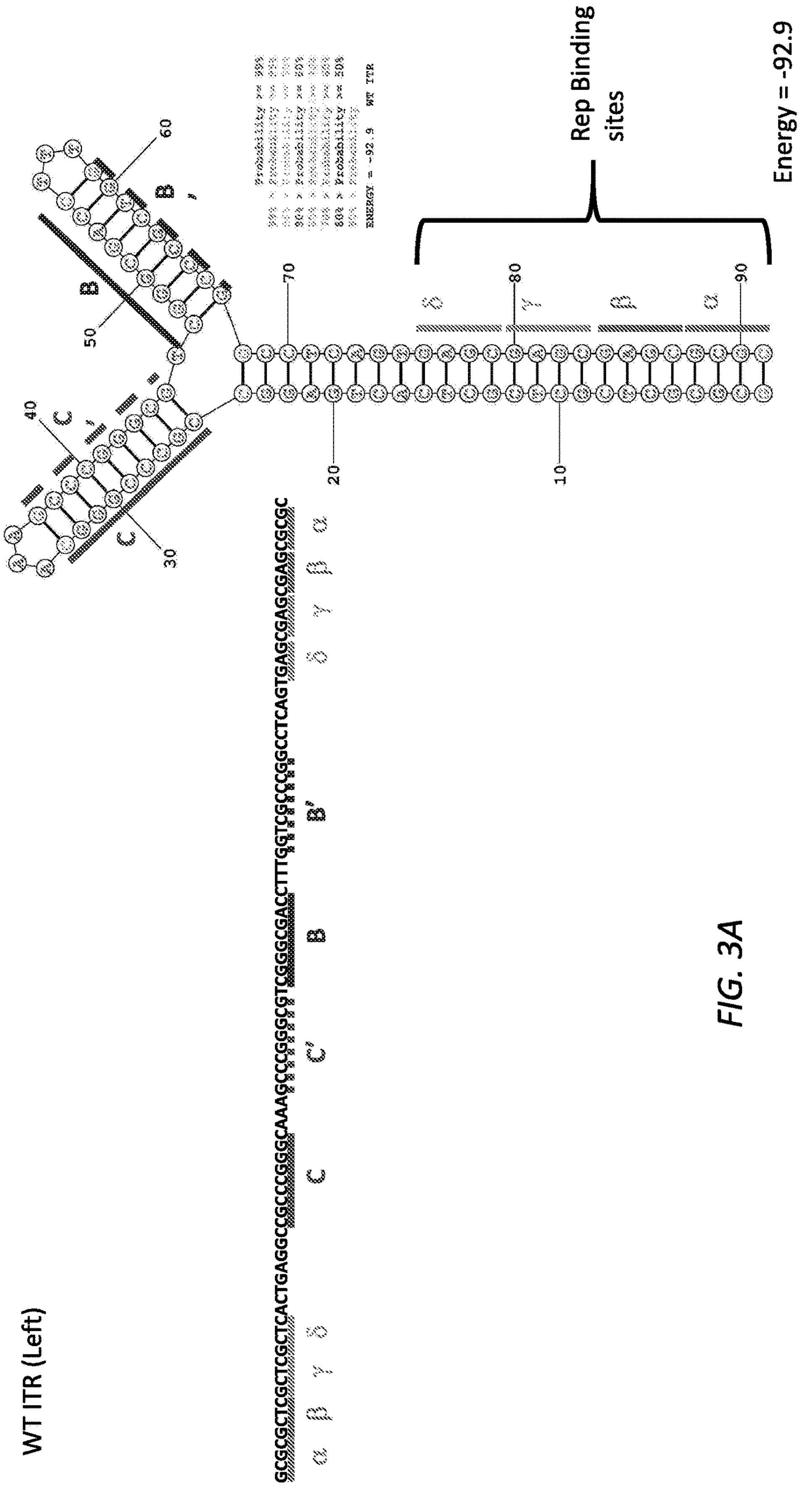
FIG. 3A provides the primary structure (polynucleotide sequence) (left) and the secondary structure (right) of the RBE-containing portions of the A-A' arm, and the C-C' and B-B' arm of the wild type left AAV2 ITR (SEQ ID NO: 54).

The ceDNA vector described herein can include WT-ITR structures that retains an operable RBE, trs and RBE' portion. FIG. 2A and FIG. 2B, using wild-type ITRs for exemplary purposes, show one possible mechanism for the operation of a trs site within a wild type ITR structure portion of a ceDNA vector. In some embodiments, the ceDNA vector contains one or more functional WT-ITR polynucleotide sequences that comprise a Rep-binding site (RBS; 5'-GCGCGCTCGCTCGCTC-3' (SEQ ID NO: 60) for AAV2) and a terminal resolution site (TRS; 5'-AGTT (SEQ ID NO: 62)). In some embodiments, at least one WT-ITR is functional. In alternative embodiments, where a ceDNA vector comprises two WT-ITRs that are substantially symmetrical to each other, at least one WT-ITR is functional and at least one WT-ITR is non-functional.

B. Modified ITRs (Mod-ITRs) in General for ceDNA Vectors Comprising Asymmetric ITR Pairs or Symmetric ITR Pairs As discussed herein, a synthetically produced ceDNA vector can comprise a symmetrical ITR pair or an asymmetrical ITR pair. In both instances, one or both of the ITRs can be modified ITRs—the difference being that in the first instance (i.e., symmetric mod-ITRs), the mod-ITRs have the same three-dimensional spatial organization (i.e., have the same A-A', C-C' and B-B' arm configurations), whereas in the second instance (i.e., asymmetric mod-ITRs), the mod-ITRs have a different three-dimensional spatial organization (i.e., have a different configuration of A-A', C-C' and B-B' arms).

In some embodiments, a modified ITR is an ITRs that is modified by deletion, insertion, and/or substitution as compared to a wild-type ITR sequence (e.g. AAV ITR). In some embodiments, at least one of the ITRs in the ceDNA vector comprises a functional Rep binding site (RBS; e.g. 5'-GCGCGCTCGCTCGCTC-3' for AAV2, SEQ ID NO: 60) and a functional terminal resolution site (TRS; e.g. 5'-AGTT-3', SEQ ID NO: 62.) In one embodiment, at least one of the ITRs is a non-functional ITR. In one embodiment, the different or modified ITRs are not each wild type ITRs from different serotypes.

Specific alterations and mutations in the ITRs are described in detail herein, but in the context of ITRs, "altered" or "mutated" or "modified", it indicates that nucleotides have been inserted, deleted, and/or substituted relative to the wild-type, reference, or original ITR sequence. The altered or mutated ITR can be an engineered ITR. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature.

In some embodiments, a mod-ITR may be synthetic. In one embodiment, a synthetic ITR is based on ITR sequences from more than one AAV serotype. In another embodiment, a synthetic ITR includes no AAV-based sequence. In yet another embodiment, a synthetic ITR preserves the ITR structure described above although having only some or no AAV-sourced sequence. In some aspects, a synthetic ITR may interact preferentially with a wild type Rep or a Rep of a specific serotype, or in some instances will not be recognized by a wild-type Rep and be recognized only by a mutated Rep.

The skilled artisan can determine the corresponding sequence in other serotypes by known means. For example, determining if the change is in the A, A', B, B', C, C' or D region and determine the corresponding region in another serotype. One can use BLAST® (Basic Local Alignment Search Tool) or other homology alignment programs at default status to determine the corresponding sequence. The invention further provides populations and pluralities of ceDNA vectors comprising mod-ITRs from a combination of different AAV serotypes—that is, one mod-ITR can be from one AAV serotype and the other mod-ITR can be from a different serotype. Without wishing to be bound by theory, in one embodiment one ITR can be from or based on an AAV2 ITR sequence and the other ITR of the ceDNA vector can be from or be based on any one or more ITR sequence of AAV serotype 1 (AAV1), AAV serotype 4 (AAV4), AAV serotype 5 (AAV5), AAV serotype 6 (AAV6), AAV serotype 7 (AAV7), AAV serotype 8 (AAV8), AAV serotype 9 (AAV9), AAV serotype 10 (AAV10), AAV serotype 11 (AAV11), or AAV serotype 12 (AAV12).

Any parvovirus ITR can be used as an ITR or as a base ITR for modification. Preferably, the parvovirus is a dependovirus. More preferably AAV. The serotype chosen can be based upon the tissue tropism of the serotype. AAV2 has a broad tissue tropism, AAV1 preferentially targets to neuronal and skeletal muscle, and AAV5 preferentially targets neuronal, retinal pigmented epithelia, and photoreceptors. AAV6 preferentially targets skeletal muscle and lung. AAV8 preferentially targets liver, skeletal muscle, heart, and pancreatic tissues. AAV9 preferentially targets liver, skeletal and lung tissue. In one embodiment, the modified ITR is based on an AAV2 ITR.

More specifically, the ability of a structural element to functionally interact with a particular large Rep protein can be altered by modifying the structural element. For example, the nucleotide sequence of the structural element can be modified as compared to the wild-type sequence of the ITR. In one embodiment, the structural element (e.g., A arm, A' arm, B arm, B' arm, C arm, C' arm, D arm, RBE, RBE', and trs) of an ITR can be removed and replaced with a wild-type structural element from a different parvovirus. For example, the replacement structure can be from AAV1, AAV2, AAV3, AAV4, AAV5, AAV6, AAV7, AAV8, AAV9, AAV10, AAV11, AAV12, AAV13, snake parvovirus (e.g., royal python parvovirus), bovine parvovirus, goat parvovirus, avian parvovirus, canine parvovirus, equine parvovirus, shrimp parvovirus, porcine parvovirus, or insect AAV. For example, the ITR can be an AAV2 ITR and the A or A' arm or RBE can be replaced with a structural element from AAV5. In another example, the ITR can be an AAV5 ITR and the C or C' arms, the RBE, and the trs can be replaced with a structural element from AAV2. In another example, the AAV ITR can be an AAV5 ITR with the B and B' arms replaced with the AAV2 ITR B and B' arms.

By way of example only, Table 3 indicates exemplary modifications of at least one nucleotide (e.g., a deletion, insertion and/or substitution) in regions of a modified ITR, where X is indicative of a modification of at least one nucleic acid (e.g., a deletion, insertion and/or substitution) in that section relative to the corresponding wild-type ITR. In some embodiments, any modification of at least one nucleotide (e.g., a deletion, insertion and/or substitution) in any of the regions of C and/or C' and/or B and/or B' retains three sequential T nucleotides (i.e., TTT) in at least one terminal loop. For example, if the modification results in any of: a single arm ITR (e.g., single C-C' arm, or a single B-B' arm), or a modified C-B' arm or C'-B arm, or a two arm ITR with at least one truncated arm (e.g., a truncated C-C' arm and/or truncated B-B' arm), at least the single arm, or at least one of the arms of a two arm ITR (where one arm can be truncated) retains three sequential T nucleotides (i.e., TTT) in at least one terminal loop. In some embodiments, a truncated C-C' arm and/or a truncated B-B' arm has three sequential T nucleotides (i.e., TTT) in the terminal loop.

TABLE 3

Exemplary combinations of modifications of at least one nucleotide (e.g., a deletion, insertion and/ or substitution) to different B-B' and C-C' regions or arms of ITRs (X indicates a nucleotide modification, e.g., addition, deletion or substitution of at least one nucleotide in the region).

| B region | B' region | C region | C' region |
|---|---|---|---|
| X | | | |
| | X | | |
| X | X | | |
| | | X | |
| | | | X |
| | | X | X |
| X | | X | |
| X | | | X |
| | X | X | |
| | X | | X |
| X | X | X | |
| X | X | | X |
| X | | X | X |
| | X | X | X |
| X | X | X | X |

In some embodiments, mod-ITR for use in a synthetically produced ceDNA vector comprising an asymmetric ITR pair, or a symmetric mod-ITR pair as disclosed herein can comprise any one of the combinations of modifications shown in Table 3, and also a modification of at least one nucleotide in any one or more of the regions selected from: between A' and C, between C and C', between C' and B, between B and B' and between B' and A. In some embodiments, any modification of at least one nucleotide (e.g., a deletion, insertion and/or substitution) in the C or C' or B or B' regions, still preserves the terminal loop of the stem-loop. In some embodiments, any modification of at least one nucleotide (e.g., a deletion, insertion and/or substitution) between C and C' and/or B and B' retains three sequential T nucleotides (i.e., TTT) in at least one terminal loop. In alternative embodiments, any modification of at least one nucleotide (e.g., a deletion, insertion and/or substitution) between C and C' and/or B and B' retains three sequential A nucleotides (i.e., AAA) in at least one terminal loop In some embodiments, a modified ITR for use herein can comprise any one of the combinations of modifications shown in Table 3, and also a modification of at least one nucleotide (e.g., a deletion, insertion and/or substitution) in any one or more of the regions selected from: A', A and/or D. For example, in some embodiments, a modified ITR for use herein can comprise any one of the combinations of modifications shown in Table 3, and also a modification of at least one nucleotide (e.g., a deletion, insertion and/or substitution) in the A region. In some embodiments, a modified ITR for use herein can comprise any one of the combinations of modifications shown in Table 3, and also a modification of at least one nucleotide (e.g., a deletion, insertion and/or substitution) in the A' region. In some embodiments, a modified ITR for use herein can comprise any one of the combinations of modifications shown in Table 3, and also a modification of at least one nucleotide (e.g., a deletion, insertion and/or substitution) in the A and/or A' region. In some embodiments, a modified ITR for use herein can comprise any one of the combinations of modifications shown in Table 3, and also a modification of at least one nucleotide (e.g., a deletion, insertion and/or substitution) in the D region.

In one embodiment, the nucleotide sequence of the structural element can be modified (e.g., by modifying 1, 2, 3, 4, 5, 6, 7, 8, 9, 10, 11, 12, 13, 14, 15, 16, 17, 18, 19, or 20 or more nucleotides or any range therein) to produce a modified structural element. In one embodiment, the specific modifications to the ITRs are exemplified herein (e.g., SEQ ID NOS: 3, 4, 15-47, 101-116 or 165-187, or shown in FIG. 7A-7B of PCT/US2018/064242, filed on Dec. 6, 2018 (e.g., SEQ ID Nos 97-98, 101-103, 105-108, 111-112, 117-134, 545-54 in PCT/US2018/064242). In some embodiments, an ITR can be modified (e.g., by modifying 1, 2, 3, 4, 5, 6, 7, 8, 9, 10, 11, 12, 13, 14, 15, 16, 17, 18, 19, or 20 or more nucleotides or any range therein). In other embodiments, the ITR can have at least 80%, at least 85%, at least 90%, at least 95%, at least 96%, at least 97%, at least 98%, at least 99%, or more sequence identity with one of the modified ITRs of SEQ ID NOS: 3, 4, 15-47, 101-116 or 165-187, or the RBE-containing section of the A-A' arm and C-C' and B-B' arms of SEQ ID NO: 3, 4, 15-47, 101-116 or 165-187, or shown in Tables 2-9 (i.e., SEQ ID NO: 110-112, 115-190, 200-468) of International application PCT/US18/49996, which is incorporated herein in its entirety by reference.

Figure 3B:
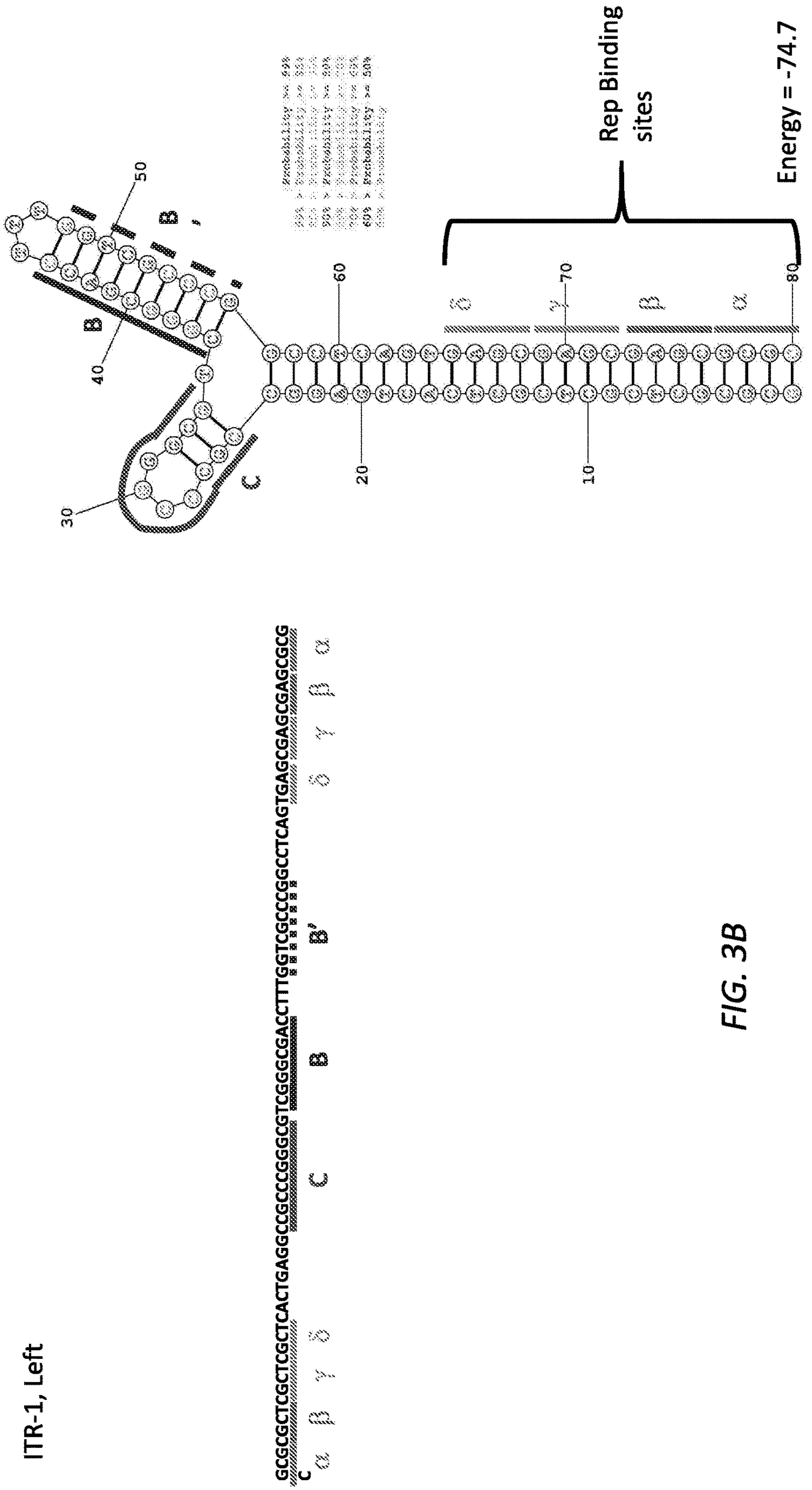
FIG. 3B shows an exemplary mutated ITR (also referred to as a modified ITR) sequence for the left ITR. Shown is the primary structure (left) and the predicted secondary structure (right) of the RBE portion of the A-A' arm, the C arm and B-B' arm of an exemplary mutated left ITR (ITR-1, left) (SEQ ID NO: 113).
Figure 3C:
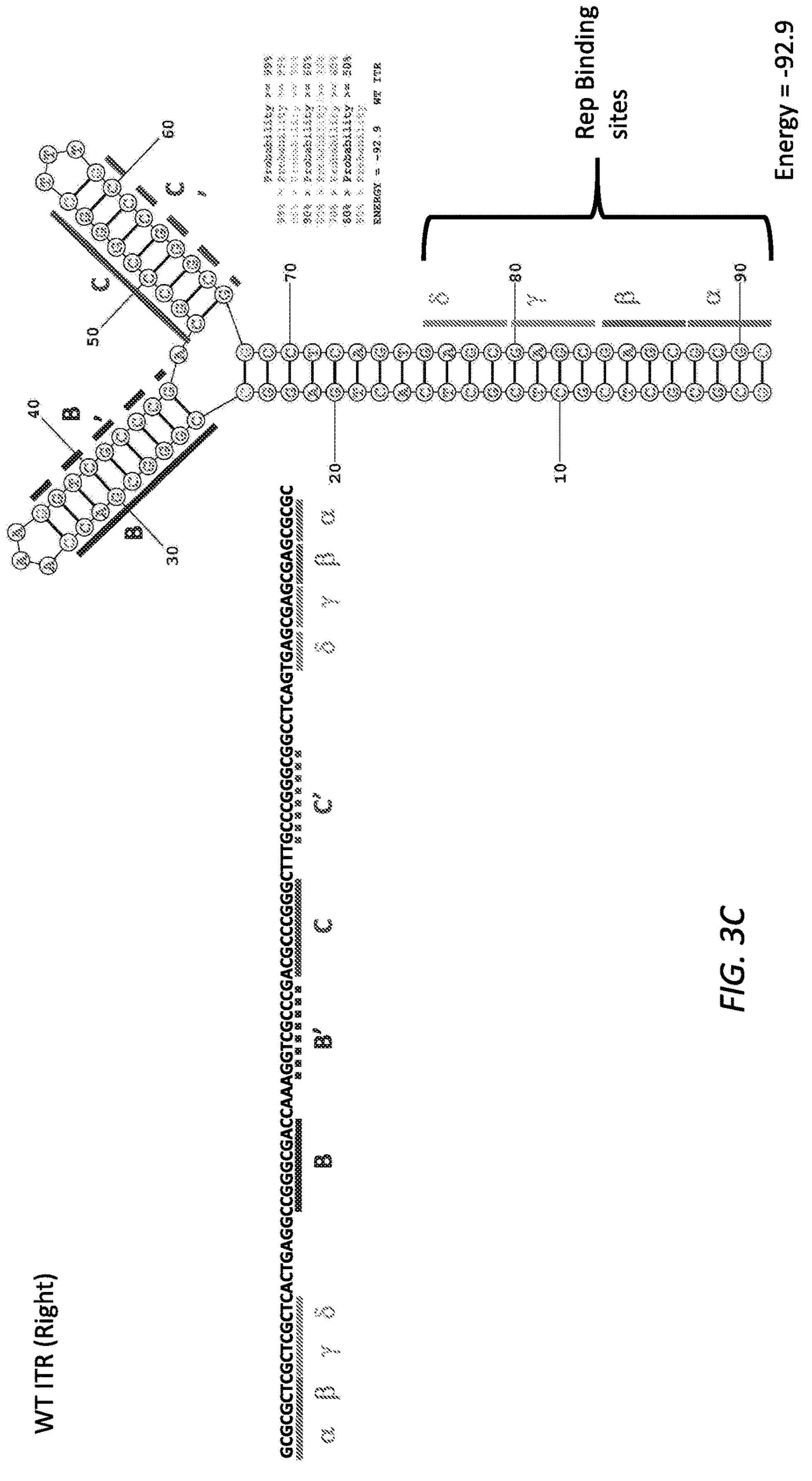
FIG. 3C shows the primary structure (left) and the secondary structure (right) of the RBE-containing portion of the A-A' loop, and the B-B' and C-C' arms of wild type right AAV2 ITR (SEQ ID NO: 55).
Figure 3D:
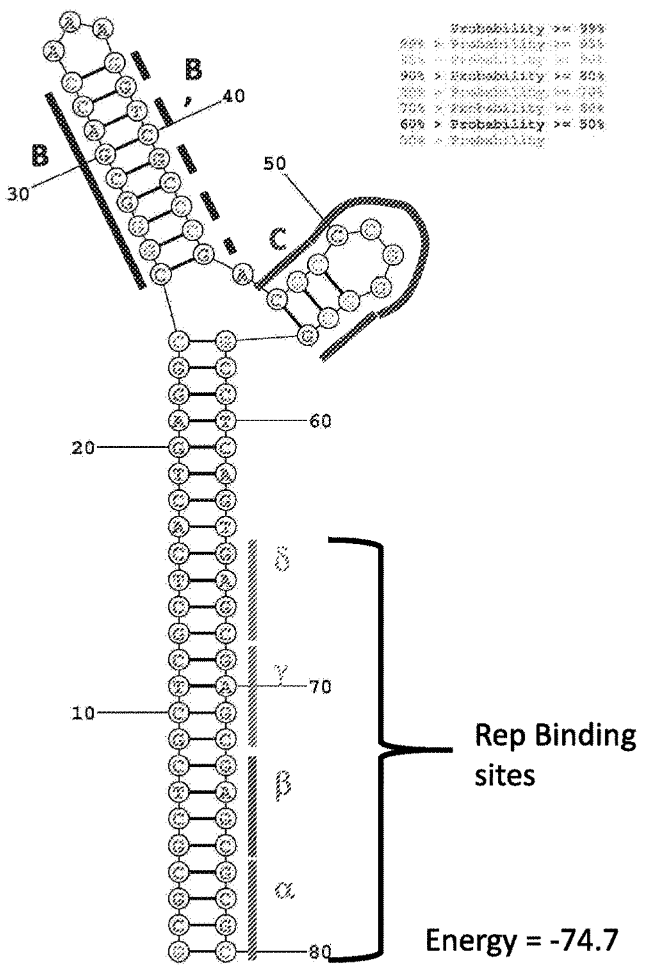
FIG. 3D shows an exemplary right modified ITR. Shown is the primary structure (left) and the predicted secondary structure (right) of the RBE containing portion of the A-A' arm, the B-B' and the C arm of an exemplary mutant right ITR (ITR-1, right) (SEQ ID NO: 114). Any combination of left and right ITR (e.g., AAV2 ITRs or other viral serotype or synthetic ITRs) can be used as taught herein. Each of FIGS. 3A-3D polynucleotide sequences refer to the sequence used to produce the ceDNA as described herein. Also included in each of FIGS. 3A-3D are corresponding ceDNA secondary structures inferred from the ceDNA vector configurations in the plasmid or bacmid/baculovirus genome and the predicted Gibbs free energy values.
Figure 7A:
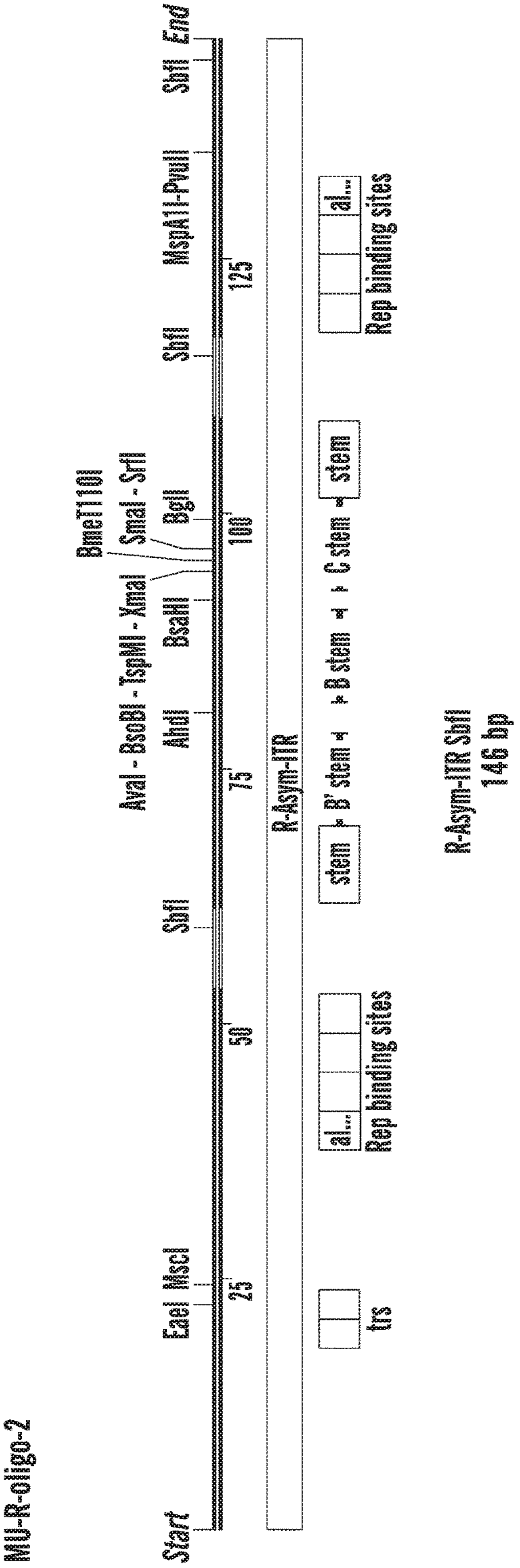
FIG. 7A-7E show exemplary ITRs and exemplary oligos for synthesizing ceDNA vectors using the cell-free synthesis as described herein.
Figure 7A:
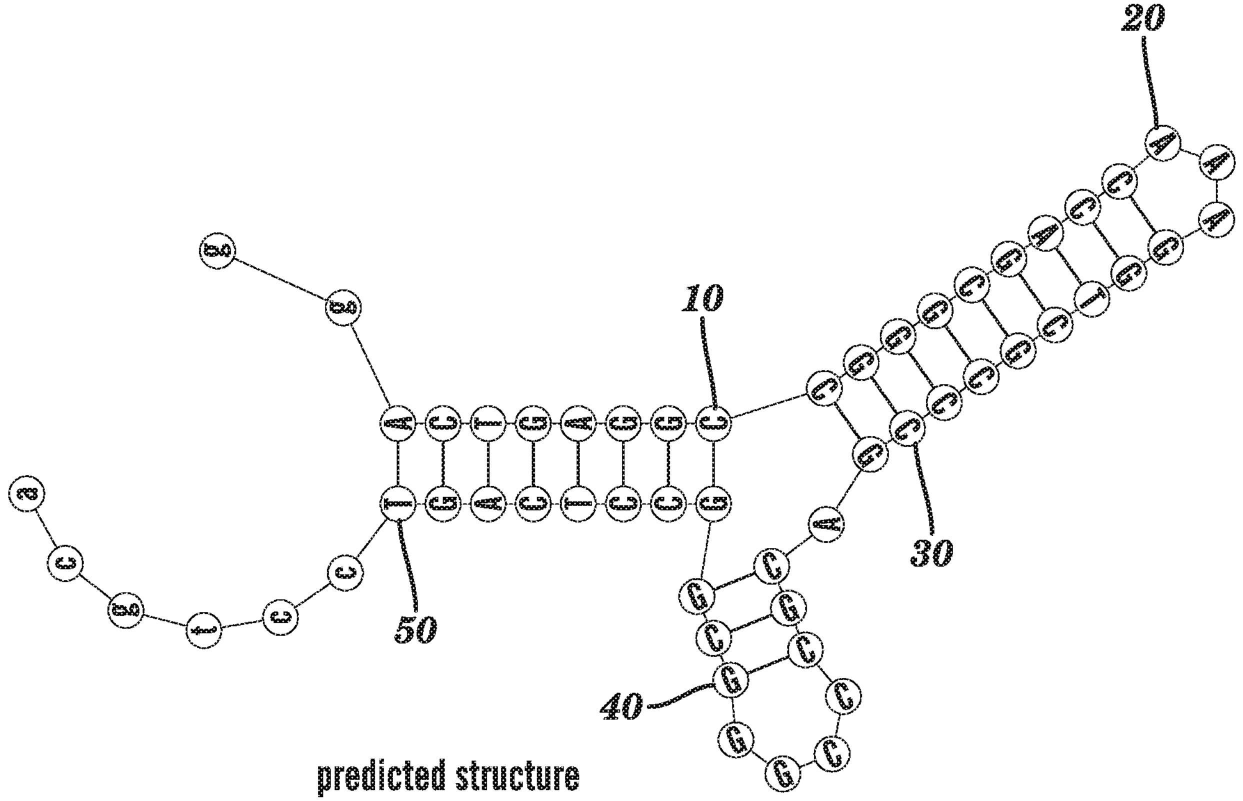

In some embodiments, a modified ITR can for example, comprise removal or deletion of all of a particular arm, e.g., all or part of the A-A' arm, or all or part of the B-B' arm or all or part of the C-C' arm, or alternatively, the removal of 1, 2, 3, 4, 5, 6, 7, 8, 9 or more base pairs forming the stem of the loop so long as the final loop capping the stem (e.g., single arm) is still present (e.g., see ITR-21 in FIG. 7A of PCT/US2018/064242, filed on Dec. 6, 2018). In some embodiments, a modified ITR can comprise the removal of 1, 2, 3, 4, 5, 6, 7, 8, 9 or more base pairs from the B-B' arm. In some embodiments, a modified ITR can comprise the removal of 1, 2, 3, 4, 5, 6, 7, 8, 9 or more base pairs from the C-C' arm (see, e.g., ITR-1 in FIG. 3B, or ITR-45 in FIG. 7A of PCT/US2018/064242, filed on Dec. 6, 2018). In some embodiments, a modified ITR can comprise the removal of 1, 2, 3, 4, 5, 6, 7, 8, 9 or more base pairs from the C-C' arm and the removal of 1, 2, 3, 4, 5, 6, 7, 8, 9 or more base pairs from the B-B' arm. Any combination of removal of base pairs is envisioned, for example, 6 base pairs can be removed in the C-C' arm and 2 base pairs in the B-B' arm. As an illustrative example, FIG. 3B shows an exemplary modified ITR with at least 7 base pairs deleted from each of the C portion and the C' portion, a substitution of a nucleotide in the loop between C and C' region, and at least one base pair deletion from each of the B region and B' regions such that the modified ITR comprises two arms where at least one arm (e.g., C-C') is truncated. In some embodiments, the modified ITR also comprises at least one base pair deletion from each of the B region and B' regions, such that the B-B' arm is also truncated relative to WT ITR.

In some embodiments, a modified ITR can have between 1 and 50 (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) nucleotide deletions relative to a full-length wild-type ITR sequence. In some embodiments, a modified ITR can have between 1 and 30 nucleotide deletions relative to a full-length WT ITR sequence. In some embodiments, a modified ITR has between 2 and 20 nucleotide deletions relative to a full-length wild-type ITR sequence.

In some embodiments, a modified ITR does not contain any nucleotide deletions in the RBE-containing portion of the A or A' regions, so as not to interfere with DNA replication (e.g. binding to an RBE by Rep protein, or nicking at a terminal resolution site). In some embodiments, a modified ITR encompassed for use herein has one or more deletions in the B, B', C, and/or C region as described herein.

In some embodiments, a synthetically produced ceDNA vector comprising a symmetric ITR pair or asymmetric ITR pair comprises a regulatory switch as disclosed herein and at least one modified ITR selected having the nucleotide sequence selected from any of the group consisting of: SEQ ID NO: 3, 4, 15-47, 101-116 or 165-187.

In another embodiment, the structure of the structural element can be modified. For example, the structural element a change in the height of the stem and/or the number of nucleotides in the loop. For example, the height of the stem can be about 2, 3, 4, 5, 6, 7, 8, or 9 nucleotides or more or any range therein. In one embodiment, the stem height can be about 5 nucleotides to about 9 nucleotides and functionally interacts with Rep. In another embodiment, the stem height can be about 7 nucleotides and functionally interacts with Rep. In another example, the loop can have 3, 4, 5, 6, 7, 8, 9, or 10 nucleotides or more or any range therein.

In another embodiment, the number of GAGY binding sites or GAGY-related binding sites within the RBE or extended RBE can be increased or decreased. In one example, the RBE or extended RBE, can comprise 1, 2, 3, 4, 5, or 6 or more GAGY binding sites or any range therein. Each GAGY binding site can independently be an exact GAGY sequence or a sequence similar to GAGY as long as the sequence is sufficient to bind a Rep protein.

In another embodiment, the spacing between two elements (such as but not limited to the RBE and a hairpin) can be altered (e.g., increased or decreased) to alter functional interaction with a large Rep protein. For example, the spacing can be about 1, 2, 3, 4, 5, 6, 7, 8, 9, 10, 11, 12, 13, 14, 15, 16, 17, 18, 19, 20, or 21 nucleotides or more or any range therein.

The synthetically produced ceDNA vector described herein can include an ITR structure that is modified with respect to the wild type AAV2 ITR structure disclosed herein, but still retains an operable RBE, trs and RBE' portion. FIG. 2A and FIG. 2B show one possible mechanism for the operation of a trs site within a wild type ITR structure portion of a ceDNA vector. In some embodiments, the ceDNA vector contains one or more functional ITR polynucleotide sequences that comprise a Rep-binding site (RBS; 5'-GCGCGCTCGCTCGCTC-3' (SEQ ID NO: 60) for AAV2) and a terminal resolution site (TRS; 5'-AGTT (SEQ ID NO: 62)). In some embodiments, at least one ITR (wt or modified ITR) is functional. In alternative embodiments, where a ceDNA vector comprises two modified ITRs that are different or asymmetrical to each other, at least one modified ITR is functional and at least one modified ITR is non-functional.

In some embodiments, a synthetically produced ceDNA vector does not have a modified ITR selected from any sequence consisting of, or consisting essentially of: SEQ ID NOs:500-529, as provided herein. In some embodiments, a ceDNA vector does not have an ITR that is selected from any sequence selected from SEQ ID NOs: 500-529.

In some embodiments, the modified ITR (e.g., the left or right ITR) of the synthetically produced ceDNA vector described herein has modifications within the loop arm, the truncated arm, or the spacer. Exemplary sequences of TRs having modifications within the loop arm, the truncated arm, or the spacer are listed in Table 2 (i.e., SEQ ID NOS: 135-190, 200-233); Table 3 (e.g., SEQ ID Nos: 234-263); Table 4 (e.g., SEQ ID NOs: 264-293); Table 5 (e.g., SEQ ID Nos: 294-318 herein); Table 6 (e.g., SEQ ID NO: 319-468; and Tables 7-9 (e.g., SEQ ID Nos: 101-110, 111-112, 115-134) or Table 10A or 10B (e.g., SEQ ID Nos: 9, 100, 469-483, 484-499) of International application PCT/US18/49996, which is incorporated herein in its entirety by reference.

In some embodiments, the modified ITR for use in a synthetically produced ceDNA vector comprising an asymmetric ITR pair, or symmetric mod-ITR pair is selected from any or a combination of those shown in Tables 2, 3, 4, 5, 6, 7, 8, 9 and 10A-101B of International application PCT/US 18/49996 which is incorporated herein in its entirety by reference.

Figure 7B:
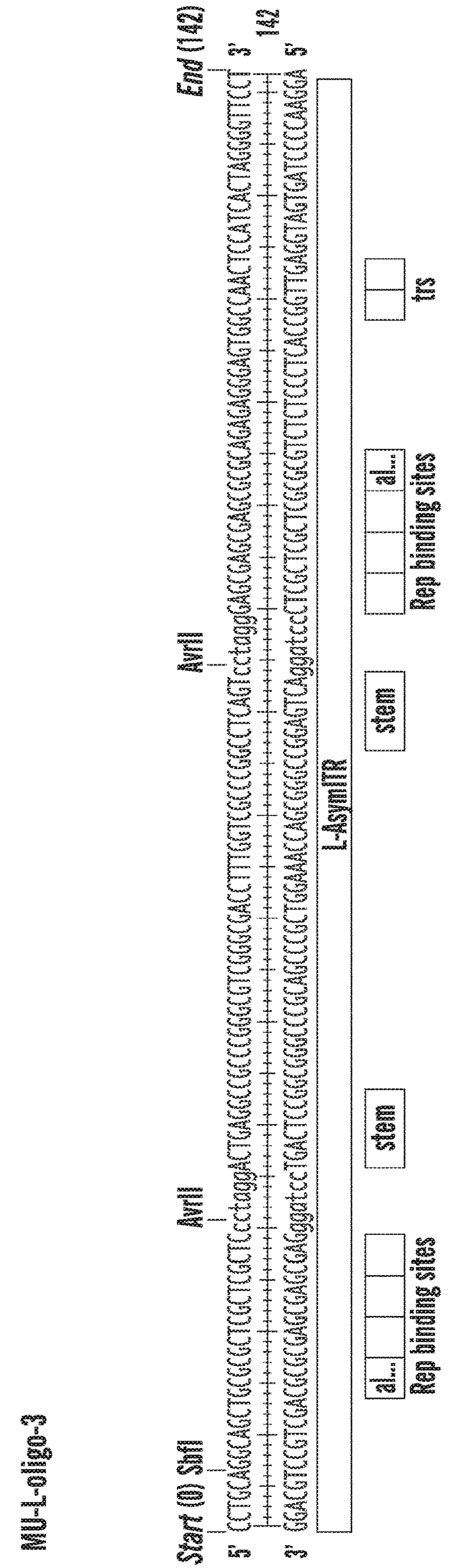
Figure 7B:
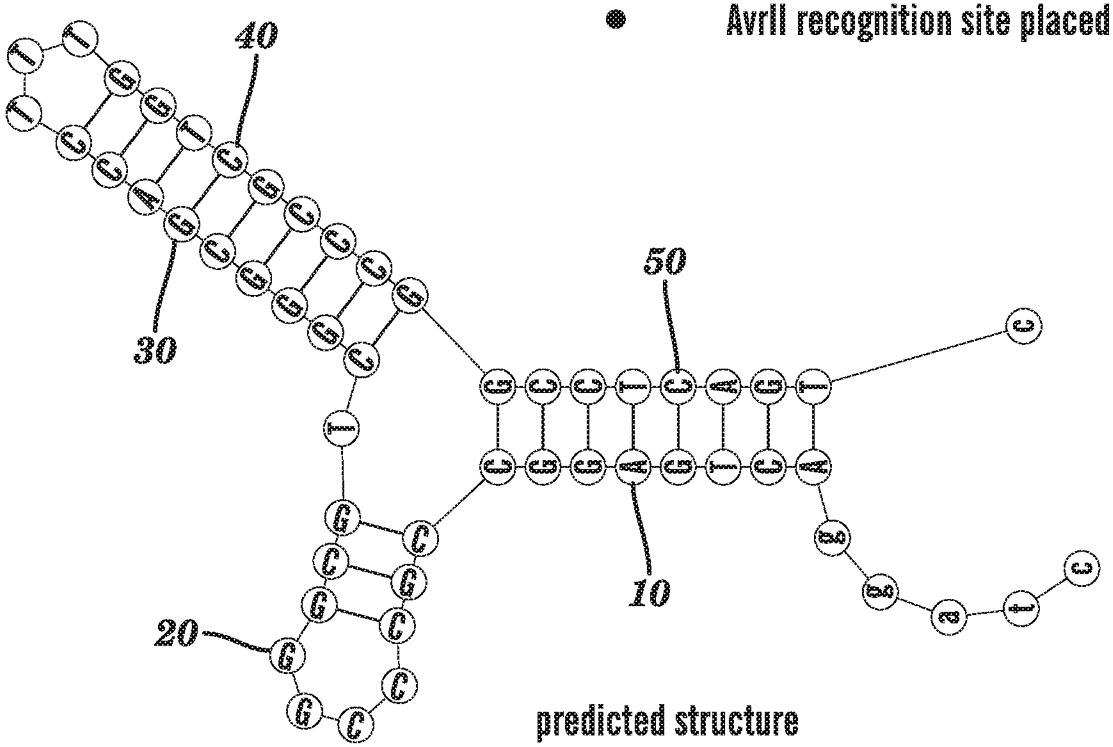
Figure 7C:
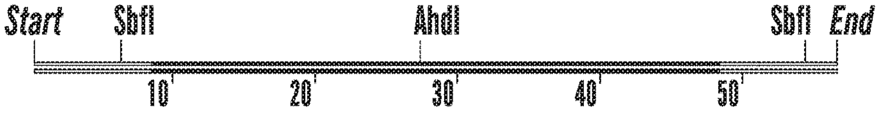
Figure 7C:
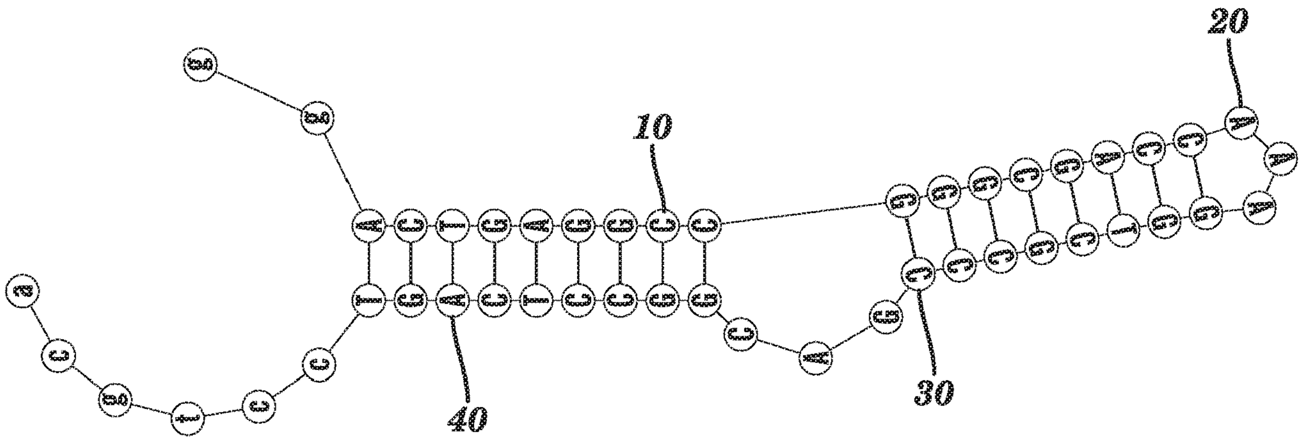
Figure 7D:
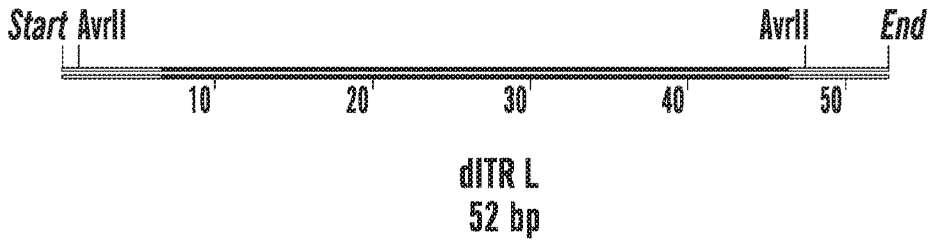
Figure 7D:
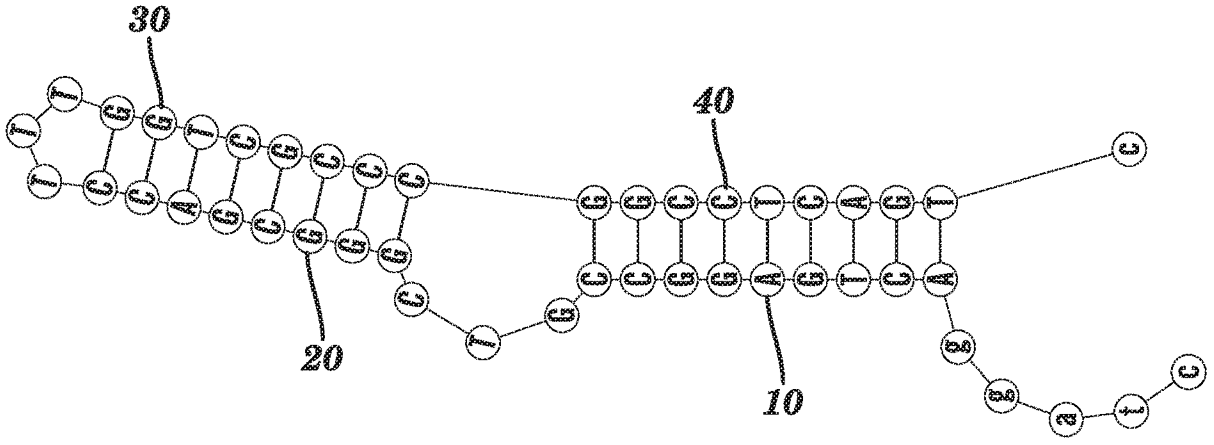
Figure 7E:
Figure 7E:
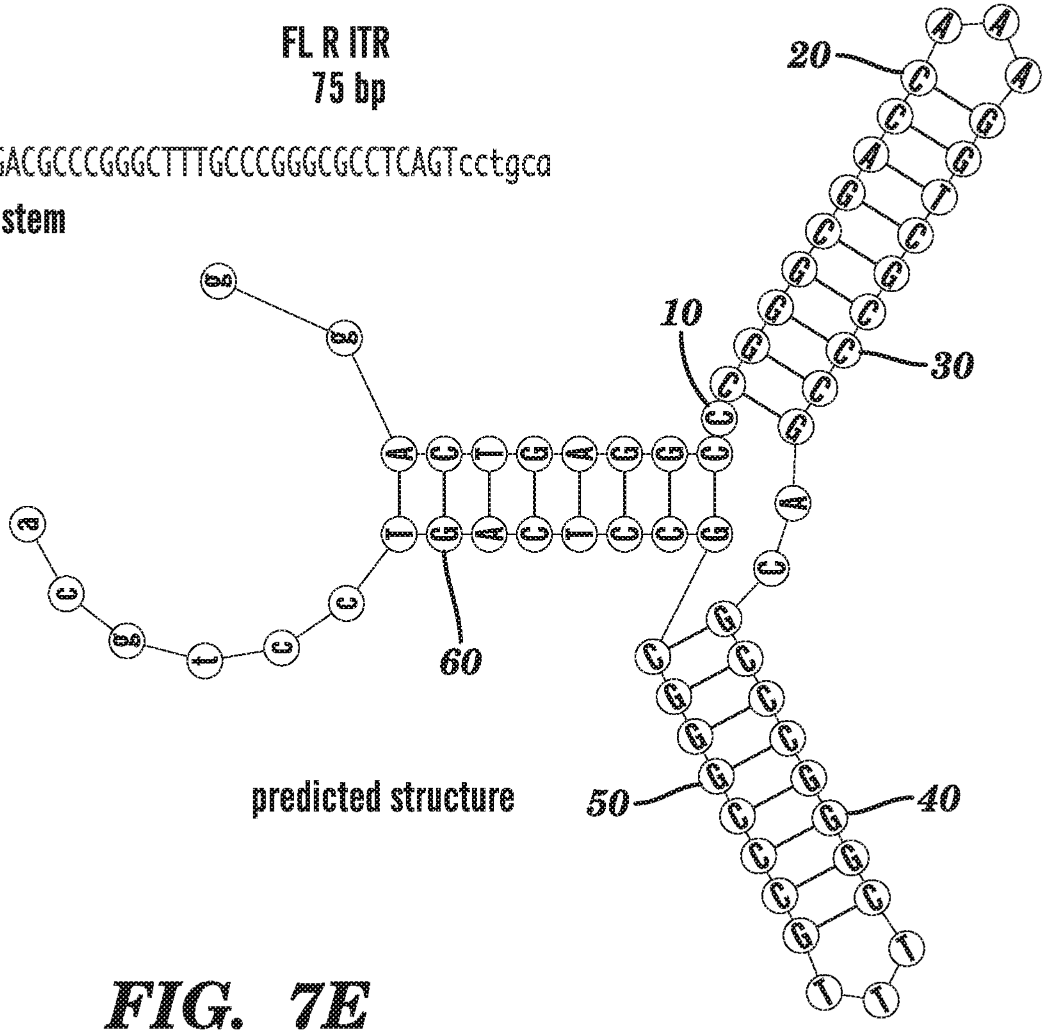
Figure 8:
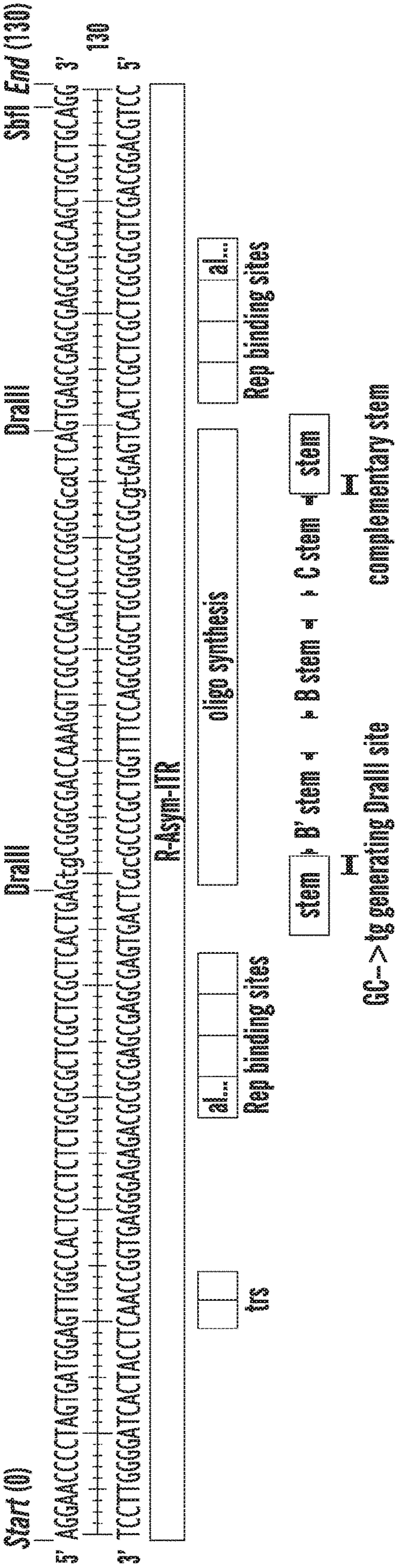
FIG. 8 shows exemplary oligonucleotide used to generate a 3' modified ITR.
Figure 8:
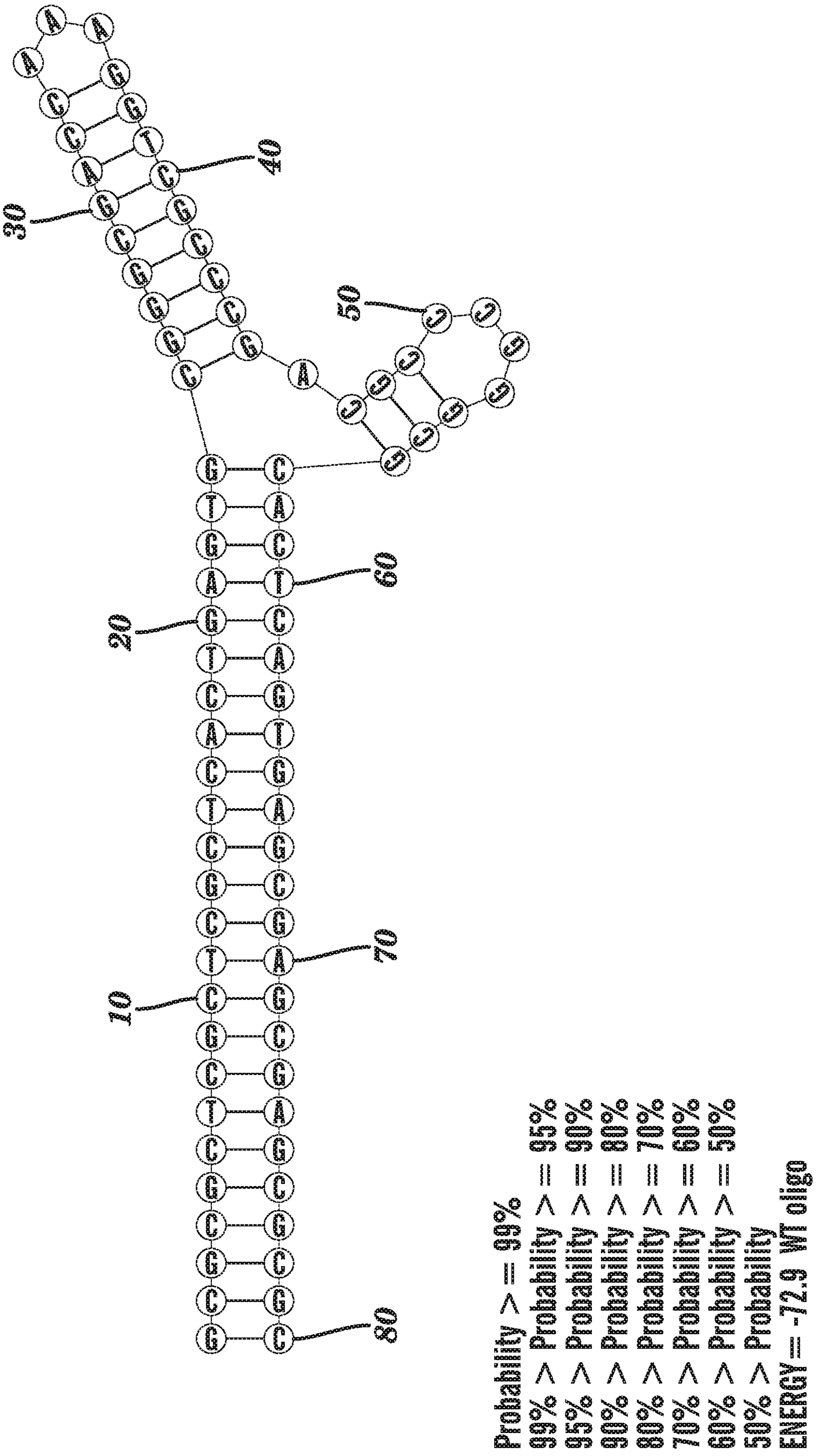

Additional exemplary modified ITRs for use in a synthetically produced ceDNA vector comprising an asymmetric ITR pair, or symmetric mod-FIR pair in each of the above classes are provided in Tables 4A and 4B. The predicted secondary structure of the Right modified ITRs in Table 4A are shown in FIG. 7A of International Application PCT/US2018/064242, filed on Dec. 6, 2018, and the predicted secondary structure of the Left modified ITRs in Table 4B are shown in FIG. 7B of International Application PCT/US2018/064242, filed on Dec. 6, 2018, which is incorporated in its entirety herein.

Table 4A and Table 4B show exemplary right and left modified ITRs.

TABLE 4A

Exemplary modified right ITRs. These exemplary modified right ITRs can comprise the RBE of GCGCGCTCGCTCGCTC-3' (SEQ ID NO: 60), spacer of ACTGAGGC (SEQ ID NO: 69), the spacer complement GCCTCAGT (SEQ ID NO: 70) and RBE' (i.e., complement to RBE) of GAGCGAGCGAGCGCGC (SEQ ID NO: 71).
Table 4A: Exemplary Right modified ITRs

| ITR Construct | Sequence | SEQ ID NO: |
|---|---|---|
| ITR-18 Right | AGGAACCCCTAGTGATGGAGTTGGCCACTCCCTCTCTGCGCGCTCG CTCGCTCACTGAGGCGCACGCCCGGGTTTCCCGGGCGGCCTCAGTG AGCGAGCGAGCGCGCAGCTGCCTGCAGG | 15 |
| ITR-19 Right | AGGAACCCCTAGTGATGGAGTTGGCCACTCCCTCTCTGCGCGCTCG CTCGCTCACTGAGGCCGACGCCCGGGCTTTGCCCGGGCGGCCTCA GTGAGCGAGCGAGCGCGCAGCTGCCTGCAGG | 16 |
| ITR-20 Right | AGGAACCCCTAGTGATGGAGTTGGCCACTCCCTCTCTGCGCGCTCG CTCGCTCACTGAGGCCGGGCGACCAAAGGTCGCCCGACGCCCGGG CGCCTCAGTGAGCGAGCGAGCGCGCAGCTGCCTGCAGG | 17 |
| ITR-21 Right | AGGAACCCCTAGTGATGGAGTTGGCCACTCCCTCTCTGCGCGCTCG CTCGCTCACTGAGGCTTTGCCTCAGTGAGCGAGCGAGCGCGCAGC TGCCTGCAGG | 18 |
| ITR-22 Right | AGGAACCCCTAGTGATGGAGTTGGCCACTCCCTCTCTGCGCGCTCG CTCGCTCACTGAGGCCGGGCGACAAAGTCGCCCGACGCCCGGGCT TTGCCCGGGCGGCCTCAGTGAGCGAGCGAGCGCGCAGCTGCCTGC AGG | 19 |
| ITR-23 Right | AGGAACCCCTAGTGATGGAGTTGGCCACTCCCTCTCTGCGCGCTCG CTCGCTCACTGAGGCCGGGCGAAAATCGCCCGACGCCCGGGCTTT GCCCGGGCGGCCTCAGTGAGCGAGCGAGCGCGCAGCTGCCTGCAG G | 20 |
| ITR-24 Right | AGGAACCCCTAGTGATGGAGTTGGCCACTCCCTCTCTGCGCGCTCG CTCGCTCACTGAGGCCGGGCGAAACGCCCGACGCCCGGGCTTTGC CCGGGCGGCCTCAGTGAGCGAGCGAGCGCGCAGCTGCCTGCAGG | 21 |
| ITR-25 Right | AGGAACCCCTAGTGATGGAGTTGGCCACTCCCTCTCTGCGCGCTCG CTCGCTCACTGAGGCCGGGCAAAGCCCGACGCCCGGGCTTTGCCC GGGCGGCCTCAGTGAGCGAGCGAGCGCGCAGCTGCCTGCAGG | 22 |
| ITR-26 Right | AGGAACCCCTAGTGATGGAGTTGGCCACTCCCTCTCTGCGCGCTCG CTCGCTCACTGAGGCCGGGCGACCAAAGGTCGCCCGACGCCCGGG TTTCCCGGGCGGCCTCAGTGAGCGAGCGAGCGCGCAGCTGCCTGC AGG | 23 |
| ITR-27 Right | AGGAACCCCTAGTGATGGAGTTGGCCACTCCCTCTCTGCGCGCTCG CTCGCTCACTGAGGCCGGGCGACCAAAGGTCGCCCGACGCCCGGT TTCCGGGCGGCCTCAGTGAGCGAGCGAGCGCGCAGCTGCCTGCAG G | 24 |
| ITR-28 Right | AGGAACCCCTAGTGATGGAGTTGGCCACTCCCTCTCTGCGCGCTCG CTCGCTCACTGAGGCCGGGCGACCAAAGGTCGCCCGACGCCCGTT TCGGGCGGCCTCAGTGAGCGAGCGAGCGCGCAGCTGCCTGCAGG | 25 |
| ITR-29 Right | AGGAACCCCTAGTGATGGAGTTGGCCACTCCCTCTCTGCGCGCTCG CTCGCTCACTGAGGCCGGGCGACCAAAGGTCGCCCGACGCCCTTT GGGCGGCCTCAGTGAGCGAGCGAGCGCGCAGCTGCCTGCAGG | 26 |
| ITR-30 Right | AGGAACCCCTAGTGATGGAGTTGGCCACTCCCTCTCTGCGCGCTCG CTCGCTCACTGAGGCCGGGCGACCAAAGGTCGCCCGACGCCTTTG GCGGCCTCAGTGAGCGAGCGAGCGCGCAGCTGCCTGCAGG | 27 |
| ITR-31 Right | AGGAACCCCTAGTGATGGAGTTGGCCACTCCCTCTCTGCGCGCTCG CTCGCTCACTGAGGCCGGGCGACCAAAGGTCGCCCGACGCTTTGC GGCCTCAGTGAGCGAGCGAGCGCGCAGCTGCCTGCAGG | 28 |
| ITR-32 Right | AGGAACCCCTAGTGATGGAGTTGGCCACTCCCTCTCTGCGCGCTCG CTCGCTCACTGAGGCCGGGCGACCAAAGGTCGCCCGACGTTTCGG CCTCAGTGAGCGAGCGAGCGCGCAGCTGCCTGCAGG | 29 |
| ITR-49 Right | AGGAACCCCTAGTGATGGAGTTGGCCACTCCCTCTCTGCGCGCTCG CTCGCTCACTGAGGCCGGGCGACCAAAGGTCGCCCGACGGCCTCA GTGAGCGAGCGAGCGCGCAGCTGCCTGCAGG | 30 |

TABLE 4A-continued

Exemplary modified right ITRs. These exemplary modified right ITRs can comprise the RBE of GCGCGCTCGCTCGCTC-3' (SEQ ID NO: 60), spacer of ACTGAGGC (SEQ ID NO: 69), the spacer complement GCCTCAGT (SEQ ID NO: 70) and RBE' (i.e., complement to RBE) of GAGCGAGCGAGCGCGC (SEQ ID NO: 71).
Table 4A: Exemplary Right modified ITRs

| ITR Construct | Sequence | SEQ ID NO: |
|---|---|---|
| ITR-50 right | AGGAACCCCTAGTGATGGAGTTGGCCACTCCCTCTCTGCGCGCTCG CTCGCTCACTGAGGCCGGGCGACCAAAGGTCGCCCGACGCCCGGG CGGCCTCAGTGAGCGAGCGAGCGCGCAGCTGCCTGCAGG | 31 |

TABLE 4B

Exemplary modified left ITRs. These exemplary modified left ITRs can comprise the RBE of GCGCGCTCGCTCGCTC-3' (SEQ ID NO: 60), spacer of ACTGAGGC (SEQ ID NO: 69), the spacer complement GCCTCAGT (SEQ ID NO: 70) and RBE complement (RBE') of GAGCGAGCGAGCGCGC (SEQ ID NO: 71).
Table 4B: Exemplary modified left ITRs

| | | |
|---|---|---|
| ITR-33 Left | CCTGCAGGCAGCTGCGCGCTCGCTCGCTCACTGAGGCCGCCCGGG AAACCCGGGCGTGCGCCTCAGTGAGCGAGCGAGCGCGCAGAGAG GGAGTGGCCAACTCCATCACTAGGGGTTCCT | 32 |
| ITR-34 Left | CCTGCAGGCAGCTGCGCGCTCGCTCGCTCACTGAGGCCGTCGGGC GACCTTTGGTCGCCCGGCCTCAGTGAGCGAGCGAGCGCGCAGAGA GGGAGTGGCCAACTCCATCACTAGGGGTTCCT | 33 |
| ITR-35 Left | CCTGCAGGCAGCTGCGCGCTCGCTCGCTCACTGAGGCCGCCCGGG CAAAGCCCGGGCGTCGGCCTCAGTGAGCGAGCGAGCGCGCAGAG AGGGAGTGGCCAACTCCATCACTAGGGGTTCCT | 34 |
| ITR-36 Left | CCTGCAGGCAGCTGCGCGCTCGCTCGCTCACTGAGGCGCCCGGGC GTCGGGCGACCTTTGGTCGCCCGGCCTCAGTGAGCGAGCGAGCGC GCAGAGAGGGAGTGGCCAACTCCATCACTAGGGGTTCCT | 35 |
| ITR-37 Left | CCTGCAGGCAGCTGCGCGCTCGCTCGCTCACTGAGGCAAAGCCTC AGTGAGCGAGCGAGCGCGCAGAGAGGGAGTGGCCAACTCCATCA CTAGGGGTTCCT | 36 |
| ITR-38 Left | CCTGCAGGCAGCTGCGCGCTCGCTCGCTCACTGAGGCCGCCCGGG CAAAGCCCGGGCGTCGGGCGACTTTGTCGCCCGGCCTCAGTGAGC GAGCGAGCGCGCAGAGAGGGAGTGGCCAACTCCATCACTAGGGGT TCCT | 37 |
| ITR-39 Left | CCTGCAGGCAGCTGCGCGCTCGCTCGCTCACTGAGGCCGCCCGGG CAAAGCCCGGGCGTCGGGCGATTTTCGCCCGGCCTCAGTGAGCGA GCGAGCGCGCAGAGAGGGAGTGGCCAACTCCATCACTAGGGGTTC CT | 38 |
| ITR-40 Left | CCTGCAGGCAGCTGCGCGCTCGCTCGCTCACTGAGGCCGCCCGGG CAAAGCCCGGGCGTCGGGCGTTTCGCCCGGCCTCAGTGAGCGAGC GAGCGCGCAGAGAGGGAGTGGCCAACTCCATCACTAGGGGTTCCT | 39 |
| ITR-41 Left | CCTGCAGGCAGCTGCGCGCTCGCTCGCTCACTGAGGCCGCCCGGG CAAAGCCCGGGCGTCGGGCTTTGCCCGGCCTCAGTGAGCGAGCGA GCGCGCAGAGAGGGAGTGGCCAACTCCATCACTAGGGGTTCCT | 40 |
| ITR-42 Left | CCTGCAGGCAGCTGCGCGCTCGCTCGCTCACTGAGGCCGCCCGGG AAACCCGGGCGTCGGGCGACCTTTGGTCGCCCGGCCTCAGTGAGC GAGCGAGCGCGCAGAGAGGGAGTGGCCAACTCCATCACTAGGGGT TCCT | 41 |
| ITR-43 Left | CCTGCAGGCAGCTGCGCGCTCGCTCGCTCACTGAGGCCGCCCGGA AACCGGGCGTCGGGCGACCTTTGGTCGCCCGGCCTCAGTGAGCGA GCGAGCGCGCAGAGAGGGAGTGGCCAACTCCATCACTAGGGGTTC CT | 42 |
| ITR-44 Left | CCTGCAGGCAGCTGCGCGCTCGCTCGCTCACTGAGGCCGCCCGAA ACGGGCGTCGGGCGACCTTTGGTCGCCCGGCCTCAGTGAGCGAGC GAGCGCGCAGAGAGGGAGTGGCCAACTCCATCACTAGGGGTTCCT | 43 |

TABLE 4B-continued

Exemplary modified left ITRs. These exemplary modified left ITRs can comprise the RBE of GCGCGCTCGCTCGCTC-3' (SEQ ID NO: 60), spacer of ACTGAGGC (SEQ ID NO: 69), the spacer complement GCCTCAGT (SEQ ID NO: 70) and RBE complement (RBE') of GAGCGAGCGAGCGCGC (SEQ ID NO: 71). Table 4B: Exemplary modified left ITRs

| | | |
|---|---|---|
| ITR-45 Left | CCTGCAGGCAGCTGCGCGCTCGCTCGCTCACTGAGGCCGCCCAAAGGGCGTCGGGCGACCTTTGGTCGCCCGGCCTCAGTGAGCGAGCGAGCGCGCAGAGAGGGAGTGGCCAACTCCATCACTAGGGGTTCCT | 44 |
| ITR-46 Left | CCTGCAGGCAGCTGCGCGCTCGCTCGCTCACTGAGGCCGCCAAAGGCGTCGGGCGACCTTTGGTCGCCCGGCCTCAGTGAGCGAGCGAGCGCGCAGAGAGGGAGTGGCCAACTCCATCACTAGGGGTTCCT | 45 |
| ITR-47 Left | CCTGCAGGCAGCTGCGCGCTCGCTCGCTCACTGAGGCCGCAAAGCGTCGGGCGACCTTTGGTCGCCCGGCCTCAGTGAGCGAGCGAGCGCGCAGAGAGGGAGTGGCCAACTCCATCACTAGGGGTTCCT | 46 |
| ITR-48 Left | CCTGCAGGCAGCTGCGCGCTCGCTCGCTCACTGAGGCCGAAACGTCGGGCGACCTTTGGTCGCCCGGCCTCAGTGAGCGAGCGAGCGCGCAGAGAGGGAGTGGCCAACTCCATCACTAGGGGTTCCT | 47 |

In one embodiment, a synthetically produced ceDNA vector comprises, in the 5' to 3' direction: a first adeno-associated virus (AAV) inverted terminal repeat (ITR), a nucleotide sequence of interest (for example an expression cassette as described herein) and a second AAV ITR, where the first ITR (5' ITR) and the second ITR (3' ITR) are asymmetric with respect to each other—that is, they have a different 3D-spatial configuration from one another. As an exemplary embodiment, the first ITR can be a wild-type ITR and the second ITR can be a mutated or modified ITR, or vice versa, where the first ITR can be a mutated or modified ITR and the second ITR a wild-type ITR. In some embodiment, the first ITR and the second ITR are both mod-ITRs, but have different sequences, or have different modifications, and thus are not the same modified ITRs, and have different 3D spatial configurations. Stated differently, a ceDNA vector with asymmetric ITRs comprises ITRs where any changes in one ITR relative to the WT-ITR are not reflected in the other ITR; or alternatively, where the asymmetric ITRs have a the modified asymmetric ITR pair can have a different sequence and different three-dimensional shape with respect to each other. Exemplary asymmetric ITRs in the ceDNA vector and for use to generate a ceDNA-plasmid are shown in Table 4A and 4B.

In an alternative embodiment, a synthetically produced ceDNA vector comprises two symmetrical mod-ITRs—that is, both ITRs have the same sequence, but are reverse complements (inverted) of each other. In some embodiments, a symmetrical mod-ITR pair comprises at least one or any combination of a deletion, insertion, or substitution relative to wild type ITR sequence from the same AAV serotype. The additions, deletions, or substitutions in the symmetrical ITR are the same but the reverse complement of each other. For example, an insertion of 3 nucleotides in the C region of the 5' ITR would be reflected in the insertion of 3 reverse complement nucleotides in the corresponding section in the C' region of the 3' ITR. Solely for illustration purposes only, if the addition is AACG in the 5' ITR, the addition is CGTT in the 3' ITR at the corresponding site. For example, if the 5' ITR sense strand is ATCGATCG with an addition of AACG between the G and A to result in the sequence ATCGAACGATCG (SEQ ID NO: 51). The corresponding 3' ITR sense strand is CGATCGAT (the reverse complement of ATCGATCG) with an addition of CGTT (i.e. the reverse complement of AACG) between the T and C to result in the sequence CGATCGTTCGAT (SEQ ID NO: 49) (the reverse complement of ATCGAACGATCG) (SEQ ID NO: 51).

In alternative embodiments, the modified ITR pair are substantially symmetrical as defined herein—that is, the modified ITR pair can have a different sequence but have corresponding or the same symmetrical three-dimensional shape. For example, one modified ITR can be from one serotype and the other modified ITR be from a different serotype, but they have the same mutation (e.g., nucleotide insertion, deletion or substitution) in the same region. Stated differently, for illustrative purposes only, a 5' mod-ITR can be from AAV2 and have a deletion in the C region, and the 3' mod-ITR can be from AAV5 and have the corresponding deletion in the C' region, and provided the 5' mod-ITR and the 3' mod-ITR have the same or symmetrical three-dimensional spatial organization, they are encompassed for use herein as a modified ITR pair.

In some embodiments, a substantially symmetrical mod-ITR pair has the same A, C-C' and B-B' loops in 3D space, e.g., if a modified ITR in a substantially symmetrical mod-ITR pair has a deletion of a C-C' arm, then the cognate mod-ITR has the corresponding deletion of the C-C' loop and also has a similar 3D structure of the remaining A and B-B' loops in the same shape in geometric space of its cognate mod-ITR. By way of example only, substantially symmetrical ITRs can have a symmetrical spatial organization such that their structure is the same shape in geometrical space. This can occur, e.g., when a G-C pair is modified, for example, to a C-G pair or vice versa, or A-T pair is modified to a T-A pair, or vice versa. Therefore, using the exemplary example above of modified 5' ITR as a ATCGAACGATCG (SEQ ID NO: 51), and modified 3' ITR as CGATCG7TCGAT (SEQ ID NO: 49) (i.e., the reverse complement of ATCGAACGATCG (SEQ ID NO: 51)), these modified ITRs would still be symmetrical if, for example, the 5' ITR had the sequence of ATCGAACCATCG (SEQ ID NO: 50), where G in the addition is modified to C, and the substantially symmetrical 3' ITR has the sequence of CGATCGTTCGAT (SEQ ID NO: 49), without the corresponding modification of the T in the addition to a. In some embodiments, such a modified ITR pair are substantially symmetrical as the modified ITR pair has symmetrical stereochemistry.

Table 5 shows exemplary symmetric modified ITR pairs (i.e. a left modified ITRs and the symmetric right modified ITR). The bold (red) portion of the sequences identify partial ITR sequences (i.e., sequences of A-A', C-C' and B-B' loops). These exemplary modified ITRs can comprise the RBE of GCGCGCTCGCTCGCTC-3' (SEQ ID NO: 60), spacer of ACTGAGGC (SEQ ID NO: 69), the spacer complement GCCTCAGT (SEQ ID NO: 70) and RBE' (i.e., complement to RBE) of GAGCGAGCGAGCGCGC (SEQ ID NO: 71).

TABLE 5 exemplary symmetric modified ITR pairs

| LEFT modified ITR (modified 5' ITR | | Symmetric RIGHT modified ITR (modified 3' ITR | |
|---|---|---|---|
| SEQ ID NO: 32 (ITR-33 left) | CCTGCAGGCAGCT**GCGCGCTCGCTCGCTCACTGAGGCCGCCCGGGAAACCCGGGCGTGCGCCTCAGTGAGCGAGCGAGCGCGC**AGAGAGGGAGTGGCCAACTCCATCACTAGGGGTTCCT | SEQ ID NO: 15 (ITR-18, right) | AGGAACCCCTAGTGATGGAGTTGGCCACTCCCTCTCT**GCGCGCTCGCTCGCTCACTGAGGCGCACGCCCGGGTTTCCCGGGCGGCCTCAGTGAGCGAGCGAGCGCGC**AGCTGCCTGCAGG |
| SEQ ID NO: 33 (ITR-34 left) | CCTGCAGGCAGCT**GCGCGCTCGCTCGCTCACTGAGGCCGTCGGGCGACCTTTGGTCGCCCGGCCTCAGTGAGCGAGCGAGCGCGC**AGAGAGGGAGTGGCCAACTCCATCACTAGGGGTTCCT | SEQ ID NO: 48 (ITR-51, right) | AGGAACCCCTAGTGATGGAGTTGGCCACTCCCTCTCT**GCGCGCTCGCTCGCTCACTGAGGCCGGGCGACCAAAGGTCGCCCGACGGCCTCAGTGAGCGAGCGAGCGCGC**AGCTGCCTGCAGG |
| SEQ ID NO: 34 (ITR-35 left) | CCTGCAGGCAGCT**GCGCGCTCGCTCGCTCACTGAGGCCGCCCGGGCAAAGCCCGGGCGTCGGCCTCAGTGAGCGAGCGAGCGCGC**AGAGAGGGAGTGGCCAACTCCATCACTAGGGGTTCCT | SEQ ID NO: 16 (ITR-19, right) | AGGAACCCCTAGTGATGGAGTTGGCCACTCCCTCTCT**GCGCGCTCGCTCGCTCACTGAGGCCGACGCCCGGGCTTTGCCCGGGCGGCCTCAGTGAGCGAGCGAGCGCGC**AGCTGCCTGCAGG |
| SEQ ID NO: 35 (ITR-36 left) | CCTGCAGGCAGCT**GCGCGCTCGCTCGCTCACTGAGGCGCCCGGGCGTCGGGCGACCTTTGGTCGCCCGGCCTCAGTGAGCGAGCGAGCGCGC**AGAGAGGGAGTGGCCAACTCCATCACTAGGGGTTCCT | SEQ ID NO: 17 (ITR-20, right) | AGGAACCCCTAGTGATGGAGTTGGCCACTCCCTCTCT**GCGCGCTCGCTCGCTCACTGAGGCCGGGCGACCAAAGGTCGCCCGACGCCCGGGCGCCTCAGTGAGCGAGCGAGCGCGC**AGCTGCCTGCAGG |
| SEQ ID NO: 36 (ITR-37 left) | CCTGCAGGCAGCT**GCGCGCTCGCTCGCTCACTGAGGCAAAGCCTCAGTGAGCGAGCGAGCGCGC**AGAGAGGGAGTGGCCAACTCCATCACTAGGGGTTCCT | SEQ ID NO: 18 (ITR-21, right) | AGGAACCCCTAGTGATGGAGTTGGCCACTCCCTCTCT**GCGCGCTCGCTCGCTCACTGAGGCTTTGCCTCAGTGAGCGAGCGAGCGCGC**AGCTGCCTGCAGG |
| SEQ ID NO: 37 (ITR-38 left) | CCTGCAGGCAGCT**GCGCGCTCGCTCGCTCACTGAGGCCGCCCGGGCAAAGCCCGGGCGTCGGGCGACTTTGTCGCCCGGCCTCAGTGAGCGAGCGAGCGCGC**AGAGAGGGAGTGGCCAACTCCATCACTAGGGGTTCCT | SEQ ID NO: 19 (ITR-22 right) | AGGAACCCCTAGTGATGGAGTTGGCCACTCCCTCTCT**GCGCGCTCGCTCGCTCACTGAGGCCGGGCGACAAAGTCGCCCGACGCCCGGGCTTTGCCCGGGCGGCCTCAGTGAGCGAGCGAGCGCGC**AGCTGCCTGCAGG |
| SEQ ID NO: 38 (ITR-39 left) | CCTGCAGGCAGCT**GCGCGCTCGCTCGCTCACTGAGGCCGCCCGGGCAAAGCCCGGGCGTCGGGCGATTTTCGCCCGGCCTCAGTGAGCGAGCGAGCGCGC**AGAGAGGGAGTGGCCAACTCCATCACTAGGGGTTCCT | SEQ ID NO: 20 (ITR-23, right) | AGGAACCCCTAGTGATGGAGTTGGCCACTCCCTCTCT**GCGCGCTCGCTCGCTCACTGAGGCCGGGCGAAAATCGCCCGACGCCCGGGCTTTGCCCGGGCGGCCTCAGTGAGCGAGCGAGCGCGC**AGCTGCCTGCAGG |
| SEQ ID NO: 39 (ITR-40 left) | CCTGCAGGCAGCT**GCGCGCTCGCTCGCTCACTGAGGCCGCCCGGGCAAAGCCCGGGCGTCGGGCGTTTCGCCCGGCCTCAGTGAGCGAGCGAGCGCGC**AGAGAGGGAGTGGCCAACTCCATCACTAGGGGTTCCT | SEQ ID NO: 21 (ITR-24, right) | AGGAACCCCTAGTGATGGAGTTGGCCACTCCCTCTCT**GCGCGCTCGCTCGCTCACTGAGGCCGGGCGAAACGCCCGACGCCCGGGCTTTGCCCGGGCGGCCTCAGTGAGCGAGCGAGCGCGC**AGCTGCCTGCAGG |

TABLE 5-continued

| exemplary symmetric modified ITR pairs | | | |
|---|---|---|---|
| LEFT modified ITR (modified 5' ITR | | Symmetric RIGHT modified ITR (modified 3' ITR | |
| SEQ ID NO: 40 (ITR-41 left) | CCTGCAGGCAGCT**GCGCGCTCGCTCGCTCACTGAGGCCGCCCGGGCAAAGCCCGGGCGTCGGGCTTTGCCCGGCCTCAGTGAGCGAGCGAGCGCGC**AGAGAGGGAGTGGCCAACTCCATCACTAGGGGTTCCT | SEQ ID NO: 22 (ITR-25 right) | AGGAACCCCTAGTGATGGAGTTGGCCACTCCCTCTCT**GCGCGCTCGCTCGCTCACTGAGGCCGGGCAAAGCCCGACGCCCGGGCTTTGCCCGGGCGGCCTCAGTGAGCGAGCGAGCGCGC**AGCTGCCTGCAGG |
| SEQ ID NO: 41 (ITR-42 left) | CCTGCAGGCAGCT**GCGCGCTCGCTCGCTCACTGAGGCCGCCCGGGAAACCCGGGCGTCGGGCGACCTTTGGTCGCCCGGCCTCAGTGAGCGAGCGAGCGCGC**AGAGAGGGAGTGGCCAACTCCATCACTAGGGGTTCCT | SEQ ID NO: 23 (ITR-26 right) | AGGAACCCCTAGTGATGGAGTTGGCCACTCCCTCTCT**GCGCGCTCGCTCGCTCACTGAGGCCGGGCGACCAAAGGTCGCCCGACGCCCGGGTTTCCCGGGCGGCCTCAGTGAGCGAGCGAGCGCGC**AGCTGCCTGCAGG |
| SEQ ID NO: 42 (ITR-43 left) | CCTGCAGGCAGCT**GCGCGCTCGCTCGCTCACTGAGGCCGCCCGGAAACCGGGCGTCGGGCGACCTTTGGTCGCCCGGCCTCAGTGAGCGAGCGAGCGCGC**AGAGAGGGAGTGGCCAACTCCATCACTAGGGGTTCCT | SEQ ID NO: 24 (ITR-27 right) | AGGAACCCCTAGTGATGGAGTTGGCCACTCCCTCTCT**GCGCGCTCGCTCGCTCACTGAGGCCGGGCGACCAAAGGTCGCCCGACGCCCGGTTTCCGGGCGGCCTCAGTGAGCGAGCGAGCGCGC**AGCTGCCTGCAGG |
| SEQ ID NO: 43 (ITR-44 left) | CCTGCAGGCAGCT**GCGCGCTCGCTCGCTCACTGAGGCCGCCCGAAACGGGCGTCGGGCGACCTTTGGTCGCCCGGCCTCAGTGAGCGAGCGAGCGCGC**AGAGAGGGAGTGGCCAACTCCATCACTAGGGGTTCCT | SEQ ID NO: 25 (ITR-28 right) | AGGAACCCCTAGTGATGGAGTTGGCCACTCCCTCTCT**GCGCGCTCGCTCGCTCACTGAGGCCGGGCGACCAAAGGTCGCCCGACGCCCGTTTCGGGCGGCCTCAGTGAGCGAGCGAGCGCGC**AGCTGCCTGCAGG |
| SEQ ID NO: 44 (ITR-45 left) | CCTGCAGGCAGCT**GCGCGCTCGCTCGCTCACTGAGGCCGCCCAAAGGGCGTCGGGCGACCTTTGGTCGCCCGGCCTCAGTGAGCGAGCGAGCGCGC**AGAGAGGGAGTGGCCAACTCCATCACTAGGGGTTCCT | SEQ ID NO: 26 (ITR-29, right) | AGGAACCCCTAGTGATGGAGTTGGCCACTCCCTCTCT**GCGCGCTCGCTCGCTCACTGAGGCCGGGCGACCAAAGGTCGCCCGACGCCCTTTGGGCGGCCTCAGTGAGCGAGCGAGCGCGC**AGCTGCCTGCAGG |
| SEQ ID NO:45 (ITR-46 left) | CCTGCAGGCAGCT**GCGCGCTCGCTCGCTCACTGAGGCCGCCAAAGGCGTCGGGCGACCTTTGGTCGCCCGGCCTCAGTGAGCGAGCGAGCGCGC**AGAGAGGGAGTGGCCAACTCCATCACTAGGGGTTCCT | SEQ ID NO: 27 (ITR-30, right) | AGGAACCCCTAGTGATGGAGTTGGCCACTCCCTCTCT**GCGCGCTCGCTCGCTCACTGAGGCCGGGCGACCAAAGGTCGCCCGACGCCTTTGGCGGCCTCAGTGAGCGAGCGAGCGCGC**AGCTGCCTGCAGG |
| SEQ ID NO: 46 (ITR-47, left) | CCTGCAGGCAGCT**GCGCGCTCGCTCGCTCACTGAGGCCGCAAAGCGTCGGGCGACCTTTGGTCGCCCGGCCTCAGTGAGCGAGCGAGCGCGC**AGAGAGGGAGTGGCCAACTCCATCACTAGGGGTTCCT | SEQ ID NO: 28 (ITR-31, right) | AGGAACCCCTAGTGATGGAGTTGGCCACTCCCTCTCT**GCGCGCTCGCTCGCTCACTGAGGCCGGGCGACCAAAGGTCGCCCGACGCTTTGCGGCCTCAGTGAGCGAGCGAGCGCGC**AGCTGCCTGCAGG |
| SEQ ID NO: 47 (ITR-48, left) | CCTGCAGGCAGCT**GCGCGCTCGCTCGCTCACTGAGGCCGAAACGTCGGGCGACCTTTGGTCGCCCGGCCTCAGTGAGCGAGCGAGCGCGC**AGAGAGGGAGTGGCCAACTCCATCACTAGGGGTTCCT | SEQ ID NO: 29 (ITR-32 right) | AGGAACCCCTAGTGATGGAGTTGGCCACTCCCTCTCT**GCGCGCTCGCTCGCTCACTGAGGCCGGGCGACCAAAGGTCGCCCGACGTTTCGGCCTCAGTGAGCGAGCGAGCGCGC**AGCTGCCTGCAGG |

In some embodiments, a ceDNA vector comprising an asymmetric ITR pair can comprise an ITR with a modification corresponding to any of the modifications in ITR sequences or ITR partial sequences shown in any one or more of Tables 4A-4B herein or the sequences shown in FIG. 7A or 7B of International Application PCT/US2018/064242, filed on Dec. 6, 2018, which is incorporated in its entirety herein, or disclosed in Tables 2, 3, 4, 5, 6, 7, 8, 9 or 10A-10B3 of International application PCT/US18/49996 filed Sep. 7, 2018 which is incorporated herein in its entirety by reference.

V. Exemplary ceDNA Vectors

As described above, the present disclosure relates to synthetically produced recombinant ceDNA expression vectors and ceDNA vectors that encode a transgene comprising any one of: an asymmetrical ITR pair, a symmetrical ITR pair, or substantially symmetrical ITR pair as described above. In certain embodiments, the disclosure relates to synthetically produced recombinant ceDNA vectors having flanking ITR sequences and a transgene, where the ITR sequences are asymmetrical, symmetrical or substantially symmetrical relative to each other as defined herein, and the ceDNA further comprises a nucleotide sequence of interest (for example an expression cassette comprising the nucleic acid of a transgene) located between the flanking ITRs, wherein said nucleic acid molecule is devoid of viral capsid protein coding sequences.

The synthetically produced ceDNA expression vector may be any ceDNA vector that can be conveniently subjected to recombinant DNA procedures including nucleotide sequence(s) as described herein, provided at least one ITR is altered. The synthetically produced ceDNA vectors of the present disclosure are compatible with the host cell into which the ceDNA vector is to be introduced. In certain embodiments, the synthetically produced ceDNA vectors may be linear. In certain embodiments, the synthetically produced ceDNA vectors may exist as an extrachromosomal entity. In certain embodiments, the synthetically produced ceDNA vectors of the present disclosure may contain an element(s) that permits integration of a donor sequence into the host cell's genome. As used herein "transgene" and "heterologous nucleotide sequence" are synonymous.

Referring now to FIGS. 1A-1G, schematics of the functional components of two non-limiting plasmids useful in synthetically producing the ceDNA vectors of the present disclosure are shown. FIG. 1A, 1B, 1D, 1F show the construct of ceDNA vectors or the corresponding sequences of ceDNA plasmids, where the first and second ITR sequences are asymmetrical, symmetrical or substantially symmetrical relative to each other as defined herein. In some embodiments, the expressible transgene cassette includes, as needed: an enhancer/promoter, one or more homology arms, a donor sequence, a post-transcription regulatory element (e.g., WPRE, e.g., SEQ ID NO: 67)), and a polyadenylation and termination signal (e.g., BGH polyA, e.g., SEQ ID NO: 68).

FIG. 5 is a gel confirming the production of ceDNA vector produced using the synthetic process as described herein and in the Examples. The generation of a ceDNA vector is confirmed by a characteristic band pattern in the gel, as discussed with respect to FIG. 4B above and in the Examples.

A. Regulatory Elements.

The ceDNA vectors as described herein and produced using the synthetic process as described herein can comprise an asymmetric ITR pair or symmetric ITR pair as defined herein, can be further comprise a specific combination of cis-regulatory elements. The cis-regulatory elements include, but are not limited to, a promoter, a riboswitch, an insulator, a mir-regulatable element, a post-transcriptional regulatory element, a tissue- and cell type-specific promoter and an enhancer. In some embodiments, the ITR can act as the promoter for the transgene. In some embodiments, the ceDNA vector comprises additional components to regulate expression of the transgene, for example, regulatory switches as described herein, to regulate the expression of the transgene, or a kill switch, which can kill a cell comprising the ceDNA vector. Regulatory elements, including Regulatory Switches that can be used in the present invention are more fully discussed in International application PCT/US18/49996, which is incorporated herein in its entirety by reference.

In embodiments, the second nucleotide sequence includes a regulatory sequence, and a nucleotide sequence encoding a nuclease. In certain embodiments the gene regulatory sequence is operably linked to the nucleotide sequence encoding the nuclease. In certain embodiments, the regulatory sequence is suitable for controlling the expression of the nuclease in a host cell. In certain embodiments, the regulatory sequence includes a suitable promoter sequence, being able to direct transcription of a gene operably linked to the promoter sequence, such as a nucleotide sequence encoding the nuclease(s) of the present disclosure. In certain embodiments, the second nucleotide sequence includes an intron sequence linked to the 5' terminus of the nucleotide sequence encoding the nuclease. In certain embodiments, an enhancer sequence is provided upstream of the promoter to increase the efficacy of the promoter. In certain embodiments, the regulatory sequence includes an enhancer and a promoter, wherein the second nucleotide sequence includes an intron sequence upstream of the nucleotide sequence encoding a nuclease, wherein the intron includes one or more nuclease cleavage site(s), and wherein the promoter is operably linked to the nucleotide sequence encoding the nuclease.

The ceDNA vectors produced using the synthetic process as described herein can further comprise a specific combination of cis-regulatory elements such as WHP posttranscriptional regulatory element (WPRE) (e.g., SEQ ID NO: 67) and BGH polyA (SEQ ID NO: 68). Suitable expression cassettes for use in expression constructs are not limited by the packaging constraint imposed by the viral capsid.

(i). Promoters:

It will be appreciated by one of ordinary skill in the art that promoters used in the synthetically produced ceDNA vectors of the invention should be tailored as appropriate for the specific sequences they are promoting. For example, a guide RNA may not require a promoter at all, since its function is to form a duplex with a specific target sequence on the native DNA to effect a recombination event. In contrast, a nuclease encoded by the ceDNA vector would benefit from a promoter so that it can be efficiently expressed from the vector—and, optionally, in a regulatable fashion.

Expression cassettes of the present invention include a promoter, which can influence overall expression levels as well as cell-specificity. For transgene expression, they can include a highly active virus-derived immediate early promoter. Expression cassettes can contain tissue-specific eukaryotic promoters to limit transgene expression to specific cell types and reduce toxic effects and immune responses resulting from unregulated, ectopic expression. In preferred embodiments, an expression cassette can contain a synthetic regulatory element, such as a CAG promoter (SEQ ID NO: 72). The CAG promoter comprises (i) the cytomegalovirus (CMV) early enhancer element, (ii) the promoter, the first exon and the first intron of chicken beta-actin gene, and (iii) the splice acceptor of the rabbit beta-globin gene. Alternatively, an expression cassette can contain an Alpha-1-antitrypsin (AAT) promoter (SEQ ID NO: 73 or SEQ ID NO: 74), a liver specific (LP1) promoter (SEQ ID NO: 75 or SEQ ID NO: 76), or a Human elongation factor-1 alpha (EF1a) promoter (e.g., SEQ ID NO: 77 or SEQ ID NO: 78). In some embodiments, the expression cassette includes one or more constitutive promoters, for example, a retroviral Rous sarcoma virus (RSV) LTR promoter (optionally with the RSV enhancer), or a cytomegalovirus (CMV) immediate early promoter (optionally with the CMV enhancer, e.g., SEQ ID NO: 79). Alternatively, an inducible promoter, a native promoter for a transgene, a tissue-specific promoter, or various promoters known in the art can be used.

Suitable promoters, including those described above, can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6, e.g., SEQ ID NO: 80) (Miyagishi et al., *Nature Biotechnology* 20, 497-500 (2002)), an enhanced U6 promoter (e.g., Xia et al., *Nucleic Acids Res.* 2003 Sep. 1; 31(17)), a human H1 promoter (H1) (e.g., SEQ ID NO: 81 or SEQ ID NO: 155), a CAG promoter, a human alpha 1-antitypsin (HAAT) promoter (e.g., SEQ ID NO: 82), and the like. In certain embodiments, these promoters are altered at their downstream intron containing end to include one or more nuclease cleavage sites. In certain embodiments, the DNA containing the nuclease cleavage site(s) is foreign to the promoter DNA.

In one embodiment, the promoter used is the native promoter of the gene encoding the therapeutic protein. The promoters and other regulatory sequences for the respective genes encoding the therapeutic proteins are known and have been characterized. The promoter region used may further include one or more additional regulatory sequences (e.g., native), e.g., enhancers, (e.g. SEQ ID NO: 79 and SEQ ID NO: 83).

Non-limiting examples of suitable promoters for use in accordance with the present invention include the CAG promoter of, for example (SEQ ID NO: 72), the HAAT promoter (SEQ ID NO: 82), the human EF1-α promoter (SEQ ID NO: 77) or a fragment of the EF1a promoter (SEQ ID NO: 78), IE2 promoter (e.g., SEQ ID NO: 84) and the rat EF1-α promoter (SEQ ID NO: 85), or IE1 promoter fragment (SEQ ID NO: 125).

(ii). Polyadenylation Sequences:

A sequence encoding a polyadenylation sequence can be included in the synthetically produced ceDNA vector to stabilize an mRNA expressed from the ceDNA vector, and to aid in nuclear export and translation. In one embodiment, the synthetically produced ceDNA vector does not include a polyadenylation sequence. In other embodiments, the vector includes at least 1, at least 2, at least 3, at least 4, at least 5, at least 10, at least 15, at least 20, at least 25, at least 30, at least 40, least 45, at least 50 or more adenine dinucleotides. In some embodiments, the polyadenylation sequence comprises about 43 nucleotides, about 40-50 nucleotides, about 40-55 nucleotides, about 45-50 nucleotides, about 35-50 nucleotides, or any range there between.

The expression cassettes can include a poly-adenylation sequence known in the art or a variation thereof, such as a naturally occurring sequence isolated from bovine BGHpA (e.g., SEQ ID NO: 68) or a virus SV40 pA (e.g., SEQ ID NO: 86), or a synthetic sequence (e.g., SEQ ID NO: 87). Some expression cassettes can also include SV40 late polyA signal upstream enhancer (USE) sequence. In some embodiments, the, USE can be used in combination with SV40 pA or heterologous poly-A signal.

The expression cassettes can also include a post-transcriptional element to increase the expression of a transgene. In some embodiments, Woodchuck Hepatitis Virus (WHP) posttranscriptional regulatory element (WPRE) (e.g., SEQ ID NO: 67) is used to increase the expression of a transgene. Other posttranscriptional processing elements such as the post-transcriptional element from the thymidine kinase gene of herpes simplex virus, or hepatitis B virus (HBV) can be used. Secretory sequences can be linked to the transgenes, e.g., VH-02 and VK-A26 sequences, e.g., SEQ ID NO: 88 and SEQ ID NO: 89.

(iii). Nuclear Localization Sequences

In some embodiments, the vector encoding an RNA guided endonuclease comprises one or more nuclear localization sequences (NLSs), for example, 1, 2, 3, 4, 5, 6, 7, 8, 9, 10, or more NLSs. In some embodiments, the one or more NLSs are located at or near the amino-terminus, at or near the carboxy-terminus, or a combination of these (e.g., one or more NLS at the amino-terminus and/or one or more NLS at the carboxy terminus). When more than one NLS is present, each can be selected independently of the others, such that a single NLS is present in more than one copy and/or in combination with one or more other NLSs present in one or more copies. Non-limiting examples of NLSs are shown in Table 6.

TABLE 6

Nuclear Localization Signals

| SOURCE | SEQUENCE | SEQ ID NO. |
|---|---|---|
| SV40 virus large T-antigen | PKKKRKV (encoded by CCCAAGAAGAAGAGGAAGGTG; SEQ ID NO: 91) | 90 |
| nucleoplasmin | KRPAATKKAGQAKKKK | 92 |
| c-myc | PAAKRVKLD<br>RQRRNELKRSP | 93<br>94 |
| hRNPA1 M9 | NQSSNFGPMKGGNFGGRSSGPYGGGG QYFAKPRNQGGY | 95 |
| IBB domain from importin-alpha | RMRIZFKNKGKDTAELRRRRVEVSVE LRKAKKDEQILKRRNV | 96 |
| myoma T protein | VSRKRPRP<br>PPKKARED | 97<br>98 |
| human p53 | PQPKKKPL | 99 |
| mouse c-abl IV | SALIKKKKKMAP | 100 |
| influenza virus NS1 | DRLRR<br>PKQKKRK | 117<br>118 |
| Hepatitis virus delta antigen | RKLKKKIKKL | 119 |
| mouse Mx1 protein | REKKKFLKRR | 120 |
| human poly(ADP-ribose) polymerase | KRKGDEVDGVDEVAKKKSKK | 121 |
| steroid hormone receptors (human) glucocorticoid | RKCLQAGMNLEARKTKK | 122 |

E. Additional Components of ceDNA Vectors

The ceDNA vectors produced using the synthetic process as described herein may contain nucleotides that encode other components for gene expression. For example, to select for specific gene targeting events, a protective shRNA may be embedded in a microRNA and inserted into a recombinant ceDNA vector designed to integrate site—specifically into the highly active locus, such as an albumin locus. Such embodiments may provide a system for in vivo selection and expansion of gene-modified hepatocytes in any genetic background such as described in Nygaard et al., *A universal system to select gene-modified hepatocytes in vivo, Gene Therapy*, Jun. 8, 2016. The ceDNA vectors of the present disclosure may contain one or more selectable markers that permit selection of transformed, transfected, transduced, or the like cells. A selectable marker is a gene the product of which provides for biocide or viral resistance, resistance to heavy metals, prototrophy to auxotrophs, NeoR, and the like. In certain embodiments, positive selection markers are incorporated into the donor sequences such as NeoR. Negative selections markers may be incorporated downstream the donor sequences, for example a nucleic acid sequence HSV-tk encoding a negative selection marker may be incorporated into a nucleic acid construct downstream the donor sequence.

In embodiments, the ceDNA vector produced using the synthetic process as described herein can be used for gene editing, for example, as disclosed in International Application PCT/US2018/064242, filed on Dec. 6, 2018, which is incorporated herein in its entirety by reference, and may include one or more of: a 5' homology arm, a 3' homology arm, a polyadenylation site upstream and proximate to the 5' homology arm. Exemplary homology arms are 5' and 3' albumin homology arms (SEQ ID NO: 151 and 152) or CCR5 5'- and 3' homology arms (e.g., SEQ ID NO: 153, 154).

F. Regulatory Switches

A molecular regulatory switch is one which generates a measurable change in state in response to a signal. Such regulatory switches can be usefully combined with the ceDNA vectors produced using the synthetic process as described herein to control the output of expression of the transgene from the ceDNA vector. In some embodiments, the ceDNA vector comprises a regulatory switch that serves to fine tune expression of the transgene. For example, it can serve as a biocontainment function of the ceDNA vector. In some embodiments, the switch is an "ON/OFF" switch that is designed to start or stop (i.e., shut down) expression of the gene of interest in the ceDNA in a controllable and regulatable fashion. In some embodiments, the switch can include a "kill switch" that can instruct the cell comprising the ceDNA vector to undergo cell programmed death once the switch is activated. Exemplary regulatory switches encompassed for use in a ceDNA vector can be used to regulate the expression of a transgene, and are more fully discussed in International application PCT/US18/49996, which is incorporated herein in its entirety by reference (i) Binary Regulatory Switches In some embodiments, the ceDNA vector produced using the synthetic process as described herein comprises a regulatory switch that can serve to controllably modulate expression of the transgene. For example, the expression cassette located between the ITRs of the ceDNA vector may additionally comprise a regulatory region, e.g., a promoter, cis-element, repressor, enhancer etc., that is operatively linked to the gene of interest, where the regulatory region is regulated by one or more cofactors or exogenous agents. By way of example only, regulatory regions can be modulated by small molecule switches or inducible or repressible promoters. Non-limiting examples of inducible promoters are hormone-inducible or metal-inducible promoters. Other exemplary inducible promoters/enhancer elements include, but are not limited to, an RU486-inducible promoter, an ecdysone-inducible promoter, a rapamycin-inducible promoter, and a metallothionein promoter.

(ii) Small molecule Regulatory Switches

A variety of art-known small-molecule based regulatory switches are known in the art and can be combined with the synthetically produced ceDNA vectors disclosed herein to form a regulatory-switch controlled ceDNA vector. In some embodiments, the regulatory switch can be selected from any one or a combination of: an orthogonal ligand/nuclear receptor pair, for example retinoid receptor variant/LG335 and GRQCIMFI, along with an artificial promoter controlling expression of the operatively linked transgene, such as that as disclosed in Taylor, et al. BMC Biotechnology 10 (2010): 15; engineered steroid receptors, e.g., modified progesterone receptor with a C-terminal truncation that cannot bind progesterone but binds RU486 (mifepristone) (U.S. Pat. No. 5,364,791); an ecdysone receptor from *Drosophila* and their ecdysteroid ligands (Saez, et al., PNAS, 97(26)(2000), 14512-14517; or a switch controlled by the antibiotic trimethoprim (TMP), as disclosed in Sando R 3$^{rd}$; Nat Methods. 2013, 10(11):1085-8. In some embodiments, the regulatory switch to control the transgene or expressed by the ceDNA vector is a pro-drug activation switch, such as that disclosed in U.S. Pat. Nos. 8,771,679, and 6,339,070.

(iii) "Passcode" Regulatory Switches

In some embodiments the regulatory switch can be a "passcode switch" or "passcode circuit". Passcode switches allow fine tuning of the control of the expression of the transgene from the synthetically produced ceDNA vector when specific conditions occur—that is, a combination of conditions need to be present for transgene expression and/or repression to occur. For example, for expression of a transgene to occur at least conditions A and B must occur. A passcode regulatory switch can be any number of conditions, e.g., at least 2, or at least 3, or at least 4, or at least 5, or at least 6 or at least 7 or more conditions to be present for transgene expression to occur. In some embodiments, at least 2 conditions (e.g., A, B conditions) need to occur, and in some embodiments, at least 3 conditions need to occur (e.g., A, B and C, or A, B and D). By way of an example only, for gene expression from a ceDNA to occur that has a passcode "ABC" regulatory switch, conditions A, B and C must be present. Conditions A, B and C could be as follows; condition A is the presence of a condition or disease, condition B is a hormonal response, and condition C is a response to the transgene expression. For example, if the transgene edits a defective EPO gene, Condition A is the presence of Chronic Kidney Disease (CKD), Condition B occurs if the subject has hypoxic conditions in the kidney, Condition C is that Erythropoietin-producing cells (EPC) recruitment in the kidney is impaired; or alternatively, HIF-2 activation is impaired. Once the oxygen levels increase or the desired level of EPO is reached, the transgene turns off again until 3 conditions occur, turning it back on.

In some embodiments, a passcode regulatory switch or "Passcode circuit" encompassed for use in the synthetically produced ceDNA vector comprises hybrid transcription factors (TFs) to expand the range and complexity of environmental signals used to define biocontainment conditions. As opposed to a deadman switch which triggers cell death in the presence of a predetermined condition, the "passcode circuit" allows cell survival or transgene expression in the presence of a particular "passcode", and can be easily reprogrammed to allow transgene expression and/or cell survival only when the predetermined environmental condition or passcode is present.

Any and all combinations of regulatory switches disclosed herein, e.g., small molecule switches, nucleic acid-based switches, small molecule-nucleic acid hybrid switches, post-transcriptional transgene regulation switches, post-translational regulation, radiation-controlled switches, hypoxia-mediated switches and other regulatory switches known by persons of ordinary skill in the art as disclosed herein can be used in a passcode regulatory switch as disclosed herein. Regulatory switches encompassed for use are also discussed in the review article Kis et al., J R Soc Interface. 12: 20141000 (2015), and summarized in Table 1 of Kis. In some embodiments, a regulatory switch for use in a passcode system can be selected from any or a combination of the switches in Table 11.

(iv). Nucleic Acid-Based Regulatory Switches to Control Transgene Expression

In some embodiments, the regulatory switch to control the transgene expressed by the synthetically produced ceDNA vector is based on a nucleic-acid based control mechanism. Exemplary nucleic acid control mechanisms are known in the art and are envisioned for use. For example, such mechanisms include riboswitches, such as those disclosed in, e.g., US2009/0305253, US2008/0269258, US2017/0204477, WO2018026762A1, U.S. Pat. No. 9,222,093 and EP application EP288071, and also disclosed in the review by Villa J K et al., Microbiol Spectr. 2018 May; 6(3). Also included are metabolite-responsive transcription biosensors, such as those disclosed in WO2018/075486 and WO2017/147585. Other art-known mechanisms envisioned for use include silencing of the transgene with an siRNA or RNAi molecule (e.g., miR, shRNA). For example, the ceDNA vector can comprise a regulatory switch that encodes a RNAi molecule that is complementary to the transgene expressed by the ceDNA vector. When such RNAi is expressed even if the transgene is expressed by the ceDNA vector, it will be silenced by the complementary RNAi molecule, and when the RNAi is not expressed when the transgene is expressed by the ceDNA vector the transgene is not silenced by the RNAi.

In some embodiments, the regulatory switch is a tissue-specific self-inactivating regulatory switch, for example as disclosed in US2002/0022018, whereby the regulatory switch deliberately switches transgene expression off at a site where transgene expression might otherwise be disadvantageous. In some embodiments, the regulatory switch is a recombinase reversible gene expression system, for example as disclosed in US2014/0127162 and U.S. Pat. No. 8,324,436.

(v). Post-Transcriptional and Post-Translational Regulatory Switches.

In some embodiments, the regulatory switch to control the transgene or gene of interest expressed by the synthetically produced ceDNA vector is a post-transcriptional modification system. For example, such a regulatory switch can be an aptazyme riboswitch that is sensitive to tetracycline or theophylline, as disclosed in US2018/0119156, GB201107768, WO2001/064956A3, EP Patent 2707487 and Beilstein et al., ACS Synth. Biol., 2015, 4 (5), pp 526-534; Zhong et al., Elife. 2016 Nov. 2; 5. pii: e18858. In some embodiments, it is envisioned that a person of ordinary skill in the art could encode both the transgene and an inhibitory siRNA which contains a ligand sensitive (OFF-switch) aptamer, the net result being a ligand sensitive ON-switch.

(vi). Other Exemplary Regulatory Switches

Any known regulatory switch can be used in the synthetically produced ceDNA vector to control the gene expression of the transgene expressed by the ceDNA vector, including those triggered by environmental changes. Additional examples include, but are not limited to; the BOC method of Suzuki et al., Scientific Reports 8; 10051 (2018); genetic code expansion and a non-physiologic amino acid; radiation-controlled or ultra-sound controlled on/off switches (see, e.g., Scott S et al., Gene Ther. 2000 July; 7(13):1121-5; U.S. Pat. Nos. 5,612,318; 5,571,797; 5,770,581; 5,817,636; and WO1999/025385A1. In some embodiments, the regulatory switch is controlled by an implantable system, e.g., as disclosed in U.S. Pat. No. 7,840,263; US2007/0190028A1 where gene expression is controlled by one or more forms of energy, including electromagnetic energy, that activates promoters operatively linked to the transgene in the ceDNA vector.

In some embodiments, a regulatory switch envisioned for use in the synthetically produced ceDNA vector is a hypoxia-mediated or stress-activated switch, e.g., such as those disclosed in WO1999060142A2, U.S. Pat. Nos. 5,834,306; 6,218,179; 6,709,858; US2015/0322410; Greco et al., (2004) Targeted Cancer Therapies 9, S368, as well as FROG, TOAD and NRSE elements and conditionally inducible silence elements, including hypoxia response elements (HREs), inflammatory response elements (IREs) and shear-stress activated elements (SSAEs), e.g., as disclosed in U.S. Pat. No. 9,394,526. Such an embodiment is useful for turning on expression of the transgene from the ceDNA vector after ischemia or in ischemic tissues, and/or tumors.

(iv). Kill Switches

Other embodiments of the invention relate to a synthetically produced ceDNA vector comprising a kill switch. A kill switch as disclosed herein enables a cell comprising the ceDNA vector to be killed or undergo programmed cell death as a means to permanently remove an introduced ceDNA vector from the subject's system. It will be appreciated by one of ordinary skill in the art that use of kill switches in the synthetically produced ceDNA vectors of the invention would be typically coupled with targeting of the ceDNA vector to a limited number of cells that the subject can acceptably lose or to a cell type where apoptosis is desirable (e.g., cancer cells). In all aspects, a "kill switch" as disclosed herein is designed to provide rapid and robust cell killing of the cell comprising the ceDNA vector in the absence of an input survival signal or other specified condition. Stated another way, a kill switch encoded by a ceDNA vector herein can restrict cell survival of a cell comprising a ceDNA vector to an environment defined by specific input signals. Such kill switches serve as a biological biocontainment function should it be desirable to remove the synthetically produced ceDNA vector from a subject or to ensure that it will not express the encoded transgene.

VI. Pharmaceutical Compositions

In another aspect, pharmaceutical compositions are provided. The pharmaceutical composition comprises a closed-ended DNA vector, e.g., ceDNA vector produced using the synthetic process as described herein and a pharmaceutically acceptable carrier or diluent.

A closed-ended DNA vector, including a ceDNA vector, produced using the synthetic process as described herein can be incorporated into pharmaceutical compositions suitable for administration to a subject for in vivo delivery to cells, tissues, or organs of the subject. Typically, the pharmaceutical composition comprises a ceDNA vector as disclosed herein and a pharmaceutically acceptable carrier. For example, a closed-ended DNA vector, including a ceDNA vector, produced using the synthetic process as described herein can be incorporated into a pharmaceutical composition suitable for a desired route of therapeutic administration (e.g., parenteral administration). Passive tissue transduction via high pressure intravenous or intra-arterial infusion, as well as intracellular injection, such as intranuclear microinjection or intracytoplasmic injection, are also contemplated. Pharmaceutical compositions for therapeutic purposes can be formulated as a solution, microemulsion, dispersion, liposomes, or other ordered structure suitable to high synthetically produced closed-ended DNA vector, e.g., ceDNA vector concentration. Sterile injectable solutions can be prepared by incorporating the synthetically produced closed-ended DNA vector, e.g., ceDNA vector compound in the required amount in an appropriate buffer with one or a combination of ingredients enumerated above, as required, followed by filtered sterilization including a ceDNA vector can be formulated to deliver a transgene in the nucleic acid to the cells of a recipient, resulting in the therapeutic expression of the transgene or donor sequence therein. The composition can also include a pharmaceutically acceptable carrier.

Pharmaceutically active compositions comprising a closed-ended DNA vector, including a ceDNA vector, produced using the synthetic process as described herein can be formulated to deliver a transgene for various purposes to the cell, e.g., cells of a subject.

Pharmaceutical compositions for therapeutic purposes typically must be sterile and stable under the conditions of manufacture and storage. The composition can be formulated as a solution, microemulsion, dispersion, liposomes, or other ordered structure suitable to high synthetically produced closed-ended DNA vector, e.g. ceDNA vector concentration. Sterile injectable solutions can be prepared by incorporating the synthetically produced closed-ended DNA vector, e.g., ceDNA vector compound in the required amount in an appropriate buffer with one or a combination of ingredients enumerated above, as required, followed by filtered sterilization.

A closed-ended DNA vector, including a ceDNA vector, produced using the synthetic process as described herein as disclosed herein can be incorporated into a pharmaceutical composition suitable for topical, systemic, intra-amniotic, intrathecal, intracranial, intra-arterial, intravenous, intralymphatic, intraperitoneal, subcutaneous, tracheal, intra-tissue (e.g., intramuscular, intracardiac, intrahepatic, intrarenal, intracerebral), intrathecal, intravesical, conjunctival (e.g., extra-orbital, intraorbital, retroorbital, intraretinal, subretinal, choroidal, sub-choroidal, intrastromal, intracameral and intravitreal), intracochlear, and mucosal (e.g., oral, rectal, nasal) administration. Passive tissue transduction via high pressure intravenous or intraarterial infusion, as well as intracellular injection, such as intranuclear microinjection or intracytoplasmic injection, are also contemplated.

In some aspects, the methods provided herein comprise delivering one or more closed-ended DNA vector, including a ceDNA vector, produced using the synthetic process as described herein to a host cell. Also provided herein are cells produced by such methods, and organisms (such as animals, plants, or fungi) comprising or produced from such cells. Methods of delivery of nucleic acids can include lipofection, nucleofection, microinjection, biolistics, liposomes, immunoliposomes, polycation or lipid:nucleic acid conjugates, naked DNA, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Delivery can be to cells (e.g., in vitro or ex vivo administration) or target tissues (e.g., in vivo administration).

Various techniques and methods are known in the art for delivering nucleic acids to cells. For example, a closed-ended DNA vector, including a ceDNA vector, produced using the synthetic process as described herein can be formulated into lipid nanoparticles (LNPs), lipidoids, liposomes, lipid nanoparticles, lipoplexes, or core-shell nanoparticles. Typically, LNPs are composed of nucleic acid (e.g., ceDNA) molecules, one or more ionizable or cationic lipids (or salts thereof), one or more non-ionic or neutral lipids (e.g., a phospholipid), a molecule that prevents aggregation (e.g., PEG or a PEG-lipid conjugate), and optionally a sterol (e.g., cholesterol).

Another method for delivering a closed-ended DNA vector, including a ceDNA vector, produced using the synthetic process as described herein to a cell is by conjugating the nucleic acid with a ligand that is internalized by the cell. For example, the ligand can bind a receptor on the cell surface and internalized via endocytosis. The ligand can be covalently linked to a nucleotide in the nucleic acid. Exemplary conjugates for delivering nucleic acids into a cell are described, example, in WO2015/006740, WO2014/025805, WO2012/037254, WO2009/082606, WO2009/073809, WO2009/018332, WO2006/112872, WO2004/090108, WO2004/091515 and WO2017/177326.

Nucleic acids and closed-ended DNA vector, including a ceDNA vector, produced using the synthetic process as described herein can also be delivered to a cell by transfection. Useful transfection methods include, but are not limited to, lipid-mediated transfection, cationic polymer-mediated transfection, or calcium phosphate precipitation. Transfection reagents are well known in the art and include, but are not limited to, TurboFect Transfection Reagent (Thermo Fisher Scientific), Pro-Ject Reagent (Thermo Fisher Scientific), TRANSPASS™ P Protein Transfection Reagent (New England Biolabs), CHARIOT™ Protein Delivery Reagent (Active Motif), PROTEOJUICE™ Protein Transfection Reagent (EMD Millipore), 293fectin, LIPOFECTAMINE™ 2000, LIPOFECTAMINE™ 3000 (Thermo Fisher Scientific), LIPOFECTAMINE™ (Thermo Fisher Scientific), LIPOFECTIN™ (Thermo Fisher Scientific), DMRIE-C, CELLFECTIN™ (Thermo Fisher Scientific), OLIGOFECTAMINE™ (Thermo Fisher Scientific), LIPOFECTACE™, FUGENE™ (Roche, Basel, Switzerland), FUGENE™ HD (Roche), TRANSFECTAM™ (Transfectam, Promega, Madison, Wis.), TFX-10™ (Promega), TFX-20™ (Promega), TFX-50™ (Promega), TRANSFECTIN™ (BioRad, Hercules, Calif.), SILENTFECT™ (BioRad), Effectene™ (Qiagen, Valencia, Calif.), DC-chol (Avanti Polar Lipids), GENEPORTER™ (Gene Therapy Systems, San Diego, Calif.), DHARMAFECT 1™ (Dharmacon, Lafayette, Colo.), DHARMAFECT 2™ (Dharmacon), DHARMAFECT 3™ (Dharmacon), DHARMAFECT 4™ (Dharmacon), ESCORT™ III (Sigma, St. Louis, Mo.), and ESCORT™ IV (Sigma Chemical Co.). Nucleic acids, such as ceDNA, can also be delivered to a cell via microfluidics methods known to those of skill in the art.

A closed-ended DNA vector, including a ceDNA vector, produced using the synthetic process as described herein can also be administered directly to an organism for transduction of cells in vivo. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of a closed-ended DNA vector, including a ceDNA vector, produced using the synthetic process as described herein can be delivered into hematopoietic stem cells, for example, by the methods as described, for example, in U.S. Pat. No. 5,928,638.

A closed-ended DNA vector, including a ceDNA vector, produced using the synthetic process as described herein can be added to liposomes for delivery to a cell or target organ in a subject. Liposomes are vesicles that possess at least one lipid bilayer. Liposomes are typical used as carriers for drug/therapeutic delivery in the context of pharmaceutical development. They work by fusing with a cellular membrane and repositioning its lipid structure to deliver a drug or active pharmaceutical ingredient (API). Liposome compositions for such delivery are composed of phospholipids, especially compounds having a phosphatidylcholine group, however these compositions may also include other lipids. Exemplary liposomes and liposome formulations are disclosed in International Application PCT/US2018/050042, filed on Sep. 7, 2018 and in International application PCT/US2018/064242, filed on Dec. 6, 2018, e.g., see the section entitled "Pharmaceutical Formulations".

Various delivery methods known in the art or modifications thereof can be used to deliver a closed-ended DNA vector, including a ceDNA vector, produced using the synthetic process as described herein in vitro or in vivo. For example, in some embodiments, ceDNA vectors are delivered by making transient penetration in cell membrane by mechanical, electrical, ultrasonic, hydrodynamic, or laser-based energy so that DNA entrance into the targeted cells is facilitated. For example, a ceDNA vector can be delivered by transiently disrupting cell membrane by squeezing the cell through a size-restricted channel or by other means known in the art. In some cases, a ceDNA vector alone is directly injected as naked DNA into skin, thymus, cardiac muscle, skeletal muscle, or liver cells. In some cases, a ceDNA vector is delivered by gene gun. Gold or tungsten spherical particles (1-3 μm diameter) coated with capsid-free AAV vectors can be accelerated to high speed by pressurized gas to penetrate into target tissue cells.

Compositions comprising a closed-ended DNA vector, including a ceDNA vector, produced using the synthetic process as described herein and a pharmaceutically acceptable carrier are specifically contemplated herein. In some embodiments, the ceDNA vector is formulated with a lipid delivery system, for example, liposomes as described herein. In some embodiments, such compositions are administered by any route desired by a skilled practitioner. The compositions may be administered to a subject by different routes including orally, parenterally, sublingually, transdermally, rectally, transmucosally, topically, via inhalation, via buccal administration, intrapleurally, intravenous, intra-arterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian may readily determine the dosing regimen and route of administration that is most appropriate for a particular animal. The compositions may be administered by traditional syringes, needleless injection devices, "microprojectile bombardment gene guns", or other physical methods such as electroporation ("EP"), hydrodynamic methods or ultrasound.

In some cases, a closed-ended DNA vector, including a ceDNA vector, produced using the synthetic process as described herein is delivered by hydrodynamic injection, which is a simple and highly efficient method for direct intracellular delivery of any water-soluble compounds and particles into internal organs and skeletal muscle in an entire limb.

In some cases, a closed-ended DNA vector, including a ceDNA vector, produced using the synthetic process as described herein is delivered by ultrasound by making nanoscopic pores in membrane to facilitate intracellular delivery of DNA particles into cells of internal organs or tumors, so the size and concentration of the closed-ended DNA vector have a great role in efficiency of the system. In some cases, closed-ended DNA vectors, including a ceDNA vector, produced using the synthetic process as described herein are delivered by magnetofection by using magnetic fields to concentrate particles containing nucleic acid into the target cells.

In some cases, chemical delivery systems can be used, for example, by using nanomeric complexes, which include compaction of negatively charged nucleic acid by polycationic nanomeric particles, belonging to cationic liposome/micelle or cationic polymers. Cationic lipids used for the delivery method includes, but not limited to monovalent cationic lipids, polyvalent cationic lipids, guanidine containing compounds, cholesterol derivative compounds, cationic polymers, (e.g., poly(ethylenimine), poly-L-lysine, protamine, other cationic polymers), and lipid-polymer hybrid.

A. Exosomes:

In some embodiments, a closed-ended DNA vector, including a ceDNA vector, produced using the synthetic process as described herein is delivered by being packaged in an exosome. Exosomes are small membrane vesicles of endocytic origin that are released into the extracellular environment following fusion of multivesicular bodies with the plasma membrane. Their surface consists of a lipid bilayer from the donor cell's cell membrane, they contain cytosol from the cell that produced the exosome, and exhibit membrane proteins from the parental cell on the surface. Exosomes are produced by various cell types including epithelial cells, B and T lymphocytes, mast cells (MC) as well as dendritic cells (DC). Some embodiments, exosomes with a diameter between 10 nm and 1 μm, between 20 nm and 500 nm, between 30 nm and 250 nm, between 50 nm and 100 nm are envisioned for use. Exosomes can be isolated for a delivery to target cells using either their donor cells or by introducing specific nucleic acids into them. Various approaches known in the art can be used to produce exosomes containing capsid-free AAV vectors of the present invention.

B. Microparticle/Nanoparticles:

In some embodiments, a closed-ended DNA vector, including a ceDNA vector, produced using the synthetic process as described herein is delivered by a lipid nanoparticle. Generally, lipid nanoparticles comprise an ionizable amino lipid (e.g., heptatriaconta-6,9,28,31-tetraen-19-yl 4-(dimethylamino)butanoate, DLin-MC3-DMA, a phosphatidylcholine (1,2-distearoyl-sn-glycero-3-phosphocholine, DSPC), cholesterol and a coat lipid (polyethylene glycol-dimyristolglycerol, PEG-DMG), for example as disclosed by Tam et al. (2013). *Advances in Lipid Nanoparticlesfor siRNA delivery*. Pharmaceuticals 5(3): 498-507.

In some embodiments, a lipid nanoparticle has a mean diameter between about 10 and about 1000 nm. In some embodiments, a lipid nanoparticle has a diameter that is less than 300 nm. In some embodiments, a lipid nanoparticle has a diameter between about 10 and about 300 nm. In some embodiments, a lipid nanoparticle has a diameter that is less than 200 nm. In some embodiments, a lipid nanoparticle has a diameter between about 25 and about 200 nm. In some embodiments, a lipid nanoparticle preparation (e.g., composition comprising a plurality of lipid nanoparticles) has a size distribution in which the mean size (e.g., diameter) is about 70 nm to about 200 nm, and more typically the mean size is about 100 nm or less.

Various lipid nanoparticles known in the art can be used to deliver a closed-ended DNA vector, including a ceDNA vector produced using the synthetic process as described herein. For example, various delivery methods using lipid nanoparticles are described in U.S. Pat. Nos. 9,404,127, 9,006,417 and 9,518,272.

In some embodiments, a closed-ended DNA vector, including a ceDNA vector, produced using the synthetic process as described herein is delivered by a gold nanoparticle. Generally, a nucleic acid can be covalently bound to a gold nanoparticle or non-covalently bound to a gold nanoparticle (e.g., bound by a charge-charge interaction), for example as described by Ding et al. (2014). *Gold Nanoparticlesfor Nucleic Acid Delivery*. Mol. Ther. 22(6); 1075-1083. In some embodiments, gold nanoparticle-nucleic acid conjugates are produced using methods described, for example, in U.S. Pat. No. 6,812,334.

C. Conjugates

In some embodiments, a closed-ended DNA vector, including a ceDNA vector, produced using the synthetic process as described herein as disclosed herein is conjugated (e.g., covalently bound to an agent that increases cellular uptake. An "agent that increases cellular uptake" is a molecule that facilitates transport of a nucleic acid across a lipid membrane. For example, a nucleic acid can be conjugated to a lipophilic compound (e.g., cholesterol, tocopherol, etc.), a cell penetrating peptide (CPP) (e.g., penetratin, TAT, Syn1B, etc.), and polyamines (e.g., spermine). Further examples of agents that increase cellular uptake are disclosed, for example, in Winkler (2013). *Oligonucleotide conjugates for therapeutic applications*. Ther. Deliv. 4(7); 791-809.

In some embodiments, a closed-ended DNA vector, including a ceDNA vector, produced using the synthetic process as described herein as disclosed herein is conjugated to a polymer (e.g., a polymeric molecule) or a folate molecule (e.g., folic acid molecule). Generally, delivery of nucleic acids conjugated to polymers is known in the art, for example as described in WO2000/34343 and WO2008/022309. In some embodiments, a ceDNA vector as disclosed herein is conjugated to a poly(amide) polymer, for example as described by U.S. Pat. No. 8,987,377. In some embodiments, a nucleic acid described by the disclosure is conjugated to a folic acid molecule as described in U.S. Pat. No. 8,507,455.

In some embodiments, a closed-ended DNA vector, including a ceDNA vector, produced using the synthetic process as described herein as disclosed herein is conjugated to a carbohydrate, for example as described in U.S. Pat. No. 8,450,467.

D. Nanocapsule

Alternatively, nanocapsule formulations of a closed-ended DNA vector, including a ceDNA vector, produced using the synthetic process as described herein as disclosed herein can be used. Nanocapsules can generally entrap substances in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use.

E. Liposomes

A closed-ended DNA vector, including a ceDNA vector, produced using the synthetic process as described herein can be added to liposomes for delivery to a cell or target organ in a subject. Liposomes are vesicles that possess at least one lipid bilayer. Liposomes are typical used as carriers for drug/therapeutic delivery in the context of pharmaceutical development. They work by fusing with a cellular membrane and repositioning its lipid structure to deliver a drug or active pharmaceutical ingredient (API). Liposome compositions for such delivery are composed of phospholipids, especially compounds having a phosphatidylcholine group, however these compositions may also include other lipids.

The formation and use of liposomes is generally known to those of skill in the art. Liposomes have been developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

F. Exemplary liposome and Lipid Nanoparticle (LNP) Compositions

A closed-ended DNA vector, including a ceDNA vector, produced using the synthetic process as described herein can be added to liposomes for delivery to a cell, e.g., a cell in need of expression of the transgene. Liposomes are vesicles that possess at least one lipid bilayer. Liposomes are typical used as carriers for drug/therapeutic delivery in the context of pharmaceutical development. They work by fusing with a cellular membrane and repositioning its lipid structure to deliver a drug or active pharmaceutical ingredient (API). Liposome compositions for such delivery are composed of phospholipids, especially compounds having a phosphatidylcholine group, however these compositions may also include other lipids.

Lipid nanoparticles (LNPs) comprising ceDNA are disclosed in International Application PCT/US2018/050042, filed on Sep. 7, 2018, and International Application PCT/US2018/064242, filed on Dec. 6, 2018, which are each incorporated herein by reference in their entirety and envisioned for use in the methods and compositions as disclosed herein.

In some aspects, the disclosure provides for a liposome formulation that includes one or more compounds with a polyethylene glycol (PEG) functional group (so-called "PEG-ylated compounds") which can reduce the immunogenicity/antigenicity of, provide hydrophilicity and hydrophobicity to the compound(s) and reduce dosage frequency. Or the liposome formulation simply includes polyethylene glycol (PEG) polymer as an additional component. In such aspects, the molecular weight of the PEG or PEG functional group can be from 62 Da to about 5,000 Da.

In some aspects, the disclosure provides for a liposome formulation that will deliver an API with extended release or controlled release profile over a period of hours to weeks. In some related aspects, the liposome formulation may comprise aqueous chambers that are bound by lipid bilayers. In other related aspects, the liposome formulation encapsulates an API with components that undergo a physical transition at elevated temperature which releases the API over a period of hours to weeks.

In some aspects, the liposome formulation comprises sphingomyelin and one or more lipids disclosed herein. In some aspects, the liposome formulation comprises optisomes.

In some aspects, the disclosure provides for a liposome formulation that includes one or more lipids selected from: N-(carbonyl-methoxypolyethylene glycol 2000)-1,2-distearoyl-sn-glycero-3-phosphoethanolamine sodium salt, (distearoyl-sn-glycero-phosphoethanolamine), MPEG (methoxy polyethylene glycol)-conjugated lipid, HSPC (hydrogenated soy phosphatidylcholine); PEG (polyethylene glycol); DSPE (distearoyl-sn-glycero-phosphoethanolamine); DSPC (distearoylphosphatidylcholine); DOPC (dioleoylphosphatidylcholine); DPPG (dipalmitoylphosphatidylglycerol); EPC (egg phosphatidylcholine); DOPS (dioleoylphosphatidylserine); POPC (palmitoyloleoylphosphatidylcholine); SM (sphingomyelin); MPEG (methoxy polyethylene glycol); DMPC (dimyristoyl phosphatidylcholine); DMPG (dimyristoyl phosphatidylglycerol); DSPG (distearoylphosphatidylglycerol); DEPC (dierucoylphosphatidylcholine); DOPE (dioleoly-sn-glycero-phophoethanolamine). cholesteryl sulphate (CS), dipalmitoylphosphatidylglycerol (DPPG), DOPC (dioleoly-sn-glycero-phosphatidylcholine) or any combination thereof.

In some aspects, the disclosure provides for a liposome formulation comprising phospholipid, cholesterol and a PEG-ylated lipid in a molar ratio of 56:38:5. In some aspects, the liposome formulation's overall lipid content is from 2-16 mg/mL. In some aspects, the disclosure provides for a liposome formulation comprising a lipid containing a phosphatidylcholine functional group, a lipid containing an ethanolamine functional group and a PEG-ylated lipid. In some aspects, the disclosure provides for a liposome formulation comprising a lipid containing a phosphatidylcholine functional group, a lipid containing an ethanolamine functional group and a PEG-ylated lipid in a molar ratio of 3:0.015:2 respectively. In some aspects, the disclosure provides for a liposome formulation comprising a lipid containing a phosphatidylcholine functional group, cholesterol and a PEG-ylated lipid. In some aspects, the disclosure provides for a liposome formulation comprising a lipid containing a phosphatidylcholine functional group and cholesterol. In some aspects, the PEG-ylated lipid is PEG-2000-DSPE. In some aspects, the disclosure provides for a liposome formulation comprising DPPG, soy PC, MPEG-DSPE lipid conjugate and cholesterol.

In some aspects, the disclosure provides for a liposome formulation comprising one or more lipids containing a phosphatidylcholine functional group and one or more lipids containing an ethanolamine functional group. In some aspects, the disclosure provides for a liposome formulation comprising one or more: lipids containing a phosphatidylcholine functional group, lipids containing an ethanolamine functional group, and sterols, e.g. cholesterol. In some aspects, the liposome formulation comprises DOPC/DEPC; and DOPE.

In some aspects, the disclosure provides for a liposome formulation further comprising one or more pharmaceutical excipients, e.g. sucrose and/or glycine.

In some aspects, the disclosure provides for a liposome formulation that is either unilamellar or multilamellar in structure. In some aspects, the disclosure provides for a liposome formulation that comprises multi-vesicular particles and/or foam-based particles. In some aspects, the disclosure provides for a liposome formulation that are larger in relative size to common nanoparticles and about 150 to 250 nm in size. In some aspects, the liposome formulation is a lyophilized powder.

In some aspects, the disclosure provides for a liposome formulation that is made and loaded with ceDNA vectors disclosed or described herein, by adding a weak base to a mixture having the isolated ceDNA outside the liposome. This addition increases the pH outside the liposomes to approximately 7.3 and drives the API into the liposome. In some aspects, the disclosure provides for a liposome formulation having a pH that is acidic on the inside of the liposome. In such cases the inside of the liposome can be at pH 4-6.9, and more preferably pH 6.5. In other aspects, the disclosure provides for a liposome formulation made by using intra-liposomal drug stabilization technology. In such cases, polymeric or non-polymeric highly charged anions and intra-liposomal trapping agents are utilized, e.g. polyphosphate or sucrose octasulfate.

In some aspects, the disclosure provides for a lipid nanoparticle comprising a DNA vector, including a ceDNA vector produced using the synthetic process as described herein and an ionizable lipid. For example, a lipid nanoparticle formulation that is made and loaded with ceDNA obtained by the process as disclosed in International Application PCT/US2018/050042, filed on Sep. 7, 2018, which is incorporated herein. This can be accomplished by high energy mixing of ethanolic lipids with aqueous ceDNA at low pH which protonates the ionizable lipid and provides favorable energetics for ceDNA/lipid association and nucleation of particles. The particles can be further stabilized through aqueous dilution and removal of the organic solvent. The particles can be concentrated to the desired level.

Generally, the lipid particles are prepared at a total lipid to ceDNA (mass or weight) ratio of from about 10:1 to 30:1. In some embodiments, the lipid to ceDNA ratio (mass/mass ratio; w/w ratio) can be in the range of from about 1:1 to about 25:1, from about 10:1 to about 14:1, from about 3:1 to about 15:1, from about 4:1 to about 10:1, from about 5:1 to about 9:1, or about 6:1 to about 9:1. The amounts of lipids and ceDNA can be adjusted to provide a desired N/P ratio, for example, N/P ratio of 3, 4, 5, 6, 7, 8, 9, 10 or higher. Generally, the lipid particle formulation's overall lipid content can range from about 5 mg/ml to about 30 mg/mL.

The ionizable lipid is typically employed to condense the nucleic acid cargo, e.g., ceDNA at low pH and to drive membrane association and fusogenicity. Generally, ionizable lipids are lipids comprising at least one amino group that is positively charged or becomes protonated under acidic conditions, for example at pH of 6.5 or lower. Ionizable lipids are also referred to as cationic lipids herein.

Exemplary ionizable lipids are described in International PCT patent publications WO2015/095340, WO2015/199952, WO2018/011633, WO2017/049245, WO2015/061467, WO2012/040184, WO2012/000104, WO2015/074085, WO2016/081029, WO2017/004143, WO2017/075531, WO2017/117528, WO2011/022460, WO2013/148541, WO2013/116126, WO2011/153120, WO2012/044638, WO2012/054365, WO2011/090965, WO2013/016058, WO2012/162210, WO2008/042973, WO2010/129709, WO2010/144740, WO2012/099755, WO2013/049328, WO2013/086322, WO2013/086373, WO2011/071860, WO2009/132131, WO2010/048536, WO2010/088537, WO2010/054401, WO2010/054406, WO2010/054405, WO2010/054384, WO2012/016184, WO2009/086558, WO2010/042877, WO2011/000106, WO2011/000107, WO2005/120152, WO2011/141705, WO2013/

126803, WO2006/007712, WO2011/038160, WO2005/121348, WO2011/066651, WO2009/127060, WO2011/141704, WO2006/069782, WO2012/031043, WO2013/006825, WO2013/033563, WO2013/089151, WO2017/099823, WO2015/095346, and WO2013/086354, and US patent publications US2016/0311759, US2015/0376115, US2016/0151284, US2017/0210697, US2015/0140070, US2013/0178541, US2013/0303587, US2015/0141678, US2015/0239926, US2016/0376224, US2017/0119904, US2012/0149894, US2015/0057373, US2013/0090372, US2013/0274523, US2013/0274504, US2013/0274504, US2009/0023673, US2012/0128760, US2010/0324120, US2014/0200257, US2015/0203446, US2018/0005363, US2014/0308304, US2013/0338210, US2012/0101148, US2012/0027796, US2012/0058144, US2013/0323269, US2011/0117125, US2011/0256175, US2012/0202871, US2011/0076335, US2006/0083780, US2013/0123338, US2015/0064242, US2006/0051405, US2013/0065939, US2006/0008910, US2003/0022649, US2010/0130588, US2013/0116307, US2010/0062967, US2013/0202684, US2014/0141070, US2014/0255472, US2014/0039032, US2018/0028664, US2016/0317458, and US2013/0195920, the contents of all of which are incorporated herein by reference in their entirety.

In some embodiments, the ionizable lipid is MC3 (6Z,9Z,28Z,31Z)-heptatriaconta-6,9,28,31-tetraen-19-yl-4-(dimethylamino) butanoate (DLin-MC3-DMA or MC3) having the following structure:

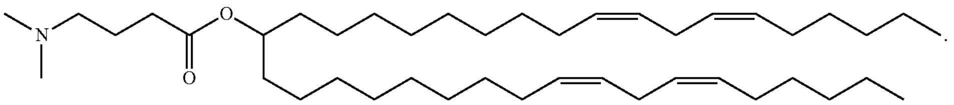

DLin-M-C3-DMA ("MC3")

The lipid DLin-MC3-DMA is described in Jayaraman et al., Angew. Chem. Int. Ed Engl. (2012), 51(34): 8529-8533, content of which is incorporated herein by reference in its entirety.

In some embodiments, the ionizable lipid is the lipid ATX-002 as described in WO2015/074085, content of which is incorporated herein by reference in its entirety.

In some embodiments, the ionizable lipid is (13Z,16Z)—N,N-dimethyl-3-nonyldocosa-13,16-dien-1-amine (Compound 32), as described in WO2012/040184, content of which is incorporated herein by reference in its entirety.

In some embodiments, the ionizable lipid is Compound 6 or Compound 22 as described in WO2015/199952, content of which is incorporated herein by reference in its entirety.

Without limitations, ionizable lipid can comprise 20-90% (mol) of the total lipid present in the lipid nanoparticle. For example, ionizable lipid molar content can be 20-70% (mol), 30-60% (mol) or 40-50% (mol) of the total lipid present in the lipid nanoparticle. In some embodiments, ionizable lipid comprises from about 50 mol % to about 90 mol % of the total lipid present in the lipid nanoparticle.

In some aspects, the lipid nanoparticle can further comprise a non-cationic lipid. Non-ionic lipids include amphipathic lipids, neutral lipids and anionic lipids. Accordingly, the non-cationic lipid can be a neutral uncharged, zwitterionic, or anionic lipid. Non-cationic lipids are typically employed to enhance fusogenicity.

Exemplary non-cationic lipids envisioned for use in the methods and compositions comprising a DNA vector, including a ceDNA vector produced using the synthetic process as described herein are described in International Application PCT/US2018/050042, filed on Sep. 7, 2018, and PCT/US2018/064242, filed on Dec. 6, 2018 which is incorporated herein in its entirety.

Exemplary non-cationic lipids are described in International application Publication WO2017/099823 and US patent publication US2018/0028664, the contents of both of which are incorporated herein by reference in their entirety.

The non-cationic lipid can comprise 0-30% (mol) of the total lipid present in the lipid nanoparticle. For example, the non-cationic lipid content is 5-20% (mol) or 10-15% (mol) of the total lipid present in the lipid nanoparticle. In various embodiments, the molar ratio of ionizable lipid to the neutral lipid ranges from about 2:1 to about 8:1.

In some embodiments, the lipid nanoparticles do not comprise any phospholipids. In some aspects, the lipid nanoparticle can further comprise a component, such as a sterol, to provide membrane integrity.

One exemplary sterol that can be used in the lipid nanoparticle is cholesterol and derivatives thereof. Exemplary cholesterol derivatives are described in International application WO2009/127060 and US patent publication US2010/0130588, contents of both of which are incorporated herein by reference in their entirety.

The component providing membrane integrity, such as a sterol, can comprise 0-50% (mol) of the total lipid present in the lipid nanoparticle. In some embodiments, such a component is 20-50% (mol) 30-40% (mol) of the total lipid content of the lipid nanoparticle.

In some aspects, the lipid nanoparticle can further comprise a polyethylene glycol (PEG) or a conjugated lipid molecule. Generally, these are used to inhibit aggregation of lipid nanoparticles and/or provide steric stabilization. Exemplary conjugated lipids include, but are not limited to, PEG-lipid conjugates, polyoxazoline (POZ)-lipid conjugates, polyamide-lipid conjugates (such as ATTA-lipid conjugates), cationic-polymer lipid (CPL) conjugates, and mixtures thereof. In some embodiments, the conjugated lipid molecule is a PEG-lipid conjugate, for example, a (methoxy polyethylene glycol)-conjugated lipid. Exemplary PEG-lipid conjugates include, but are not limited to, PEG-diacylglycerol (DAG) (such as 1-(monomethoxy-polyethyleneglycol)-2,3-dimyristoylglycerol (PEG-DMG)), PEG-dialkyloxypropyl (DAA), PEG-phospholipid, PEG-ceramide (Cer), a PEGylated phosphatidylethanoloamine (PEG-PE), PEG succinate diacylglycerol (PEGS-DAG) (such as 4-O-(2',3'-di(tetradecanoyloxy)propyl-1-O-(w-methoxy(polyethoxy)ethyl) butanedioate (PEG-S-DMG)), PEG dialkoxypropylcarbam, N-(carbonyl-methoxypolyethylene glycol 2000)-1,2-distearoyl-sn-glycero-3-phosphoethanolamine sodium salt, or a mixture thereof. Additional exemplary PEG-lipid conjugates are described, for example, in U.S. Pat. Nos. 5,885,613, 6,287,591, US2003/0077829, US2003/0077829, US2005/0175682, US2008/0020058, US2011/0117125, US2010/0130588, US2016/0376224, and US2017/0119904, the contents of all of which are incorporated herein by reference in their entirety.

In some embodiments, a PEG-lipid is a compound disclosed in US2018/0028664, the content of which is incorporated herein by reference in its entirety.

In some embodiments, a PEG-lipid is disclosed in US20150376115 or in US2016/0376224, the content of both of which is incorporated herein by reference in its entirety.

The PEG-DAA conjugate can be, for example, PEG-dilauryloxypropyl, PEG-dimyristyloxypropyl, PEG-dipalmityloxypropyl, or PEG-distearyloxypropyl. The PEG-lipid can be one or more of PEG-DMG, PEG-dilaurylglycerol, PEG-dipalmitoylglycerol, PEG-disterylglycerol, PEG-dilaurylglycamide, PEG-dimyristylglycamide, PEG-dipalmitoylglycamide, PEG-disterylglycamide, PEG-cholesterol (1-[8'-(Cholest-5-en-3 [beta]-oxy)carboxamido-3',6'-dioxaoctanyl]carbamoyl-[omega]-methyl-poly(ethylene glycol), PEG-DMB (3,4-Ditetradecoxylbenzyl-[omega]-methyl-poly(ethylene glycol) ether), and 1,2-dimyristoyl-sn-glycero-3-phosphoethanolamine-N-[methoxy(polyethylene glycol)-2000]. In some examples, the PEG-lipid can be selected from the group consisting of PEG-DMG, 1,2-dimyristoyl-sn-glycero-3-phosphoethanolamine-N-[methoxy(polyethylene glycol)-2000].

Lipids conjugated with a molecule other than a PEG can also be used in place of PEG-lipid. For example, polyoxazoline (POZ)-lipid conjugates, polyamide-lipid conjugates (such as ATTA-lipid conjugates), and cationic-polymer lipid (CPL) conjugates can be used in place of or in addition to the PEG-lipid. Exemplary conjugated lipids, i.e., PEG-lipids, (POZ)-lipid conjugates, ATTA-lipid conjugates and cationic polymer-lipids are described in the International patent application publications WO1996/010392, WO1998/051278, WO2002/087541, WO2005/026372, WO2008/147438, WO2009/086558, WO2012/000104, WO2017/117528, WO2017/099823, WO2015/199952, WO2017/004143, WO2015/095346, WO2012/000104, WO2012/000104, and WO2010/006282, US patent application publications US2003/0077829, US2005/0175682, US2008/0020058, US2011/0117125, US2013/0303587, US2018/0028664, US2015/0376115, US2016/0376224, US2016/0317458, US2013/0303587, US2013/0303587, and US20110123453, and U.S. Pat. Nos. 5,885,613, 6,287,591, 6,320,017, and 6,586,559, the contents of all of which are incorporated herein by reference in their entirety.

In some embodiments, the one or more additional compound can be a therapeutic agent. The therapeutic agent can be selected from any class suitable for the therapeutic objective. In other words, the therapeutic agent can be selected from any class suitable for the therapeutic objective. In other words, the therapeutic agent can be selected according to the treatment objective and biological action desired. For example, if the ceDNA within the LNP is useful for treating cancer, the additional compound can be an anti-cancer agent (e.g., a chemotherapeutic agent, a targeted cancer therapy (including, but not limited to, a small molecule, an antibody, or an antibody-drug conjugate). In another example, if the LNP containing the ceDNA is useful for treating an infection, the additional compound can be an antimicrobial agent (e.g., an antibiotic or antiviral compound). In yet another example, if the LNP containing the ceDNA is useful for treating an immune disease or disorder, the additional compound can be a compound that modulates an immune response (e.g., an immunosuppressant, immunostimulatory compound, or compound modulating one or more specific immune pathways). In some embodiments, different cocktails of different lipid nanoparticles containing different compounds, such as a ceDNA encoding a different protein or a different compound, such as a therapeutic may be used in the compositions and methods of the invention.

In some embodiments, the additional compound is an immune modulating agent. For example, the additional compound is an immunosuppressant. In some embodiments, the additional compound is immune stimulatory agent.

Also provided herein is a pharmaceutical composition comprising the lipid nanoparticle-encapsulated synthetically produced ceDNA vector and a pharmaceutically acceptable carrier or excipient.

In some aspects, the disclosure provides for a lipid nanoparticle formulation further comprising one or more pharmaceutical excipients. In some embodiments, the lipid nanoparticle formulation further comprises sucrose, tris, trehalose and/or glycine.

A closed-ended DNA vector, including a ceDNA vector, produced using the synthetic process as described herein can be complexed with the lipid portion of the particle or encapsulated in the lipid position of the lipid nanoparticle. In some embodiments, a DNA vector, including a ceDNA vector produced using the synthetic process as described herein can be fully encapsulated in the lipid position of the lipid nanoparticle, thereby protecting it from degradation by a nuclease, e.g., in an aqueous solution. In some embodiments, a DNA vector, including a ceDNA vector produced using the synthetic process as described herein in the lipid nanoparticle is not substantially degraded after exposure of the lipid nanoparticle to a nuclease at 37° C. for at least about 20, 30, 45, or 60 minutes. In some embodiments, the ceDNA in the lipid nanoparticle is not substantially degraded after incubation of the particle in serum at 37° C. for at least about 30, 45, or 60 minutes or at least about 2, 3, 4, 5, 6, 7, 8, 9, 10, 12, 14, 16, 18, 20, 22, 24, 26, 28, 30, 32, 34, or 36 hours.

In certain embodiments, the lipid nanoparticles are substantially non-toxic to a subject, e.g., to a mammal such as a human. In some aspects, the lipid nanoparticle formulation is a lyophilized powder.

In some embodiments, lipid nanoparticles are solid core particles that possess at least one lipid bilayer. In other embodiments, the lipid nanoparticles have a non-bilayer structure, i.e., a non-lamellar (i.e., non-bilayer) morphology. Without limitations, the non-bilayer morphology can include, for example, three dimensional tubes, rods, cubic symmetries, etc. For example, the morphology of the lipid nanoparticles (lamellar vs. non-lamellar) can readily be assessed and characterized using, e.g., Cryo-TEM analysis as described in US2010/0130588, the content of which is incorporated herein by reference in its entirety.

In some further embodiments, the lipid nanoparticles having a non-lamellar morphology are electron dense. In some aspects, the disclosure provides for a lipid nanoparticle that is either unilamellar or multilamellar in structure. In some aspects, the disclosure provides for a lipid nanoparticle formulation that comprises multi-vesicular particles and/or foam-based particles.

By controlling the composition and concentration of the lipid components, one can control the rate at which the lipid conjugate exchanges out of the lipid particle and, in turn, the rate at which the lipid nanoparticle becomes fusogenic. In addition, other variables including, e.g., pH, temperature, or ionic strength, can be used to vary and/or control the rate at which the lipid nanoparticle becomes fusogenic. Other methods which can be used to control the rate at which the lipid nanoparticle becomes fusogenic will be apparent to those of ordinary skill in the art based on this disclosure. It will also be apparent that by controlling the composition and concentration of the lipid conjugate, one can control the lipid particle size.

The pKa of formulated cationic lipids can be correlated with the effectiveness of the LNPs for delivery of nucleic acids (see Jayaraman et al, Angewandte Chemie, International Edition (2012), 51(34), 8529-8533; Semple et al, Nature Biotechnology 28, 172-176 (2010), both of which are incorporated by reference in their entirety). The preferred range of pKa is ~5 to ~7. The pKa of the cationic lipid can be determined in lipid nanoparticles using an assay based on fluorescence of 2-(p-toluidino)-6-napthalene sulfonic acid (TNS).

VII. Methods of Delivering Closed-Ended DNA Vectors

In some embodiments, a closed-ended DNA vector, including a ceDNA vector, produced using the synthetic process as described herein can be delivered to a target cell in vitro or in vivo by various suitable methods. A closed-ended DNA vector, including a ceDNA vector, produced using the synthetic process as described herein alone can be applied or injected. A closed-ended DNA vector, including a ceDNA vector, produced using the synthetic process as described herein can be delivered to a cell without the help of a transfection reagent or other physical means. Alternatively, a closed-ended DNA vector, including a ceDNA vector, produced using the synthetic process as described herein can be delivered using any art-known transfection reagent or other art-known physical means that facilitates entry of DNA into a cell, e.g., liposomes, alcohols, polylysine-rich compounds, arginine-rich compounds, calcium phosphate, microvesicles, microinjection, electroporation and the like.

In another embodiment, a closed-ended DNA vector, including a ceDNA vector, produced using the synthetic process as described herein is administered to the CNS (e.g., to the brain or to the eye). The, e.g., ceDNA vector may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes, cortex, basal ganglia, hippocampus and portaamygdala), limbic system, neocortex, corpus striatum, cerebrum, and inferior colliculus. The ceDNA vector may also be administered to different regions of the eye such as the retina, cornea and/or optic nerve. The ceDNA vector may be delivered into the cerebrospinal fluid (e.g., by lumbar puncture). The ceDNA vector may further be administered intravascularly to the CNS in situations in which the blood-brain barrier has been perturbed (e.g., brain tumor or cerebral infarct).

In some embodiments, a closed-ended DNA vector, including a ceDNA vector, produced using the synthetic process as described herein can be administered to the desired region(s) of the CNS by any route known in the art, including but not limited to, intrathecal, intra-ocular, intracerebral, intraventricular, intravenous (e.g., in the presence of a sugar such as mannitol), intranasal, intra-aural, intra-ocular (e.g., intra-vitreous, sub-retinal, anterior chamber) and peri-ocular (e.g., sub-Tenon's region) delivery as well as intramuscular delivery with retrograde delivery to motor neurons.

In some embodiments, a closed-ended DNA vector, including a ceDNA vector, produced using the synthetic process as described herein is administered in a liquid formulation by direct injection (e.g., stereotactic injection) to the desired region or compartment in the CNS. In other embodiments, the e.g., synthetically produced ceDNA vector can be provided by topical application to the desired region or by intra-nasal administration of an aerosol formulation. Administration to the eye may be by topical application of liquid droplets. As a further alternative, the e.g., ceDNA vector can be administered as a solid, slow-release formulation (see, e.g., U.S. Pat. No. 7,201,898). In yet additional embodiments, the e.g., synthetically produced ceDNA vector can be used for retrograde transport to treat, ameliorate, and/or prevent diseases and disorders involving motor neurons (e.g., amyotrophic lateral sclerosis (ALS); spinal muscular atrophy (SMA), etc.). For example, the e.g., synthetically produced ceDNA vector can be delivered to muscle tissue from which it can migrate into neurons.

VIII. Additional Uses of the ceDNA Vectors

The compositions and closed-ended DNA vector, including ceDNA vectors, produced using the synthetic process as described herein can be used to express a target gene or transgene for various purposes. In some embodiments, the resulting transgene encodes a protein or functional RNA that is intended to be used for research purposes, e.g., to create a somatic transgenic animal model harboring the transgene, e.g., to study the function of the transgene product. In another example, the transgene encodes a protein or functional RNA that is intended to be used to create an animal model of disease. In some embodiments, the resulting transgene encodes one or more peptides, polypeptides, or proteins, which are useful for the treatment, prevention, or amelioration of disease states or disorders in a mammalian subject. The resulting transgene can be transferred (e.g., expressed in) to a subject in a sufficient amount to treat a disease associated with reduced expression, lack of expression or dysfunction of the gene. In some embodiments the resulting transgene can be expressed in a subject in a sufficient amount to treat a disease associated with increased expression, activity of the gene product, or inappropriate upregulation of a gene that the resulting transgene suppresses or otherwise causes the expression of which to be reduced. In yet other embodiments, the resulting transgene replaces or supplements a defective copy of the native gene. It will be appreciated by one of ordinary skill in the art that the transgene may not be an open reading frame of a gene to be transcribed itself; instead it may be a promoter region or repressor region of a target gene, and the ceDNA vector may modify such region with the outcome of so modulating the expression of a gene of interest.

In some embodiments, the transgene encodes a protein or functional RNA that is intended to be used to create an animal model of disease. In some embodiments, the transgene encodes one or more peptides, polypeptides, or proteins, which are useful for the treatment or prevention of disease states in a mammalian subject. The transgene can be transferred (e.g., expressed in) to a patient in a sufficient amount to treat a disease associated with reduced expression, lack of expression or dysfunction of the gene.

IX. Methods of Use

A synthetically produced closed-ended DNA vector, e.g., ceDNA vector as disclosed herein can also be used in a method for the delivery of a nucleotide sequence of interest (e.g., a transgene) to a target cell (e.g., a host cell). The method may in particular be a method for delivering a transgene to a cell of a subject in need thereof and treating a disease of interest. The invention allows for the in vivo expression of a transgene, e.g., a protein, antibody, nucleic acid such as miRNA etc. encoded in the ceDNA vector in a cell in a subject such that therapeutic effect of the expression of the transgene occurs. These results are seen with both in vivo and in vitro modes of closed-ended DNA vector (e.g., ceDNA vector) delivery.

In addition, the invention provides a method for the delivery of a transgene in a cell of a subject in need thereof, comprising multiple administrations of the synthetically produced closed-ended DNA vector (e.g. ceDNA vector) of the invention comprising said nucleic acid or transgene of interest. Since the ceDNA vector of the invention does not induce an immune response like that typically observed against encapsidated viral vectors, such a multiple administration strategy will likely have greater success in a ceDNA-based system.

The synthetically produced closed-ended DNA vector (e.g., ceDNA vector) nucleic acid(s) are administered in sufficient amounts to transfect the cells of a desired tissue and to provide sufficient levels of gene transfer and expression without undue adverse effects. Conventional and pharmaceutically acceptable routes of administration include, but are not limited to, intravenous (e.g., in a liposome formulation), direct delivery to the selected organ (e.g., intraportal delivery to the liver), intramuscular, and other parental routes of administration. Routes of administration may be combined, if desired.

Closed-ended DNA vector (e.g. ceDNA vector) delivery is not limited to delivery gene replacements. For example, the synthetically produced closed-ended DNA vectors (e.g., ceDNA vectors) as described herein may be used with other delivery systems provided to provide a portion of the gene therapy. One non-limiting example of a system that may be combined with the synthetically produced ceDNA vectors in accordance with the present disclosure includes systems which separately deliver one or more co-factors or immune suppressors for effective gene expression of the transgene.

The invention also provides for a method of treating a disease in a subject comprising introducing into a target cell in need thereof (in particular a muscle cell or tissue) of the subject a therapeutically effective amount of a synthetically produced closed-ended DNA vector (e.g., ceDNA vector), optionally with a pharmaceutically acceptable carrier. While the, e.g., synthetically produced ceDNA vector can be introduced in the presence of a carrier, such a carrier is not required. The, e.g., synthetically produced ceDNA vector selected comprises a nucleotide sequence of interest useful for treating the disease. In particular, the, e.g., synthetically produced ceDNA vector may comprise a desired exogenous DNA sequence operably linked to control elements capable of directing transcription of the desired polypeptide, protein, or oligonucleotide encoded by the exogenous DNA sequence when introduced into the subject. The e.g., synthetically produced ceDNA vector can be administered via any suitable route as provided above, and elsewhere herein.

The synthetically produced compositions and vectors provided herein can be used to deliver a transgene for various purposes. In some embodiments, the transgene encodes a protein or functional RNA that is intended to be used for research purposes, e.g., to create a somatic transgenic animal model harboring the transgene, e.g., to study the function of the transgene product. In another example, the transgene encodes a protein or functional RNA that is intended to be used to create an animal model of disease. In some embodiments, the transgene encodes one or more peptides, polypeptides, or proteins, which are useful for the treatment or prevention of disease states in a mammalian subject. The transgene can be transferred (e.g., expressed in) to a patient in a sufficient amount to treat a disease associated with reduced expression, lack of expression or dysfunction of the gene.

In principle, the expression cassette can include a nucleic acid or any transgene that encodes a protein or polypeptide that is either reduced or absent due to a mutation or which conveys a therapeutic benefit when overexpressed is considered to be within the scope of the invention.

A synthetically produced ceDNA vector is not limited to one species of ceDNA vector. As such, in another aspect, multiple ceDNA vectors comprising different transgenes or the same transgene but operatively linked to different promoters or cis-regulatory elements can be delivered simultaneously or sequentially to the target cell, tissue, organ, or subject. Therefore, this strategy can allow for the gene therapy or gene delivery of multiple genes simultaneously. It is also possible to separate different portions of the transgene into separate ceDNA vectors (e.g., different domains and/or co-factors required for functionality of the transgene) which can be administered simultaneously or at different times, and can be separately regulatable, thereby adding an additional level of control of expression of the transgene. Delivery can also be performed multiple times and, importantly for gene therapy in the clinical setting, in subsequent increasing or decreasing doses, given the lack of an anti-capsid host immune response due to the absence of a viral capsid. It is anticipated that no anti-capsid response will occur as there is no capsid.

The invention also provides for a method of treating a disease in a subject comprising introducing into a target cell in need thereof (in particular a muscle cell or tissue) of the subject a therapeutically effective amount of a synthetically produced ceDNA vector as disclosed herein, optionally with a pharmaceutically acceptable carrier. While the ceDNA vector can be introduced in the presence of a carrier, such a carrier is not required. The ceDNA vector implemented comprises a nucleotide sequence of interest useful for treating the disease. In particular, the ceDNA vector may comprise a desired exogenous DNA sequence operably linked to control elements capable of directing transcription of the desired polypeptide, protein, or oligonucleotide encoded by the exogenous DNA sequence when introduced into the subject. The synthetically produced ceDNA vector can be administered via any suitable route as provided above, and elsewhere herein.

X. Methods of Treatment

The technology described herein also demonstrates methods for making, as well as methods of using the disclosed synthetically produced ceDNA vectors in a variety of ways, including, for example, ex situ, in vitro and in vivo applications, methodologies, diagnostic procedures, and/or gene therapy regimens.

Provided herein is a method of treating a disease or disorder in a subject comprising introducing into a target cell in need thereof (for example, a muscle cell or tissue, or other affected cell type) of the subject a therapeutically effective amount of a synthetically produced ceDNA vector, optionally with a pharmaceutically acceptable carrier. While the ceDNA vector can be introduced in the presence of a carrier, such a carrier is not required. The synthetically produced ceDNA vector implemented comprises a nucleotide sequence of interest useful for treating the disease. In particular, the synthetically produced ceDNA vector may comprise a desired exogenous DNA sequence operably linked to control elements capable of directing transcription of the desired polypeptide, protein, or oligonucleotide encoded by the exogenous DNA sequence when introduced into the subject. The synthetically produced ceDNA vector can be administered via any suitable route as provided above, and elsewhere herein.

Disclosed herein are ceDNA vector compositions and formulations that include one or more of the synthetically produced ceDNA vectors of the present invention together with one or more pharmaceutically-acceptable buffers, diluents, or excipients. Such compositions may be included in one or more diagnostic or therapeutic kits, for diagnosing, preventing, treating or ameliorating one or more symptoms of a disease, injury, disorder, trauma or dysfunction. In one aspect the disease, injury, disorder, trauma or dysfunction is a human disease, injury, disorder, trauma or dysfunction.

Another aspect of the technology described herein provides a method for providing a subject in need thereof with a diagnostically- or therapeutically-effective amount of a synthetically produced ceDNA vector, the method comprising providing to a cell, tissue or organ of a subject in need thereof, an amount of the synthetically produced ceDNA vector as disclosed herein; and for a time effective to enable expression of the transgene from the ceDNA vector thereby providing the subject with a diagnostically- or a therapeutically-effective amount of the protein, peptide, nucleic acid expressed by the ceDNA vector. In a further aspect, the subject is human.

Another aspect of the technology described herein provides a method for diagnosing, preventing, treating, or ameliorating at least one or more symptoms of a disease, a disorder, a dysfunction, an injury, an abnormal condition, or trauma in a subject. In an overall and general sense, the method includes at least the step of administering to a subject in need thereof one or more of the disclosed synthetically produced ceDNA vectors, in an amount and for a time sufficient to diagnose, prevent, treat or ameliorate the one or more symptoms of the disease, disorder, dysfunction, injury, abnormal condition, or trauma in the subject. In a further aspect, the subject is human.

Another aspect is use of the synthetically produced ceDNA vector as a tool for treating or reducing one or more symptoms of a disease or disease states. There are a number of inherited diseases in which defective genes are known, and typically fall into two classes: deficiency states, usually of enzymes, which are generally inherited in a recessive manner, and unbalanced states, which may involve regulatory or structural proteins, and which are typically but not always inherited in a dominant manner. For deficiency state diseases, synthetically produced ceDNA vectors can be used to deliver transgenes to bring a normal gene into affected tissues for replacement therapy, as well, in some embodiments, to create animal models for the disease using antisense mutations. For unbalanced disease states, synthetically produced ceDNA vectors can be used to create a disease state in a model system, which could then be used in efforts to counteract the disease state. Thus the synthetically produced ceDNA vectors and methods disclosed herein permit the treatment of genetic diseases. As used herein, a disease state is treated by partially or wholly remedying the deficiency or imbalance that causes the disease or makes it more severe.

A. Host Cells:

In some embodiments, the synthetically produced ceDNA vector delivers the transgene into a subject host cell. In some embodiments, the subject host cell is a human host cell, including, for example blood cells, stem cells, hematopoietic cells, $CD34^+$ cells, liver cells, cancer cells, vascular cells, muscle cells, pancreatic cells, neural cells, ocular or retinal cells, epithelial or endothelial cells, dendritic cells, fibroblasts, or any other cell of mammalian origin, including, without limitation, hepatic (i.e., liver) cells, lung cells, cardiac cells, pancreatic cells, intestinal cells, diaphragmatic cells, renal (i.e., kidney) cells, neural cells, blood cells, bone marrow cells, or any one or more selected tissues of a subject for which gene therapy is contemplated. In one aspect, the subject host cell is a human host cell.

The present disclosure also relates to recombinant host cells as mentioned above, including synthetically produced ceDNA vectors as described herein. Thus, one can use multiple host cells depending on the purpose as is obvious to the skilled artisan. A construct or synthetically produced ceDNA vector including donor sequence is introduced into a host cell so that the donor sequence is maintained as a chromosomal integrant as described earlier. The term host cell encompasses any progeny of a parent cell that is not identical to the parent cell due to mutations that occur during replication. The choice of a host cell will to a large extent depend upon the donor sequence and its source. The host cell may also be a eukaryote, such as a mammalian, insect, plant, or fungal cell. In one embodiment, the host cell is a human cell (e.g., a primary cell, a stem cell, or an immortalized cell line). In some embodiments, the host cell can be administered the synthetically produced ceDNA vector ex vivo and then delivered to the subject after the gene therapy event. A host cell can be any cell type, e.g., a somatic cell or a stem cell, an induced pluripotent stem cell, or a blood cell, e.g., T-cell or B-cell, or bone marrow cell. In certain embodiments, the host cell is an allogenic cell. For example, T-cell genome engineering is useful for cancer immunotherapies, disease modulation such as HIV therapy (e.g., receptor knock out, such as CXCR4 and CCR5) and immunodeficiency therapies. MHC receptors on B-cells can be targeted for immunotherapy. In some embodiments, gene modified host cells, e.g., bone marrow stem cells, e.g., $CD34^+$ cells, or induced pluripotent stem cells can be transplanted back into a patient for expression of a therapeutic protein.

B. Exemplary Transgenes and Diseases to be Treated with a ceDNA Vector

A closed-ended DNA vector, including a ceDNA vector, produced using the synthetic process as described herein are also useful for correcting a defective gene. As a non-limiting example, DMD gene of Duchene Muscular Dystrophy can be delivered using the synthetically produced ceDNA vectors as disclosed herein.

A synthetically produced ceDNA vector or a composition thereof can be used in the treatment of any hereditary disease. As a non-limiting example, the synthetically produced ceDNA vector or a composition thereof e.g. can be used in the treatment of transthyretin amyloidosis (ATTR), an orphan disease where the mutant protein misfolds and aggregates in nerves, the heart, the gastrointestinal system etc. It is contemplated herein that the disease can be treated by deletion of the mutant disease gene (mutTTR) using the synthetically produced ceDNA vector systems described herein. Such treatments of hereditary diseases can halt disease progression and may enable regression of an established disease or reduction of at least one symptom of the disease by at least 10%.

In another embodiment, a synthetically produced ceDNA vector or a composition thereof can be used in the treatment of ornithine transcarbamylase deficiency (OTC deficiency), hyperammonaemia or other urea cycle disorders, which impair a neonate or infant's ability to detoxify ammonia. As with all diseases of inborn metabolism, it is contemplated herein that even a partial restoration of enzyme activity compared to wild-type controls (e.g., at least 20%, at least 30%, at least 40%, at least 50%, at least 60%, at least 70%, at least 80%, at least 90%, at least 95% or at least 99%) may be sufficient for reduction in at least one symptom OTC and/or an improvement in the quality of life for a subject having OTC deficiency. In one embodiment, a nucleic acid encoding OTC can be inserted behind the albumin endogenous promoter for in vivo protein replacement.

In another embodiment, a synthetically produced ceDNA vector or a composition thereof can be used in the treatment of phenylketonuria (PKU) by delivering a nucleic acid sequence encoding a phenylalanine hydroxylase enzyme to reduce buildup of dietary phenylalanine, which can be toxic to PKU sufferers. As with all diseases of inborn metabolism, it is contemplated herein that even a partial restoration of enzyme activity compared to wild-type controls (e.g., at least 20%, at least 30%, at least 40%, at least 50%, at least 60%, at least 70%, at least 80%, at least 90%, at least 95% or at least 99%) may be sufficient for reduction in at least one symptom of PKU and/or an improvement in the quality of life for a subject having PKU. In one embodiment, a nucleic acid encoding phenylalanine hydroxylase can be inserted behind the albumin endogenous promoter for in vivo protein replacement.

In another embodiment, a synthetically produced ceDNA vector or a composition thereof can be used in the treatment of glycogen storage disease (GSD) by delivering a nucleic acid sequence encoding an enzyme to correct aberrant glycogen synthesis or breakdown in subjects having GSD. Non-limiting examples of enzymes that can be delivered and expressed using the synthetically produced ceDNA vectors and methods as described herein include glycogen synthase, glucose-6-phosphatase, acid-alpha glucosidase, glycogen debranching enzyme, glycogen branching enzyme, muscle glycogen phosphorylase, liver glycogen phosphorylase, muscle phosphofructokinase, phosphorylase kinase, glucose transporter-2 (GLUT-2), aldolase A, beta-enolase, phosphoglucomutase-1 (PGM-1), and glycogenin-1. As with all diseases of inborn metabolism, it is contemplated herein that even a partial restoration of enzyme activity compared to wild-type controls (e.g., at least 20%, at least 30%, at least 40%, at least 50%, at least 60%, at least 70%, at least 80%, at least 90%, at least 95% or at least 99%) may be sufficient for reduction in at least one symptom of GSD and/or an improvement in the quality of life for a subject having GSD. In one embodiment, a nucleic acid encoding an enzyme to correct aberrant glycogen storage can be inserted behind the albumin endogenous promoter for in vivo protein replacement.

The synthetically produced ceDNA vectors described herein are also contemplated for use in the treatment of any of; of Leber congenital amaurosis (LCA), polyglutamine diseases, including polyQ repeats, and alpha-1 antitrypsin deficiency (A1AT). LCA is a rare congenital eye disease resulting in blindness, which can be caused by a mutation in any one of the following genes: GUCY2D, RPE65, SPATA7, AIPL1, LCA5, RPGRIP1, CRX, CRB1, NMNAT1, CEP290, IMPDH1, RD3, RDH12, LRAT, TULP1, KCNJ13, GDF6 and/or PRPH2. It is contemplated herein that the ceDNA vectors and compositions and methods as described herein can be adapted for delivery of one or more of the genes associated with LCA in order to correct an error in the gene(s) responsible for the symptoms of LCA. Polyglutamine diseases include, but are not limited to: dentatorubropallidoluysian atrophy, Huntington's disease, spinal and bulbar muscular atrophy, and spinocerebellar ataxia types 1, 2, 3 (also known as Machado-Joseph disease), 6, 7, and 17. A1AT deficiency is a genetic disorder that causes defective production of alpha-1 antitrypsin, leading to decreased activity of the enzyme in the blood and lungs, which in turn can lead to emphysema or chronic obstructive pulmonary disease in affected subjects. Treatment of a subject with an A1AT deficiency is specifically contemplated herein using the ceDNA vectors or compositions thereof as outlined herein. It is contemplated herein that a ceDNA vector comprising a nucleic acid encoding a desired protein for the treatment of LCA, polyglutamine diseases or A1AT deficiency can be administered to a subject in need of treatment.

In further embodiments, the compositions comprising a synthetically produced ceDNA vector as described herein can be used to deliver a viral sequence, a pathogen sequence, a chromosomal sequence, a translocation junction (e.g., a translocation associated with cancer), a non-coding RNA gene or RNA sequence, a disease associated gene, among others.

Any nucleic acid or target gene of interest may be delivered or expressed by a synthetically produced ceDNA vector as disclosed herein. Target nucleic acids and target genes include, but are not limited to nucleic acids encoding polypeptides, or non-coding nucleic acids (e.g., RNAi, miRs etc.) preferably therapeutic (e.g., for medical, diagnostic, or veterinary uses) or immunogenic (e.g., for vaccines) polypeptides. In certain embodiments, the target nucleic acids or target genes that are targeted by the synthetically produced ceDNA vectors as described herein encode one or more polypeptides, peptides, ribozymes, peptide nucleic acids, siRNAs, RNAis, antisense oligonucleotides, antisense polynucleotides, antibodies, antigen binding fragments, or any combination thereof.

In particular, a gene target or transgene for expression by the synthetically produced ceDNA vector as disclosed herein can encode, for example, but is not limited to, protein(s), polypeptide(s), peptide(s), enzyme(s), antibodies, antigen binding fragments, as well as variants, and/or active fragments thereof, for use in the treatment, prophylaxis, and/or amelioration of one or more symptoms of a disease, dysfunction, injury, and/or disorder. In one aspect, the disease, dysfunction, trauma, injury and/or disorder is a human disease, dysfunction, trauma, injury, and/or disorder.

The expression cassette can also encode polypeptides, sense or antisense oligonucleotides, or RNAs (coding or non-coding; e.g., siRNAs, shRNAs, micro-RNAs, and their antisense counterparts (e.g., antagoMiR)). Expression cassettes can include an exogenous sequence that encodes a reporter protein to be used for experimental or diagnostic purposes, such as β-lactamase, β-galactosidase (LacZ), alkaline phosphatase, thymidine kinase, green fluorescent protein (GFP), chloramphenicol acetyltransferase (CAT), luciferase, and others well known in the art.

Sequences provided in the expression cassette, expression construct of a ceDNA vector described herein can be codon optimized for the host cell. As used herein, the term "codon optimized" or "codon optimization" refers to the process of modifying a nucleic acid sequence for enhanced expression in the cells of the vertebrate of interest, e.g., mouse or human, by replacing at least one, more than one, or a significant number of codons of the native sequence (e.g., a prokaryotic sequence) with codons that are more frequently or most frequently used in the genes of that vertebrate. Various species exhibit particular bias for certain codons of a particular amino acid. Typically, codon optimization does not alter the amino acid sequence of the original translated protein. Optimized codons can be determined using e.g., Aptagen's Gene Forge® codon optimization and custom gene synthesis platform (Aptagen, Inc., 2190 Fox Mill Rd. Suite 300, Herndon, Va. 20171) or another publicly available database.

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage (Nakamura, Y., et al. "Codon usage tabulated from the international DNA sequence databases: status for the year 2000" Nucl. Acids Res. 28:292 (2000)).

As noted herein, a synthetically produced ceDNA vector as disclosed herein can encode a protein or peptide, or therapeutic nucleic acid sequence or therapeutic agent, including but not limited to one or more agonists, antagonists, anti-apoptosis factors, inhibitors, receptors, cytokines, cytotoxins, erythropoietic agents, glycoproteins, growth factors, growth factor receptors, hormones, hormone receptors, interferons, interleukins, interleukin receptors, nerve growth factors, neuroactive peptides, neuroactive peptide receptors, proteases, protease inhibitors, protein decarboxylases, protein kinases, protein kinase inhibitors, enzymes, receptor binding proteins, transport proteins or one or more inhibitors thereof, serotonin receptors, or one or more uptake inhibitors thereof, serpins, serpin receptors, tumor suppressors, diagnostic molecules, chemotherapeutic agents, cytotoxins, or any combination thereof.

The synthetically produced ceDNA vectors are also useful for ablating gene expression. For example, in one embodiment a ceDNA vector can be used to express an antisense nucleic acid or functional RNA to induce knockdown of a target gene. As a non-limiting example, expression of CXCR4 and CCR5, HIV receptors, have been successfully ablated in primary human T-cells, See Schumann et al. (2015), PNAS 112(33): 10437-10442, herein incorporated by reference in its entirety. Another gene for targeted inhibition is PD-1, where the synthetically produced ceDNA vector can express an inhibitory nucleic acid or RNAi or functional RNA to inhibit the expression of PD-1. PD-1 expresses an immune checkpoint cell surface receptor on chronically active T cells that happens in malignancy. See Schumann et al. supra.

In some embodiments, a synthetically produced ceDNA vectors is useful for correcting a defective gene by expressing a transgene that targets the diseased gene. Non-limiting examples of diseases or disorders amenable to treatment by a synthetically produced ceDNA vector as disclosed herein, are listed in Tables A-C along with their and their associated genes of US patent publication 2014/0170753, which is herein incorporated by reference in its entirety.

In alternative embodiments, the synthetically produced ceDNA vectors are used for insertion of an expression cassette for expression of a therapeutic protein or reporter protein in a safe harbor gene, e.g., in an inactive intron. In certain embodiments, a promoter-less cassette is inserted into the safe harbor gene. In such embodiments, a promoter-less cassette can take advantage of the safe harbor gene regulatory elements (promoters, enhancers, and signaling peptides), a non-limiting example of insertion at the safe harbor locus is insertion into to the albumin locus that is described in *Blood* (2015) 126 (15): 1777-1784, which is incorporated herein by reference in its entirety. Insertion into Albumin has the benefit of enabling secretion of the transgene into the blood (See e.g., Example 22). In addition, a genomic safe harbor site can be determined using techniques known in the art and described in, for example, Papapetrou, ER & Schambach, A. *Molecular Therapy* 24(4):678-684 (2016) or Sadelain et al. *Nature Reviews Cancer* 12:51-58 (2012), the contents of each of which are incorporated herein by reference in their entirety. It is specifically contemplated herein that safe harbor sites in an adeno associated virus (AAV) genome (e.g., AAVS1 safe harbor site) can be used with the methods and compositions described herein (see e.g., Oceguera-Yanez et al. *Methods* 101:43-55 (2016) or Tiyaboonchai, A et al. *Stem Cell Res* 12(3):630-7 (2014), the contents of each of which are incorporated by reference in their entirety). For example, the AAVS1 genomic safe harbor site can be used with the ceDNA vectors and compositions as described herein for the purposes of hematopoietic specific transgene expression and gene silencing in embryonic stem cells (e.g., human embryonic stem cells) or induced pluripotent stem cells (iPS cells). In addition, it is contemplated herein that synthetic or commercially available homology-directed repair donor templates for insertion into an AASV1 safe harbor site on chromosome 19 can be used with the ceDNA vectors or compositions as described herein. For example, homology-directed repair templates, and guide RNA, can be purchased commercially, for example, from System Biosciences, Palo Alto, CA, and cloned into a ceDNA vector.

In some embodiments, the synthetically produced ceDNA vectors are used for expressing a transgene, or knocking out or decreasing expression of a target gene in a T cell, e.g., to engineer the T cell for improved adoptive cell transfer and/or CAR-T therapies (see, e.g., Example 24). In some embodiments, the ceDNA vector as described herein can express transgenes that knock-out genes. Non-limiting examples of therapeutically relevant knock-outs of T cells are described in PNAS (2015) 112(33):10437-10442, which is incorporated herein by reference in its entirety.

C. Additional Diseases for Gene Therapy:

In general, the ceDNA vector produced by the synthetic methods as disclosed herein can be used to deliver any transgene in accordance with the description above to treat, prevent, or ameliorate the symptoms associated with any disorder related to gene expression. Illustrative disease states include, but are not-limited to: cystic fibrosis (and other diseases of the lung), hemophilia A, hemophilia B, thalassemia, anemia and other blood disorders, AIDS, Alzheimer's disease, Parkinson's disease, Huntington's disease, amyotrophic lateral sclerosis, epilepsy, and other neurological disorders, cancer, diabetes mellitus, muscular dystrophies (e.g., Duchenne, Becker), Hurler's disease, adenosine deaminase deficiency, metabolic defects, retinal degenerative diseases (and other diseases of the eye), mitochondriopathies (e.g., Leber's hereditary optic neuropathy (LHON), Leigh syndrome, and subacute sclerosing encephalopathy), myopathies (e.g., facioscapulohumeral myopathy (FSHD) and cardiomyopathies), diseases of solid organs (e.g., brain, liver, kidney, heart), and the like. In some embodiments, a ceDNA vector produced by the synthetic production methods as described herein can be advantageously used in the treatment of individuals with metabolic disorders (e.g., ornithine transcarbamylase deficiency).

In some embodiments, a ceDNA vector produced by the synthetic production methods as described herein can be used to treat, ameliorate, and/or prevent a disease or disorder caused by mutation in a gene or gene product. Exemplary diseases or disorders that can be treated with a ceDNA vectors include, but are not limited to, metabolic diseases or disorders (e.g., Fabry disease, Gaucher disease, phenylketonuria (PKU), glycogen storage disease); urea cycle diseases or disorders (e.g., ornithine transcarbamylase (OTC) deficiency); lysosomal storage diseases or disorders (e.g., metachromatic leukodystrophy (MLD), mucopolysaccharidosis Type II (MPSII; Hunter syndrome)); liver diseases or disorders (e.g., progressive familial intrahepatic cholestasis (PFIC); blood diseases or disorders (e.g., hemophilia (A and B), thalassemia, and anemia); cancers and tumors, and genetic diseases or disorders (e.g., cystic fibrosis).

As still a further aspect, a ceDNA vector produced by the synthetic production methods as described herein may be employed to deliver a heterologous nucleotide sequence in situations in which it is desirable to regulate the level of transgene expression (e.g., transgenes encoding hormones or growth factors, as described herein).

Accordingly, in some embodiments, a ceDNA vector produced by the synthetic production methods as described herein can be used to correct an abnormal level and/or function of a gene product (e.g., an absence of, or a defect in, a protein) that results in the disease or disorder. The ceDNA vector can produce a functional protein and/or modify levels of the protein to alleviate or reduce symptoms resulting from, or confer benefit to, a particular disease or disorder caused by the absence or a defect in the protein. For example, treatment of OTC deficiency can be achieved by producing functional OTC enzyme; treatment of hemophilia A and B can be achieved by modifying levels of Factor VIII, Factor IX, and Factor X; treatment of PKU can be achieved by modifying levels of phenylalanine hydroxylase enzyme; treatment of Fabry or Gaucher disease can be achieved by producing functional alpha galactosidase or beta glucocerebrosidase, respectively; treatment of MLD or MPSII can be achieved by producing functional arylsulfatase A or iduronate-2-sulfatase, respectively; treatment of cystic fibrosis can be achieved by producing functional cystic fibrosis transmembrane conductance regulator; treatment of glycogen storage disease can be achieved by restoring functional G6Pase enzyme function; and treatment of PFIC can be achieved by producing functional ATP8B1, ABCB 11, ABCB4, or TJP2 genes.

In alternative embodiments, a ceDNA vector produced by the synthetic production methods as described herein can be used to provide an antisense nucleic acid to a cell in vitro or in vivo. For example, where the transgene is a RNAi molecule, expression of the antisense nucleic acid or RNAi in the target cell diminishes expression of a particular protein by the cell. Accordingly, transgenes which are RNAi molecules or antisense nucleic acids may be administered to decrease expression of a particular protein in a subject in need thereof. Antisense nucleic acids may also be administered to cells in vitro to regulate cell physiology, e.g., to optimize cell or tissue culture systems.

In some embodiments, exemplary transgenes encoded by a ceDNA vector produced by the synthetic production methods as described herein, include, but are not limited to: X, lysosomal enzymes (e.g., hexosaminidase A, associated with Tay-Sachs disease, or iduronate sulfatase, associated, with Hunter Syndrome/MPS II), erythropoietin, angiostatin, endostatin, superoxide dismutase, globin, leptin, catalase, tyrosine hydroxylase, as well as cytokines (e.g., a interferon, β-interferon, interferon-γ, interleukin-2, interleukin-4, interleukin 12, granulocyte-macrophage colony stimulating factor, lymphotoxin, and the like), peptide growth factors and hormones (e.g., somatotropin, insulin, insulin-like growth factors 1 and 2, platelet derived growth factor (PDGF), epidermal growth factor (EGF), fibroblast growth factor (FGF), nerve growth factor (NGF), neurotrophic factor-3 and 4, brain-derived neurotrophic factor (BDNF), glial derived growth factor (GDNF), transforming growth factor-α and -β, and the like), receptors (e.g., tumor necrosis factor receptor). In some exemplary embodiments, the transgene encodes a monoclonal antibody specific for one or more desired targets. In some exemplary embodiments, more than one transgene is encoded by the ceDNA vector. In some exemplary embodiments, the transgene encodes a fusion protein comprising two different polypeptides of interest. In some embodiments, the transgene encodes an antibody, including a full-length antibody or antibody fragment, as defined herein. In some embodiments, the antibody is an antigen-binding domain or an immunoglobulin variable domain sequence, as that is defined herein. Other illustrative transgene sequences encode suicide gene products (thymidine kinase, cytosine deaminase, diphtheria toxin, cytochrome P450, deoxycytidine kinase, and tumor necrosis factor), proteins conferring resistance to a drug used in cancer therapy, and tumor suppressor gene products.

In a representative embodiment, the transgene expressed by a ceDNA vector produced by the synthetic production methods as described herein can be used for the treatment of muscular dystrophy in a subject in need thereof, the method comprising: administering a treatment-, amelioration- or prevention-effective amount of ceDNA vector described herein, wherein the ceDNA vector comprises a heterologous nucleic acid encoding dystrophin, a mini-dystrophin, a micro-dystrophin, myostatin propeptide, follistatin, activin type II soluble receptor, IGF-1, anti-inflammatory polypeptides such as the Ikappa B dominant mutant, sarcospan, utrophin, a micro-dystrophin, laminin-α2, α-sarcoglycan, β-sarcoglycan, γ-sarcoglycan, δ-sarcoglycan, IGF-1, an antibody or antibody fragment against myostatin or myostatin propeptide, and/or RNAi against myostatin. In particular embodiments, the synthetically produced ceDNA vector can be administered to skeletal, diaphragm and/or cardiac muscle as described elsewhere herein.

In some embodiments, a ceDNA vector produced by the synthetic production methods as described herein can be used to deliver a transgene to skeletal, cardiac or diaphragm muscle, for production of a polypeptide (e.g., an enzyme) or functional RNA (e.g., RNAi, microRNA, antisense RNA) that normally circulates in the blood or for systemic delivery to other tissues to treat, ameliorate, and/or prevent a disorder (e.g., a metabolic disorder, such as diabetes (e.g., insulin), hemophilia (e.g., VIII), a mucopolysaccharide disorder (e.g., Sly syndrome, Hurler Syndrome, Scheie Syndrome, Hurler-Scheie Syndrome, Hunter's Syndrome, Sanfilippo Syndrome A, B, C, D, Morquio Syndrome, Maroteaux-Lamy Syndrome, etc.) or a lysosomal storage disorder (such as Gaucher's disease [glucocerebrosidase], Pompe disease [lysosomal acid .alpha.-glucosidase] or Fabry disease [.alpha.-galactosidase A]) or a glycogen storage disorder (such as Pompe disease [lysosomal acid a glucosidase]). Other suitable proteins for treating, ameliorating, and/or preventing metabolic disorders are described above.

In other embodiments, a ceDNA vector produced by the synthetic production methods as described herein can be used to deliver a transgene in a method of treating, ameliorating, and/or preventing a metabolic disorder in a subject in need thereof. Illustrative metabolic disorders and transgenes encoding polypeptides are described herein. Optionally, the polypeptide is secreted (e.g., a polypeptide that is a secreted polypeptide in its native state or that has been engineered to be secreted, for example, by operable association with a secretory signal sequence as is known in the art).

Another aspect of the invention relates to a method of treating, ameliorating, and/or preventing congenital heart failure or PAD in a subject in need thereof, the method comprising administering a ceDNA vector produced by the synthetic production methods as described herein to a mammalian subject, wherein the ceDNA vector comprises a transgene encoding, for example, a sarcoplasmic endoreticulum $Ca^{2+}$-ATPase (SERCA2a), an angiogenic factor, phosphatase inhibitor I (I-1), RNAi against phospholamban; a phospholamban inhibitory or dominant-negative molecule such as phospholamban S16E, a zinc finger protein that regulates the phospholamban gene, β2-adrenergic receptor, .beta.2-adrenergic receptor kinase (BARK), PI3 kinase, calsarcan, a .beta.-adrenergic receptor kinase inhibitor (βARKct), inhibitor 1 of protein phosphatase 1, S100A1, parvalbumin, adenylyl cyclase type 6, a molecule that effects G-protein coupled receptor kinase type 2 knockdown such as a truncated constitutively active βARKct, Pim-1, PGC-1α, SOD-1, SOD-2, EC-SOD, kallikrein, HIF, thymosin-β4, mir-1, mir-133, mir-206 and/or mir-208.

In some embodiments, a ceDNA vector produced by the synthetic production methods as described herein can be administered to the lungs of a subject by any suitable means, optionally by administering an aerosol suspension of respirable particles comprising the ceDNA vectors, which the subject inhales. The respirable particles can be liquid or solid. Aerosols of liquid particles comprising the ceDNA vectors may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising a ceDNA vector produced by the synthetic production methods as described herein may likewise be produced with any solid particulate medicament aerosol generator, by techniques known in the pharmaceutical art.

In some embodiments, a ceDNA vector produced by the synthetic production methods as described herein can be administered to tissues of the CNS (e.g., brain, eye). In particular embodiments, a ceDNA vector produced by the synthetic production methods as described herein may be administered to treat, ameliorate, or prevent diseases of the CNS, including genetic disorders, neurodegenerative disorders, psychiatric disorders and tumors. Illustrative diseases of the CNS include, but are not limited to Alzheimer's disease, Parkinson's disease, Huntington's disease, Canavan disease, Leigh's disease, Refsum disease, Tourette syndrome, primary lateral sclerosis, amyotrophic lateral sclerosis, progressive muscular atrophy, Pick's disease, muscular dystrophy, multiple sclerosis, myasthenia gravis, Binswanger's disease, trauma due to spinal cord or head injury, Tay Sachs disease, Lesch-Nyan disease, epilepsy, cerebral infarcts, psychiatric disorders including mood disorders (e.g., depression, bipolar affective disorder, persistent affective disorder, secondary mood disorder), schizophrenia, drug dependency (e.g., alcoholism and other substance dependencies), neuroses (e.g., anxiety, obsessional disorder, somatoform disorder, dissociative disorder, grief, post-partum depression), psychosis (e.g., hallucinations and delusions), dementia, paranoia, attention deficit disorder, psychosexual disorders, sleeping disorders, pain disorders, eating or weight disorders (e.g., obesity, cachexia, anorexia nervosa, and bulemia) and cancers and tumors (e.g., pituitary tumors) of the CNS.

Ocular disorders that may be treated, ameliorated, or prevented with a ceDNA vector produced by the synthetic production methods as described herein include ophthalmic disorders involving the retina, posterior tract, and optic nerve (e.g., retinitis pigmentosa, diabetic retinopathy and other retinal degenerative diseases, uveitis, age-related macular degeneration, glaucoma). Many ophthalmic diseases and disorders are associated with one or more of three types of indications: (1) angiogenesis, (2) inflammation, and (3) degeneration. In some embodiments, a ceDNA vector produced by the synthetic production methods as described herein can be employed to deliver anti-angiogenic factors; anti-inflammatory factors; factors that retard cell degeneration, promote cell sparing, or promote cell growth and combinations of the foregoing. Diabetic retinopathy, for example, is characterized by angiogenesis. Diabetic retinopathy can be treated by delivering one or more anti-angiogenic factors either intraocularly (e.g., in the vitreous) or periocularly (e.g., in the sub-Tenon's region). One or more neurotrophic factors may also be co-delivered, either intraocularly (e.g., intravitreally) or periocularly. Additional ocular diseases that may be treated, ameliorated, or prevented with the ceDNA vectors of the invention include geographic atrophy, vascular or "wet" macular degeneration, Stargardt disease, Leber Congenital Amaurosis (LCA), Usher syndrome, pseudoxanthoma elasticum (PXE), x-linked retinitis pigmentosa (XLRP), x-linked retinoschisis (XLRS), Choroideremia, Leber hereditary optic neuropathy (LHON), Archomatopsia, cone-rod dystrophy, Fuchs endothelial corneal dystrophy, diabetic macular edema and ocular cancer and tumors.

In some embodiments, inflammatory ocular diseases or disorders (e.g., uveitis) can be treated, ameliorated, or prevented by a ceDNA vector produced by the synthetic production methods as described herein. One or more anti-inflammatory factors can be expressed by intraocular (e.g., vitreous or anterior chamber) administration of a ceDNA vector produced by the synthetic production methods as described herein. In other embodiments, ocular diseases or disorders characterized by retinal degeneration (e.g., retinitis pigmentosa) can be treated, ameliorated, or prevented by the ceDNA vectors of the invention. Intraocular (e.g., vitreal administration) of a ceDNA vector produced by the synthetic production methods as described herein encoding one or more neurotrophic factors can be used to treat such retinal degeneration-based diseases. In some embodiments, diseases or disorders that involve both angiogenesis and retinal degeneration (e.g., age-related macular degeneration) can be treated with a ceDNA vector produced by the synthetic production methods as described herein. Age-related macular degeneration can be treated by administering a ceDNA vector produced by the synthetic production methods as described herein encoding one or more neurotrophic factors intraocularly (e.g., vitreous) and/or one or more anti-angiogenic factors intraocularly or periocularly (e.g., in the sub- Tenon's region). Glaucoma is characterized by increased ocular pressure and loss of retinal ganglion cells. Treatments for glaucoma include administration of one or more neuroprotective agents that protect cells from excitotoxic damage using the ceDNA vector as disclosed herein. Accordingly, such agents include N-methyl-D-aspartate (NMDA) antagonists, cytokines, and neurotrophic factors, can be delivered intraocularly, optionally intravitreally using a ceDNA vector produced by the synthetic production methods as described herein.

In other embodiments, a ceDNA vector produced by the synthetic production methods as described herein may be used to treat seizures, e.g., to reduce the onset, incidence or severity of seizures. The efficacy of a therapeutic treatment for seizures can be assessed by behavioral (e.g., shaking, tics of the eye or mouth) and/or electrographic means (most seizures have signature electrographic abnormalities). Thus, a ceDNA vector produced by the synthetic production methods as described herein can also be used to treat epilepsy, which is marked by multiple seizures over time. In one representative embodiment, somatostatin (or an active fragment thereof) is administered to the brain using a ceDNA vector produced by the synthetic production methods as described herein to treat a pituitary tumor. According to this embodiment, a ceDNA vector produced by the synthetic production methods as described herein encoding somatostatin (or an active fragment thereof) is administered by microinfusion into the pituitary. Likewise, such treatment can be used to treat acromegaly (abnormal growth hormone secretion from the pituitary). The nucleic acid (e.g., GenBank Accession No. J00306) and amino acid (e.g., GenBank Accession No. P01166; contains processed active peptides somatostatin-28 and somatostatin-14) sequences of somatostatins as are known in the art. In particular embodiments, the ceDNA vector can encode a transgene that comprises a secretory signal as described in U.S. Pat. No. 7,071,172.

Another aspect of the invention relates to the use of a ceDNA vector produced by the synthetic production methods as described herein to produce antisense RNA, RNAi or other functional RNA (e.g., a ribozyme) for systemic delivery to a subject in vivo. Accordingly, in some embodiments, a ceDNA vector produced by the synthetic production methods as described herein can comprise a transgene that encodes an antisense nucleic acid, a ribozyme (e.g., as described in U.S. Pat. No. 5,877,022), RNAs that affect spliceosome-mediated trans-splicing (see, Puttaraju et al., (1999) Nature Biotech. 17:246; U.S. Pat. Nos. 6,013,487; 6,083,702), interfering RNAs (RNAi) that mediate gene silencing (see, Sharp et al., (2000) Science 287:2431) or other non-translated RNAs, such as "guide" RNAs (Gorman et al., (1998) Proc. Nat. Acad. Sci. USA 95:4929; U.S. Pat. No. 5,869,248 to Yuan et al.), and the like.

In some embodiments, a ceDNA vector produced by the synthetic production methods as described herein can further also comprise a transgene that encodes a reporter polypeptide (e.g., an enzyme such as Green Fluorescent Protein, or alkaline phosphatase). In some embodiments, a transgene that encodes a reporter protein useful for experimental or diagnostic purposes, is selected from any of: β-lactamase, β-galactosidase (LacZ), alkaline phosphatase, thymidine kinase, green fluorescent protein (GFP), chloramphenicol acetyltransferase (CAT), luciferase, and others well known in the art. In some aspects, synthetically produced ceDNA vectors comprising a transgene encoding a reporter polypeptide may be used for diagnostic purposes or as markers of the ceDNA vector's activity in the subject to which they are administered.

In some embodiments, a ceDNA vector produced by the synthetic production methods as described herein can comprise a transgene or a heterologous nucleotide sequence that shares homology with, and recombines with a locus on the host chromosome. This approach may be utilized to correct a genetic defect in the host cell.

In some embodiments, a ceDNA vector produced by the synthetic production methods as described herein can comprise a transgene that can be used to express an immunogenic polypeptide in a subject, e.g., for vaccination. The transgene may encode any immunogen of interest known in the art including, but not limited to, immunogens from human immunodeficiency virus, influenza virus, gag proteins, tumor antigens, cancer antigens, bacterial antigens, viral antigens, and the like.

D. Testing for Successful Gene Expression Using a ceDNA Vector

Assays well known in the art can be used to test the efficiency of gene delivery by a synthetically produced ceDNA vector and can be performed in both in vitro and in vivo models. Knock-in or knock-out of a desired transgene by a synthetically produced ceDNA can be assessed by one skilled in the art by measuring mRNA and protein levels of the desired transgene (e.g., reverse transcription PCR, western blot analysis, and enzyme-linked immunosorbent assay (ELISA)). Nucleic acid alterations by synthetically produced ceDNA (e.g., point mutations, or deletion of DNA regions) can be assessed by deep sequencing of genomic target DNA. In one embodiment, synthetically produced ceDNA comprises a reporter protein that can be used to assess the expression of the desired transgene, for example by examining the expression of the reporter protein by fluorescence microscopy or a luminescence plate reader. For in vivo applications, protein function assays can be used to test the functionality of a given gene and/or gene product to determine if gene expression has successfully occurred. For example, it is envisioned that a point mutation in the cystic fibrosis transmembrane conductance regulator gene (CFTR) inhibits the capacity of CFTR to move anions (e.g., $Cl^-$) through the anion channel, can be corrected by delivering a functional (i.e., non-mutated) CFTR gene to the subject with a ceDNA vector. Following administration of a ceDNA vector, one skilled in the art can assess the capacity for anions to move through the anion channel to determine if the CFTR gene has been delivered and expressed. One skilled will be able to determine the best test for measuring functionality of a protein in vitro or in vivo.

It is contemplated herein that the effects of gene expression of the transgene from the ceDNA vector in a cell or subject can last for at least 1 month, at least 2 months, at least 3 months, at least four months, at least 5 months, at least six months, at least 10 months, at least 12 months, at least 18 months, at least 2 years, at least 5 years, at least 10 years, at least 20 years, or can be permanent.

In some embodiments, a transgene in the expression cassette, expression construct, or ceDNA vector described herein can be codon optimized for the host cell. As used herein, the term "codon optimized" or "codon optimization" refers to the process of modifying a nucleic acid sequence for enhanced expression in the cells of the vertebrate of interest, e.g., mouse or human (e.g., humanized), by replacing at least one, more than one, or a significant number of codons of the native sequence (e.g., a prokaryotic sequence) with codons that are more frequently or most frequently used in the genes of that vertebrate. Various species exhibit particular bias for certain codons of a particular amino acid. Typically, codon optimization does not alter the amino acid sequence of the original translated protein. Optimized codons can be determined using e.g., Aptagen's Gene Forge® codon optimization and custom gene synthesis platform (Aptagen, Inc.) or another publicly available database.

XI. Administration

In particular embodiments, more than one administration (e.g., two, three, four or more administrations) may be employed to achieve the desired level of gene expression over a period of various intervals, e.g., daily, weekly, monthly, yearly, etc.

Exemplary modes of administration of a closed-ended DNA vector, including a ceDNA vector, produced using the synthetic process as described herein includes oral, rectal, transmucosal, intranasal, inhalation (e.g., via an aerosol), buccal (e.g., sublingual), vaginal, intrathecal, intraocular, transdermal, intraendothelial, in utero (or in ovo), parenteral (e.g., intravenous, subcutaneous, intradermal, intracranial, intramuscular [including administration to skeletal, diaphragm and/or cardiac muscle], intrapleural, intracerebral, and intraarticular), topical (e.g., to both skin and mucosal surfaces, including airway surfaces, and transdermal administration), intralymphatic, and the like, as well as direct tissue or organ injection (e.g., to liver, eye, skeletal muscle, cardiac muscle, diaphragm muscle or brain).

Administration of a closed-ended DNA vector, including a ceDNA vector, produced using the synthetic process as described herein can be to any site in a subject, including, without limitation, a site selected from the group consisting of the brain, a skeletal muscle, a smooth muscle, the heart, the diaphragm, the airway epithelium, the liver, the kidney, the spleen, the pancreas, the skin, and the eye. Administration of the synthetically produced ceDNA vector can also be to a tumor (e.g., in or near a tumor or a lymph node). The most suitable route in any given case will depend on the nature and severity of the condition being treated, ameliorated, and/or prevented and on the nature of the particular ceDNA vector that is being used. Additionally, a ceDNA vector produced using the synthetic process as described herein permits one to administer more than one transgene in a single vector, or multiple ceDNA vectors (e.g. a ceDNA cocktail).

Administration of a closed-ended DNA vector, including a ceDNA vector, produced using the synthetic process as described herein to skeletal muscle according to the present invention includes but is not limited to administration to skeletal muscle in the limbs (e.g., upper arm, lower arm, upper leg, and/or lower leg), back, neck, head (e.g., tongue), thorax, abdomen, pelvis/perineum, and/or digits. The synthetically produced ceDNA vector can be delivered to skeletal muscle by intravenous administration, intra-arterial administration, intraperitoneal administration, limb perfusion, (optionally, isolated limb perfusion of a leg and/or arm; see, e.g. Arruda et al., (2005) Blood 105: 3458-3464), and/or direct intramuscular injection. In particular embodiments, the ceDNA vector as disclosed herein is administered to a limb (arm and/or leg) of a subject (e.g., a subject with muscular dystrophy such as DMD) by limb perfusion, optionally isolated limb perfusion (e.g., by intravenous or intra-articular administration. In certain embodiments, a DNA vector, including a ceDNA vector produced using the synthetic process as described herein can be administered without employing "hydrodynamic" techniques.

Administration of a closed-ended DNA vector, including a ceDNA vector, produced using the synthetic process as described herein to cardiac muscle includes administration to the left atrium, right atrium, left ventricle, right ventricle and/or septum. The synthetically produced ceDNA vector as described herein can be delivered to cardiac muscle by intravenous administration, intra-arterial administration such as intra-aortic administration, direct cardiac injection (e.g., into left atrium, right atrium, left ventricle, right ventricle), and/or coronary artery perfusion. Administration to diaphragm muscle can be by any suitable method including intravenous administration, intra-arterial administration, and/or intra-peritoneal administration. Administration to smooth muscle can be by any suitable method including intravenous administration, intra-arterial administration, and/or intra-peritoneal administration. In one embodiment, administration can be to endothelial cells present in, near, and/or on smooth muscle.

In some embodiments, a DNA vector, including a ceDNA vector produced using the synthetic process as described herein is administered to skeletal muscle, diaphragm muscle and/or cardiac muscle (e.g., to treat, ameliorate and/or prevent muscular dystrophy or heart disease (e.g., PAD or congestive heart failure).

A. Ex Vivo Treatment

In some embodiments, cells are removed from a subject, a closed-ended DNA vector, including a ceDNA vector, produced using the synthetic process as described herein is introduced therein, and the cells are then replaced back into the subject. Methods of removing cells from subject for treatment ex vivo, followed by introduction back into the subject are known in the art (see, e.g., U.S. Pat. No. 5,399,346; the disclosure of which is incorporated herein in its entirety). Alternatively, a closed-ended DNA vector, including a ceDNA vector, produced using the synthetic process as described herein is introduced into cells from another subject, into cultured cells, or into cells from any other suitable source, and the cells are administered to a subject in need thereof.

Cells transduced with a closed-ended DNA vector, including a ceDNA vector, produced using the synthetic process as described herein are preferably administered to the subject in a "therapeutically-effective amount" in combination with a pharmaceutical carrier. Those of ordinary skill in the art will appreciate that the therapeutic effects need not be complete or curative, as long as some benefit is provided to the subject.

In some embodiments, a closed-ended DNA vector, including a ceDNA vector, produced using the synthetic process as described herein can encode a transgene (sometimes called a heterologous nucleotide sequence) that is any polypeptide that is desirably produced in a cell in vitro, ex vivo, or in vivo. For example, in contrast to the use of the ceDNA vectors in a method of treatment as previously discussed herein, in some embodiments a closed-ended DNA vector, including a ceDNA vector, produced using the synthetic process as described herein may be introduced into cultured cells and the expressed gene product isolated therefrom, e.g., for the production of antigens or vaccines.

A closed-ended DNA vector, including a ceDNA vector, produced using the synthetic process as described herein can be used in both veterinary and medical applications. Suitable subjects for ex vivo gene delivery methods as described above include both avians (e.g., chickens, ducks, geese, quail, turkeys and pheasants) and mammals (e.g., humans, bovines, ovines, caprines, equines, felines, canines, and lagomorphs), with mammals being preferred. Human subjects are most preferred. Human subjects include neonates, infants, juveniles, and adults.

One aspect of the technology described herein relates to a method of delivering a transgene to a cell. Typically, for in vitro methods, a closed-ended DNA vector, including a ceDNA vector, produced using the synthetic process as described herein may be introduced into the cell using the methods as disclosed herein, as well as other methods known in the art. A closed-ended DNA vector, including a ceDNA vector, produced using the synthetic process as described herein disclosed herein are preferably administered to the cell in a biologically-effective amount. If a closed-ended DNA vector, including a ceDNA vector, produced using the synthetic process as described herein is administered to a cell in vivo (e.g., to a subject), a biologically-effective amount of the ceDNA vector is an amount that is sufficient to result in transduction and expression of the transgene in a target cell.

B. Dose Ranges

In vivo and/or in vitro assays can optionally be employed to help identify optimal dosage ranges for use of the synthetically produced ceDNA vector. The precise dose to be employed in the formulation will also depend on the route of administration, and the seriousness of the condition, and should be decided according to the judgment of the person of ordinary skill in the art and each subject's circumstances. Effective doses can be extrapolated from dose-response curves derived from in vitro or animal model test systems.

A closed-ended DNA vector, including a ceDNA vector, produced using the synthetic process as described herein is administered in sufficient amounts to transfect the cells of a desired tissue and to provide sufficient levels of gene transfer and expression without undue adverse effects. Conventional and pharmaceutically acceptable routes of administration include, but are not limited to, those described above in the "Administration" section, such as direct delivery to the selected organ (e.g., intraportal delivery to the liver), oral, inhalation (including intranasal and intratracheal delivery), intraocular, intravenous, intramuscular, subcutaneous, intradermal, intratumoral, and other parental routes of administration. Routes of administration can be combined, if desired.

The dose of the amount of a synthetically produced ceDNA vector required to achieve a particular "therapeutic effect," will vary based on several factors including, but not limited to: the route of nucleic acid administration, the level of gene or RNA expression required to achieve a therapeutic effect, the specific disease or disorder being treated, and the stability of the gene(s), RNA product(s), or resulting expressed protein(s). One of skill in the art can readily determine a synthetically produced ceDNA vector dose range to treat a patient having a particular disease or disorder based on the aforementioned factors, as well as other factors that are well known in the art.

Dosage regime can be adjusted to provide the optimum therapeutic response. For example, the oligonucleotide can be repeatedly administered, e.g., several doses can be administered daily or the dose can be proportionally reduced as indicated by the exigencies of the therapeutic situation. One of ordinary skill in the art will readily be able to determine appropriate doses and schedules of administration of the subject oligonucleotides, whether the oligonucleotides are to be administered to cells or to subjects.

A "therapeutically effective dose" will fall in a relatively broad range that can be determined through clinical trials and will depend on the particular application (neural cells will require very small amounts, while systemic injection would require large amounts). For example, for direct in vivo injection into skeletal or cardiac muscle of a human subject, a therapeutically effective dose will be on the order of from about 1 μg to 100 g of the ceDNA vector. If exosomes or microparticles are used to deliver a DNA vector, including a ceDNA vector produced using the synthetic process as described herein, then a therapeutically effective dose can be determined experimentally, but is expected to deliver from 1 μg to about 100 g of vector. Moreover, a therapeutically effective dose is an amount ceDNA vector that expresses a sufficient amount of the transgene to have an effect on the subject that results in a reduction in one or more symptoms of the disease, but does not result in significant off-target or significant adverse side effects.

Formulation of pharmaceutically-acceptable excipients and carrier solutions is well-known to those of skill in the art, as is the development of suitable dosing and treatment regimens for using the particular compositions described herein in a variety of treatment regimens.

For in vitro transfection, an effective amount of a closed-ended DNA vector, including a ceDNA vector, produced using the synthetic process as described herein to be delivered to cells ($1\times10^6$ cells) will be on the order of 0.1 to 100 μg ceDNA vector, preferably 1 to 20 μg, and more preferably 1 to 15 μg or 8 to 10 μg. Larger ceDNA vectors will require higher doses. If exosomes or microparticles are used, an effective in vitro dose can be determined experimentally but would be intended to deliver generally the same amount of the ceDNA vector.

Treatment can involve administration of a single dose or multiple doses. In some embodiments, more than one dose can be administered to a subject; in fact multiple doses can be administered as needed, because the synthetically produced ceDNA vector elicits does not elicit an anti-capsid host immune response due to the absence of a viral capsid, and its formulation does not contain unwanted cellular contaminants due to its synthetic production. As such, one of skill in the art can readily determine an appropriate number of doses. The number of doses administered can, for example, be on the order of 1-100, preferably 2-20 doses.

Without wishing to be bound by any particular theory, the lack of typical anti-viral immune response elicited by administration of a synthetically produced ceDNA vector as described by the disclosure (i.e., the absence of capsid components) allows the synthetically produced ceDNA vector to be administered to a host on multiple occasions. In some embodiments, the number of occasions in which a heterologous nucleic acid is delivered to a subject is in a range of 2 to 10 times (e.g., 2, 3, 4, 5, 6, 7, 8, 9, or 10 times). In some embodiments, a synthetically produced ceDNA vector is delivered to a subject more than 10 times.

In some embodiments, a dose of a synthetically produced ceDNA vector is administered to a subject no more than once per calendar day (e.g., a 24-hour period). In some embodiments, a dose of a synthetically produced ceDNA vector is administered to a subject no more than once per 2, 3, 4, 5, 6, or 7 calendar days. In some embodiments, a dose of a synthetically produced ceDNA vector is administered to a subject no more than once per calendar week (e.g., 7 calendar days). In some embodiments, a dose of a synthetically produced ceDNA vector is administered to a subject no more than bi-weekly (e.g., once in a two calendar week period). In some embodiments, a dose of a synthetically produced ceDNA vector is administered to a subject no more than once per calendar month (e.g., once in 30 calendar days). In some embodiments, a dose of a synthetically produced ceDNA vector is administered to a subject no more than once per six calendar months. In some embodiments, a dose of a synthetically produced ceDNA vector is administered to a subject no more than once per calendar year (e.g., 365 days or 366 days in a leap year).

C. Unit Dosage Forms

In some embodiments, the pharmaceutical compositions can conveniently be presented in unit dosage form. A unit dosage form will typically be adapted to one or more specific routes of administration of the pharmaceutical composition. In some embodiments, the unit dosage form is adapted for administration by inhalation. In some embodiments, the unit dosage form is adapted for administration by a vaporizer. In some embodiments, the unit dosage form is adapted for administration by a nebulizer. In some embodiments, the unit dosage form is adapted for administration by an aerosolizer. In some embodiments, the unit dosage form is adapted for oral administration, for buccal administration, or for sublingual administration. In some embodiments, the unit dosage form is adapted for intravenous, intramuscular, or subcutaneous administration. In some embodiments, the unit dosage form is adapted for intrathecal or intracerebroventricular administration. In some embodiments, the pharmaceutical composition is formulated for topical administration. The amount of active ingredient which can be combined with a carrier material to produce a single dosage form will generally be that amount of the compound which produces a therapeutic effect.

XII. Various Applications

The compositions and closed-ended DNA vector, including ceDNA vectors, produced using the synthetic process as described herein can be used to deliver a transgene for various purposes as described above. In some embodiments, a transgene can encode a protein or be a functional RNA, and in some embodiments, can be a protein or functional RNA that is modified for research purposes, e.g., to create a somatic transgenic animal model harboring one or more mutations or a corrected gene sequence, e.g., to study the function of the target gene. In another example, the transgene encodes a protein or functional RNA to create an animal model of disease.

In some embodiments, the transgene encodes one or more peptides, polypeptides, or proteins, which are useful for the treatment, amelioration, or prevention of disease states in a mammalian subject. The transgene expressed by the synthetically produced ceDNA vector is administered to a patient in a sufficient amount to treat a disease associated with an abnormal gene sequence, which can result in any one or more of the following: reduced expression, lack of expression or dysfunction of the target gene.

In some embodiments, a DNA vector, including a ceDNA vector, produced using the synthetic process as described herein are envisioned for use in diagnostic and screening methods, whereby a transgene is transiently or stably expressed in a cell culture system, or alternatively, a transgenic animal model.

Another aspect of the technology described herein provides a method of transducing a population of mammalian cells. In an overall and general sense, the method includes at least the step of introducing into one or more cells of the population, a composition that comprises an effective amount of one or more of the synthetically produced ceDNA disclosed herein.

Additionally, the present invention provides compositions, as well as therapeutic and/or diagnostic kits that include one or more of the disclosed closed-ended DNA vector, including a ceDNA vector composition, produced using the synthetic process as described herein, formulated with one or more additional ingredients, or prepared with one or more instructions for their use.

A cell to be administered a closed-ended DNA vector, including a ceDNA vector, produced using the synthetic process as described herein may be of any type, including but not limited to neural cells (including cells of the peripheral and central nervous systems, in particular, brain cells), lung cells, retinal cells, epithelial cells (e.g., gut and respiratory epithelial cells), muscle cells, dendritic cells, pancreatic cells (including islet cells), hepatic cells, myocardial cells, bone cells (e.g., bone marrow stem cells), hematopoietic stem cells, spleen cells, keratinocytes, fibroblasts, endothelial cells, prostate cells, germ cells, and the like. Alternatively, the cell may be any progenitor cell. As a further alternative, the cell can be a stem cell (e.g., neural stem cell, liver stem cell). As still a further alternative, the cell may be a cancer or tumor cell. Moreover, the cells can be from any species of origin, as indicated above.

In some embodiments, the present application may be defined in any of the following paragraphs:

1. A method of preparing a DNA vector comprising:
   contacting a double-stranded DNA construct comprising:
      an expression cassette;
      an ITR on the upstream (5'-end) of the expression cassette;
      an ITR on the downstream (3'-end) of the expression cassette;
      and at least two restriction endonuclease sites flanking the ITRs such that the restriction
      endonucleases are distal to the expression cassette
   with one or more restriction endonucleases that can cleave the double-stranded DNA construct at the restriction endonuclease sites to excise the sequences between the restriction endonuclease sites from the DNA construct; and
   ligating the 5' and 3' ends of the excised sequence to form a DNA vector, wherein at least one ITR is a modified ITR.
2. The method of paragraph 1, wherein the double-stranded DNA construct is a bacmid, plasmid, minicircle, or a linear double-stranded DNA molecule.
3. The method of any of paragraphs 1-2, wherein the ITR upstream of the expression cassette is a wild-type ITR.
4. The method of paragraph 3, wherein the wild-type ITR comprises a polynucleotide of SEQ ID NO: 1, 2, or 5-14.
5. The method of any of paragraphs 1-4, wherein the ITR downstream of the expression cassette is a modified ITR.
6. The method of paragraph 5, wherein the modified ITR comprises a polynucleotide of SEQ ID NO: 3.
7. The method of any of paragraphs 1-2, wherein the ITR upstream of the expression cassette is a modified ITR.
8. The method of paragraph 7, wherein the modified ITR comprises a polynucleotide of SEQ ID NO: 4.
9. The method of any of paragraphs 7-8, wherein the ITR downstream of the expression cassette is a wild-type ITR.
10. The method of paragraph 9, wherein the wild-type ITR comprises a polynucleotide of SEQ ID NO: 1.
11. The method of any of paragraphs 1-10, wherein the ITR is a replication-competent.
12, The method of any of paragraphs 1-11 wherein the ITR is a AAV ITR.
13. The method of any of paragraphs 1-12, wherein the expression cassette comprises a cis-regulatory element.

14. The method of paragraph 13, wherein the cis-regulatory element is selected from the group consisting of a posttranscriptional regulatory element, and a BGH poly-A signal.
15. The method of paragraph 14, wherein the posttranscriptional regulatory element comprises a WHP posttranscriptional regulatory element (WPRE).
16. The method of any of paragraphs 1-15, wherein the expression cassette further comprises a promoter selected from the group consisting of CAG promoter, AAT promoter, LP1 promoter, and EF1a promoter.
17. The method of paragraph 16, wherein said expression cassette comprises polynucleotides of SEQ ID NO: 72, SEQ ID NO: 123 or SEQ ID NO: 124, SEQ ID NO: 67 and SEQ ID NO: 68.
18. The method of any of paragraphs 1-17, wherein said expression cassette further comprises an exogenous sequence.
19. The method of paragraphs 1-18, wherein the exogenous sequence comprises at least 2000 or 5000 nucleotides.
20. The method of paragraph 19, wherein the exogenous sequence encodes a protein.
21. The method of paragraph 20, wherein the exogenous sequence encodes a reporter protein, therapeutic protein, an antigen, a gene editing protein, or a cytotoxic protein.
22. The method of any of paragraphs 1-21, wherein the DNA vector has a linear and continuous structure.
23. A DNA vector generated by the method of any of paragraphs 1-22.
24. A pharmaceutical composition comprising: the DNA vector of paragraph 23; and optionally, an excipient.
25. A polynucleotide for generating a DNA vector comprising:
   an expression cassette;
   an ITR on the upstream (5'-end) of the expression cassette;
   an ITR on the downstream (3'-end) of the expression cassette;
   and at least two restriction endonuclease sites flanking the ITRs such that the restriction endonucleases are distal to the expression cassette, wherein at least one ITR is a modified ITR.
26. The polynucleotide of paragraph 25, wherein the polynucleotide is a bacmid, plasmid, minicircle, or a linear double-stranded DNA molecule.
27. The polynucleotide of any of paragraphs 25-26, wherein the ITR upstream of the expression cassette is a wild-type ITR.
28. The polynucleotide of paragraph 27, wherein the wild-type ITR comprises a polynucleotide of SEQ ID NO: 2.
29. The polynucleotide of any of paragraphs 25-28, wherein the ITR downstream of the expression cassette is a modified ITR.
30. The polynucleotide of paragraph 29, wherein the modified ITR comprises a polynucleotide of SEQ ID NO: 3.
31. The polynucleotide of any of paragraphs 25-26, wherein the ITR upstream of the expression cassette is a modified ITR.
32. The polynucleotide of paragraph 31, wherein the modified ITR comprises a polynucleotide of SEQ ID NO: 4.
33. The polynucleotide of any of paragraphs 31-32, wherein the ITR downstream of the expression cassette is a wild-type ITR.
34. The polynucleotide of paragraph 33, wherein the wild-type ITR comprises a polynucleotide of SEQ ID NO: 1.
35. The polynucleotide of any of paragraphs 25-34, wherein the wild-type ITR is replication-competent.
36. The polynucleotide of any of paragraphs 25-35, wherein the ITR is a AAV ITR.
37. The polynucleotide of any of paragraphs 25-36, wherein the expression cassette comprises a cis-regulatory element.
38. The polynucleotide of paragraph 37, wherein the cis-regulatory element is selected from the group consisting of a posttranscriptional regulatory element, and a BGH poly-A signal.
39. The polynucleotide of paragraph 38, wherein the posttranscriptional regulatory element comprises a WHP posttranscriptional regulatory element (WPRE).
40. The polynucleotide of any of paragraphs 25-39, wherein the expression cassette further comprises a promoter selected from the group consisting of CAG promoter, AAT promoter, LP1 promoter, and EF1a promoter.
41. The polynucleotide of paragraph 40, wherein said expression cassette comprises polynucleotides of SEQ ID NO: 72, SEQ ID NO: 123 or SEQ ID NO: 124, SEQ ID NO: 67 and SEQ ID NO: 68.
42. The polynucleotide of any of paragraphs 25-41, wherein said expression cassette further comprises an exogenous sequence.
43. The polynucleotide of paragraph 42, wherein the exogenous sequence comprises at least 5000 nucleotides.
44. The polynucleotide of paragraph 43, wherein the exogenous sequence encodes a protein.
45. The polynucleotide of paragraph 44, wherein the exogenous sequence encodes a reporter protein, therapeutic protein, an antigen, a gene editing protein, or a cytotoxic protein.
46. The polynucleotide of any of paragraphs 25-45, wherein the DNA vector has a linear and continuous structure.
47. A method of preparing a DNA vector comprising:
synthesizing a single-stranded molecule comprising, from 5' to 3':
   a sense first ITR;
   a sense expression cassette sequence;
   a sense second ITR;
   a hairpin sequence;
   an antisense second ITR;
   an antisense expression cassette sequence; and
   an antisense first ITR;
   forming a hairpin polynucleotide from the single-stranded molecule;
and ligating the 5' and 3' ends to form the DNA vector, wherein one at least one ITR is a modified ITR.
48. The method of paragraph 47, wherein the first ITR is a wild-type ITR.
49. The method of paragraph 48, wherein the wild-type ITR comprises a polynucleotide of SEQ ID NO: 2.
50. The method of any of paragraphs 4749, wherein the second ITR is a modified ITR.
51. The method of paragraph 50, wherein the modified ITR comprises a polynucleotide of SEQ ID NO: 3.

52. The method of paragraph 47, wherein the first ITR upstream is a modified ITR.
53. The method of paragraph 52, wherein the modified ITR comprises a polynucleotide of SEQ ID NO: 4.
54. The method of any of paragraphs 52-53, wherein the second ITR is a wild-type ITR.
55. The method of paragraph 54, wherein the wild-type ITR comprises a polynucleotide of SEQ ID NO: 1.
56. The method of any of paragraphs 47-55, wherein the wild-type ITR is replication-competent.
57. The method of any of paragraphs 47-56, wherein the ITR is a AAV ITR.
58. The method of any of paragraphs 47-57, wherein the expression cassette comprises a cis-regulatory element.
59. The method of paragraph 58, wherein the cis-regulatory element is selected from the group consisting of a posttranscriptional regulatory element, and a BGH poly-A signal
60. The method of paragraph 59, wherein the posttranscriptional regulatory element comprises a WHP posttranscriptional regulatory element (WPRE).
61. The method of any of paragraphs 47-60, wherein the expression cassette further comprises a promoter selected from the group consisting of CAG promoter, AAT promoter, LP1 promoter, and EF1a promoter.
62. The method of paragraph 61, wherein said expression cassette comprises polynucleotides of SEQ ID NO: 72, SEQ ID NO: 123 or SEQ ID NO: 124, SEQ ID NO: 67 and SEQ ID NO: 68.
63. The method of any of paragraphs 47-62, wherein said expression cassette further comprises an exogenous sequence.
64. The method of paragraph 63, wherein the exogenous sequence comprises at least 2000 nucleotides.
65. The method of paragraph 63, wherein the exogenous sequence encodes a protein.
66. The method of paragraph 65, wherein the exogenous sequence encodes a reporter protein, therapeutic protein, an antigen, a gene editing protein, or a cytotoxic protein.
67. The method of any of paragraphs 47-66, wherein the DNA vector has a linear and continuous structure.
68. A DNA vector generated by the method of any of paragraphs 47-67.
69. A pharmaceutical composition comprising:
the DNA vector of paragraph 68; and
optionally, an excipient.
70. A method of preparing a DNA vector comprising:
synthesizing a first single-stranded ITR molecule comprising a first ITR;
synthesizing a second single-stranded ITR molecule comprising a second ITR;
providing a double-stranded polynucleotide comprising an expression cassette sequence; and
ligating the 5' and 3' ends of the first ITR molecule to a first end of the double-stranded molecule and ligating the 5' and 3' ends of the second ITR molecule to the second end of the double stranded molecule to form the DNA vector.
71. The method of paragraph 70, wherein the double-stranded polynucleotide is provided by excising the double-stranded molecule from a double-stranded DNA construct.
72. The method of any of paragraphs 70-71, wherein the first ITR is a wild-type ITR.
73. The method of paragraph 72, wherein the wild-type ITR comprises a polynucleotide of SEQ ID NO: 2.
74. The method of any of paragraphs 70-73, wherein the second ITR is a modified ITR.
75. The method of paragraph 74, wherein the modified ITR comprises a polynucleotide of SEQ ID NO: 3.
76. The method of any of paragraphs 70-71, wherein the first ITR upstream is a modified ITR.
77. The method of paragraph 76, wherein the modified ITR comprises a polynucleotide of SEQ ID NO: 4.
78. The method of any of paragraphs 76-77, wherein the second ITR is a wild-type ITR.
79. The method of paragraph 78, wherein the wild-type ITR comprises a polynucleotide of SEQ ID NO: 1.
80. The method of any of paragraphs 70-79, wherein the wild-type ITR is replication-competent.
81. The method of any of paragraphs 70-80, wherein the ITR is a AAV ITR.
82. The method of any of paragraphs 70-81, wherein the expression cassette comprises a cis-regulatory element.
83. The method of paragraph 82, wherein the cis-regulatory element is selected from the group consisting of a posttranscriptional regulatory element, and a BGH poly-A signal
84. The method of paragraph 83, wherein the posttranscriptional regulatory element comprises a WHP posttranscriptional regulatory element (WPRE).
85. The method of any of paragraphs 70-84, wherein the expression cassette further comprises a promoter selected from the group consisting of CAG promoter, AAT promoter, LP1 promoter, and EF1a promoter.
86. The method of paragraph 70-85, wherein said expression cassette comprises polynucleotides of SEQ ID NO: 72, SEQ ID NO: 123 or SEQ ID NO: 124, SEQ ID NO: 67 and SEQ ID NO: 68.
87. The method of any of paragraphs 70-86, wherein said expression cassette further comprises an exogenous sequence.
88. The method of paragraph 70-87, wherein the exogenous sequence comprises at least 2000 nucleotides.
89. The method of paragraph 88, wherein the exogenous sequence encodes a protein.
90. The method of paragraph 88, wherein the exogenous sequence encodes a reporter protein, therapeutic protein, an antigen, a gene editing protein, or a cytotoxic protein.
91. The method of any of paragraphs 70-90, wherein the DNA vector has a linear and continuous structure.
92. A DNA vector generated by the method of any of paragraphs 70-91.
93. A pharmaceutical composition comprising: the DNA vector of paragraph 92; and optionally, an excipient.
94. The method of any of paragraphs 1-22, 47-67, and 70-91, wherein the ligation step comprises chemical ligation.
95. The method of any of paragraphs 1-22, 47-67, and 70-91, wherein the ligation step comprises ligation with a ligation-competent protein.
96. The method of paragraph 95, wherein the ligation-competent protein is AAV Rep.
97. The method of any of paragraphs 1, 25, 47, and 70, wherein the ITRS are selected from a pair of ITRs selected from the group consisting of: SEQ ID NO:101 and SEQ ID NO:102; SEQ ID NO:103, and SEQ ID NO:104, SEQ ID NO:105, and SEQ ID NO:106; SEQ ID NO: 107, and SEQ ID NO:108; SEQ ID NO:109, and SEQ ID NO: 110; SEQ ID NO:111, and SEQ ID NO: 112; SEQ ID NO:113 and SEQ ID NO:114; and SEQ ID NO:115 and SEQ ID NO:116 or any of SEQ ID NO: 1-48 SEQ ID NO: 165-187, or from the sequences listing in any of Tables 2, 4A, 4B or 5.

98. An isolated DNA vector obtained by or obtainable by a process comprising the steps of one or methods disclosed herein.

99. An isolated DNA vector obtained by a method comprising the steps of any one of paragraphs 1-22.

100. An isolated DNA vector obtainable by a method comprising the steps of any one of paragraphs 1-22.

101. An isolated DNA vector obtained by a method comprising the steps of any one of paragraphs 47-67.

102. An isolated DNA vector obtainable by a method comprising the steps of any one of paragraphs 47-67.

103. An isolated DNA vector obtained by a method comprising the steps of any one of paragraphs 70-96.

104. An isolated DNA vector obtainable by a method comprising the steps of any one of paragraphs 70-96.

105. A genetic medicine comprising an isolated DNA vector as disclosed herein.

106. A genetic medicine comprising an isolated DNA vector of any one of paragraphs 23-46.

107. A genetic medicine comprising the isolated DNA vector of any one of paragraphs 97-103.

EXAMPLES

The following examples are provided by way of illustration not limitation. It will be appreciated by one of ordinary skill in the art that a DNA vector, including a ceDNA vector produced using the synthetic process as described herein can be constructed from any of the symmetric or asymmetric ITR configurations, comprising any of wild-type or modified ITRs as described herein, and that the following exemplary methods can be used to construct and assess the activity of such ceDNA vectors. While the methods are exemplified with certain ceDNA vectors, they are applicable to any DNA vector, including any ceDNA vector, in keeping with the description.

Example 1: Constructing ceDNA Vectors Using Insect Cell-Based Method

For comparative purposes, Example 1 describes the production of ceDNA vectors using an insect cell based method and a polynucleotide construct template, and is also described in Example 1 of PCT/US18/49996, which is incorporated herein in its entirety by reference. For example, a polynucleotide construct template used for generating the ceDNA vectors of the present invention according to Example 1 can be a ceDNA-plasmid, a ceDNA-Bacmid, and/or a ceDNA-baculovirus. Without being limited to theory, in a permissive host cell, in the presence of e.g., Rep, the polynucleotide construct template having two symmetric ITRs and an expression construct, where at least one of the ITRs is modified relative to a wild-type ITR sequence, replicates to produce ceDNA vectors. ceDNA vector production undergoes two steps: first, excision ("rescue") of template from the template backbone (e.g. ceDNA-plasmid, ceDNA-bacmid, ceDNA-baculovirus genome etc.) via Rep proteins, and second, Rep mediated replication of the excised ceDNA vector.

Figure 1B:
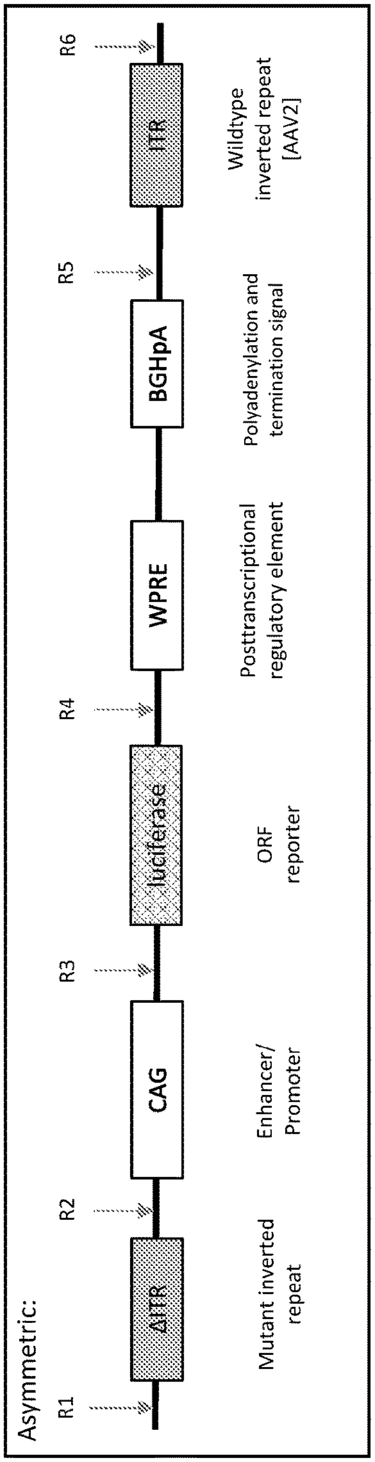
FIG. 1B illustrates an exemplary structure of a ceDNA vector comprising asymmetric ITRs with an expression cassette containing CAG promoter, WPRE, and BGHpA. An open reading frame (ORF) encoding a transgene, e.g., a Luciferase transgene is inserted into the cloning site between CAG promoter and WPRE. The expression cassette is flanked by two inverted terminal repeats (ITRs)—a modified ITR on the upstream (5'-end) and a wild-type ITR on the downstream (3'-end) of the expression cassette.
Figure 1C:
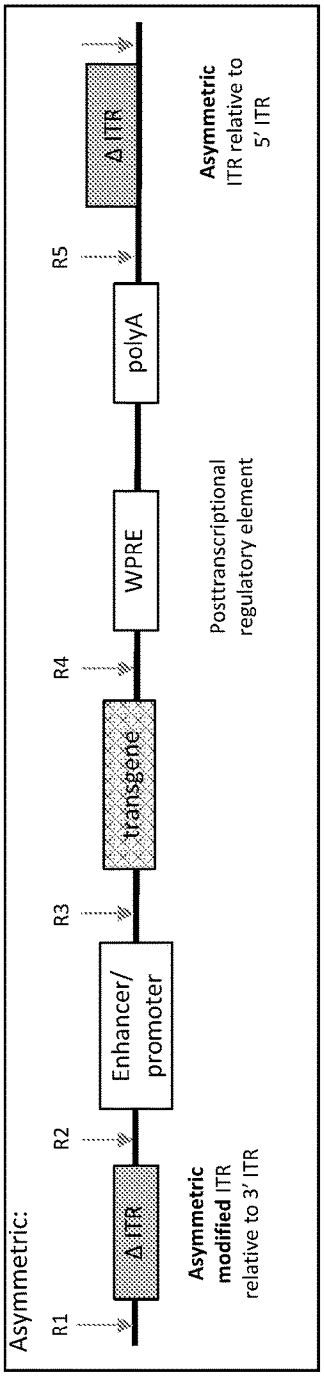
FIG. 1C illustrates an exemplary structure of a ceDNA vector for comprising asymmetric ITRs, with an expression cassette containing an enhancer/promoter, a transgene, a post transcriptional element (WPRE), and a polyA signal. An open reading frame (ORF) allows insertion of a transgene, into the cloning site between CAG promoter and WPRE. The expression cassette is flanked by two inverted terminal repeats (ITRs) that are asymmetrical with respect to each other; a modified ITR on the upstream (5'-end) and a modified ITR on the downstream (3'-end) of the expression cassette, where the 5' ITR and the 3'ITR are both modified ITRs but have different modifications (i.e., they do not have the same modifications).
Figure 1D:
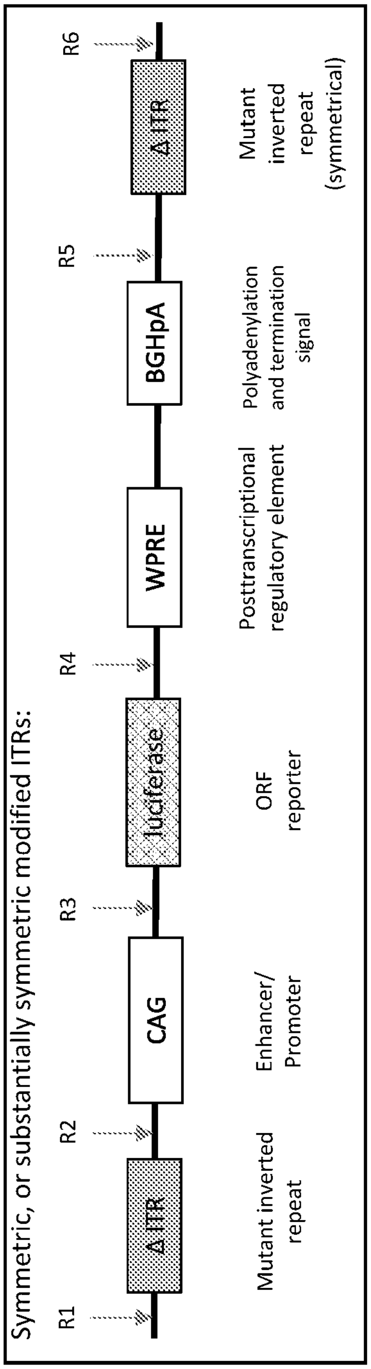
FIG. 1D illustrates an exemplary structure of a ceDNA vector comprising symmetric modified ITRs, or substantially symmetrical modified ITRs as defined herein, with an expression cassette containing CAG promoter, WPRE, and BGHpA. An open reading frame (ORF) encoding a transgene, e.g., a Luciferase transgene is inserted into the cloning site between CAG promoter and WPRE. The expression cassette is flanked by two modified inverted terminal repeats (ITRs), where the 5' modified ITR and the 3' modified ITR are symmetrical or substantially symmetrical.
Figure 1E:
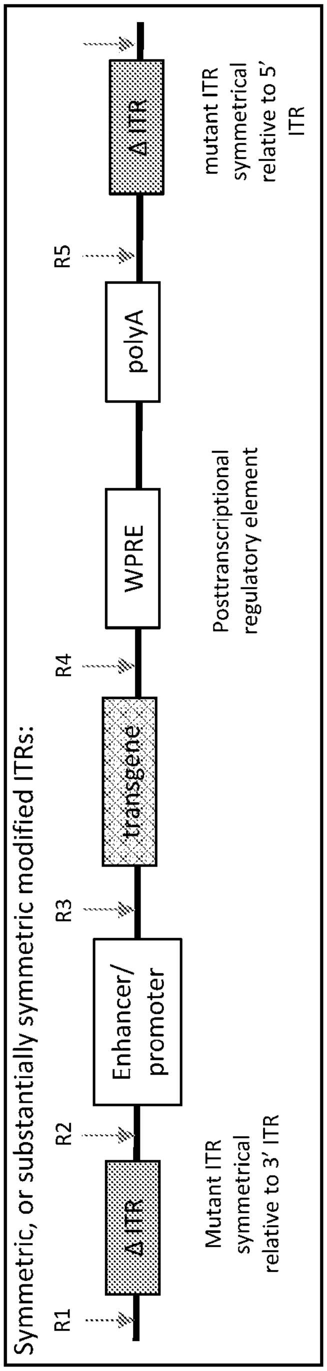
FIG. 1E illustrates an exemplary structure of a ceDNA vector comprising symmetric modified ITRs, or substantially symmetrical modified ITRs as defined herein, with an expression cassette containing an enhancer/promoter, a transgene, a post transcriptional element (WPRE), and a polyA signal. An open reading frame (ORF) allows insertion of a transgene into the cloning site between CAG promoter and WPRE. The expression cassette is flanked by two modified inverted terminal repeats (ITRs), where the 5' modified ITR and the 3' modified ITR are symmetrical or substantially symmetrical.
Figure 1F:
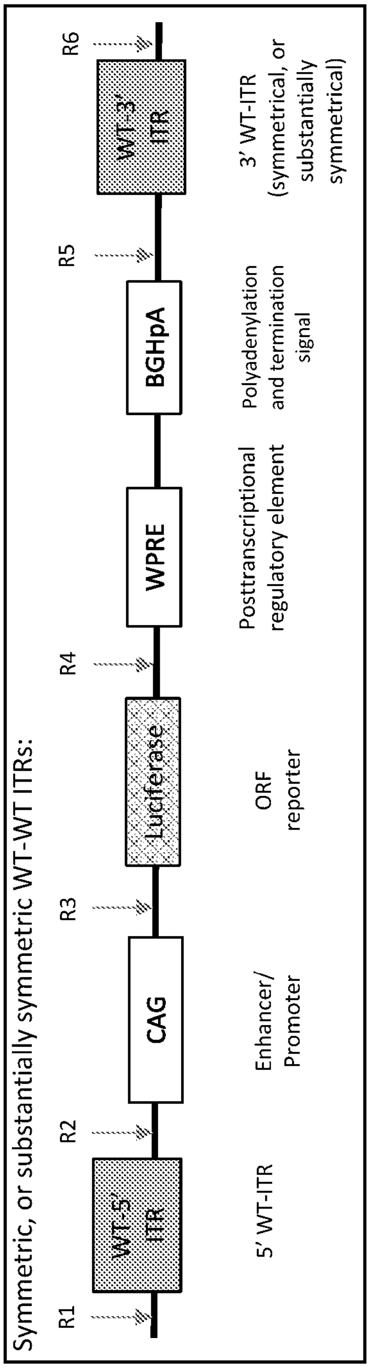
FIG. 1F illustrates an exemplary structure of a ceDNA vector comprising symmetric WT-ITRs, or substantially symmetrical WT-ITRs as defined herein, with an expression cassette containing CAG promoter, WPRE, and BGHpA. An open reading frame (ORF) encoding a transgene, e.g., a Luciferase transgene is inserted into the cloning site between CAG promoter and WPRE. The expression cassette is flanked by two wild type inverted terminal repeats (WT-ITRs), where the 5' WT-ITR and the 3' WT ITR are symmetrical or substantially symmetrical.
Figure 1G:
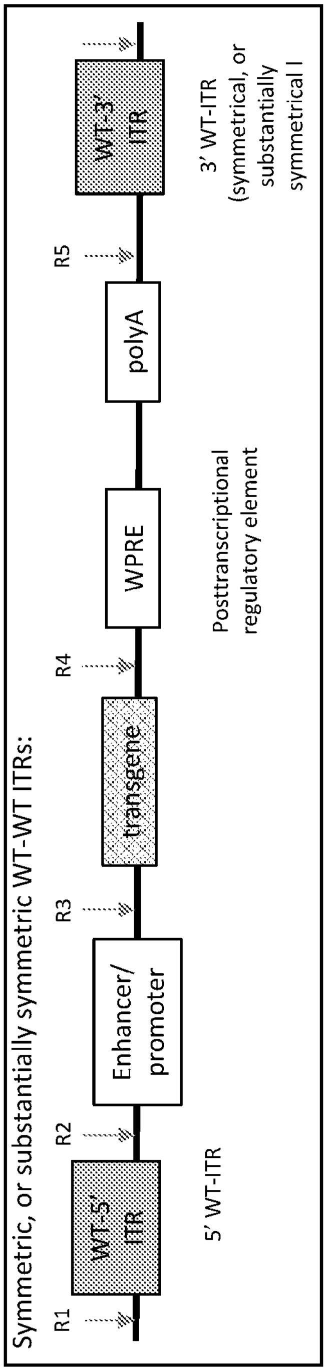
FIG. 1G illustrates an exemplary structure of a ceDNA vector comprising symmetric modified ITRs, or substantially symmetrical modified ITRs as defined herein, with an expression cassette containing an enhancer/promoter, a transgene, a post transcriptional element (WPRE), and a polyA signal. An open reading frame (ORF) allows insertion of a transgene into the cloning site between CAG promoter and WPRE. The expression cassette is flanked by two wild type inverted terminal repeats (WT-ITRs), where the 5' WT-ITR and the 3' WT ITR are symmetrical or substantially symmetrical.

An exemplary method to produce ceDNA vectors in a method using insect cell is from a ceDNA-plasmid as described herein. Referring to FIGS. 1A and 1B, the polynucleotide construct template of each of the ceDNA-plasmids includes both a left modified ITR and a right modified ITR with the following between the ITR sequences: (i) an enhancer/promoter; (ii) a cloning site for a transgene; (iii) a posttranscriptional response element (e.g. the woodchuck hepatitis virus posttranscriptional regulatory element (WPRE)); and (iv) a poly-adenylation signal (e.g. from bovine growth hormone gene (BGHpA). Unique restriction endonuclease recognition sites (R1-R6) (shown in FIG. 1A and FIG. 1B) were also introduced between each component to facilitate the introduction of new genetic components into the specific sites in the construct. R3 (PmeI) GTTTAAAC (SEQ ID NO: 123) and R4 (PacI) TTAATTAA (SEQ ID NO: 124) enzyme sites are engineered into the cloning site to introduce an open reading frame of a transgene. These sequences were cloned into a pFastBac HT B plasmid obtained from ThermoFisher Scientific.

Production of ceDNA-Bacmids:

DH10Bac competent cells (MAX EFFICIENCY® DH10Bac™ Competent Cells, Thermo Fisher) were transformed with either test or control plasmids following a protocol according to the manufacturer's instructions. Recombination between the plasmid and a baculovirus shuttle vector in the DH10Bac cells were induced to generate recombinant ceDNA-bacmids. The recombinant bacmids were selected by screening a positive selection based on blue-white screening in *E. coli* (($\Phi$80dlacZ$\Delta$M15 marker provides $\alpha$-complementation of the $\beta$-galactosidase gene from the bacmid vector) on a bacterial agar plate containing X-gal and IPTG with antibiotics to select for transformants and maintenance of the bacmid and transposase plasmids. White colonies caused by transposition that disrupts the $\beta$-galactoside indicator gene were picked and cultured in 10 ml of media.

The recombinant ceDNA-bacmids were isolated from the *E. coli* and transfected into Sf9 or Sf21 insect cells using FugeneHD to produce infectious baculovirus. The adherent Sf9 or Sf21 insect cells were cultured in 50 ml of media in T25 flasks at 25° C. Four days later, culture medium (containing the P0 virus) was removed from the cells, filtered through a 0.45 μm filter, separating the infectious baculovirus particles from cells or cell debris.

Optionally, the first generation of the baculovirus (P0) was amplified by infecting naïve Sf9 or Sf21 insect cells in 50 to 500 ml of media. Cells were maintained in suspension cultures in an orbital shaker incubator at 130 rpm at 25° C., monitoring cell diameter and viability, until cells reach a diameter of 18-19 nm (from a naïve diameter of 14-15 nm), and a density of ~4.0E+6 cells/mL. Between 3 and 8 days post-infection, the P1 baculovirus particles in the medium were collected following centrifugation to remove cells and debris then filtration through a 0.45 μm filter.

The ceDNA-baculovirus comprising the test constructs were collected and the infectious activity, or titer, of the baculovirus was determined. Specifically, four×20 ml Sf9 cell cultures at 2.5E+6 cells/ml were treated with P1 baculovirus at the following dilutions: 1/1000, 1/10,000, 1/50,000, 1/100,000, and incubated at 25-27° C. Infectivity was determined by the rate of cell diameter increase and cell cycle arrest, and change in cell viability every day for 4 to 5 days.

A "Rep-plasmid" was produced in a pFASTBAC™-Dual expression vector (ThermoFisher) comprising both the Rep78 (SEQ ID NO: 131 or 133) or Rep68 (SEQ ID NO: 130) and Rep52 (SEQ ID NO: 132) or Rep40 (SEQ ID NO: 129). The Rep-plasmid was transformed into the DH10Bac competent cells (MAX EFFICIENCY® DH10Bac™ Competent Cells (Thermo Fisher) following a protocol provided by the manufacturer. Recombination between the Rep-plasmid and a baculovirus shuttle vector in the DH10Bac cells were induced to generate recombinant bacmids ("Rep-bacmids"). The recombinant bacmids were selected by a positive selection that included-blue-white screening in *E. coli* (Φ80dlacZΔM15 marker provides α-complementation of the β-galactosidase gene from the bacmid vector) on a bacterial agar plate containing X-gal and IPTG. Isolated white colonies were picked and inoculated in 10 ml of selection media (kanamycin, gentamicin, tetracycline in LB broth). The recombinant bacmids (Rep-bacmids) were isolated from the *E. coli* and the Rep-bacmids were transfected into Sf9 or Sf21 insect cells to produce infectious baculovirus.

The Sf9 or Sf21 insect cells were cultured in 50 ml of media for 4 days, and infectious recombinant baculovirus ("Rep-baculovirus") were isolated from the culture. Optionally, the first generation Rep-baculovirus (P0) were amplified by infecting naïve Sf9 or Sf21 insect cells and cultured in 50 to 500 ml of media. Between 3 and 8 days post-infection, the P1 baculovirus particles in the medium were collected either by separating cells by centrifugation or filtration or another fractionation process. The Rep-baculovirus were collected and the infectious activity of the baculovirus was determined. Specifically, four×20 mL Sf9 cell cultures at $2.5\times10^6$ cells/mL were treated with P1 baculovirus at the following dilutions, 1/1000, 1/10,000, 1/50,000, 1/100,000, and incubated. Infectivity was determined by the rate of cell diameter increase and cell cycle arrest, and change in cell viability every day for 4 to 5 days.

ceDNA Vector Generation and Characterization

Sf9 insect cell culture media containing either (1) a sample-containing a ceDNA-bacmid or a ceDNA-baculovirus, and (2) Rep-baculovirus described above were then added to a fresh culture of Sf9 cells (2.5E+6 cells/ml, 20 ml) at a ratio of 1:1000 and 1:10,000, respectively. The cells were then cultured at 130 rpm at 25° C. 4-5 days after the co-infection, cell diameter and viability are detected. When cell diameters reached 18-20 nm with a viability of ~70-80%, the cell cultures were centrifuged, the medium was removed, and the cell pellets were collected. The cell pellets are first resuspended in an adequate volume of aqueous medium, either water or buffer. The ceDNA vector was isolated and purified from the cells using Qiagen MIDI PLUS™ purification protocol (Qiagen, 0.2 mg of cell pellet mass processed per column).

Yields of ceDNA vectors produced and purified from the Sf9 insect cells were initially determined based on UV absorbance at 260 nm. The purified ceDNA vectors can be assessed for proper closed-ended configuration using the electrophoretic methodology described in Example 5.

Example 2: ceDNA Production Via Excision from a Double-Stranded DNA Molecule

One exemplary method of producing a ceDNA vector using a synthetic method that involves the excision of a double-stranded DNA molecule. In brief, a ceDNA vector can be generated using a double stranded DNA construct, e.g., see FIGS. 7A-8E. In some embodiments, the double stranded DNA construct is a ceDNA plasmid, e.g., see, e.g., FIG. 6 in International patent application PCT/US2018/064242, filed Dec. 6, 2018).

In some embodiments, a construct to make a ceDNA vector comprises a regulatory switch as described herein.

For illustrative purposes, Example 3 describes producing ceDNA vectors as exemplary closed-ended DNA vectors generated using this method. However, while ceDNA vectors are exemplified in this Example to illustrate in vitro synthetic production methods to generate a closed-ended DNA vector by excision of a double-stranded polynucleotide comprising the ITRs and expression cassette (e.g., heterologous nucleic acid sequence) followed by ligation of the free 3' and 5' ends as described herein, one of ordinary skill in the art is aware that one can, as illustrated above, modify the double stranded DNA polynucleotide molecule such that any desired closed-ended DNA vector is generated, including but not limited to, doggybone DNA, dumbbell DNA and the like. Exemplary DNA vectors that can be produced by the synthetic production method described in Example 3 are discussed in the sections entitled "II D. DNA vectors produced using the synthetic production method", "III. ceDNA vectors in general" and "IV. Exemplary ceDNA vectors".

The method involves (i) excising a sequence encoding the expression cassette from a double-stranded DNA construct and (ii) forming hairpin structures at one or more of the ITRs and (iii) joining the free 5' and 3' ends by ligation, e.g., by T4 DNA ligase.

Figure 9:
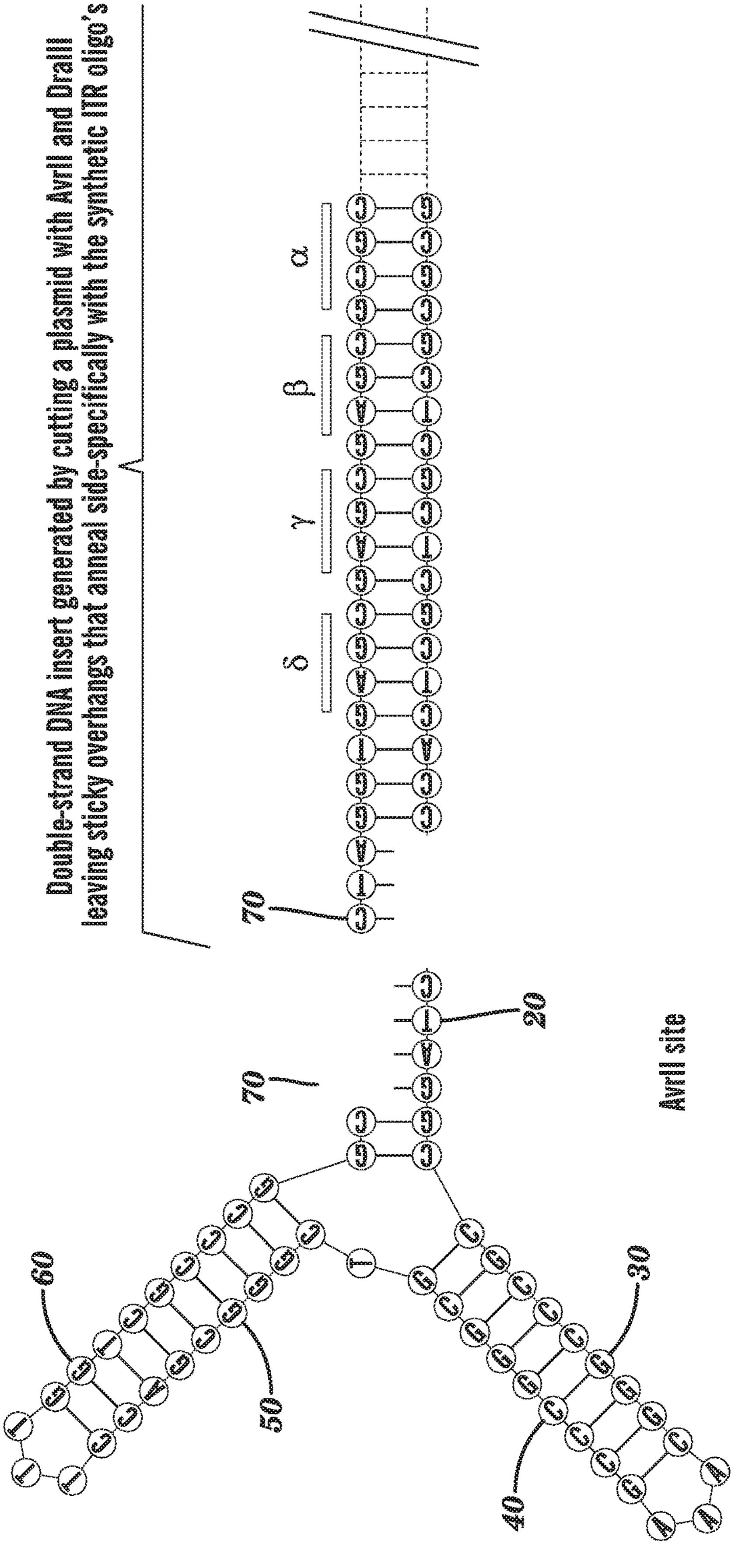
FIG. 9 depicts a diagram of an exemplary DNA vector and its assembly according to certain embodiments described herein. In particular, a 5' ITR oligonucleotide is ligated to the 5' end of the double stranded DNA molecule, a 3' ITR oligonucleotide is ligated to the 3' of the double stranded DNA molecule. The ends of the 5' ITR oligonucleotide are complementary to the '5 sense strand and 3' antisense strand of the double stranded DNA molecule (i.e., they have the same restriction endonuclease site), and similarly, the ends of the 3' ITR oligonucleotide are complementary to the '3 sense strand and 5' antisense strand of the double stranded DNA molecule.
Figure 9:
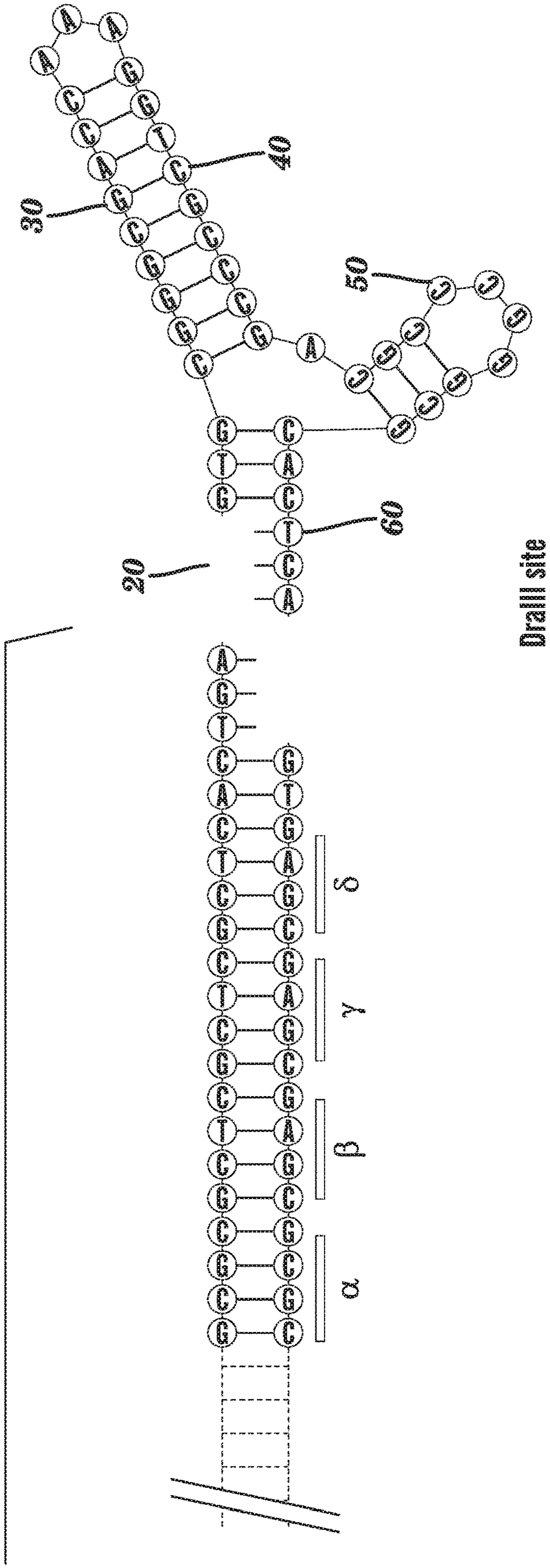

The double-stranded DNA construct comprises, in 5' to 3' order: a first restriction endonuclease site; an upstream ITR; an expression cassette; a downstream ITR; and a second restriction endonuclease site. The double-stranded DNA construct is then contacted with one or more restriction endonucleases to generate double-stranded breaks at both of the restriction endonuclease sites. One endonuclease can target both sites, or each site can be targeted by a different endonuclease as long as the restriction sites are not present in the ceDNA vector template. This excises the sequence between the restriction endonuclease sites from the rest of the double-stranded DNA construct (see FIG. 9). Upon ligation a closed-ended DNA vector is formed.

One or both of the ITRs used in the method may be wild-type ITRs. Modified ITRs may also be used, where the modification can include deletion, insertion, or substitution of one or more nucleotides from the wild-type ITR in the sequences forming B and B' arm and/or C and C' arm (see, e.g., FIGS. 6-8 and 10), and may have two or more hairpin loops (see, e.g., FIG. 6-8) or a single hairpin loop (see, e.g., FIG. 10A-10B). The hairpin loop modified ITR can be generated by genetic modification of an existing oligo or by de novo biological and/or chemical synthesis.

Figure 10B:
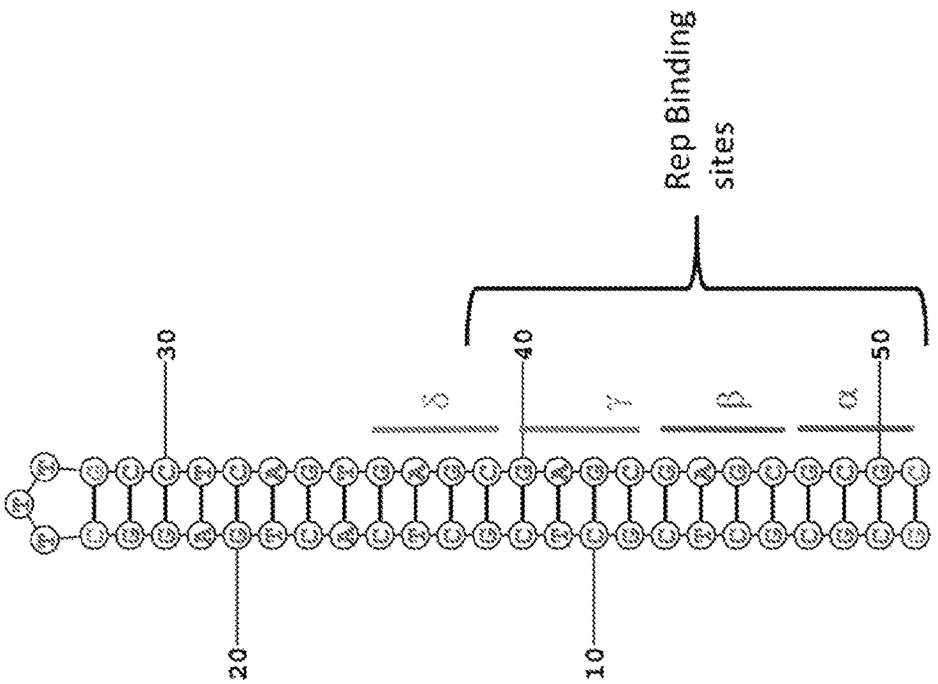
FIG. 10A provides a lowest energy structure of a modified ITR (“ITR-6 (Left)” SEQ ID NO: 111) and FIG. 10B provides a lowest energy structure of a modified ITR (“ITR-6 (Right)” SEQ ID NO: 112). They are predicted to form a hairpin structure with a single arm. Their Gibbs' free energies of unfolding are predicted to be −54.4 kcal/mol.
Figure 10A:
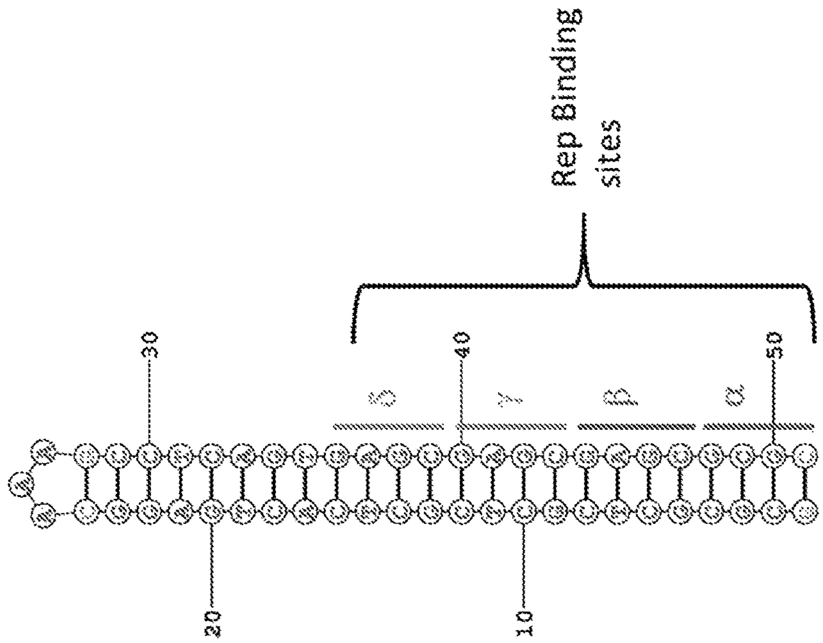

In a nonlimiting example, ITR-6 Left and Right provided in FIGS. 10A-10B (SEQ ID NOS: 111 and 112), include 40 nucleotide deletions in the B-B' and C-C' arms from the wild-type ITR of AAV2. Nucleotides remaining in the modified ITR are predicted to form a single hairpin structure. Gibbs free energy of unfolding the structure is about −54.4 kcal/mol. Other modifications to the ITR may also be made, including optional deletion of a functional Rep binding site or a Trs site.

Example 3: ceDNA Production Via Oligonucleotide Construction

Another exemplary method of producing a ceDNA vector using a synthetic method that involves assembly of various oligonucleotides, is provided. In this example, the ceDNA vector is produced by synthesizing a 5' oligonucleotide and a 3' ITR oligonucleotide and ligating the ITR oligonucleotides to a double-stranded polynucleotide comprising an expression cassette. FIG. 11B shows an exemplary method of ligating a 5' ITR oligonucleotide and a 3' ITR oligonucleotide to a double stranded polynucleotide comprising an expression cassette.

For illustrative purposes, Example 3 describes generating ceDNA vectors as exemplary closed-ended DNA vectors generated using this method. However, while ceDNA vectors are exemplified in this Example to illustrate in vitro synthetic production methods to generate a closed-ended DNA vector by ligating ITR-oligonucleotides to a double-stranded polynucleotide comprising the expression cassette (e.g., heterologous nucleic acid sequence) as described herein, one of ordinary skill in the art is aware that one can, as illustrated above, modify the parameters of the method such that any desired closed-ended DNA vector is generated, including but not limited to, doggybone DNA, dumbbell DNA and the like. Exemplary DNA vectors that can be produced by the synthetic production method described in Example 3 are discussed in the sections entitled "II D. DNA vectors produced using the synthetic production method", "III. ceDNA vectors in general" and "IV. Exemplary ceDNA vectors".

ITR oligonucleotides can be provided by any method of DNA synthesis (e.g., in vitro DNA synthesis methodologies) and are provided as linear molecules with a free 5' end and free 3' end. The ITR oligonucleotides may form secondary base-pairing structures (e.g., stem-loops or hairpins), but the primary structure is a linear single-strand molecule. Table 7 shows exemplary ITR oligonucleotides, which can be ligated to the 5' and 3' of a double stranded DNA construct as illustrated in FIG. 11.

TABLE 7

| Synthetic ITR oligonucleotide | Synthetic ITR oligonucleotide | SEQ ID NO: | |
|---|---|---|---|
| WT-L-oligo-1 | ctAGGCCGCCCGGGCAAAGCC CGGGCGTCGGGCGACCTTTG GTCGCCCGGC | 134 | AvrII recognition placed in the stem, to recover rep binding sites if needed |
| WT-L-oligo-2 | ctaggACTGAGGCCGCCCGGGC AAAGCCCGGGCGTCGGGCGA CCTTTGGTCGCCCGGCCTCAG Tc | 135 | AvrII recognition site placed at end of the stem |
| WT-R-oligo-3 | ggACTGAGGCCGCCCGGGCA AAGCCCGGGCGTCGGGCGAC CTTTGGTCGCCCGGCCTCAGT cctgca | 136 | Sbf1 recognition site placed at end of the stem |
| MU-R-oligo-1 | GtgCGGGCGACCAAAGGTCGC CCGACGCCCGGGCGcaCTCA | 137 | DraIII recognition placed in the stem, to recover rep binding sites if needed |
| MU-R-oligo-2 | ggACTGAGGCCGGGCGACCA AAGGTCGCCCGACGCCCGGG CGGCCTCAGTcctgca | 138 | Sbf1 recognition site placed at end of the stem |
| MU-L-oligo-3 | ctaggACTGAGGCCGCCCGGGC GTCGGGCGACCTTTGGTCGC CCGGCCTCAGTc | 139 | AvrII recognition site placed at end of the stem |
| MU-L-oligo-4 | ggACTGAGGCCGGGCGACCA AAGGTCGCCCGACGGCCTCA GTcctgca | 140 | Sbf1 recognition site placed at end of the stem [dITR R] |
| MU-L-oligo-5 | ctaggACTGAGGCCGTCGGGCG ACCTTTGGTCGCCCGGCCTCA GTc | 141 | AvrII recognition site placed at end of the stem [dITR L] |
| MU-R-oligo-6 | ggACTGAGGCCCGGGCGACC AAAGGTCGCCCGACGCCCGG GCTTTGCCCGGGCGCCTCAG Tcctgca | 142 | Sbf1 recognition site placed at end of the stem [FL R ITR] |
| FBGR-sense-1 | atacctaggcacgcgtgtta ctagttattaatagt aatcaattacgg | 143 | 3NT overhang-AvrII-5' sense (38 bp, Tm 60 C.)-primer |
| FBGR-sense-2 | atacctaggggccgcacgcg tgttactag | 144 | 3NT overhang-AvrII-5' sense (20 bp, Tm 62 C.)-primer |
| FBGR-as-1 | AtaCactcagtgcctgcagg cacgtggtccg gagatccagac | 145 | 3NT overhang-DraIII-Sbf1-3'anti-sense (22 bp, Tm 62 C.)-primer |

As disclosed herein, the ITR oligonucleotides can comprise WT-ITRs (e.g., see FIG. 6A, FIG. 6B), or modified ITRs (e.g., see, FIG. 7A and FIG. 7B). Modified ITRs can include deletion, insertion, or substitution of one or more nucleotides from the wild-type ITR in the sequences forming B and B' arm and/or C and C' arm. ITR oligonucleotides, comprising WT-ITRs or mod-ITRs as described herein, to be used in the cell-free synthesis, can be generated by genetic modification or biological and/or chemical synthesis. As discussed herein, the ITR oligonucleotides in Examples 2 and 3 can comprise WT-ITRs, or modified ITRs (mod-ITRs) in symmetrical or asymmetrical configurations, as discussed herein.

As part of the synthesis process, one or more restriction endonuclease sites can be introduced into the stem portion of the ITR. FIGS. 6A-7E provide exemplary ITR oligonucleotide sequences and structures, including embodiments where restriction endonuclease sites are incorporated.

The double-stranded polynucleotide comprising the expression cassette is provided as a linear molecule with free 5' and 3' ends on each strand. The double-stranded polynucleotide can be provided via DNA synthesis, by PCR chain assembly, or by excising such a molecule from a plasmid or other vector. See e.g. FIG. 11B.

The double-stranded polynucleotide is then contacted with the 5' and 3' ITR oligonucleotides, either sequentially or concurrently and the ITR oligonucleotides are ligated to the double-stranded polynucleotide to form a ceDNA vector. A standard ligation reaction is performed, e.g. using T4 DNA ligase.

In some embodiments, such as those illustrated in FIG. 11B, the ITR oligonucleotides and the double-stranded polynucleotide can be provided with complementary overhangs and their ends and/or cleaved with the same restriction endonuclease in order to provide complementary overhangs. Blunt end ligations can also be performed.

The molecules can be assembled in a step-wise fashion. For example, oligos are annealed followed by ligation of annealed double-stranded oligos to one another. To anneal two oligo strands, the oligos are mixed in equal molar amounts in a suitable buffer: e.g. 100 mM potassium acetate; 30 mM HEPES, pH 7.5) and heated to 94° C. for 2 minutes and gradually cooled. For oligos without significant secondary structure, the cooling step can be as simple as transferring samples from the heat block or water bath to room-temperature. For oligos predicted to have a lot of secondary structure, a more gradual cooling/annealing step is beneficial. This is done by placing the oligo solution in a water bath or heat block and unplugging/turning off the machine. The annealed oligonucleotides can be diluted in a nuclease free buffer and stored in their double-stranded annealed form at 4° C.

Example 4: ceDNA Production Via a Single-Stranded DNA Molecule

Another exemplary method of producing a ceDNA vector using a synthetic method uses a single-stranded linear DNA comprising two sense ITRs which flank a sense expression cassette sequence and are attached covalently to two antisense ITRs which flank an antisense expression cassette, the ends of which single stranded linear DNA are then ligated to form a closed-ended single-stranded molecule. One nonlimiting example comprises synthesizing and/or producing a single-stranded DNA molecule, annealing portions of the molecule to form a single linear DNA molecule which has one or more base-paired regions of secondary structure, and then ligating the free 5' and 3' ends to each other to form a closed single-stranded molecule.

For illustrative purposes, Example 4 describes producing ceDNA vectors as exemplary DNA vectors generated using this method. However, while ceDNA vectors are exemplified in this Example to illustrate in vitro synthetic production methods to generate a closed-ended DNA vector by as described herein, one of ordinary skill in the art is aware that one can, as illustrated above, modify the parameters of the method such that any desired closed-ended DNA vector is generated, including but not limited to, doggybone DNA, dumbbell DNA and the like. Exemplary DNA vectors that can be produced by the synthetic production method described in Example 3 are discussed in the sections entitled "II D. DNA vectors produced using the synthetic production method", "III. ceDNA vectors in general" and "IV. Exemplary ceDNA vectors".

An exemplary single-stranded DNA molecule for production of a ceDNA vector comprises, from 5' to 3':

a sense first ITR;

a sense expression cassette sequence;

a sense second ITR;

an antisense second ITR;

an antisense expression cassette sequence; and an antisense first ITR.

A single-stranded DNA molecule for use in the exemplary method of Example 4 can be formed by any DNA synthesis methodology described herein, e.g., in vitro DNA synthesis, or provided by cleaving a DNA construct (e.g., a plasmid) with nucleases and melting the resulting dsDNA fragments to provide ssDNA fragments.

Annealing can be accomplished by lowering the temperature below the calculated melting temperatures of the sense and antisense sequence pairs. The melting temperature is dependent upon the specific nucleotide base content and the characteristics of the solution being used, e.g., the salt concentration. Melting temperatures for any given sequence and solution combination are readily calculated by one of ordinary skill in the art.

The free 5' and 3' ends of the annealed molecule can be ligated to each other, or ligated to a hairpin molecule to form the ceDNA vector. Suitable exemplary ligation methodologies and hairpin molecules are described in Examples 2 and 3.

Example 5: Purifying and/or Confirming Production of ceDNA

Any of the DNA vector products produced by the methods described herein, e.g., including the methods described in Examples 1-4 can be purified, e.g., to remove impurities, unused components, or byproducts using methods commonly known by a skilled artisan; and/or can be analysed to confirm that DNA vector produced, (in this instance, a ceDNA vector) is the desired molecule. An exemplary method for purification of the DNA vector, e.g., ceDNA is using Qiagen Midi Plus purification protocol (Qiagen) and/or by gel purification, The following is an exemplary method for confirming the identity of ceDNA vectors.

ceDNA vectors can be assessed by identified by agarose gel electrophoresis under native or denaturing conditions as illustrated in FIG. 4C, where (a) the presence of characteristic bands migrating at twice the size on denaturing gels versus native gels after restriction endonuclease cleavage and gel electrophoretic analysis and (b) the presence of monomer and dimer (2×) bands on denaturing gels for uncleaved material is characteristic of the presence of ceDNA vector.

Figure 4D:
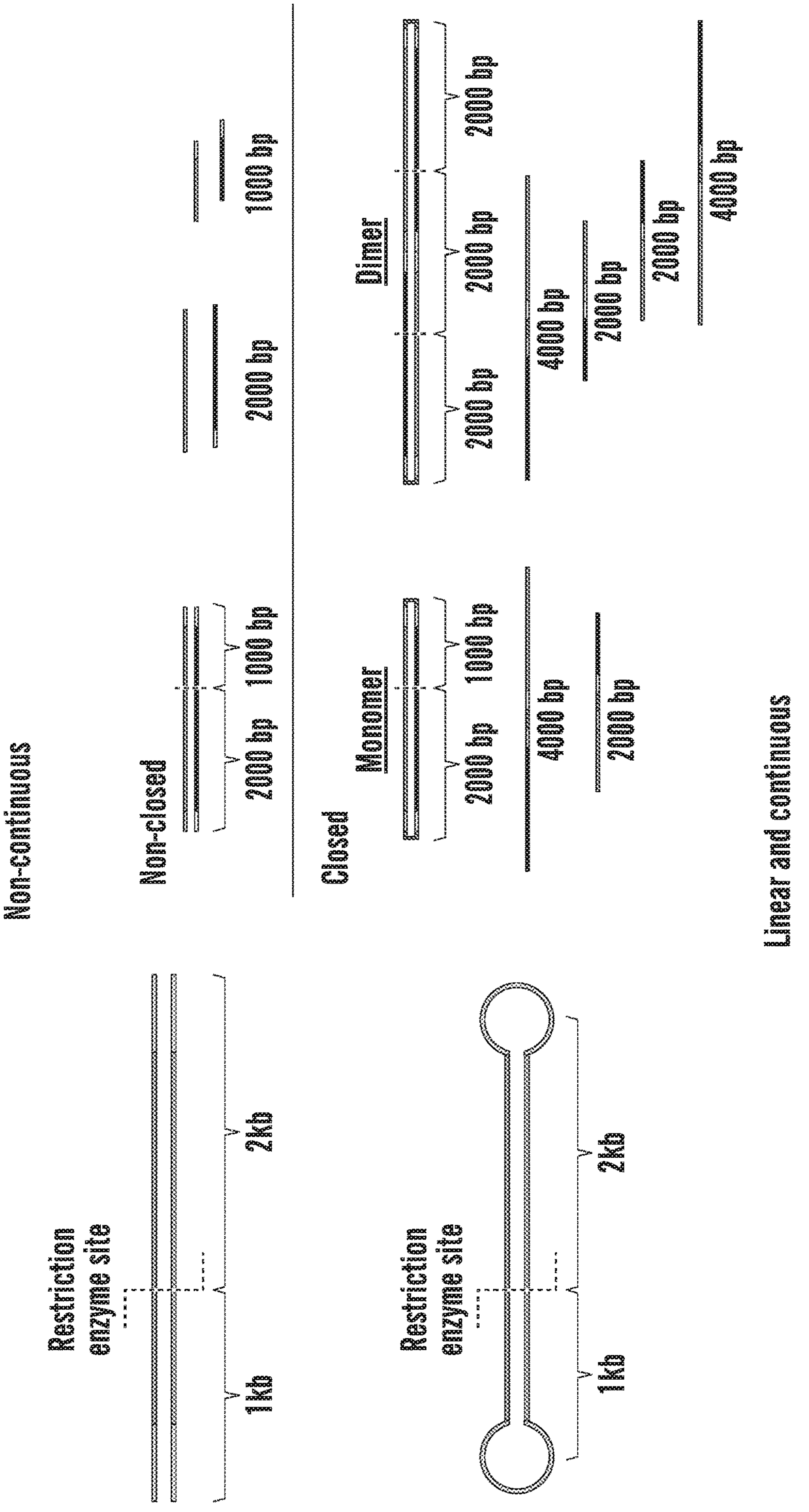

Structures of the isolated ceDNA vectors were further analyzed by digesting the purified DNA with restriction endonucleases selected for a) the presence of only a single cut site within the ceDNA vectors, and b) resulting fragments that were large enough to be seen clearly when fractionated on a 0.8% denaturing agarose gel (>800 bp). As illustrated in FIGS. 4C and 4D, linear DNA vectors with a non-continuous structure and ceDNA vector with the linear and continuous structure can be distinguished by sizes of their reaction products—for example, a DNA vector with a non-continuous structure is expected to produce 1 kb and 2 kb fragments, while a ceDNA vector with the continuous structure is expected to produce 2 kb and 4 kb fragments.

Therefore, to demonstrate in a qualitative fashion that isolated ceDNA vectors are covalently closed-ended as is required by definition, the samples were digested with a restriction endonuclease identified in the context of the specific DNA vector sequence as having a single restriction site, preferably resulting in two cleavage products of unequal size (e.g., 1000 bp and 2000 bp). Following digestion and electrophoresis on a denaturing gel (which separates the two complementary DNA strands), a linear, non-covalently closed DNA will resolve at sizes 1000 bp and 2000 bp, while a covalently closed DNA (i.e., a ceDNA vector) will resolve at 2× sizes (2000 bp and 4000 bp), as the two DNA strands are linked and are now unfolded and twice the length (though single stranded). Furthermore, digestion of monomeric, dimeric, and n-meric forms of the DNA vectors will all resolve as the same size fragments due to the end-to-end linking of the multimeric DNA vectors (see FIG. 4C).

As used herein, the phrase "assay for the Identification of DNA vectors by agarose gel electrophoresis under native gel and denaturing conditions" refers to an assay to assess the close-endedness of the ceDNA by performing restriction endonuclease digestion followed by electrophoretic assessment of the digest products. One such exemplary assay follows, though one of ordinary skill in the art will appreciate that many art-known variations on this example are possible. The restriction endonuclease is selected to be a single cut enzyme for the ceDNA vector of interest that will generate products of approximately 1/3× and 2/3× of the DNA vector length. This resolves the bands on both native and denaturing gels. Before denaturation, it is important to remove the buffer from the sample. The Qiagen PCR clean-up kit or desalting "spin columns," e.g. GE HEALTHCARE ILUSTRA™ MICROSPIN™ G-25 columns are some art-known options for the endonuclease digestion. The assay includes for example, i) digest DNA with appropriate restriction endonuclease(s), 2) apply to e.g., a Qiagen PCR clean-up kit, elute with distilled water, iii) adding 10× denaturing solution (10×=0.5 M NaOH, 10 mM EDTA), add 10× dye, not buffered, and analyzing, together with DNA ladders prepared by adding 10× denaturing solution to 4×, on a 0.8-1.0% gel previously incubated with 1 mM EDTA and 200 mM NaOH to ensure that the NaOH concentration is uniform in the gel and gel box, and running the gel in the presence of 1× denaturing solution (50 mM NaOH, 1 mM EDTA). One of ordinary skill in the art will appreciate what voltage to use to run the electrophoresis based on size and desired timing of results. After electrophoresis, the gels are drained and neutralized in 1×TBE or TAE and transferred to distilled water or 1×TBE/TAE with 1×SYBR Gold. Bands can then be visualized with e.g. Thermo Fisher, SYBR® Gold Nucleic Acid Gel Stain (10,000× Concentrate in DMSO) and epifluorescent light (blue) or UV (312 nm). The foregoing gel-based method can be adapted to purification purposes by isolating the ceDNA vector from the gel band and permitting it to renature.

The purity of the generated ceDNA vector can be assessed using any art-known method. As one exemplary and non-limiting method, contribution of ceDNA-plasmid to the overall UV absorbance of a sample can be estimated by comparing the fluorescent intensity of ceDNA vector to a standard. For example, if based on UV absorbance 4 μg of ceDNA vector was loaded on the gel, and the ceDNA vector fluorescent intensity is equivalent to a 2 kb band which is known to be 1 μg, then there is 1 μg of ceDNA vector, and the ceDNA vector is 25% of the total UV absorbing material. Band intensity on the gel is then plotted against the calculated input that band represents—for example, if the total ceDNA vector is 8 kb, and the excised comparative band is 2 kb, then the band intensity would be plotted as 25% of the total input, which in this case would be 0.25 μg for 1.0 μg input. Using the ceDNA vector plasmid titration to plot a standard curve, a regression line equation is then used to calculate the quantity of the ceDNA vector band, which can then be used to determine the percent of total input represented by the ceDNA vector, or percent purity.

Example 6: Constructing ceDNA Vectors Using a Synthetic Approach

As one example of the synthetic construction of ceDNA vectors described herein, the following procedure was used. A schematic representation of a ceDNA vector is shown in FIG. 11A, showing the hairpin loop ITRs flanking the cassette with the gene of interest and optionally a promoter/enhancer, posttranscriptional regulatory element, and/or polyadenylation sequence. Briefly, the construction method involved the construction of several segments of the ceDNA vector with complementary overhanging DNA ends to facilitate correct ligation to properly form the ceDNA vector (see FIG. 11A and FIG. 11B), followed by purification to remove the unwanted ligation products.

In more detail, single-stranded oligodeoxynucleotides were designed for each ITR comprising (a) the desired ITR structure (e.g., wild-type or mutant) and (b) an overhang region in the A-stem of the ITR sequence between the hairpin loop sequences B and C and the RPE element that is complementary to the overhang created by endonuclease cleavage at a restriction site engineered into the cassette oligodeoxynucleotide ("oligo"), where ligation between the two overhang regions is desired. The overhangs in each of the two ITR oligos are labeled as R1 and R2, respectively in Figure A(B). Each ITR oligo was synthesized using traditional methods, including gel or column purification and with a final concentration of between 10 and 100 μM in water, followed by annealing at 95° C. for 2 minutes and rapid cooling an ice bath. To construct the ceDNA vector with wild-type AAV2 ITRs, the synthesized oligodeoxynucleotides were:

```
Left ITR ("left oligo-1") (containing R1
overhang complementary to AvrII restriction
site cleavage overhang):
                                        (SEQ ID NO: 135)
5'CTAGGACTGAGGCCGCCCGGGCAAAGCCCGGGCGTCGGGCGACCTTT

GGTCGCCCGGCCTCAGTC3'
and

Right ITR (Right oligo-2") (containing R2
overhang complementary to Sbf1 restriction
site cleavage overhang):
                                        (SEQ ID NO: 136)
5'GGACTGAGGCCGCCCGGGCAAAGCCCGGGCGTCGGGCGACCTTTGGT

CGCCCGGCCTCAGTCCTGCA3'.
```

The cassette region (labeled "gene expression unit" in Figure A(B)) may be made by any traditional nucleotide construction method, but in this example was conveniently produced using a plasmid production system. The CAG promoter, green fluorescent protein (GFP) open reading frame, bovine growth hormone polyadenylation sequence, and ITR D- and RPE regions (collectively, SEQ ID NO: 146) were inserted into a parental plasmid (SEQ ID NO: 147).

The restriction sites in the gene expression unit and the overhangs on each of the ITR oligos were selected in order to facilitate specific ligation of the ITR oligos to the gene expression unit in the correct orientation, due to complementary overhangs. In this particular example, an overhang region was designed in the left ITR to be complementary to the 5' gene expression unit AvrII cleavage-resulting overhang. However, the terminal residues of the left ITR oligo do not themselves constitute an AvrII restriction site, thus the enzyme does not cleave the overhang. This same region of the oligo forms an ApaLI restriction site in the event of homodimerization, and thus ApaLI can be used to ensure that unwanted homodimers of the left ITR oligo are cleaved and returned to their monomeric state. A similar approach was taken in the right ITR, where the overhang region was designed to be complementary to the overhang generated by cleavage at the SbfI site engineered at the 3' end of the gene expression unit. The terminal region of the right ITR oligo is designed to not be recognized by SbfI, but instead to form a Nhe1 site in the event of homodimerization of the oligo, so that homodimerization can be controlled by cleavage with that enzyme. Finally, the restriction sites DraIII and BsaI existed as unique sites in the parental plasmid backbone and were exploited to facilitate removal of the unwanted backbone fragment. These various restriction sites were selected for convenience and one of ordinary skill in the art can readily engineer any combination of restriction sites to accomplish the same outcomes that are compatible with available reagents and the underlying nucleotide constructs.

Plasmids containing the gene expression unit were used to transform *E. coli*, and selective pressure to maintain the plasmid was maintained through inclusion of Ampicillin in the medium, using standard techniques. Plasmid DNA was harvested using DNA extraction kit (Qiagen) and the manufacturer's recommended methods for purification. Excision of the gene expression unit from the plasmid (step 1B as set forth in FIG. 12) was performed by a restriction endonuclease cleavage step. In a 100 μL reaction volume, 20 pmol of parental plasmid was combined with 3% of each of the three restriction enzymes AvrII, SbfI, and ApaLI. The reaction was incubated at 37° C. for 4 hrs.

Figure 12:
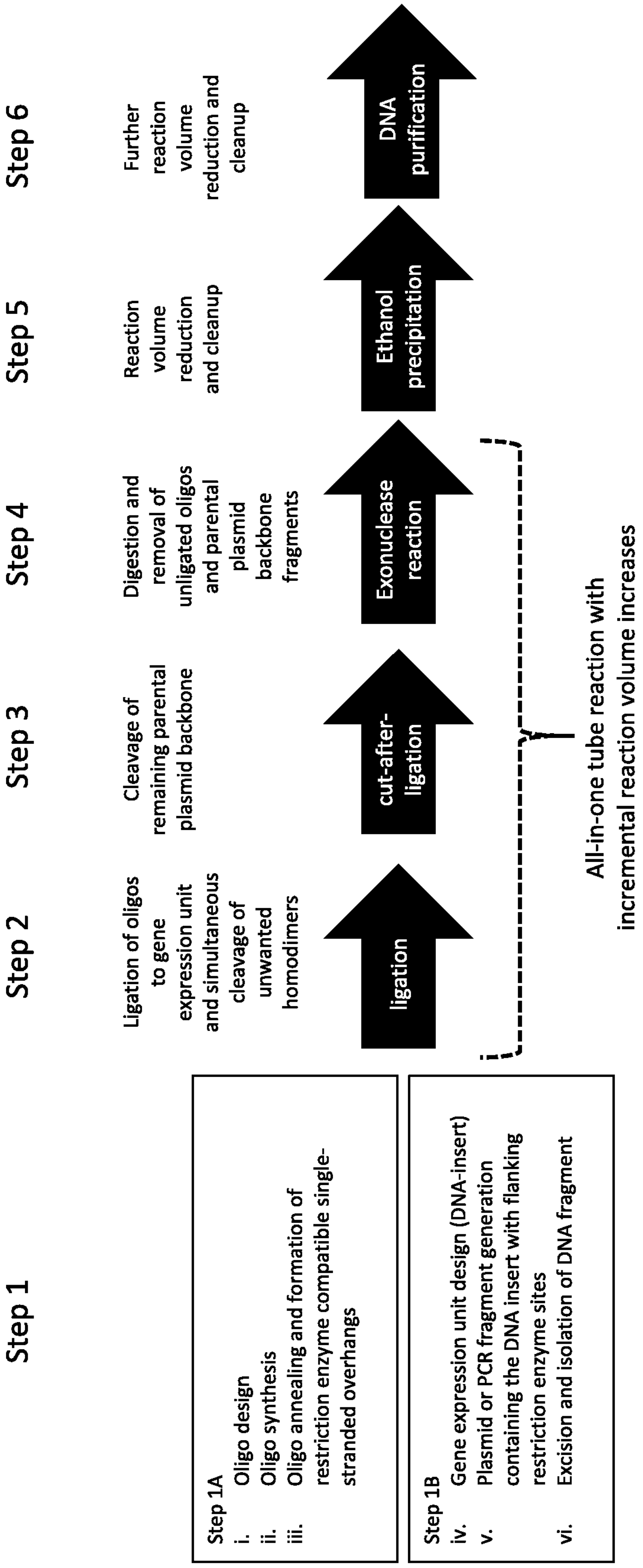
FIG. 12 is a schematic description of an exemplary method used to prepare ceDNA vector synthetically.

Next, the ITR oligos and the gene expression unit DNA segment were ligated (Step 2 of FIG. 12). To a total volume of 400 μL, 20 pmol of the digested parental plasmid reaction (100 μL) was combined with 160 pmol of each of the left and right annealed ITR oligos, with 10% of an ATP-containing ligation buffer, 2% T4 DNA ligase, and 2% of each of these restriction endonucleases: AvrII, SbfI, ApaLI, NheI. The ligase effected the ligation, while the AvrII and SbfI enzymes ensured that the gene expression unit did not homodimerize, and the ApaL1 and NheI enzymes ensured that the ITR oligos did not homodimerize. The reaction was incubated from 4 to 16 hours at 22° C., after which the T4 DNA ligase was inactivated by heating the reaction at 65° C. for 20 minutes.

To remove remaining parental plasmid from the reaction, the mixture was treated with restriction endonuclease enzymes known to cut solely in the parental plasmid backbone, but not in either ITR oligo or the gene expression unit (see step 3 of FIG. 12). Accordingly, 400 μL of the immediately prior reaction mixture is combined with 10% of the manufacturer recommended restriction enzyme buffer, 3% of the DraIII restriction endonuclease enzyme and 5% of the BsaI restriction endonuclease enzyme to a total reaction volume of 1 mL in water. The reaction was incubated at 37° C. for 1-2 hours.

Unwanted unligated oligos and the remaining pieces of the parental plasmid backbone were then removed by exonuclease digestion (step 4 of FIG. 12). To the 1 mL prior reaction were added 10% of the manufacturer recommended exonuclease reaction buffer, 10% ATP (10 mM), and 8% T5 exonuclease and sufficient water to bring the total reaction volume to 5 mL. The reaction was incubated at 37° C. for 1 to 4 hours. The T5 exonuclease cleaves single-stranded DNA, thus any of the oligos or backbone pieces with an unligated overhang are digested by the enzyme.

The reaction was subjected to ethanol precipitation (step 5 of FIG. 12) to concentrate the DNA in preparation for purification. The entire 5 mL reaction volume from the T5 exonuclease cleavage was combined in a total reaction volume of >12.5 mL with 10% 3M sodium acetate and 2.5-fold ethanol by volume. The mixture was incubated for at least 20 minutes at −80° C. and then the DNA was pelleted by centrifugation at 4° C. The pellet was washed with 70% ethanol and re-pelleted by centrifugation. The resulting washed DNA pellet was resuspended in 1 mL water. The ceDNA vector was purified using a standard DNA purification silica column (Zymo Research), eliminating proteins and residual small DNA fragments (step 6 of FIG. 12).

Figure 13A:
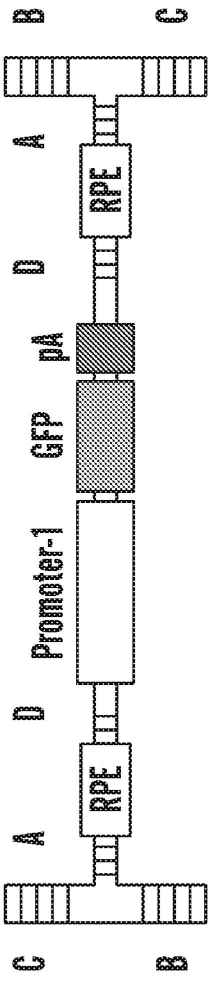
FIG. 13A depicts a schematic representation of a ceDNA vector with two wild-type AAV2 ITRs that is produced synthetically according to Example 6.
Figure 13B:
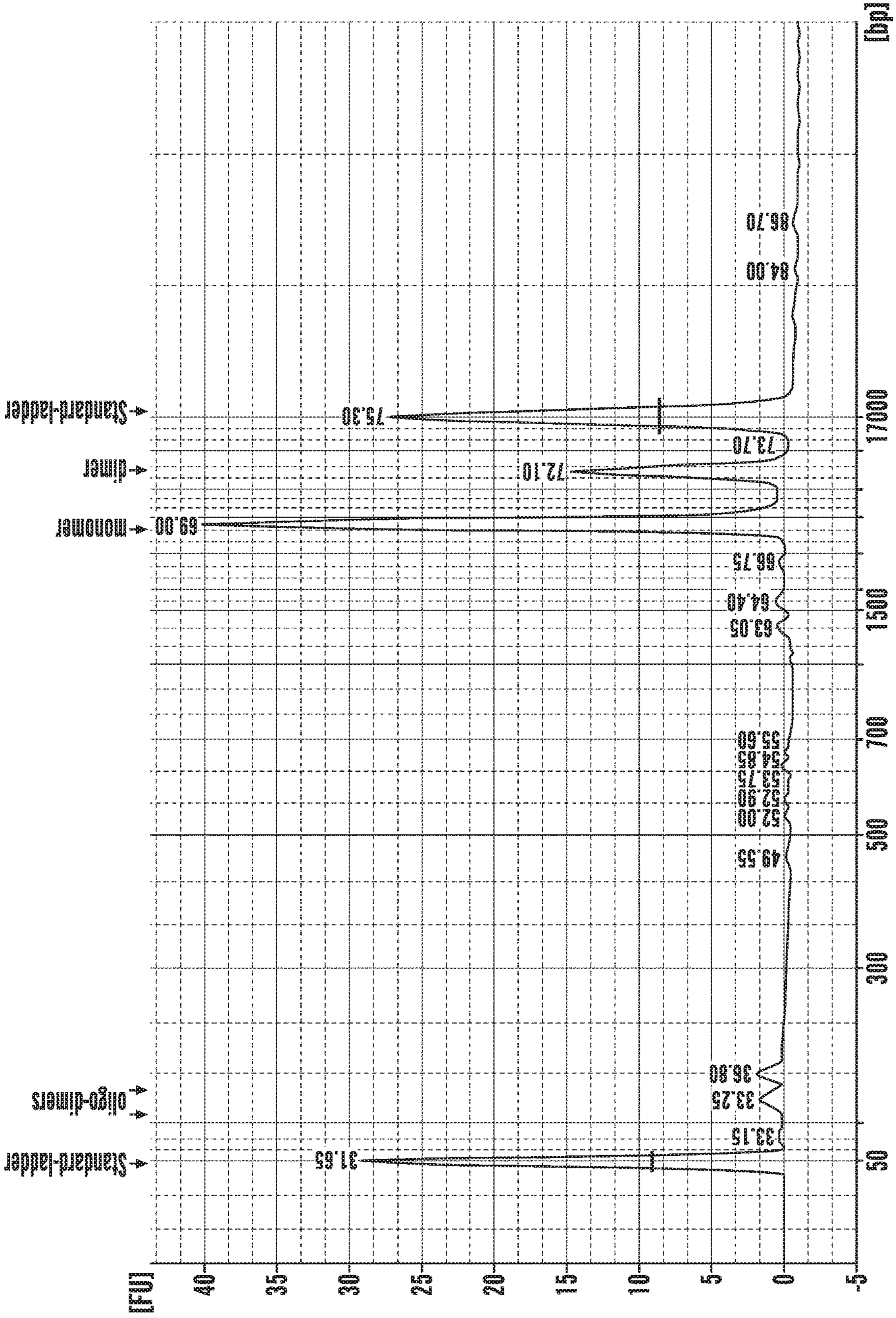
FIG. 13B is a chromatogram resulting from the bioanalyzer analysis of the purified ceDNA vector with WT/WT ITRs according to Example 6. Data from each of the peaks on the chromatogram is set forth in Table 8.

A sample of the resulting purified WT/WT ITR ceDNA vector was spiked with a standard ladder and was analyzed using a Bioanalyzer (Agilent Technologies) using the manufacturer recommended conditions and kit (Agilent Technologies, DNA-12000 Kit). The resulting chromatograph is shown in FIG. 13B. The two largest peaks correspond to the expected sizes for monomeric and dimeric ceDNA vector, and very minor peaks were seen at the expected sizes for oligo dimers, illustrating that the overall sample after the final purification step was substantially pure ceDNA vector. The tabular peak data from the chromatograph is given in Table 8.

TABLE 8

Peak parameters corresponding to the chromatograph in FIG. 13B.

| Size [bp] | Conc. [ng/μL] | Molarity [nmol/L] | Notes | Area | Aligned Migration Time [s] | Peak Height | Peak Width | % of Total | Time corrected area |
|---|---|---|---|---|---|---|---|---|---|
| 50 | 8.3 | 251.5 | Lower Marker | 17.6 | 31.65 | 29.2 | 1.4 | 0 | 54.9 |
| 84 | 0.04 | 0.7 | | 0.1 | 33.15 | 0.2 | 0.8 | 0.3 | 0.4 |
| 131 | 0.4 | 4.6 | | 1.3 | 35.25 | 1.5 | 1.5 | 2.9 | 3.7 |
| 165 | 0.35 | 3.2 | | 1.2 | 36.8 | 1.7 | 1.2 | 2.6 | 3.2 |
| 468 | 0.03 | 0.1 | | 0.2 | 49.55 | 0.3 | 0.8 | 0.4 | 0.3 |
| 543 | 0.02 | 0.1 | | 0.1 | 52 | 0.2 | 0.6 | 0.2 | 0.2 |
| 576 | 0.02 | 0.1 | | 0.1 | 52.9 | 0.2 | 0.7 | 0.2 | 0.2 |
| 606 | 0.01 | 0 | | 0 | 53.75 | 0.1 | 0.6 | 0.1 | 0.1 |
| 646 | 0.05 | 0.1 | | 0.2 | 54.85 | 0.5 | 0.8 | 0.5 | 0.4 |
| 673 | 0.01 | 0 | | 0.1 | 55.6 | 0.2 | 0.5 | 0.1 | 0.1 |
| 1,352 | 0.11 | 0.1 | | 0.7 | 63.05 | 0.8 | 1.4 | 1.5 | 1.1 |
| 1,660 | 0.09 | 0.1 | | 0.5 | 64.4 | 0.7 | 1.2 | 1.2 | 0.8 |
| 2,732 | 0.04 | 0 | | 0.2 | 66.75 | 0.3 | 1.1 | 0.5 | 0.3 |
| 4,545 | 4.45 | 1.5 | | 29 | 69 | 40.5 | 2.2 | 64 | 41.8 |
| 8,543 | 1.74 | 0.3 | | 11.4 | 72.1 | 15 | 2.3 | 25.2 | 15.7 |
| 11,568 | 0.02 | 0 | | 0.1 | 73.7 | 0.2 | 0.5 | 0.3 | 0.1 |
| 17,000 | 4.2 | 0.4 | Upper Marker | 26.3 | 75.3 | 27.7 | 2.6 | 0 | 34.7 |
| 46,535 | 0 | 0 | | 0 | 84 | 0.1 | 0.5 | 0 | 0.1 |
| 55,701 | 0 | 0 | | 0.3 | 86.7 | 0.4 | 1.2 | 0 | 0.3 |

Figure 14A:
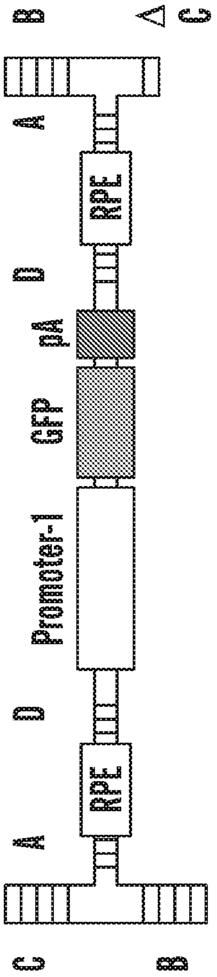
FIG. 14A depicts a schematic representation of a ceDNA vector with a left wild-type AAV2 ITR and a right truncation mutant ITR that is produced synthetically according to Example 5.
Figure 14B:
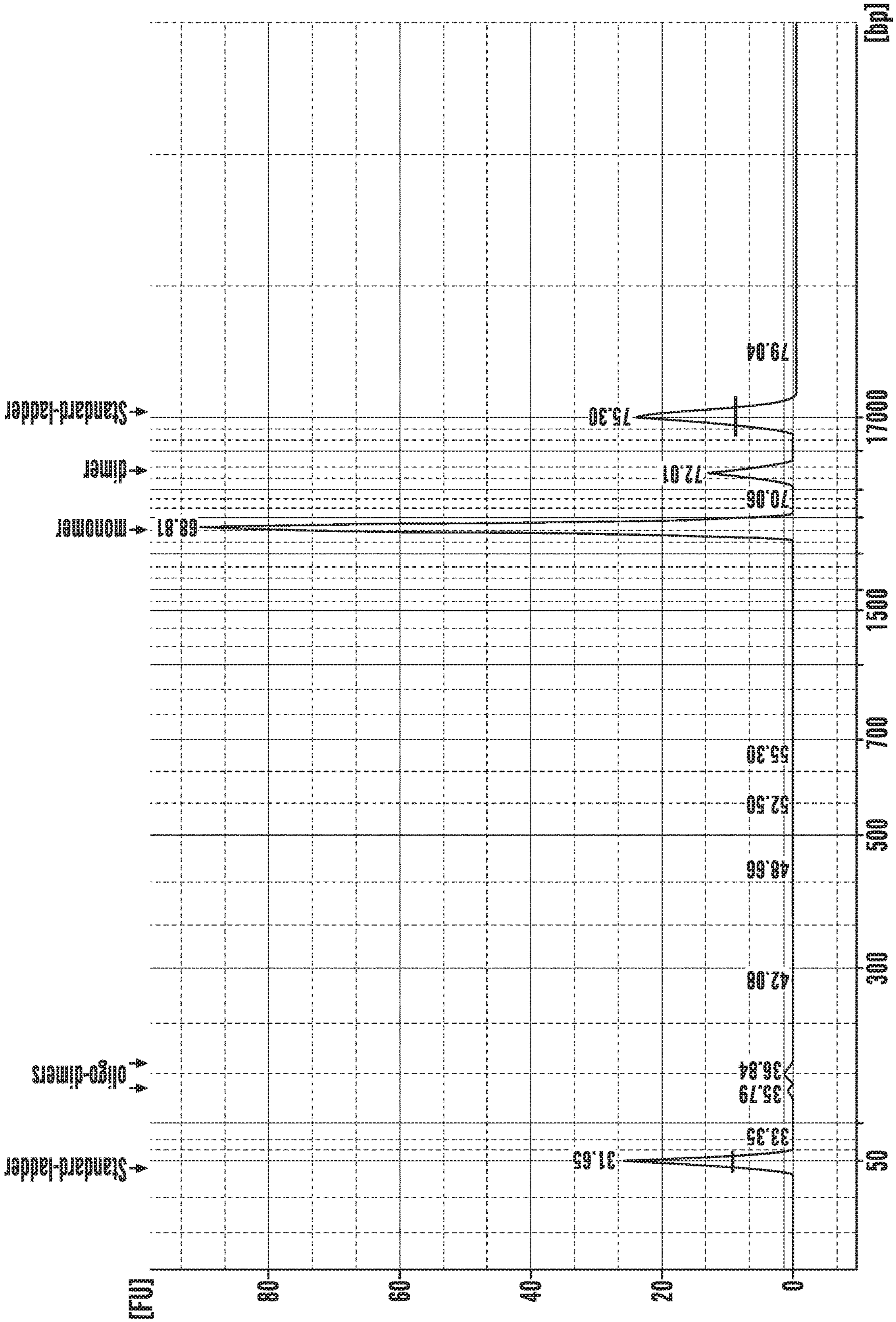
FIG. 14B is a chromatogram resulting from the bioanalyzer analysis of the purified ceDNA vector with WT/mutant ITRs according to Example 6. Data from each of the peaks on the chromatogram is set forth in Table 9.
Figure 15A:
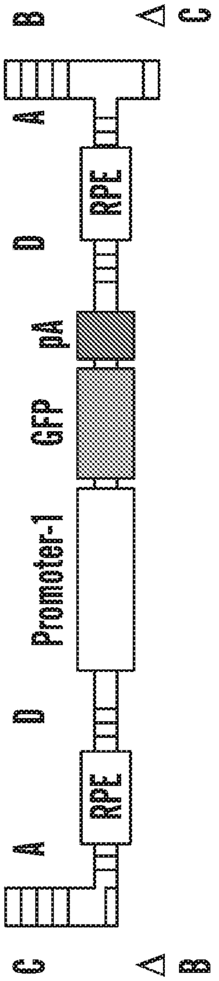
FIG. 15A depicts a schematic representation of a ceDNA vector with a left truncation mutant ITR and a different right truncation mutant ITR that is produced synthetically according to Example 6.
Figure 15B:
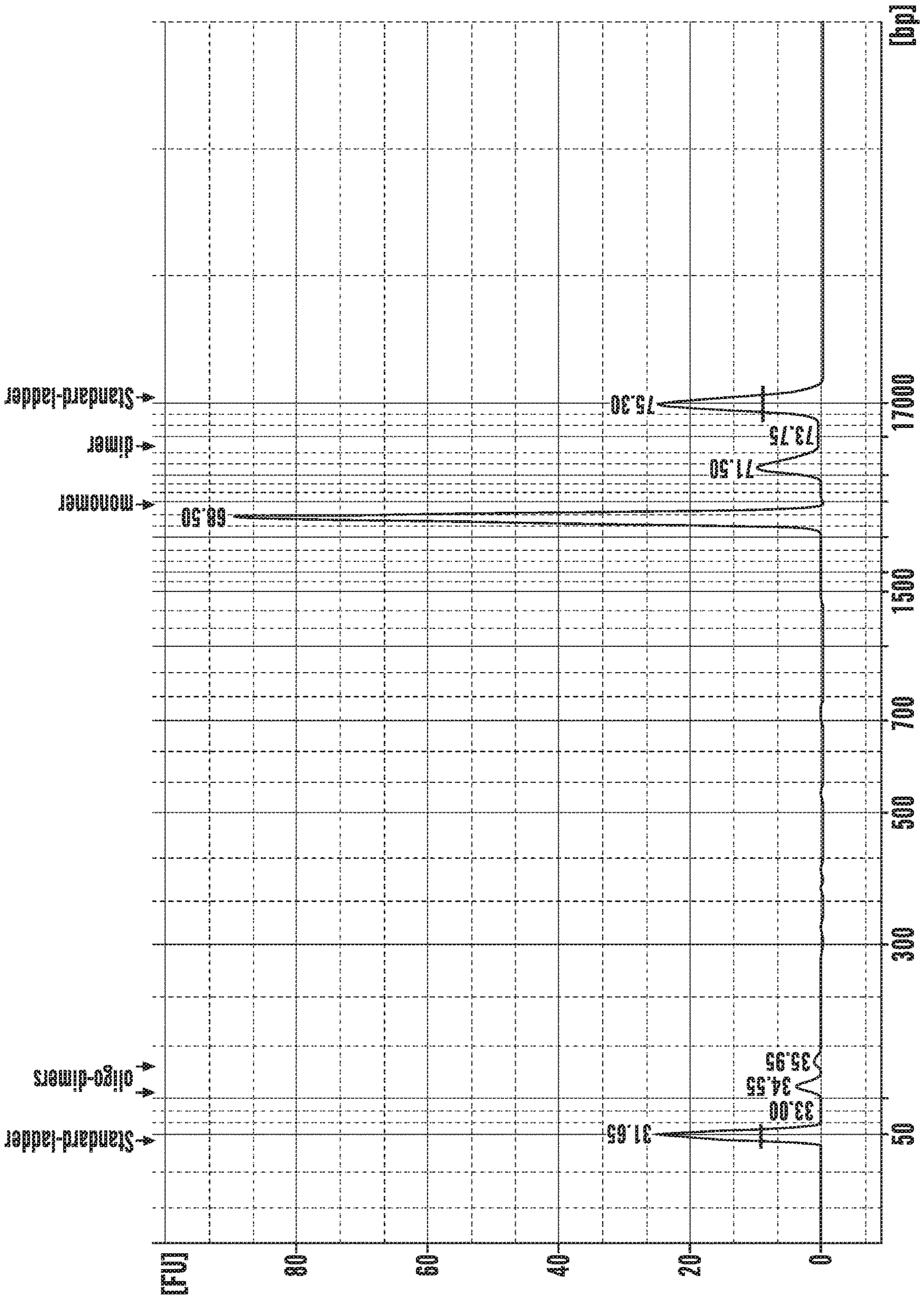
FIG. 15B is a chromatogram resulting from the bioanalyzer analysis of the purified ceDNA vector with asymmetric mutant/mutant ITRs according to Example 6. Data from each of the peaks on the chromatogram is set forth in Table 10.

This methodology was repeated several times with different ITR oligos to result in the synthetic production of different ceDNA vectors, including a WT/mutant ceDNA vector as shown in FIG. 14A, and an asymmetric mutant/mutant ceDNA vector as shown in FIG. 15A, as well as alternate ceDNA vector variants comprising luciferase in the gene expression unit cassette rather than green fluorescent protein in the context of each of those ITR pairs. Their bioanalyzer results for the GFP ceDNA constructs are shown in FIG. 14B and FIG. 15B, respectively, and were very similar to that obtained for the WT/WT ceDNA vector sample (FIG. 13B)). The peak data tables for each are set forth below in Table 9 and Table 10, respectively.

TABLE 9

Peak parameters corresponding to the chromatograph in FIG. 14B.

| Size [bp] | Conc. [ng/μL] | Molarity [nmol/L] | Notes | Area | Aligned Migration Time [s] | Peak Height | Peak Width | % of Total | Time corrected area |
|---|---|---|---|---|---|---|---|---|---|
| 50 | 8.3 | 251.5 | Lower Marker | 15.8 | 31.65 | 25.9 | 1.4 | 0 | 48.6 |
| 89 | 0.04 | 0.7 | | 0.1 | 33.35 | 0.2 | 1.1 | 0.2 | 0.3 |
| 143 | 0.17 | 1.8 | | 0.5 | 35.79 | 0.7 | 1 | 0.7 | 1.3 |
| 166 | 0.35 | 3.2 | | 1 | 36.84 | 1.4 | 1.2 | 1.5 | 2.7 |
| 281 | 0.02 | 0.1 | | 0.1 | 42.08 | 0.1 | 0.6 | 0.1 | 0.1 |
| 446 | 0.01 | 0 | | 0.1 | 48.66 | 0.1 | 0.6 | 0.1 | 0.1 |
| 561 | 0.01 | 0 | | 0.1 | 52.5 | 0.2 | 0.6 | 0.1 | 0.1 |
| 662 | 0.02 | 0 | | 0.1 | 55.3 | 0.2 | 0.6 | 0.1 | 0.1 |
| 4,377 | 10.41 | 3.6 | | 57.2 | 68.81 | 91 | 2 | 83.2 | 82.1 |
| 5,725 | 0.01 | 0 | | 0 | 70.06 | 0.1 | 0.5 | 0.1 | 0.1 |
| 8,407 | 1.74 | 0.3 | | 9.6 | 72.01 | 13.1 | 2.4 | 13.9 | 13.2 |
| 17,000 | 4.2 | 0.4 | Upper Marker | 22.2 | 75.3 | 24.3 | 2.6 | 0 | 29.2 |
| 29,702 | 0 | 0 | | 0.1 | 79.04 | 0.2 | 0.6 | 0 | 0.1 |

TABLE 10

Peak parameters corresponding to the chromatograph in FIG. 15B.

| Size [bp] | Conc. [ng/μL] | Molarity [nmol/L] | Notes | Area | Aligned Migration Time [s] | Peak Height | Peak Width | % of Total | Time corrected area |
|---|---|---|---|---|---|---|---|---|---|
| 50 | 8.3 | 251.5 | Lower Marker | 15.4 | 31.65 | 25.4 | 1.5 | 0 | 47.4 |
| 81 | 0.13 | 2.5 | | 0.4 | 33 | 0.5 | 1.1 | 0.6 | 1.1 |
| 115 | 0.91 | 11.9 | | 2.4 | 34.55 | 3.8 | 1.4 | 3.6 | 6.9 |

TABLE 10-continued

Peak parameters corresponding to the chromatograph in FIG. 15B.

Figure 16A:
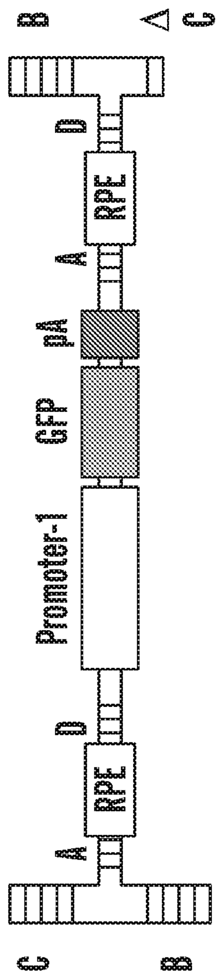
FIG. 16A depicts a schematic representation of a ceDNA vector with a left wild-type AAV2 ITR and a right truncation mutant ITR that is produced traditionally using Sf9 cell production.
Figure 16B:
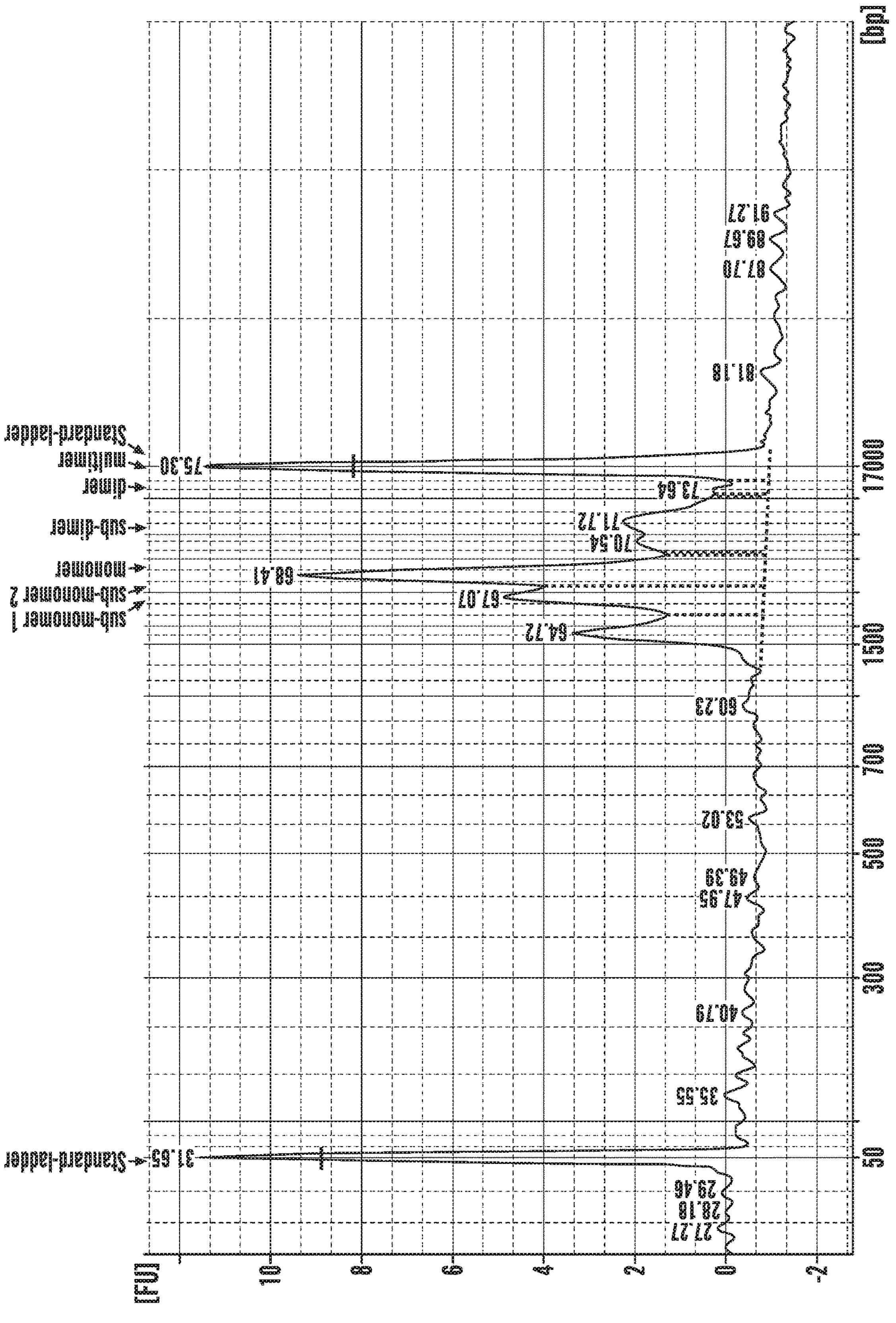
FIG. 16B is a chromatogram resulting from the bioanalyzer analysis of the purified traditionally-produced ceDNA vector with WT/mutant ITRs. Data from each of the peaks on the chromatogram is set forth in Table 11.

| Size [bp] | Conc. [ng/μL] | Molarity [nmol/L] | Notes | Area | Aligned Migration Time [s] | Peak Height | Peak Width | % of Total | Time corrected area |
|---|---|---|---|---|---|---|---|---|---|
| 146 | 0.3 | 3.1 | | 0.8 | 35.95 | 1.1 | 1.5 | 1.2 | 2.3 |
| 4,091 | 10.19 | 3.8 | | 55.3 | 68.5 | 89.6 | 1.8 | 80.8 | 79.7 |
| 7,661 | 1.66 | 0.3 | | 9 | 71.5 | 10 | 2.1 | 13.2 | 12.5 |
| 11,738 | 0.08 | 0 | | 0.4 | 73.75 | 0.6 | 0.8 | 0.6 | 0.6 |
| 17,000 | 4.2 | 0.4 | Upper Marker | 22.1 | 75.3 | 25 | 2.4 | 0 | 29 |

ceDNA vector (WT/mutant) produced by a traditional Sf9 insect cell method (FIG. 16A also underwent bioanalyzer analysis. The chromatograph is shown in FIG. 16B, and notably includes several additional species of ceDNA, including multimer and sub-monomeric peaks, more than those seen in the synthetically produced ceDNA vector analyses. As can be seen by comparing the peak parameter data in Tables 8-11, the synthetically produced samples are >65% monomeric ceDNA vector and in some cases >85% monomeric ceDNA vector, whereas the Sf9-produced ceDNA vector sample was <35% monomeric ceDNA vector and had numerous additional ceDNA vector species present in the sample.

TABLE 11

Peak parameter data corresponding to the chromatograph shown in FIG. 16B.

| Size [bp] | Conc. [ng/μL] | Molarity [nmol/L] | Notes | Area | Aligned Migration Time [s] | Peak Height | Peak Width | % of Total | Time corrected area |
|---|---|---|---|---|---|---|---|---|---|
| 11 | 0 | 0 | | 0.2 | 27.27 | 0.3 | 0.7 | 0 | 0.7 |
| 19 | 0 | 0 | | 0.1 | 28.18 | 0.3 | 0.7 | 0 | 0.5 |
| 31 | 0 | 0 | | 0.1 | 29.46 | 0.3 | 0.6 | 0 | 0.5 |
| 50 | 8.3 | 251.5 | Lower Marker | 7.2 | 31.65 | 11.8 | 1.9 | 0 | 22.5 |
| 137 | 0.15 | 1.7 | | 0.2 | 35.55 | 0.4 | 1 | 0.6 | 0.6 |
| 252 | 0.02 | 0.1 | | 0 | 40.79 | 0.1 | 0.5 | 0.1 | 0.1 |
| 427 | 0.06 | 0.2 | | 0.1 | 47.95 | 0.2 | 0.9 | 0.3 | 0.2 |
| 464 | 0.05 | 0.2 | | 0.1 | 49.39 | 0.2 | 0.6 | 0.3 | 0.2 |
| 580 | 0.06 | 0.2 | | 0.1 | 53.02 | 0.3 | 0.9 | 0.4 | 0.2 |
| 962 | 0.08 | 0.1 | | 0.2 | 60.23 | 0.4 | 0.7 | 0.5 | 0.3 |
| 1,789 | 2.39 | 2 | | 5.9 | 64.72 | 4.2 | 3.4 | 17.6 | 9.3 |
| 2,889 | 2.66 | 1.4 | | 6.8 | 67.07 | 5.8 | 1.7 | 20.4 | 10.5 |
| 4,007 | 4.25 | 1.6 | | 11.1 | 68.41 | 10.3 | 1.9 | 33.4 | 16.8 |
| 6,348 | 1.06 | 0.3 | | 2.8 | 70.54 | 2.9 | 1.1 | 8.4 | 4.1 |
| 7,985 | 2.01 | 0.4 | | 5.3 | 71.72 | 3.2 | 2.4 | 15.9 | 7.7 |
| 11,377 | 0.27 | 0 | | 0.7 | 73.64 | 1.3 | 0.7 | 2.1 | 1 |
| 17,000 | 4.2 | 0.4 | Upper Marker | 10.7 | 75.3 | 12.4 | 2.2 | 0 | 14.7 |
| 36,952 | 0 | 0 | | 0.2 | 81.18 | 0.3 | 0.8 | 0 | 0.2 |
| 59,080 | 0 | 0 | | 0.1 | 87.7 | 0.2 | 0.5 | 0 | 0.1 |
| 65,791 | 0 | 0 | | 0.1 | 89.67 | 0.3 | 0.6 | 0 | 0.1 |
| 71,232 | 0 | 0 | | 0.1 | 91.27 | 0.3 | 0.7 | 0 | 0.1 |
| 110,772 | 0 | 0 | | 0 | 102.92 | 0.1 | 0.6 | 0 | 0 |

To ensure that the obtained ceDNA vectors had the proper covalently closed-ended ceDNA vector structure, samples of each were digested with a restriction endonuclease having a single restriction site in the ceDNA vector, preferably resulting in two cleavage products of unequal size. Following digestion and electrophoresis on a denaturing gel, a linear non-covalently closed DNA will display bands migrating on the gel at sizes corresponding to the two expected fragments. A linear, covalently closed DNA (like ceDNA vector) should instead have bands migrating at 2× the expected sizes of the cleavage products because the two DNA strands are linked and upon cleavage become unfolded and twice the length. Furthermore, digestion of monomeric, dimeric, and multimeric forms of ceDNA vector will all resolve as the same size fragment due to the end-to-end linking of those multimeric DNA vectors. When each of the synthetic and Sf9-produced ceDNA vectors were assessed by this gel electrophoretic method, each of the samples had similar banding patterns, indicating that all of the ceDNA vectors had the proper covalently closed-ended structure.

It will be appreciated by one of ordinary skill in the art that the amounts of all reagents can be tailored to effect the production of the desired amount of ceDNA vector.

Example 7: ceDNA Vectors Express Transgene in Cells

To assess whether the synthetically produced ceDNA vectors were able to express transgene similarly to traditionally Sf9-produced ceDNA vectors, the expression of ceDNA vectors in cultured cells was measured by the degree of fluorescent protein (GFP) production and fluorescence emission. Human hepatic cells (HepaRG cell line, Lonza) was plated at a concentration of $7.5\times10^4$ cells/mL. The desired ceDNA vector was introduced to the cultured cells using a commercially available device (Nucleofector™, Lonza) according to the manufacturer's protocols. A 16-well strip containing 150 ng/well of each construct was nucleofected in a volume of 20 μL. Nucleofected samples were added 80 μL of media in each well of a 96-well plate for a final volume in each well of 100 μL. The media was changed 24 hours post nucleofection, and subsequently replaced twice per week. Plasmid comprising the ceDNA vector shown in FIG. 14A was used as a control. The fluorescence of each culture was measured 6 days after nucleofection using the Essen Bioscience IncuCyte® live cell imaging microscope. This system is positioned inside an incubator and automatically takes time lapse phase and fluorescence photos of cells over the desired timeframe.

Figure 17:
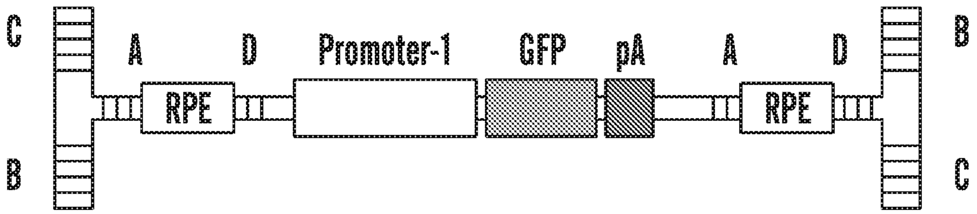
FIG. 17 depicts the results of the in vitro cell expression assays set forth in Example 7 comparing expression of transgene from synthetically-produced ceDNA vectors to that from traditionally Sf9-produced ceDNA vectors in HepaRG cells. A schematic representation of each construct used is set forth immediately above the fluorescence microscopy image for the cells treated with that ceDNA vector after 6 days of introduction of the indicated ceDNA vector by nucleofection (white spots represent GFP transgene-expressing cell populations).
Figure 17:
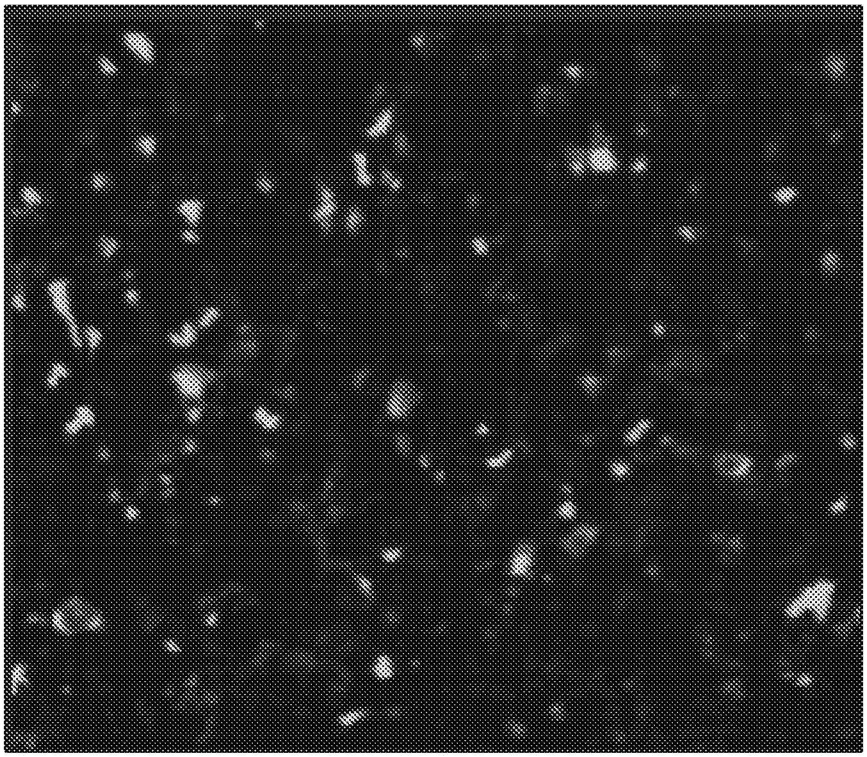
Figure 17:
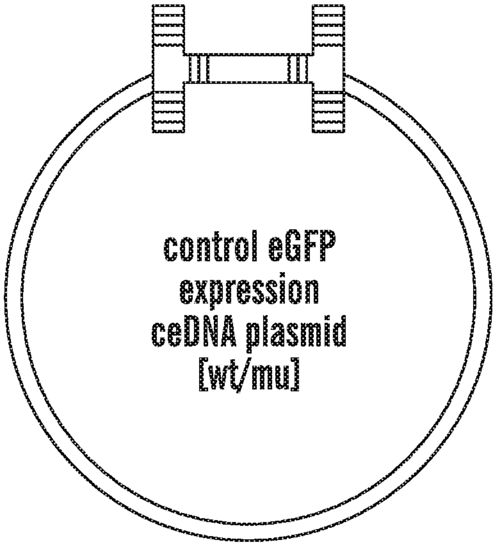
Figure 17:
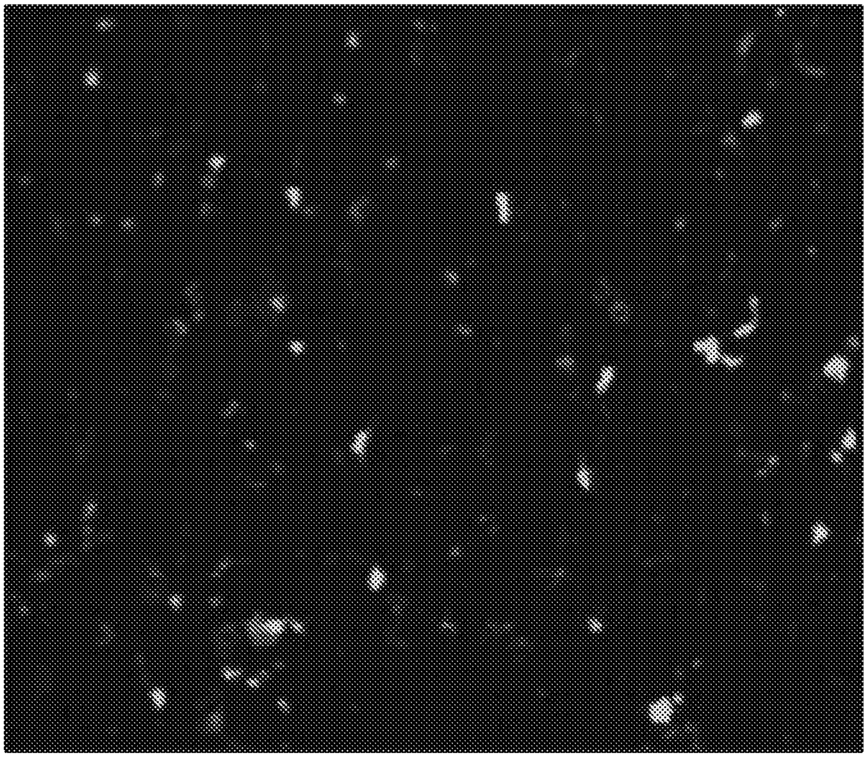
Figure 17:
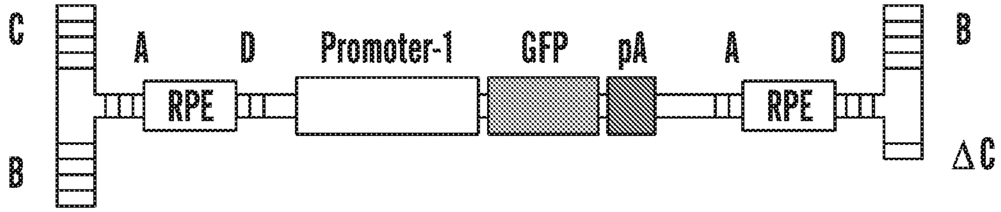
Figure 17:
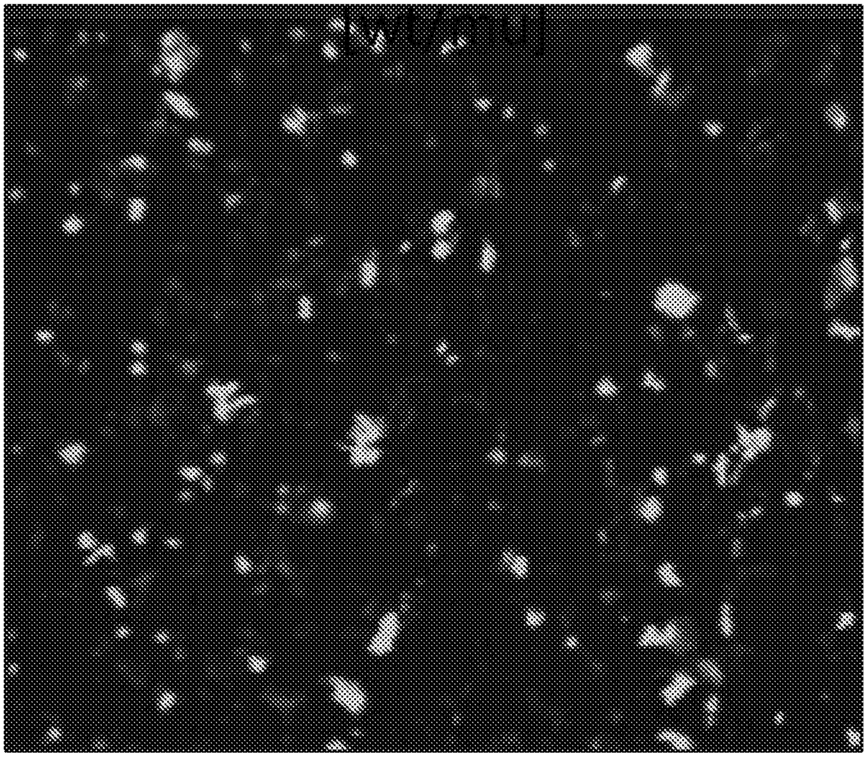
Figure 17:
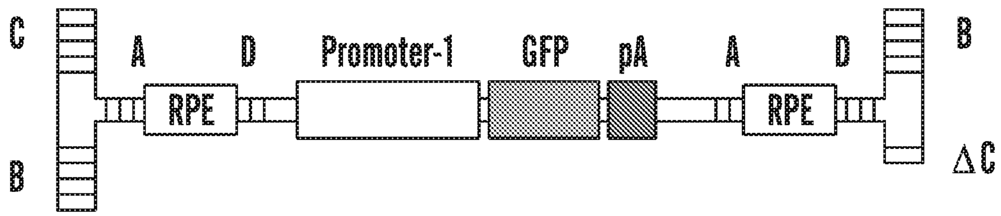
Figure 17:
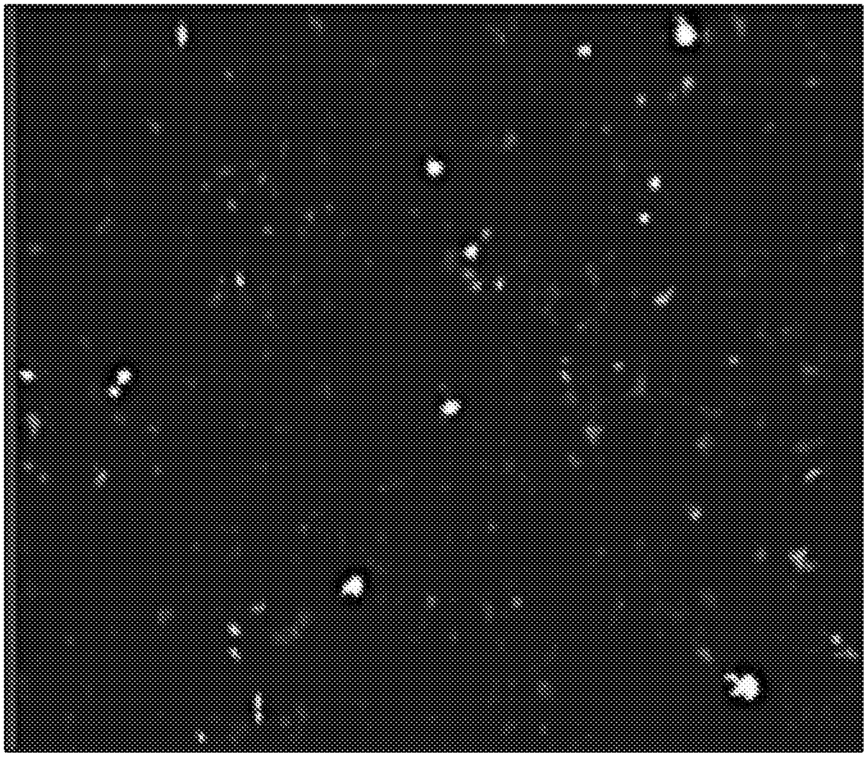
Figure 17:
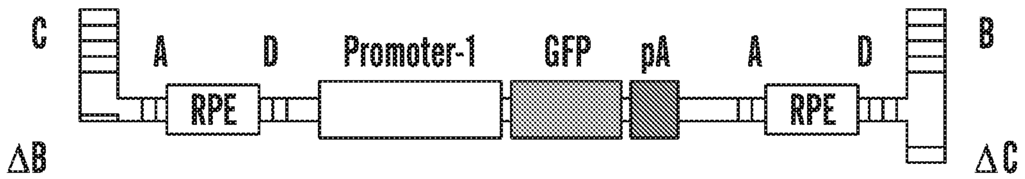
Figure 17:
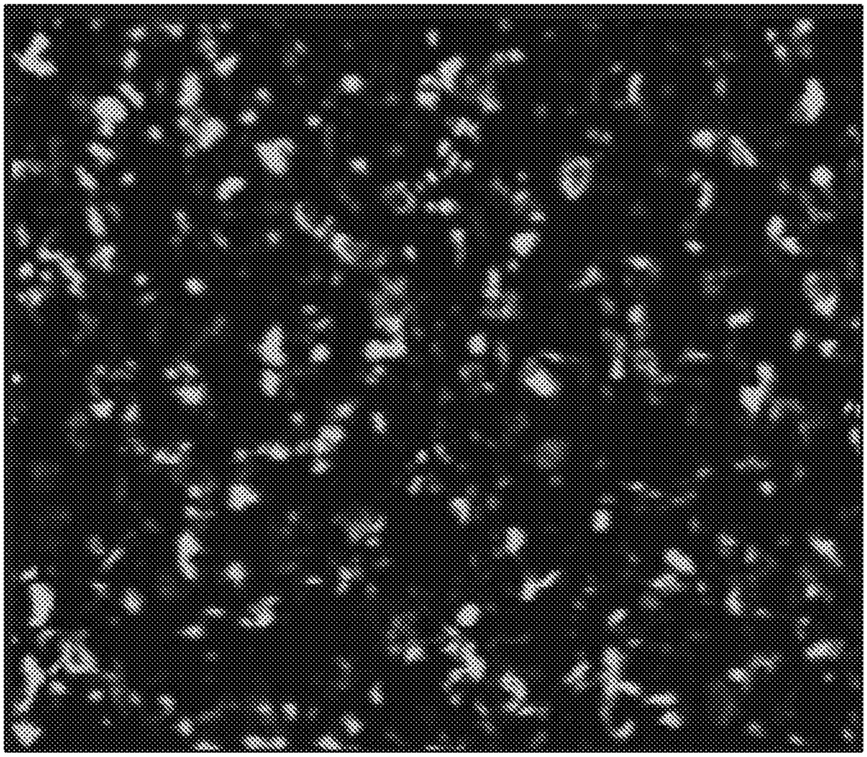

The results are shown in FIG. 17. Expression of GFP appears as bright white spots. Cells treated with the Sf9-produced ceDNA vector with WT/mutant ITRs had similar expression of GFP as seen in the plasmid-treated cells. All three of the synthetically produced ceDNA vectors (WT/WT, WT/Mut, and asymmetric mutant) demonstrated greater fluorescence and number of spots in the assay than either the plasmid control or the traditionally Sf9-produced ceDNA vector. This relative increase in fluorescence may be at least partially due to the greater purity of the synthetically produced material to that of the traditionally-produced material. The results illustrate that the synthetically produced ceDNA vector expresses the encoded transgene at least as well and possibly better than the traditionally Sf9-produced ceDNA vector, and thus that the synthetically produced material functions as expected.

Example 8: Protein Expression from ceDNA Vectors in Mice

In vivo protein expression of a firefly luciferase transgene from the synthetically produced ceDNA vectors described above was assessed in vivo in mice in comparison with traditionally produced equivalent ceDNA vectors. Thirty approximately four week old male CD-1 IGS mice (Envigo) were given a single intravenous administration of 0.5 mg/kg in a 5 mL/kg volume of (a) LNP-Sf9-produced WT/Mut ceDNA, (b) LNP-Sf9-produced Mut/Mut (asymmetric) ceDNA, (c) LNP-Sf9-produced WT/WT ceDNA vectors, (d) LNP-synthetic WT/WT ceDNA vectors, (e) LNP-synthetic WT/Mut ceDNA, or (f) control LNP-Poly C. Mice are assessed for 28 days post injection, with whole blood collection at days 0, 1, and 28. In vivo imaging (IVIS) of each whole mouse was performed on days 3, 7, 14, 21, and 28, by dosing each mouse with luciferin at 150 mg/kg (60 mg/mL) via intraperitoneal injection at 2.5 mL/kg, with shaving of the mouse hair coat as needed. Within fifteen minutes after each luciferin injection, each mouse is anaesthetized and imaged. Animals are terminated at day 28 and liver and spleen collected and imaged ex vivo by IVIS. Luciferase expression is additionally assessed in those tissues by a luciferase ELISA assay (MAXDISCOVERY®, BIOO Scientific/PerkinElmer), and qPCR for luciferase of liver samples.

Figure 18A:
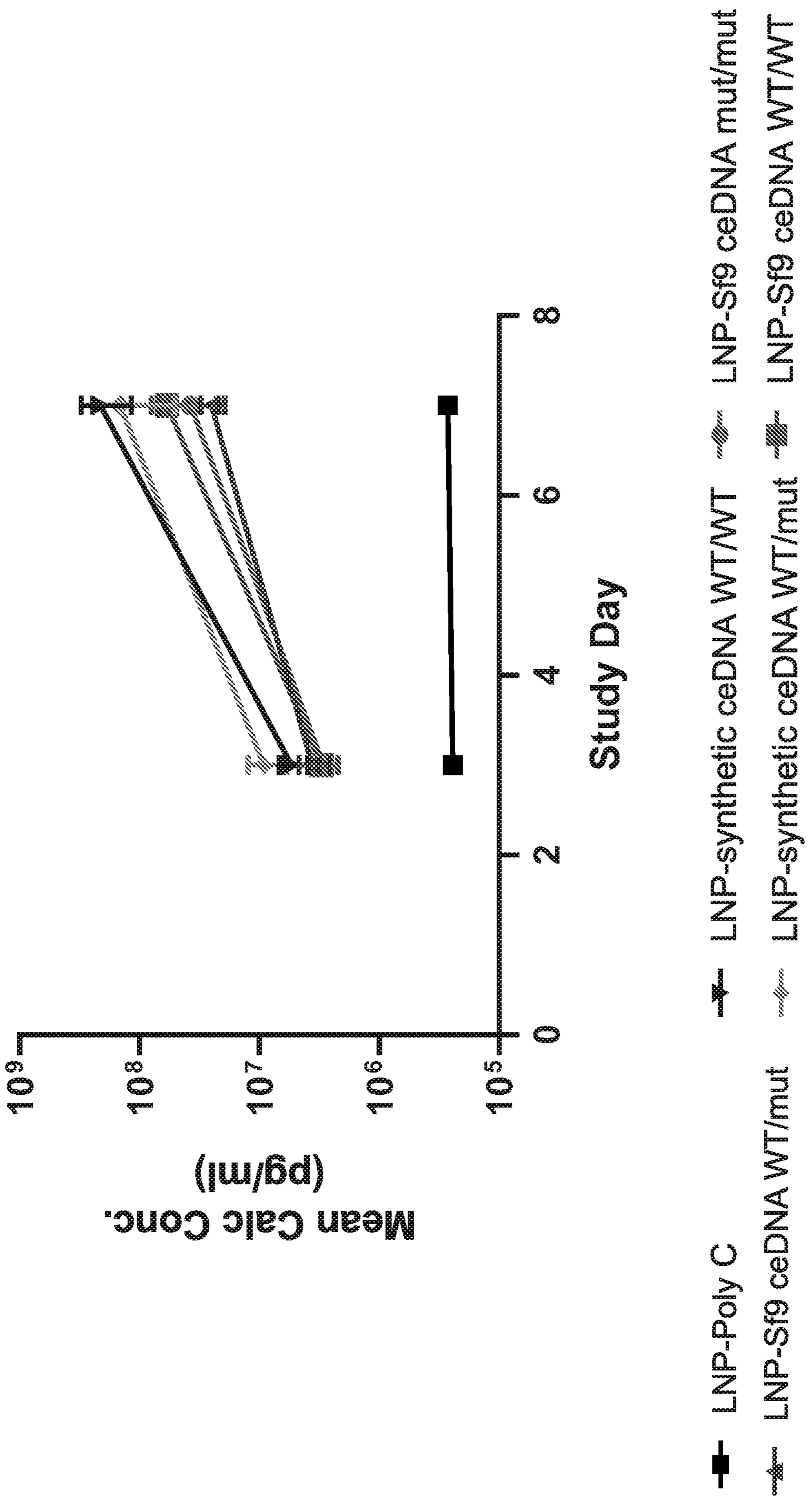
FIG. 18A provides a graph showing the quantitative day 3 and day 7 results of in vivo imaging data from mice treated with synthetically or traditionally-produced ceDNA vectors according to Example 8.
Figure 18B:
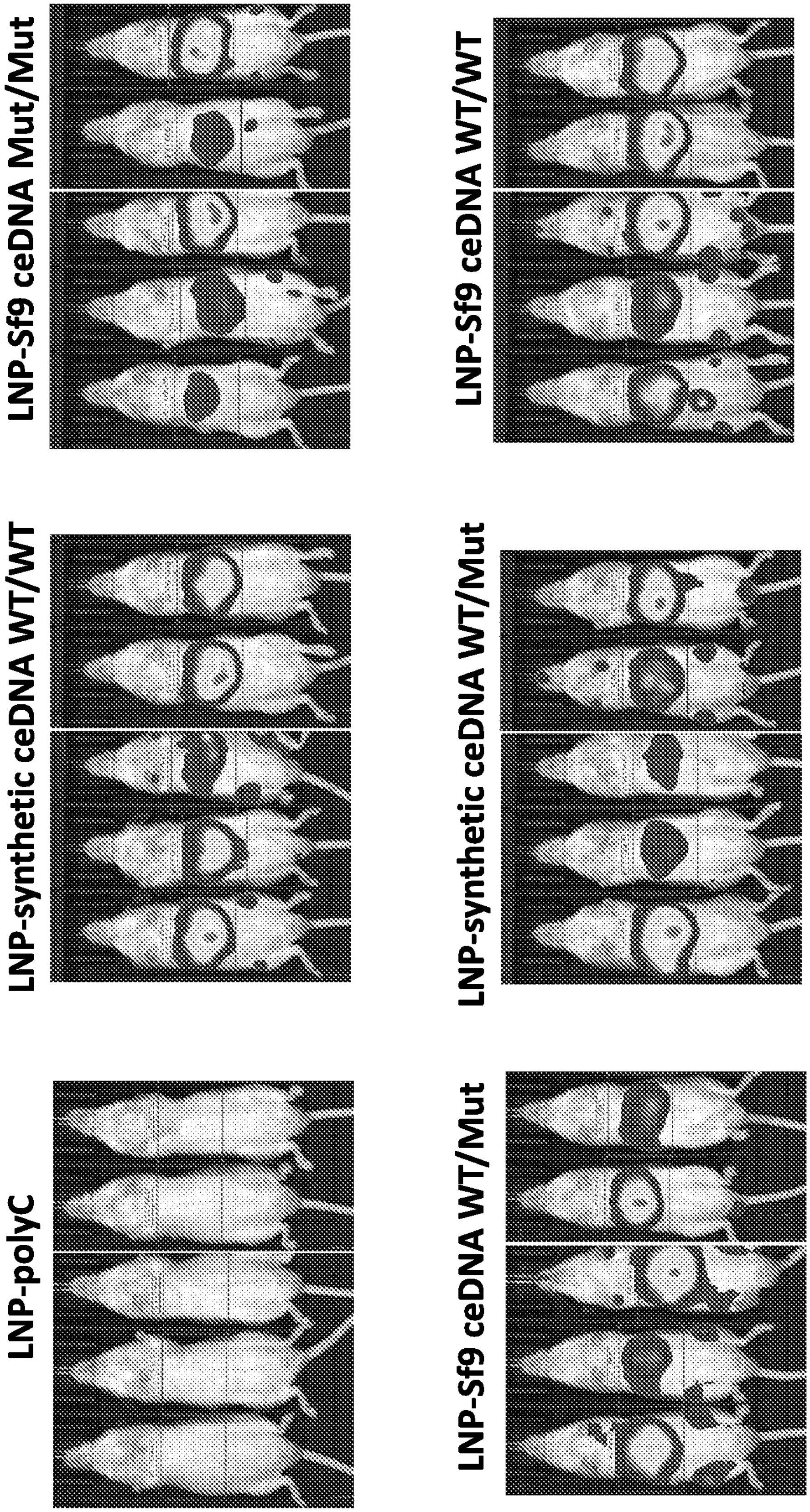
FIG. 18B provides the raw IVIS images of the treated mice (from which the quantitation was made for the FIG. 18A graph) at day 7 post treatment, and demonstrates that the majority of the luciferase expression was localized to the liver as expected regardless of the production method of the ceDNA used to treat the mice.

The results of the day 3 and 7 IVIS analyses are shown in FIGS. 18A and B (day 7 data). Significant fluorescence was seen above background levels in each of the ceDNA-treated groups of mice. The fluorescence detected in the mice treated with synthetically produced ceDNA vectors was at least as great and in some cases greater than the fluorescence detected in the mice treated with the traditionally produced ceDNA. As seen in FIG. 18B with respect to the day 7 data, the majority of the fluorescence was localized to the liver as expected for each treatment group. This result again shows that ceDNA produced by synthetic methods functions in vivo similarly to the Sf9-produced ceDNA vectors.

REFERENCES

All publications and references, including but not limited to patents and patent applications, cited in this specification and Examples herein are incorporated by reference in their entirety as if each individual publication or reference were specifically and individually indicated to be incorporated by reference herein as being fully set forth. Any patent application to which this application claims priority is also incorporated by reference herein in the manner described above for publications and references.

What is claimed is:

1. A cell-free method of preparing a non-viral, linear and closed-ended DNA (ceDNA) vector comprising:

providing a first single-stranded inverted terminal repeat (ITR) molecule comprising a first ITR;

providing a second single-stranded ITR molecule comprising a second ITR, wherein the first ITR and the second ITR are synthetic;

providing a double-stranded polynucleotide comprising a double-stranded expression cassette sequence, wherein the double-stranded polynucleotide comprising the double-stranded expression cassette is obtained by excision from a double-stranded DNA construct; and ligating the 5' and 3' ends of the first ITR molecule to a first end of the double-stranded polynucleotide and ligating the 5' and 3' ends of the second ITR molecule to a second end of the double-stranded polynucleotide to form the ceDNA vector, wherein:

the first ITR molecule comprises a first overhang region that is complementary to an overhang region on the first end of the double-stranded polynucleotide, and the second ITR molecule comprises a second overhang region that is complementary to an overhang region on the second end of the double-stranded polynucleotide;

each of the first overhang region and the second overhang region is located in an A-stem of the respective ITR; and ITR D regions are present in the double-stranded expression cassette sequence;

thereby preparing the ceDNA vector without using cells.

2. The method of claim 1, further comprising a step of synthesizing at least one of the first ITR and the second ITR using in vitro DNA synthesis prior to the providing steps.

3. The method of claim 1, wherein, within the double-stranded DNA construct, the double-stranded polynucleotide comprising the double-stranded expression cassette sequence is flanked at the 5' end by a first restriction endonuclease cleavage site and at the 3' end by a second restriction endonuclease cleavage site.

4. The method of claim 1, wherein the double-stranded DNA construct is selected from the group consisting of: a bacmid, a plasmid, a minicircle, and a linear double-stranded DNA molecule.

5. The method of claim 1, wherein at least one of the first ITR and the second ITR are annealed prior to ligation to the double-stranded polynucleotide comprising the expression cassette sequence.

6. The method of claim 1, wherein the ligation is effected by T4 ligase or an AAV Rep protein.

7. The method of claim 1, wherein the first ITR is selected from the group consisting of a wild-type ITR and a modified ITR, and/or the second ITR is selected from the group consisting of a wild-type ITR and a modified ITR.

8. The method of claim 1, wherein at least one of the first ITR and the second ITR comprises at least one RBE site.

9. The method of claim 1, wherein at least one of the first ITR and the second ITR is an AAV ITR or an AAV-derived ITR.

10. The method of claim 1, wherein the double-stranded expression cassette sequence comprises at least one cis-regulatory element.

11. The method of claim 1, wherein the double-stranded expression cassette sequence comprises a transgene sequence.

12. The method of claim 11, wherein the transgene sequence encodes a protein.

13. The method of claim 1, wherein the double stranded polynucleotide comprises at least one RBE element and an ITR D region.

14. The method of claim 1, wherein the method steps are all performed in a manner that does not involve replication of the ceDNA vector by or inside of a cell or using a cellular extract.

15. The method of claim 1, wherein the double-stranded polynucleotide comprises a first Rep binding element (RBE) and a second RBE.

16. The method of claim 1, wherein each of the first overhang region and the second overhang region is located in the A-stem of the respective ITR between: hairpin loop sequences B and C, and a Rep binding element (RBE).

* * * * *